US012605412B2

(12) United States Patent
Zitvogel et al.

(10) Patent No.: US 12,605,412 B2
(45) Date of Patent: Apr. 21, 2026

(54) MICROBIAL COMPOSITIONS FOR IMPROVING THE EFFICACY OF ANTICANCER TREATMENTS BASED ON IMMUNE CHECKPOINT INHIBITORS AND/OR TYROSINE KINASE INHIBITORS AND MARKERS OF RESPONSIVENESS TO SUCH TREATMENTS

(71) Applicants:INSTITUT GUSTAVE ROUSSY, Villejuif (FR); Institut National de la Sante et de la Recherche Medicale, Paris (FR); Universite Paris-Saclay, Gif-sur-Yvette (FR)

(72) Inventors: Laurence Zitvogel, Paris (FR); Lisa Derosa, Paris (FR)

(73) Assignees: Institut Gustave Roussy, Villejuif (FR); Institut National de la Sante et de la Recherche Medicale, Paris (FR); Universite Paris-Saclay, Gif-sur-Yvette (FR)

( * ) Notice: Subject to any disclaimer, the term of this patent is extended or adjusted under 35 U.S.C. 154(b) by 826 days.

(21) Appl. No.: 17/762,263

(22) PCT Filed: Sep. 29, 2020

(86) PCT No.: PCT/EP2020/077234
§ 371 (c)(1),
(2) Date: Mar. 21, 2022

(87) PCT Pub. No.: WO2021/063948
PCT Pub. Date: Apr. 8, 2021

(65) Prior Publication Data
US 2022/0370514 A1     Nov. 24, 2022

(30) Foreign Application Priority Data
Sep. 30, 2019     (EP) ..................................... 19306246

(51) Int. Cl.
*A61K 35/74* (2015.01)
*A61K 31/404* (2006.01)
(Continued)

(52) U.S. Cl.
CPC ............ *A61K 35/74* (2013.01); *A61K 31/404* (2013.01); *A61K 31/416* (2013.01); *A61K 31/47* (2013.01);
(Continued)

(58) Field of Classification Search
CPC .... A61K 35/74; A61K 31/404; A61K 31/416; A61K 31/47; A61K 35/741; A61K 45/06;
(Continued)

(56) References Cited

U.S. PATENT DOCUMENTS 11,684,640 B2 *   6/2023   Zitvogel ................ C12Q 1/689
424/93.45

FOREIGN PATENT DOCUMENTS

EP       2744890 A1 *   6/2014   ............. A61K 35/71
EP       3209692 B1 *   5/2024   ........... A61K 35/741
(Continued)

OTHER PUBLICATIONS

Bhullar et al (Kinase-targeted cancer therapies: progress, challenges and future directions. Mol Cancer 17, 48 (2018)) (Year: 2018).*
(Continued)

*Primary Examiner* — Thomas J. Visone
*Assistant Examiner* — Georgiana C Reglas
(74) *Attorney, Agent, or Firm* — Arrigo, Lee, Guttman & Mouta-Bellum LLP

(57) ABSTRACT

The invention pertains to the use of bacteria selected amongst *Alistipes senegalensis, Dorea longicatena* and *Eubacterium siraeum* for inducing immunostimulation in a patient in combination with an anti-cancer immunotherapy with an immune check-point inhibitor (ICI) and/or a tyrosine
(Continued)

kinase inhibitor (TKI). The invention also relates to methods for assessing the probability that N a patient respond to a treatment with an ICI and/or a TKI, based on measuring the relative abundances of immunotolerant bacterial species (*Clostridium hathewayi, Clostridium clostridioforme* and *Clostridium boltae*) and/or immunostimulatory bacterial species CN (*Akkermansia muciniphila, Bacteroides salyersiae, Alistipes senegalensis, Dorea longicatena* and *Eubacterium siraeum*) in the patient's gut microbiota.

16 Claims, 39 Drawing Sheets

Specification includes a Sequence Listing.

(51) Int. Cl.
| | |
|---|---|
| *A61K 31/416* | (2006.01) |
| *A61K 31/47* | (2006.01) |
| *A61K 35/00* | (2006.01) |
| *A61K 35/741* | (2015.01) |
| *A61K 45/06* | (2006.01) |
| *A61P 35/00* | (2006.01) |
| *C12N 9/22* | (2006.01) |
| *C12N 15/11* | (2006.01) |
| *G01N 33/569* | (2006.01) |

(52) U.S. Cl.
CPC ............ *A61K 35/741* (2013.01); *A61K 45/06* (2013.01); *A61P 35/00* (2018.01); *C12N 9/22* (2013.01); *C12N 15/11* (2013.01); *G01N 33/56911* (2013.01); *A61K 2035/115* (2013.01); *C12N 2310/20* (2017.05); *C12N 2800/80* (2013.01)

(58) Field of Classification Search
CPC ..... A61K 2035/115; A61P 35/00; C12N 9/22; C12N 15/11; C12N 2310/20; C12N 2800/80; G01N 33/56911
See application file for complete search history.

(56) References Cited

FOREIGN PATENT DOCUMENTS

| WO | WO-2016063263 A2 * | 4/2016 | .......... A61K 35/741 |
|---|---|---|---|
| WO | 2019/178542 A1 | 9/2019 | |

OTHER PUBLICATIONS

Krzyszczyk et al (The growing role of precision and personalized medicine for cancer treatment. Technology (Singap World Sci). Sep.-Dec. 2018;6(3-4):79-100) (Year: 2018).*

Fuerst, Mark. Gut Microbiome Affects Response to Immunotherapy. Oncology Times 41(8):p. 32, Apr. 20, 2019 (Year: 2019).*

Frankel et al.(Cancer Immune Checkpoint Inhibitor Therapy and the Gut Microbiota. Integrative Cancer Therapies. Apr. 23, 2019;18) (Year: 2019).*

Grüllich, C. (published Aug. 2, 2018). Cabozantinib: Multi-kinase Inhibitor of MET, AXL, RET, and VEGFR2. In: Martens, U. (eds) Small Molecules in Oncology. Recent Results in Cancer Research, vol. 211. Springer, Cham. (Year: 2018).*

National Cancer Institute "Cancer Treatment" [online. [retrieved Nov. 13, 2024] Retrieved from the Internet:<URL:https://www.cancer.gov/about-cancer/treatment> (Year: 2015).*

Bertrand Routy et al. ,Gut microbiome influences efficacy of PD-1-based immunotherapy against epithelial tumors. Science359,91-97(2018) (Year: 2018).*

Zitvogel et al. ,Cancer and the gut microbiota: An unexpected link. Sci. Transl. Med.7,271ps1-271ps1(2015) (Year: 2015).*

Zitvogel et al. ,The microbiome in cancer immunotherapy: Diagnostic tools and therapeutic strategies. Science359,1366-1370(2018) (Year: 2018).*

Tanque et al., A defined commensal consortium elicits CD8 cells and anti-cancer immunity, NATURE vol. 565, No. 7741, 600-605 (Jan. 23, 2019).

* cited by examiner

NIVOREN trial
NCT03013335

Fig. 2A
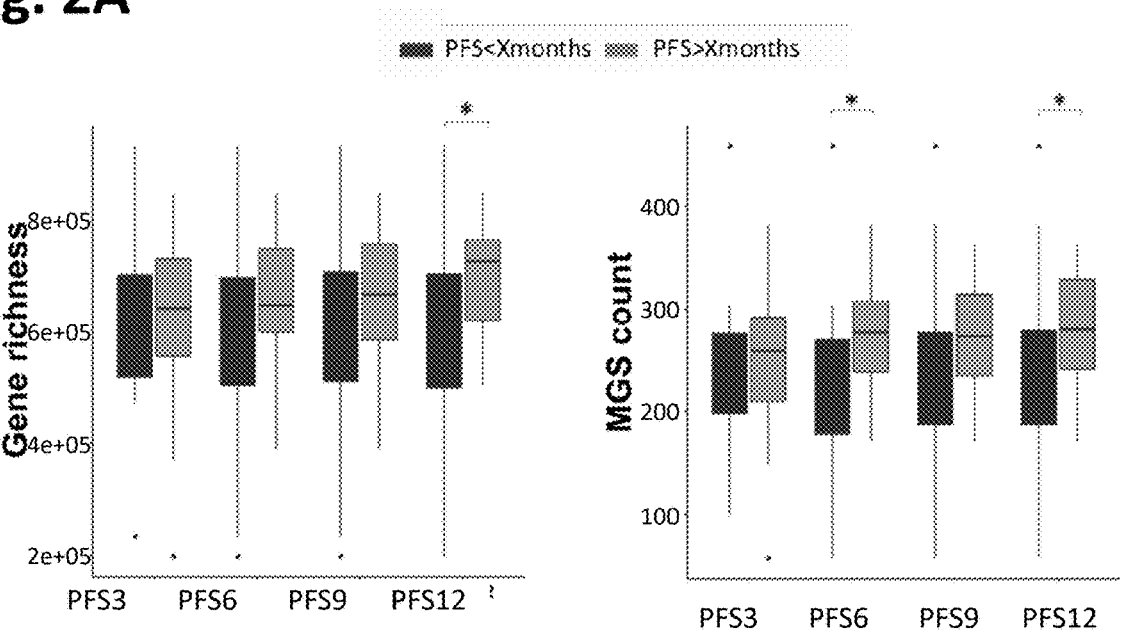
Fig. 2B
NR = 28     R = 30
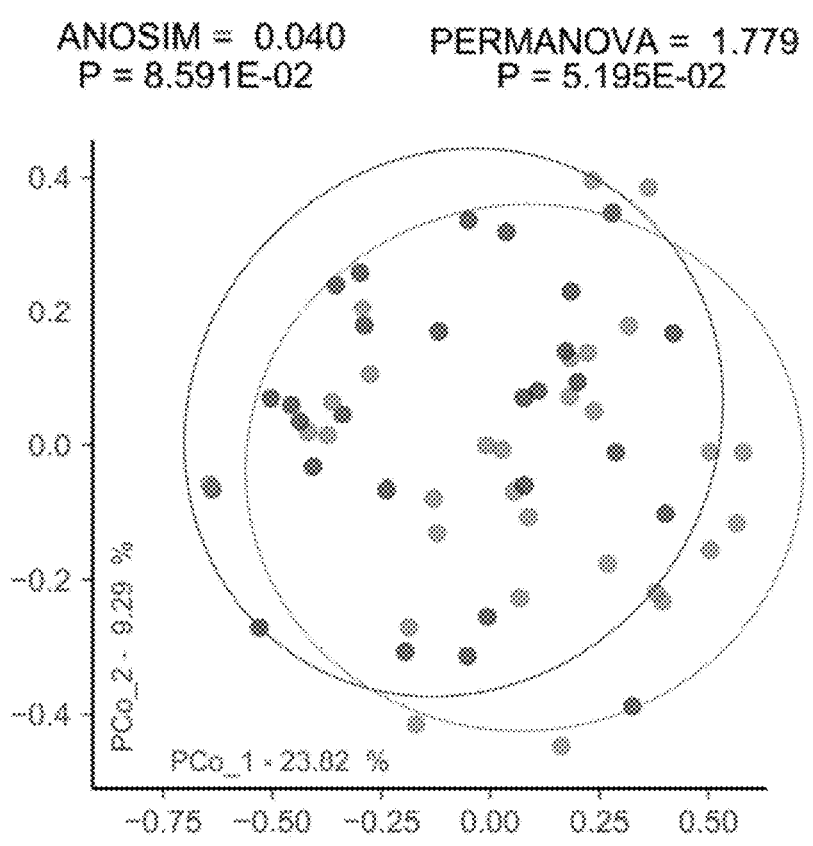

Fig. 3A

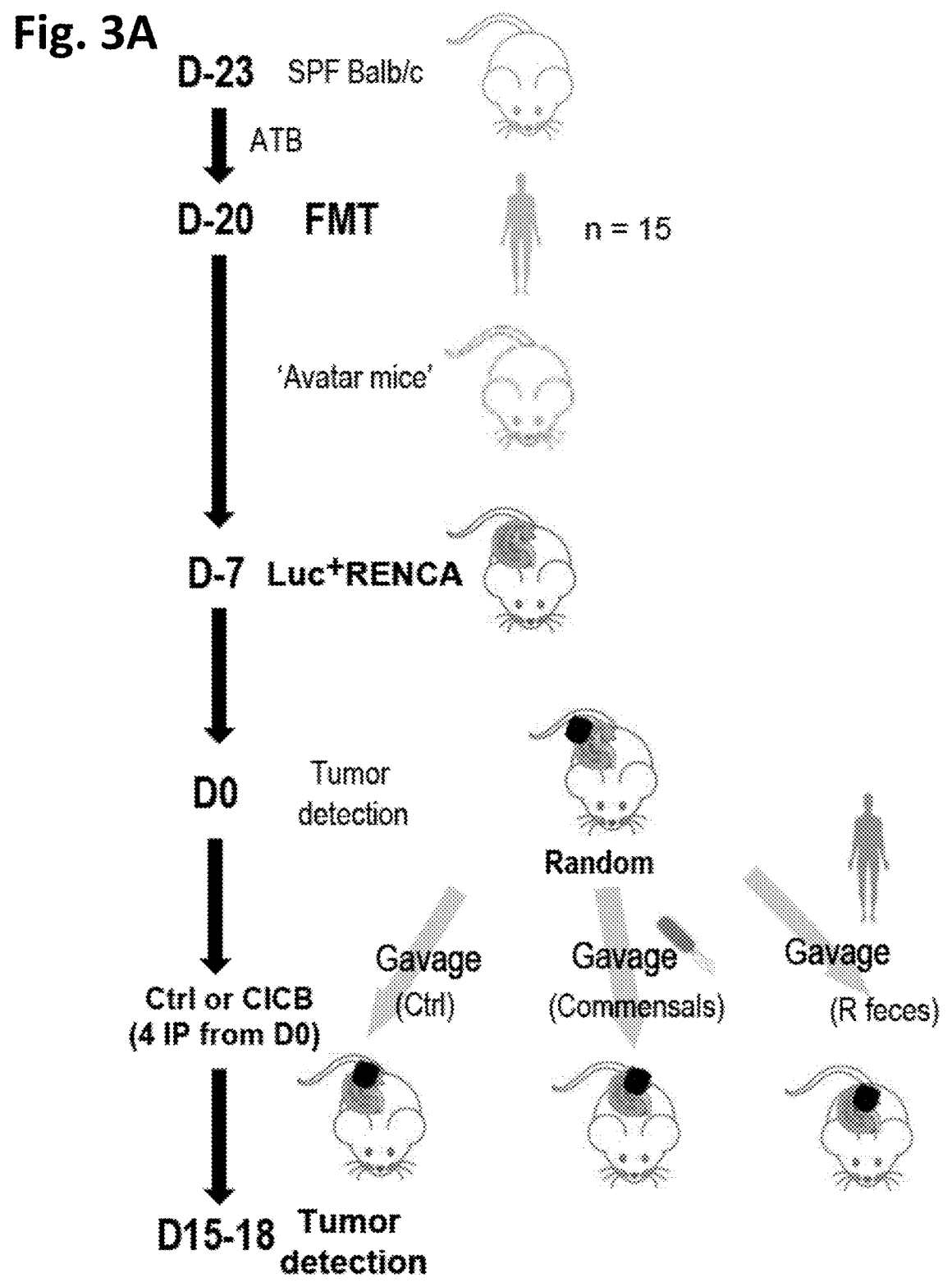

D-23   SPF Balb/c

↓ ATB

D-20   FMT     n = 15

'Avatar mice'

D-7   Luc+RENCA

D0   Tumor detection

Random

Ctrl or ClCB (4 IP from D0)

Gavage (Ctrl)    Gavage (Commensals)    Gavage (R feces)

D15-18   Tumor detection

Spleen : Ctrl

RENCA : Ctrl

RENCA : CICB on Ctrl

Fig. 5E
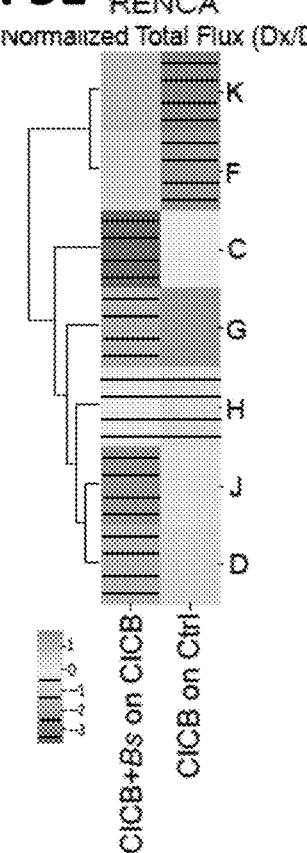
Fig. 5F
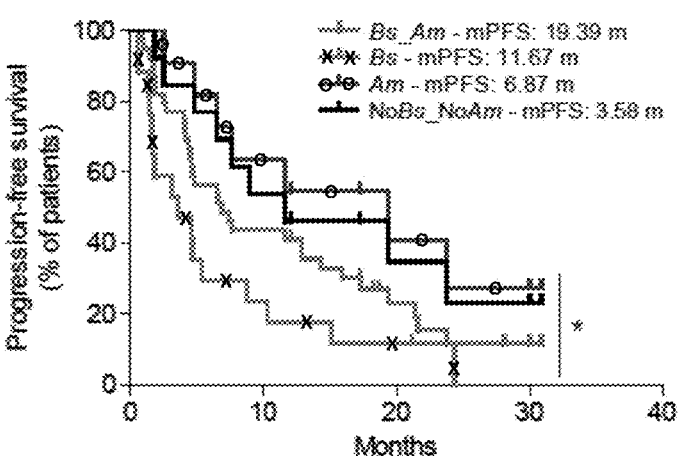
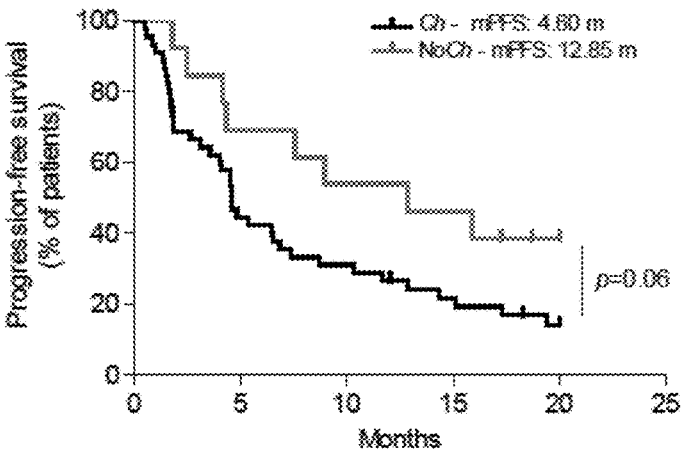
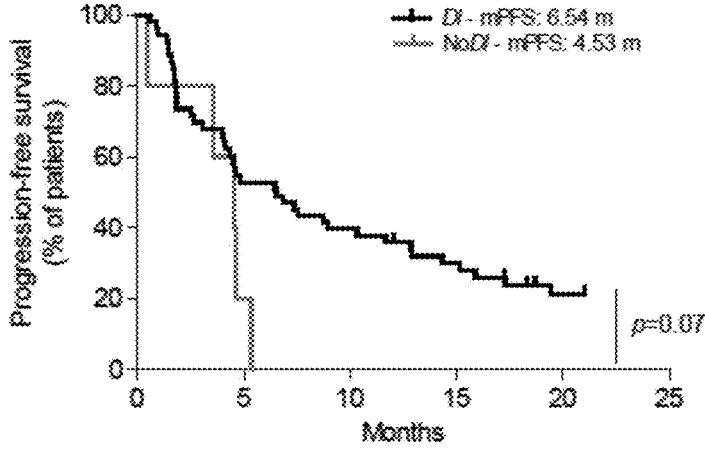

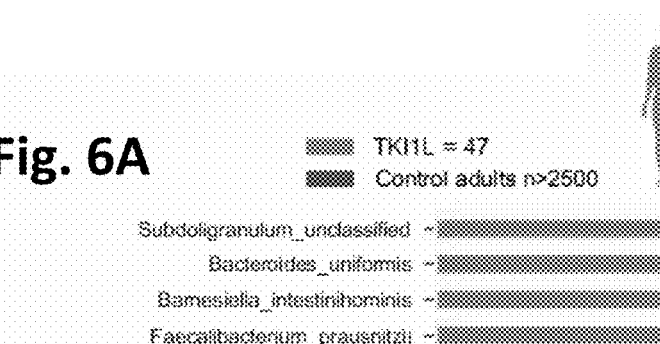
Fig. 6A
TKI1L = 47
Control adults n>2500
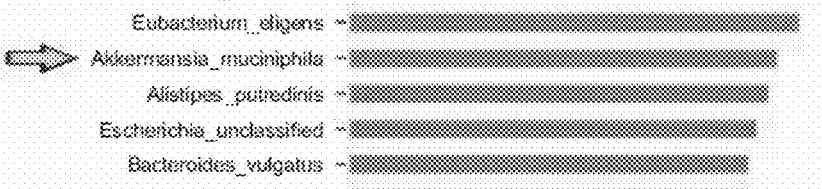
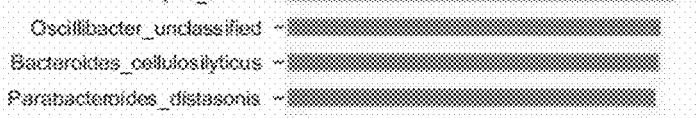
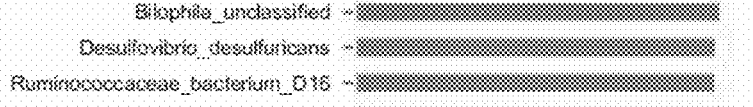
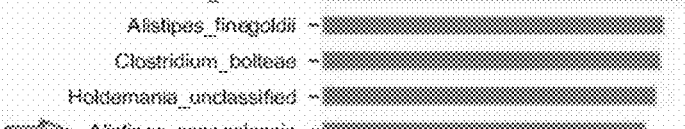
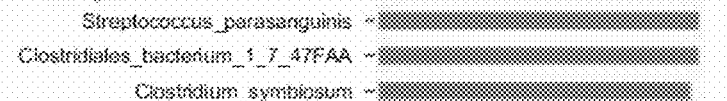
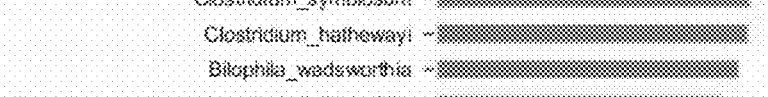
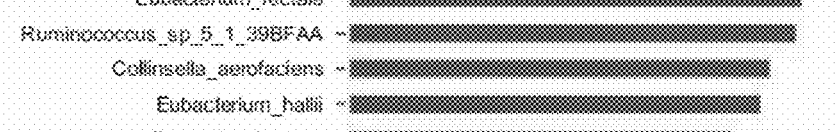
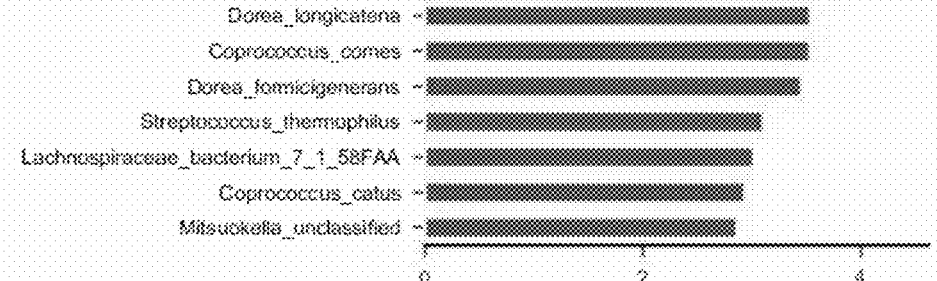
LDA score

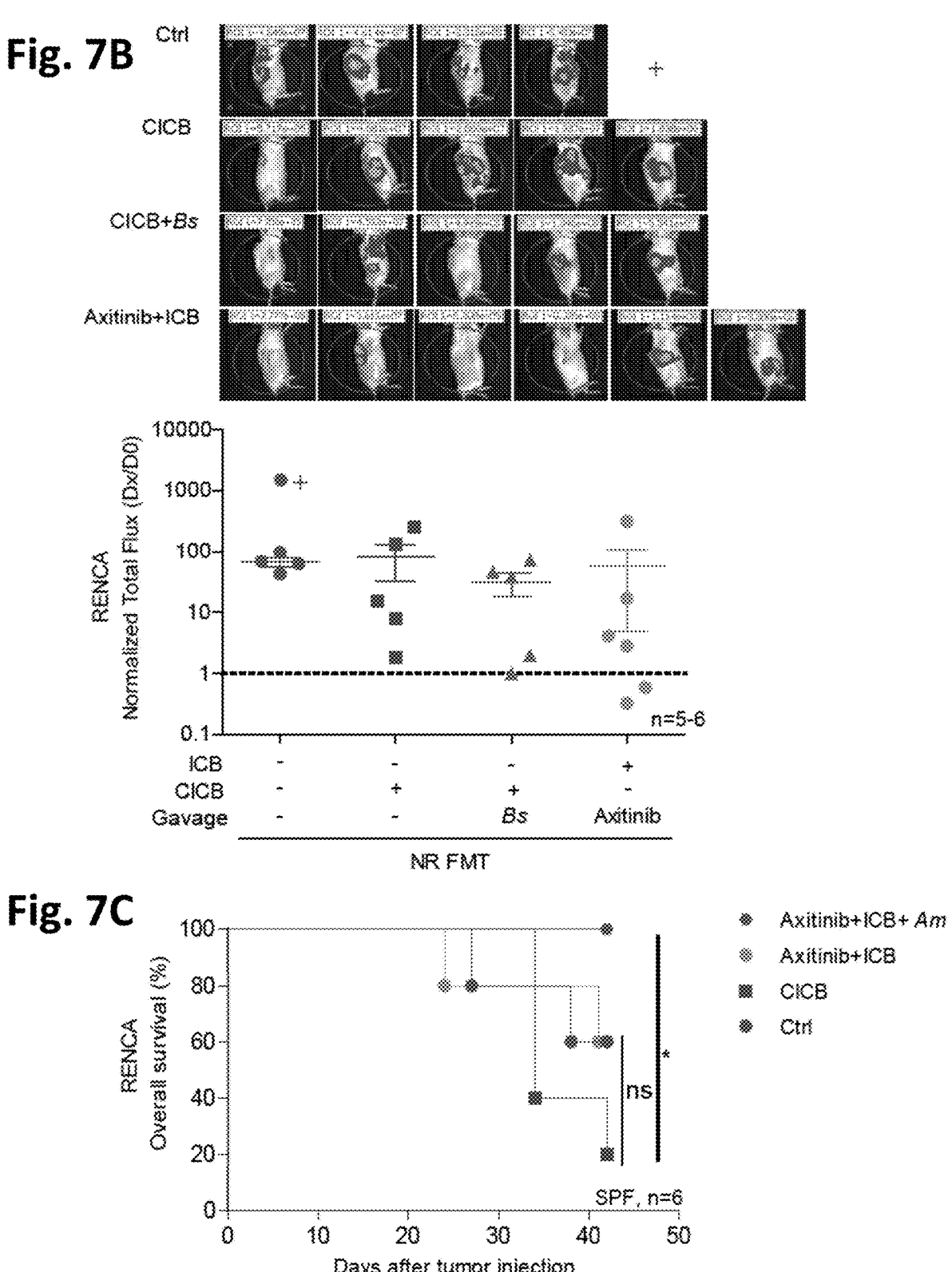

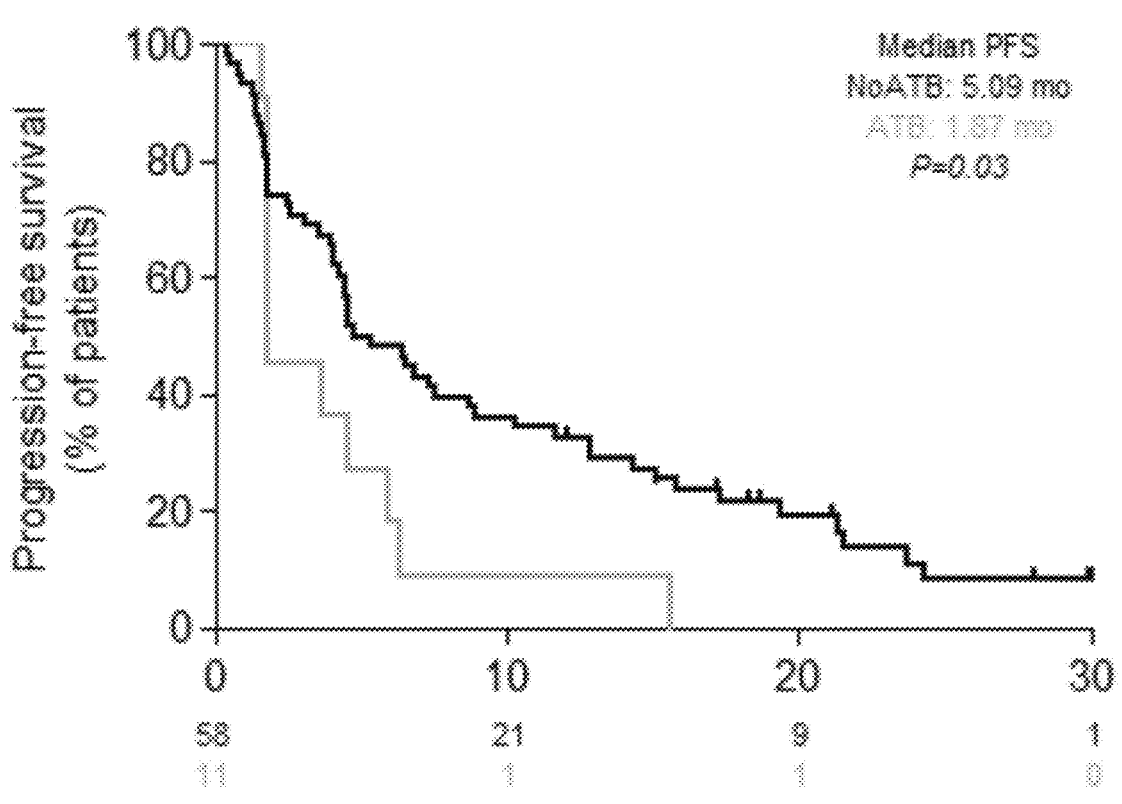
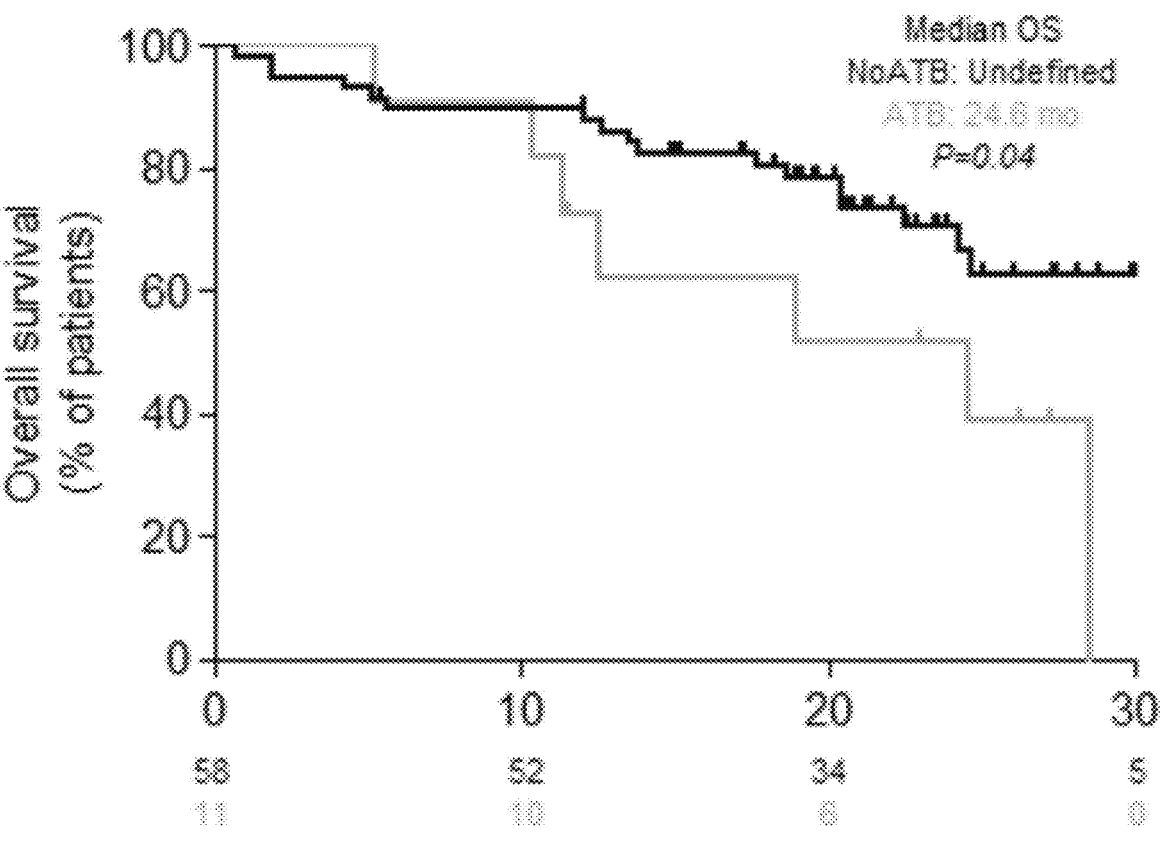
Fig. 8

Fig. 9A
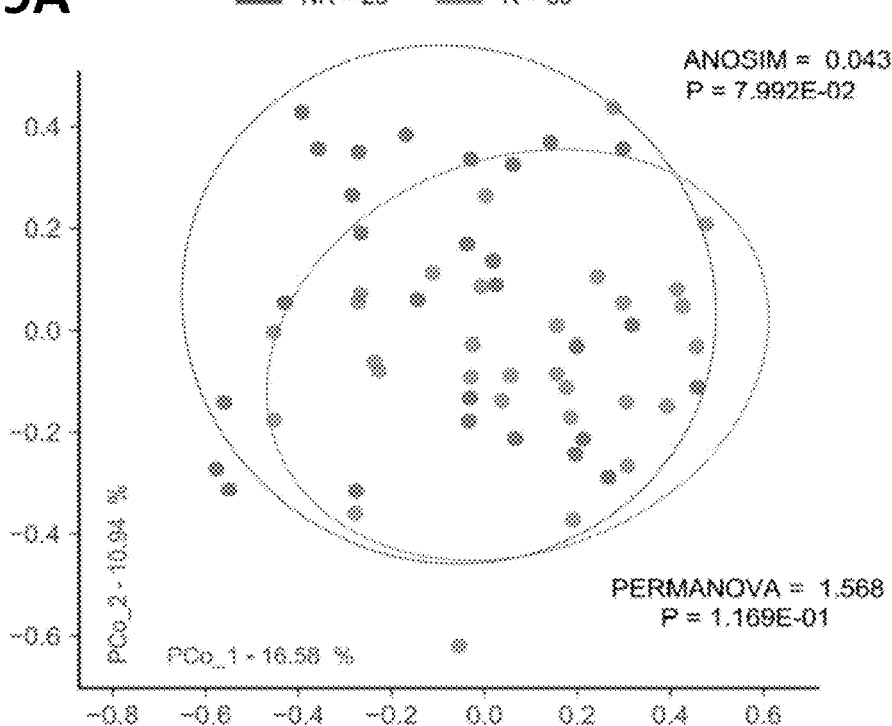
Fig. 9C   *Akkermansia muciniphila*
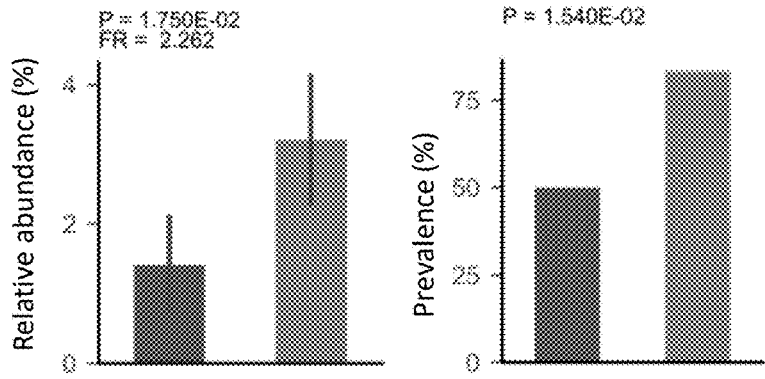
*Bacteroides salyersiae*
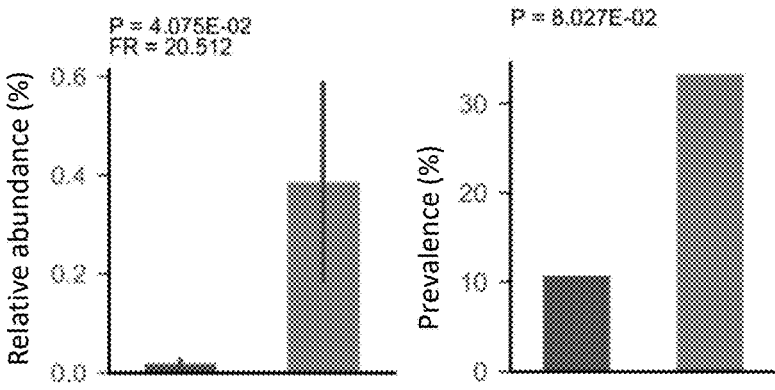

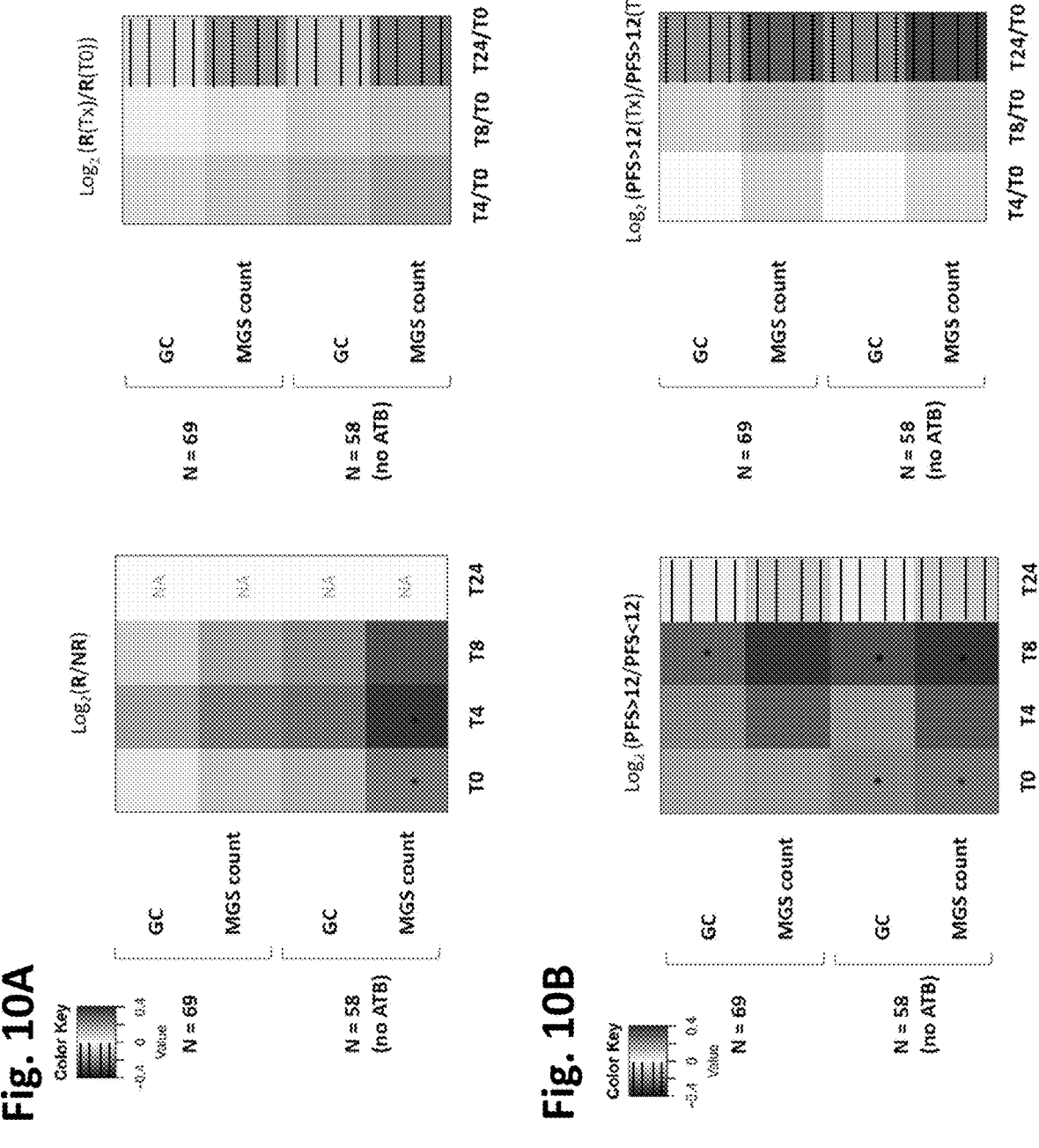

Nodes:  144
EdgesT:  372
Edges+:  79%
Edges-:  21%

| | | | |
|---|---|---|---|
| | SIG 1 | spp=31 | 25.0% |
| | SIG 2 | spp=27 | 21.8% |
| | SIG 3 | spp=18 | 14.5% |
| | SIG 4 | spp=18 | 14.5% |
| | SIG 5 | spp=10 | 8.1% |
| | SIG 6 | spp=9 | 7.3% |
| | Other | spp=11 | 8.8% |
| | | Tot=124 | 100% |

Control adults n>2500

LDA SCORE (log 10)

RCC n>69

LDA SCORE (log 10)

Fig. 15A
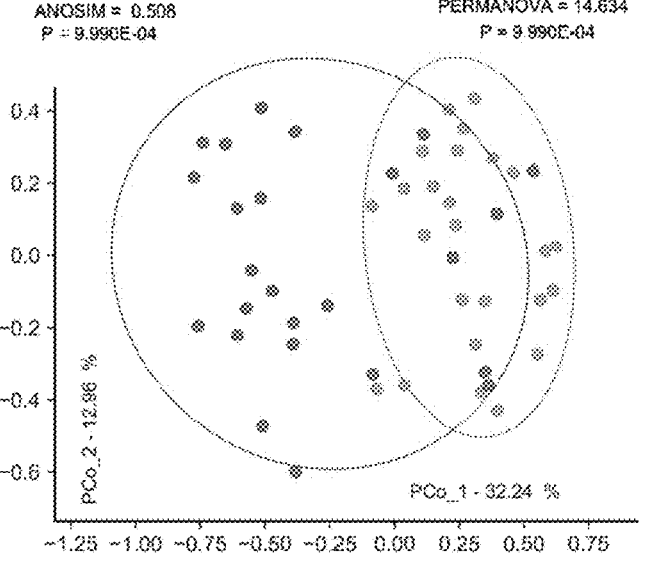
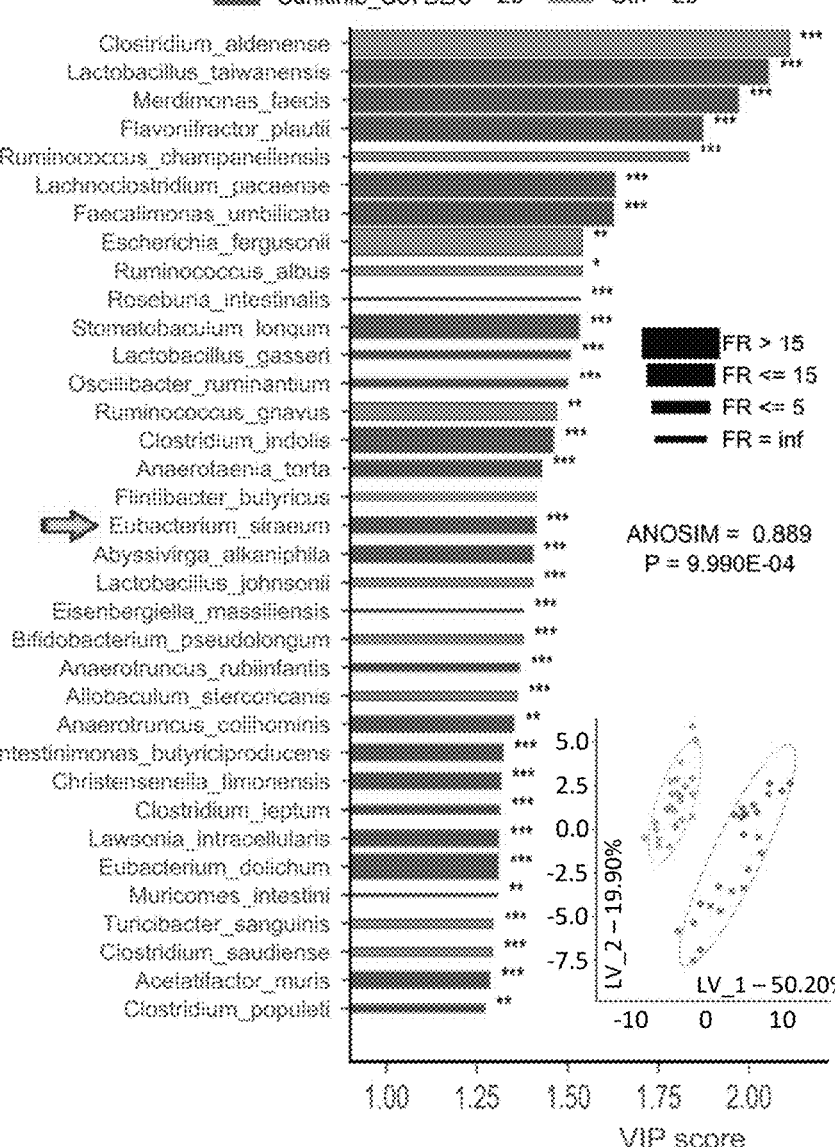

Fig. 15B
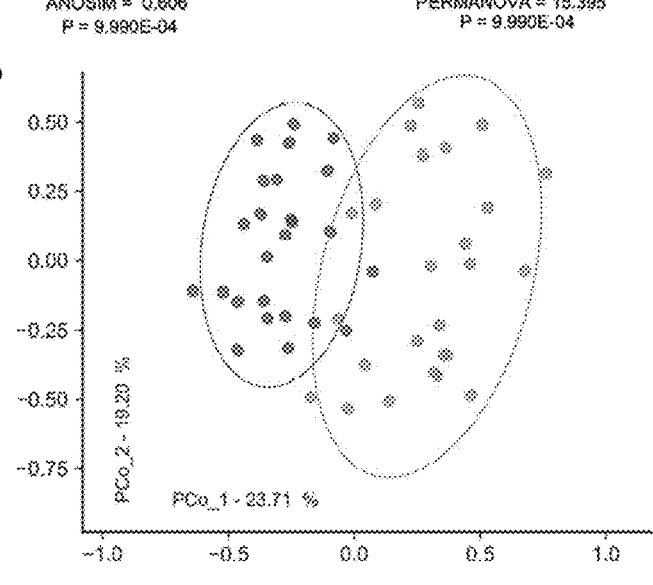
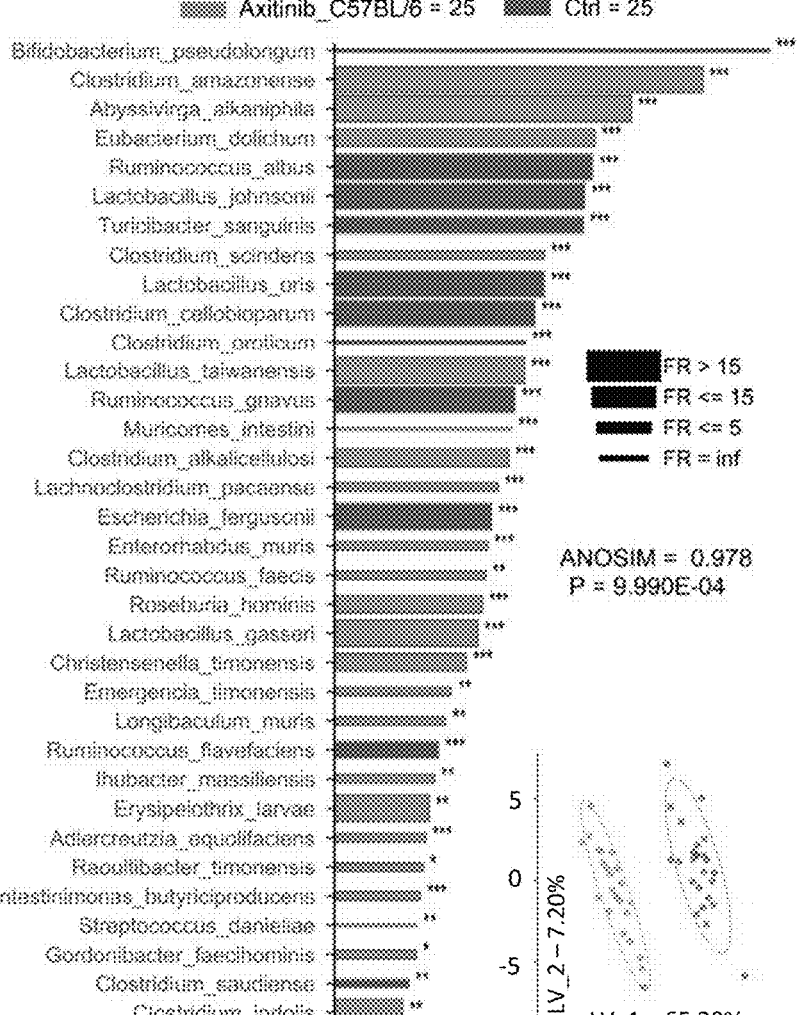

SEQUENCE LISTING

<160> NUMBER OF SEQ ID NOS: 248

<210> SEQ ID NO 1
<211> LENGTH: 3225
<212> TYPE: DNA
<213> ORGANISM: Alistipes senegalensis

<400> SEQUENCE: 1
gtgggtgcgg ctcaggatgt ccgagcctat gagggtgcga ttacgcttcc gacctatctc        60
ctggatccgg cggaaaaggc cccgatcttt gaacgggact ggtcctacca gcgcgccaaa       120
agaagtgtct atccctatcc gctcaatgac aatatgaccc gtaagaagaa ggatgtgacc       180
tacgattgtc tctatatgga gaacgagtat gtgaagttgt gcgtactccc ggagatcgga       240
ggccggttgt tgtatgccgt cgacaagacc aacggttacg acatctttta ccggaacagc       300
gtggtcaagc cggccaatgt gggaatgacc ggagcgtgga tcagtggtgg cgtagagtgg       360
aatgccttcc accatcaccg ccagaccagc catattccgt gtgactggcg gattgtcgat       420
aatcgcgacg gctcgaagac gatctggctt ggcgagactg agtatcgcca tcggatgcag       480
tgggcgatcg gaatcacgct ccgtccgggg aaatcctata tggagatcag tggacgtttg       540
atcaattcca ctcagaataa caattcgatg ctttattggt cgaatgtatc gacgctggtc       600
gacgagaatt accagatttg ttttccgcag agcacggagt cgtgacgtt ccattgtaaa       660 aactggtttg cacactggcc cgttacgcat gaacccttca acgatatgga cttctacaag       720
aatggtgtgg atgcaagctg gtggaaaaac cattacatga gcaactcgat gttcatccat       780
gaccagaagg aggattttgt ggccggatat gaccacggcc gtcatgctgg cacgatgcta       840
gtcggcaatc acaacatcat caagggtggc aagttctggc tgtggggccc caattccgag       900
tgggacaccc ggattcttac tgatacgtcg ggccattatt gcgagttgat ggtggggggcc       960 tactccgaca accagcctga ttacaattgg agtttcccct acgagagcaa ggaattcacc      1020
cattactggt atggtatccg ggacatgggt ggcgtgaagg ccggtagccg ccacgctgcg      1080
ttgaacctgg accgcctgtc gtcggaccgg gttctggtgg gggccaatgc tacggaaaaa      1140
tatgcgaaac tgacccttga actgcgccat ggggatgaag ttctttacac ccgcagcggt      1200
gcaatgtctc ctgccgaacc gatggttgat acggttgccg tggcaagcgg ggtggcagat      1260
cacgaactga cattggtcct gaaggacgag aatggaaact ggatgctctc ctatacgccg      1320
gtccgcaagg atgcgaactc tccgctgccc gagatcgttg agccgccgtt gctgcctcat      1380
cagatcgaaa acacggagga gtgttttctc gtggggcttc ggaacctgca gttccacaac      1440
ccgttcgtca atccggttga ttattttgag gaggtgctcc gccgggatcc ctcggacagc      1500
cggaccaata ccgtgctggg ctcctactat cggatgaggg gcgaatacga caaggctgcg      1560
aagtatcttc ggacggcgat tcggcgtctg acgaaggatt ataccgccc gaaggatgtc      1620 gaggcgctgt ataatctggg actgattctt cagatacagg caagcgcga ggctgcctac      1680 gatacattgt atcgggcgac ttggaattat acgtataatt cggcggccaa tacgcaactg      1740
gcccggatgt attcggagga gaagcgctgg ggcatggctc tggagcggct cgatgaggca      1800
atcgcctaca atggccgtaa ctatacggcg ctgaatctga aaggttcggt cctgaagagc      1860
ctgggccggg atgcggaggc gcggcaatgt ttcgaccgcg tgcttgccga cgatccgatc      1920
aatgcctatg cgctgcatga aaccgcttcg cacgacgact ccggcgcctt tatgcgcgaa      1980
cagccggaat cctacctcga actggccatt cagtattggc acaatggatt cacagatacg      2040
gccgtcaatc tgttgaagga gatcgatgcc cgcgtgccgt atccgaccgt gaagatgtat      2100

```
ctgggctatc tgaccggtga ggatcgctat tttggcgagg ccttgtcgct gccggtcggt    2160
tactgcgcgc cgttccggct tgagacggtc cccgttctgg agaaggctaa gtcggtttgc    2220
tcggactctt cgctgcccta ttattacctc ggcaatctgt attacaacat tcagcccgac    2280
aatgccatcc gggagtggga aaagtgtgtg gcgatacagc cggacaacga tctcgcctgg    2340
cggaacctcg gctgggccca ttggctgcat acgaaagatt acgccaagtc ggccgactgt    2400
tatcggaaag ccatcgagtt gaatcccgat gcggcgcttt acctggagga gtgcgatcag    2460
gtgctggaag ccctggggac tcccgttcag gaacgctatg atctgctcaa gagccaccat    2520
gcaacagccg agaaacgcta ttatcctttg gcgcaggagg tcataacggg tacctatgtc    2580
ggggattacg actatgtgct ggatcttctg gaccggtgct atttcccgac gcgggaaggg    2640
gtggccaact ccatgacaa ctttgtggat gcgttgatcc tggccggcga ggagaagata    2700
gcggaaggta aggtcgaaca ggccgtgacg ctttacaaga aggcgtttac ctatccggag    2760
aatcatcagg tgttcctcgt ggacgagcgg gccacgcacg atgcgcagat caactattgt    2820
ctcggagagg cttacgccgc gcttggccag gatgccgagg cggaaaagta ttggaaacta    2880
gccgccgaac aggattatga actgaaggga agcaaggatt ccgctactg gacgggcctt    2940 gcgctggagc gtctgggccg gaaagcggag gcggaggcca tcttctcggc gctggttgcc    3000
gatggcgagg ctgccgttgt cacacagcac gttaatttct acggagctga aggaactacg    3060
ggcgtgacgg tcgatattat caactcggcg gcctattata cccaggcact cggtcatctg    3120
ggactcggac ataggggaa ggcgaaacgt ctctttgccg aagtgcagcg cctgaagccg    3180
gatcacctct gggcaaacga gttcatgaag cagtttgaaa aatag    3225
```

```
<210> SEQ ID NO 2
<211> LENGTH: 3120
<212> TYPE: DNA
<213> ORGANISM: Alistipes senegalensis

<400> SEQUENCE: 2
atgatgaaag gaatcatata cgctgcggcc gtgtcgtcgt tcgtgctggc cgcatgcacc     60
tcctgcacgc acgacggcct gcccggcgcg gaggttccgg acgacggctg catcgaaatc    120
cgtttcgacg ccgatattcc gccgatgccc gtggtcgcca cccgctcggt cgatcccgac    180
ggcacgggcg tgcagaacat gacgctcttc tgtttcgaca gctacggact tttcgtcgca    240
acgacgcagg cgacgctggc gccgacatcg gacgacctgc atgaaggcac gttcacggcc    300
cgcgtgccgc agaatacgcg cctgatccat ttcctgggca accagaacat gctgggattt    360
caggaacggg atttctacaa caagtcggag gcgcaggtga tggccgcgct cgaaggctcc    420
tcgggcatga tgatctactg ggcccgtttc gcctgtgccg aggacgatcc gcgctccgtc    480
gccgagcagc tgaaagcgca gggcgggata gagctcgtcc gcaaccatgc gctgatctcg    540
gtggacaacc ccgcgggcaa cggcagtctg gacgtgaccg ggttcgtcgt ctgcaatacc    600
agcgcgttcg gcaccgtggc gccctatcac cccgagcagg gattcgtatg gccggggacg    660
gagcctttcg tgacgctgcc gaaaaatacg tcggtgatga gcgacatcct cgacgtgacg    720
accgacatgc ggcaatatgt cttcgagtgc gagaatacgc ccgacaaacc cgtcagtgtg    780
atcctgcgcg gacaccgccc cggtgaaacc gaggccgacg acctttatta ccgcgtgatg    840
ctgatcgatg cgcagggcga acagctgctc atccgccgca accaccatta cattctccat    900
atcgagggcg aactttccta cgggcagcgc tcgttcggcg aagcgctcga tgctgccgcg    960
```

-continued

```
acgaacaacg tctggatctc gatccgggac aatatcgacg aggtttcgga cggcaccttt    1020
accctgaaag tcgatcggac gagctatgtg ctggaccaga gcaacgaggg gcggcagtat    1080
tcgcttcgct acacgctccg gaggaacgac ggatcggcgg tttcggaggc cgacaaaccg    1140
tcggtgacgt ggctcgacgg caacaacgtg gcggggcaga atgtcggcaa ttcgttcgtc    1200
gtcgggagcg acggcgtggg gaacggcgaa ctcaccgtgg tgctgcgcga aatgggcggc    1260
agcgaaaagc tcgaagggac gctgctggtc aaaaaggggc ttttgcagcg caagatcaag    1320
atcatcctca tcaaaacgca gtcgttccgg cccgcatggg tggcgtcgca ggtgttcggc    1380
acaccctctg ccggagagag cggaggcacg tacggcgaac atgtgacgtt gatgttcacc    1440
gttccggaga catgtccggc ggagctgttt ccgctgcggg tgctgatcgg cgtcgaggat    1500
ctcgatgtcc gcgcggcggc cggcatgtcg ctgccggtga tccgccgcgg cgaggatggc    1560
ttcggagaga atatcctcga cgaaaagggg gagccgatcg aatacaagtt cgtctatacg    1620
gccgtacagc cgggcgtgca gcgggtgtat ttccgcacga tcctgccgca gagcggttcc    1680
ggagcgaaga ccaaggtttc ggtcgaagcc ggatacttcg ccacgcagga gaaggaggtg    1740
acctataccg gcctccgata tgtgatcgag gtcgccggat tgaacgaata tacggccaga    1800
cccgacgacg atttcgccga cgacgagaag atcttctacc ggctggtgcc gcagaagaag    1860
ggcgctttcg tccagttcac catgcatctg cacgataatt cagcggaaac atcgtccggc    1920
ggcgattacg gcgaattcgt caacgccacg gccgacgacg agtttctgat ctattcgcag    1980
tatctcgacc acattcccga cggagaggag cccgacggcg ttacgttcga ctgcacgttc    2040
tcgcccgtca acgaggatat gtggacggag aatggccgca tgtatctctt ttacccgcgc    2100
gcgggcggcg atacgccgca gtcggggacg ggcatctatt cgatttacct gcgaaccaac    2160
cgtccgcaga gtgccgaggt cgtccgcata gcctccaata tttcgggcga gaagtcgttg    2220
aaagatgtcg cccgggacta tgccggccgc ggttatcgtt cgacttcgtt cgagctggcc    2280
aactacaacc ccttccgttt tgcggcacgc atagacggtg cgggcgggga tgcctccgga    2340
agcgacgcgg agccggtgac ggaattgacg tggaattatg agaatccggc cgaaacgaac    2400
atcgacatcg agttcgacgt gaccagtttc cggggttcgg acgaccggtc ggccgatcct    2460
ttcggcgaga cgttcgaggt ctatatcgac gcgccgatgc tgaccgtgga cgaatcgcgg    2520
ctggccgagt gcaatctgac gcccgataaa ctcaaagcgg accctgaggt cgaggggcgt    2580
ttcgtttata cggtcgatgc ctcgcgcgag gaggagcgca aattcggtgt cgcagacgcg    2640
ctgatccccg atacgacgcc ggccgctgcc ggaagccctg cgccttcaca gtcgggagag    2700
cgcaagcggc tgccgttcaa gacgaactgt gtggtgagcg ccggcgacat caccctttcg    2760
tcgaacgagg agaaagtcgt cttcttccgg aagaccttcc gtgtggcgaa cgagtcggtc    2820
acggggcgga tcacctacga tccgggcacc ggggcgattc ccgtgccgcg caatgcgttc    2880
gtgtcgttca tacagtcggg aacggggagc cgcatcgggt cgatgaccgt gacggcggac    2940
ggccgctacg agttgcggtt gcgcaaggag tatgaccccg ggtggttcga tcgcatcgaa    3000
ctccgctata cgaaggacgg cgcggtttac cggaaccgga tcgacgagaa caatccgctg    3060
acgctggccc gtctggtgca gtcgcccgat atagtattgg tgaatgtggc cgctgattga    3120
```

<210> SEQ ID NO 3
<211> LENGTH: 3063
<212> TYPE: DNA
<213> ORGANISM: Alistipes senegalensis

<400> SEQUENCE: 3

-continued

```
atggcacaga atgaaataca taagatcata acgatagagt tcaaaaattc ggaacttatc      60
gacaaaatgc gagaggcgca gaatgctata aaggcactca ataccgaaac caaatatctg     120
aaagaggacc tgaatgagta tcgccagcag ctcaaatccg gagctatctc gcaagaccag     180
tttgatcgga tgatgattaa gaccaagaac gagataatca aaaacgatca ggctgtaatt     240
aaatacaaat cggatattaa agcgtacact cgtgaacttc aatccaatat ccgccaagat     300
aaggagaagg tcggttccct gaatcaactg cggtcgtccg taaagtcttt gactgcggaa     360
tacaataatt tgagcgccgc agagcgagga ggagtccggg ggaaagaaat cgtgcggcag     420
attcagaaaa caacggccga gatcggcagg caggaaaatg cactccgtaa ttatcatatc     480
ggcgtcggta attacgccgg aggcattcag aaagcgtttg ttaagatcgg ggcggcgtgg     540
atggctattc gctcggcgtt tagcctcttt cggaatagct ttaacacgat taaagatttc     600
gagcaggcca atgctaatct cggtaccatc ttgggtgcta ctaacgagga gatggataaa     660
ctacgagaat cagcacttga actggggcgg acaactgaat acacggcctc acaagttaca     720
cagttgcaaa ctgaattggc aaaattggga ttcggtccga aatccattca ggcgatgcaa     780
caaccgattt tgaatttcgc aacagccgta ggtgcaaaac tttcggatgc cgcaaaattg     840
gccggtgcga ctttgcgaat ttttggattg agtgcccatc aaaccgaaga tgccttagat     900
gtcctcgctt tgtctactaa taaatcggcc ctttcgtttg aatacttgaa tacggcgtta     960
tcaatcgttg gtcctgttgc caagacgttc ggattctccg tgcgtgatgt aacggccctt    1020
ctcgggtcat tggcaaatag tggattcgat gcttccagtg cagcgacagc aaccagaaat    1080
attttattaa atcttgctga tattaatggc aaactggcga agtctctcaa cggtccggtt    1140
aagtcattgc cggagttgat cgacggatta aaaaagctac gtgcacgggg cattgacctc    1200
gccggaacac ttgaactaac cgataaacgg agcgttgcgg catttaatac tttcttaaat    1260
ggtgctgatg atgtgaagga attacatgat gcgttgcaag atgtagatgg agcagctaaa    1320
agcattgccg aagaacgatt aaatactgtt gagggatcaa tcaaactatt gcaaagcgcc    1380
tgggaaggac ttgtgctgtc attttacaat agcaaaggca cgattaagtc cgttattgat    1440
atactgacga atgggataga ggggatcagc aatttgctaa atccggatgc ccaaaagaac    1500
aaacaaaaaa atcttttcct cgatgaattt atgaatgtat attctgccga aggagaagat    1560
gcgctgaatc ggaatattca aatcgggttg aaatattggg gcgatcaata tgaagaggcc    1620
cggaaacgct atgccggaag cggaggtctt tttggtaaat ccgaatttga tattaccgaa    1680
acgatgtata aaggcattta tcgctgctgga aatgaagctc tcgacaatgt gcagaaactc    1740
aaaaaagaac aagaaggttt agcggcacag acagaagata atggtgagaa aatcactacg    1800
ataactgaaa aagagttgaa agcacgccag caagccgcca agacacagct cgatttagag    1860
aagcaattat caaaatccat tcttgaactt agacaagcga gccttgaaaa agacctggaa    1920
ctttcccggc ttcgcttttc gtgggaacgc caagagctgg aaaacaaact caaatacgac    1980
aaaacgctga ctgcggaatc ccgggaggct ataaaccagc tgatcctgaa tatggaggaa    2040
cgcaggtata aggaggaatc cgaaatccgc cagcgttgga gcgataagga gttcgaggaa    2100
gaagcccgca atgcggagaa caggatcaag atgcggatca aagtccagga agagatggac    2160
aaactatctc ttgcgcaagt aaaaaacagg aactatgcag gattgatcgg ggacgacaag    2220
gatgcacgga ttaaagcgca gcaggccgtt gcaaatgaag aattgcgtat tgctcaaagt    2280
aaatatgacg ctatttcaca aatggatgag gagcaatgga gtgcgcaata cggttctatt    2340
```

-continued

```
caagcctatg agatggcccg actggatgca gaaaacaatg tgcaagatgc aattaagaaa      2400
acgaccgacc tgtctatcgc ctcgcaaaat caggcaataa aagtgcaact ggacgaactg      2460
gcggccgcct cctcgttagt tgggagtcta agaggtttat tcggggcgtt gggcgatgat      2520
cttgaggcat cgccattgc agagcaggca ttggccgtgg cgcaaatcat catcgacgct       2580
caaaaagcaa caatggaagc gatggttgca tcattccaac tcggacctat tgcgggacct      2640
atatggtttg caacacagaa aggaattata acagcgcagg cggcaatcgc atcggcgaca      2700
acgcttgcac aagccatccc ttcgttcttc tcggaaggcg gccttgtcac gggcccgggc      2760
accggaactt cggacagcat ccccgcaatg ttatccaacg gcgaagctgt gatgaccgcc      2820
caggctgtca cgactgggg cgcaatgctc tcggccatga acgtggcaag cggcggaaac       2880
gccatccaag tatcgaatct tccccagcgc aacgacggaa tgaaggggat ggagcgcatg      2940
atggaacggg ccctgatgaa tatgccggcg cccattgttt cggtggttga catcaacaaa      3000
gggcagaagc gggtcaaggt tcaaaacagc ctcggaaaat taggtcgaaa aaaatacgaa      3060
taa                                                                   3063
```

```
<210> SEQ ID NO 4
<211> LENGTH: 3060
<212> TYPE: DNA
<213> ORGANISM: Alistipes senegalensis

<400> SEQUENCE: 4
```

```
atgttcgtta ccgcagcggc ccagcaaaac cgccaggacg cggtcaaagg cactgtcctc        60
gacgacaaac aagcgcccgc cgtaggagcg accatcgtgg taaaaggtac gaaccgggga       120
acgatcgccg acgggcaagg aaaattctcg attgaagcct cctcacgaga taccctgcaa       180
atcagtctga tcggatacct tccccaggag ataccggtag cagccaggc cgaagtgacc        240 gtctggctga aagagaacct gctttcaatc gaagacgtgg tcgtggtcgg cttcggtgtc       300
cagcgaaaag agaccgtaac cggtgccatc aacagcatcg gctccaaaga gatcctgcgt       360
tcgccgacag ccaacgtcac taacgcgctg gcaggcaaga tggccggtct gaccgccgta      420
cagcgcggag gagagccagg caaggacgga gccacattca aaatccgcgg catcggaacg      480
ctgaacgaag gcagcgaatc cgccccgctt atcctgatcg acggcatcga acgcacctcc      540
ctggacgtaa tcgacccgaa cgagatcgaa accatcaata tcctgaaaga cgcttccgcc       600
accgcggtat atggagtccg gggagcgaac ggagtcattc tcgtcacgac caagacaggc       660
cagcccggac gcgcccaggt cacgctgaca tccaatttcg gatggcagtc ctataccatg       720
atgcccgaac tggtcaacgc ttacgaatgg gcgacccttt acaacgaagg gctcgcacac       780
gaaaacagca ccaaggcgcc gttcccgcag gaagcgctcg atgcctggaa gaaccacacg       840
aacccggtac tctatccgga cgtagactgg gtggacaaac tgctccgcaa atcggcccct       900
cagcaacagt ataacgtcaa cgtaagcggc ggaagcgacc ggaccaaata tttcgtctcc       960
ttcggaatgc tccatcaaga aggcatttac aaggagtacg acatcgacgg cgtggacttc      1020
tccgtcaatc cggattaccg cagattcaac ctgcgcgcca atctggacat cgacgtgatg      1080
aagggcatga cgctcggact ccggctcggt accatcttca cggacggcaa ctacccgaac      1140
gcatccactt ccaatatttt cgactatctg ttgcgcacgg tcccgggtgg aggtccgggt      1200
ctgatcaacg gcaagctcgt tacgggttat tcgggcgacg atccgctcga aaactacgag      1260
cgcagagtat ccaatccgat tttcgacatc ctcgaacagg ggtatcagga atacaacacc      1320
agtacctaca acctgagcgc agacctgaac tacgacctcg gattcctcgt caaagggctg      1380
```

```
tcggtacggg gcaaagtcgc ctacgacgac tacggcaccc accgggtagc atacacgacg    1440
ggaagcattc cgcaatacac ggtcgtggtg gacaacgact acgaagacgg ataccgcctc    1500
gtcaaggctt ccgacgaaac ggccttcggc gccaaggagt cttacagcac ccgttaccgt    1560
aatgtatacc tggaaggcgg catcagttat gccggccagt cggccgcca cagcgtcacc     1620 gccctggccc tctacaacca gcgggtacaa gacaatccct cgttccaata cgacctgccc    1680
aaaggcctgc tgggattcgt aggacgcatc acctacaatt cgacaaccg ctatctggcc     1740 gaattcaacg ccggctataa cggttcggaa aacttcgccg aaggcaaacg attcggcttc    1800
ttccccgcat tctccctggg ctggattctg accgaagaga aattcatacc ccgcaacaaa    1860
tttctgacct acgccaaaat ccgcgggtca tacggagaag tcggaaacga ccaaatcggc    1920
ggcgaccgct atctctacct gcctccgaca ttcgtatacg gttcgaacgg ctacaacttc    1980
ggaacattcg ggcagaattc gcagtactat cccgcctccg ccgagggaag cgtcggcaac    2040
tccgacgtga cctgggaaag ggccaagaaa gccaatatcg gactcgacct gaaaatgttc    2100
gacaaccagt tgagtttcac gggagactat ttctgggaaa aacgcgacaa catcctctgg    2160
gattacggaa ccgtcccctc gatcgtgggt acgactcttt cggccgcgaa cctgggccgg    2220
gtggacaaca aaggtttcga actcgaactg ggctggaatt ccaaagtccg gaacttcgag    2280
tattggattt ccggcgtatt ctcctatgcc aaaaacaaga tcgtctacat ggacgaagcc    2340
aagcaagcct atccctatct ggcgcaaacg ggttactccg tgggccagta caaaggctac    2400
atcaacgaag ggttcatcaa cacggatgcc gacctcgaaa accagcccgc acacggctgg    2460
ggcggcgacc ggtgggccaa aggcgagctg aatttcatcg acatcaacgg cgacggcatc    2520
gtcgatacga acgaccgtgt aacaatcggg tacggctcct atcccgaaat cacgttcggc    2580
gtgaacctcg gattccaatg gaaagggttc gaagtcagcg ccttgttaca aggagccgca    2640
aacgtctcgc tctacctgaa acagagcgcc gtctgcccgc tgtattacac ccggagcgcc    2700
cagaaatggc acatgggccg ctggaccgaa gagcggtatc tcgccggaga gaagatcacc    2760
tatccgcgca ttctgtccga caacatttcg tctccctcgt tcctgacca gaatccgctc     2820 tctacgttct ggctctacga cgcttcctac ctgcgcctgc gcaacctgga aatcgcctac    2880
acgctgaaat cgaaaacgct caaaaactcg ggcatctcct ccatccggct ctatgtcagc    2940
ggcaccaacc tgttcacaat cacaggcatg gataatttcg acccggaagc gccctccggc    3000
atcggaagtt tctacccgat gcagaaagtc tataatgtag gtgtcaaact tgttttctaa    3060
```

```
<210> SEQ ID NO 5
<211> LENGTH: 2937
<212> TYPE: DNA
<213> ORGANISM: Alistipes senegalensis

<400> SEQUENCE: 5
```

```
atgaacaaag taagcaaaga cgacgtattg caggccaccg aaggcggcaa gacggttatc      60
ctcgattatt accccgcgtc ccgggacgga ttcgagcggc gccggaattt caggctccgg     120
ccggacgacc ggaaccctcc gtgcaccgtg ttcaaccgcg acggcatctg gttcctgcaa      180
gacaagggcg gcggcgatac caaggcccgc acgccatct cgatcgtcat ggaggaagag       240
cgcctaacat acccgcaggc gatcgagttc atcgcgtcga aatacgctcc tcacctgctt     300 gccgggggcct cggcggtttc cgtacagccg gagcccgggc gggccgaaac ggccccgcag     360
gacgccatga ccgtacaacg ccgcaagggt ggaaaattct ccaaatggga actcgatctg      420
```

```
ctcggacatc agatcacgca ggaggtgtgc aacgaactcc gcctggtacc gctggactcc      480
tacatcaccc gcaaaaacga aaaggggaag agctggaaga tctcggccac ggagaactat      540
ccgatcttct actacgatta cgggacatgg ggacggctct accagccgct gtcggcccag      600
ctccgtttca tgttcgtcgg agagaagccc gccgacttca ttttcggcga ctcatggttc      660
ctcaaagcgt tcgatggttc caagcgtcgg acgcccgaca tctcggatgt cggggaagag      720
gaggaagaga cgccggaaca gggcgacgac gacgatccgg aagatgaggg cgatatggac      780
tccgcaaacg cctcgccccg gcaggagcaa tgcgacgcaa tcatcctctg ttcgggaggt      840
tccgacgccc tgaatgtccg gaacgcctgc atcaataccg gccgggccgg atggcatgtc      900
gcatggctga actccgaaac ggccgacctt ccccgggccg acatgttcca cctccggcag      960
atagccaaag aggtctacat tctctacgat caggacagca cggggagtcgc caacgccttc     1020 cggcacgcca tgaaatacct cgacctccgg atcatccgcc tcccggacga cctcaaacgc     1080
ttcaagaccc gcaaaggagg agcctgcaag gatgccaagg acctcttcat gcactaccga     1140
aagcctgcgg cacaagaccc ctacaaaatc ttcagcaacc tgctccgggt atccggatcg     1200
ctgaaattct gggtgcgttt caaagaccgc cgcggcaagg agtgtttcga catcaacaac     1260
gagcagctct actccttcct gcaagcgagc ggatactatc gcatcgaatc ctcggccacg     1320
agcaagggat tcaccttctg ctacatccgg gacaacatcg tccgcctgat cgacgagcag     1380
gccatcgcgt cggaatgcaa tgccgagttg atccgctatc tctatgctca tcccgagtac     1440
tactcgcagg cgctggccaa cgccatccac cgaagcaacc aggtgaagct cggatcgctg     1500
gagaagctgc ggatgatcgc accgaatttc cgttatttcg gggcgaattt cgaccatgtg     1560
ctattcaaga acaagatcat ccgcatcgac cgggacggcc tgcacgaaat tcgtccgcag     1620
gactggccct acttcgagta cagcaacaag attctcgacc acgaaataca actggacagg     1680
aacggtgtgc ttccgttcga catcgtggaa acgccggccg cccttgcgat acggaaagaa     1740
atgcagggcc ttaatccccg gtccctatt tataagcaaa tgcaagctgc gcttgacacg     1800
ttgacaggga cggcgaggtt caagctgcgc atcaaccgcc ccgatttctc tttcctgcgg     1860
tacatctaca acaccgggcg cgtgcattgg cgcaaggagg agatgggaca gcccctcacc     1920
gacgaagagc gcgccgagca ggatctgcac ttcatgtcaa aggtcatggc actcggatac     1980
ctgctgacca aatacaaatc ggcagccgag gcaaaggcgg tctacgccat ggagacggag     2040
atctccgacg agggccagca caagggagga accggaaagt cgctcttcct gggcagcatc     2100
gagcagatgc gcaaccagct tttcatcaat gggcaggagc tccgcccga caagatggag     2160 ttcctattcc aggggggttgt caaggggggtg acggacacga tctacttcga cgacgtgaac     2220
aagtcgatcg acctccaccg cttcatgccg gcgatcacca acaagatcac catcaacgcc     2280
aagtatgccg cggccgtaac gctcgaatac gccgagtccc cgaaaatatc cttttcgagc     2340
aaccatgcca tccgggagtt cgacaactcc ctccggcgac ggatatggtt cacggcattc     2400
tccgactact accactcggc agacccggcc gccaagcttt cgctgcggaa cccggccacg     2460
gagttcggga agaatctgat ccaggactac acgcccgagg agatgaacga attttacatt     2520
ttcatgctta catgtatgca cgtatacatc aagcatcagg tcgcgctcca gccgccgatg     2580
cacgacatcg agcagcgcaa catccagcgt cagatcggcg acgacttcat ctactgggcc     2640
gaagagtatt tcgccgcaga cggacgccga gacaccttcc tcaataaaac cgaggtattc     2700
gaggcataca aggaatcgct ccccaagcgg gcacaggaca gtgtgaagat gcagaccttc     2760
aaaggccgcc tcatccagtt ctgcgagtac aagggatggg agttcaaccc cgacgagatg     2820
```

-continued

```
ctgcaaaccg aatccgaccg gaagcggaac gagatccacc gaaaagagca gggtgtcgat    2880
gtctactact tctacattcg gacggccgaa gaggacgggg aggagaagat tttttag       2937

<210> SEQ ID NO 6
<211> LENGTH: 2754
<212> TYPE: DNA
<213> ORGANISM: Alistipes senegalensis

<400> SEQUENCE: 6
ttgctgtttg cggggtgtct gttatctgcc tccgcccggc agaacgaagg ttttccggtc      60
gtaggtgctc ccgataccat aagtctcggc tacgggatcg gtgtcgaccg ggatcggagc     120
gcctggacac aggcgggagt gggccgcgaa gtgctggaca atgcgccgca gattgatgcg     180
gccaaagccc tttacggacg aatcgccgga ctgaatgttt atcagggagt cggcacgacg     240
gccgataaca tcgcttcgct gtcgattcac ggacaggctc cgctggtact tgtcgatggt     300
ttcccgcggg atcttaagaa tcttacggta caggagatcg aatcggtcgt cgtgctgaag     360
gacgccgcag cggttgcact ctacggtgtg cgcggtgcga atggggtcgt gatggtctcc     420
acgcggcggg gaacgcccgg caagctgaaa gtgggtgtcg gctatcagta cggcgtcagc     480
acgcaatttc gcgcaccgga atttgccgat gcctttacct atgcccgttc gctcaacgag     540
gcgcttacga atgacggcct ttcgcttcgt tacaatgcct acgaactgaa tgcgttccgc     600
agcggaaaac atccgtcgta ttatccgaat gttgattggt ggaatgaagt ctacaacacc     660
acagcgtcga atcatcgcct caatcttaca ttcgatggag ggtcgcgcaa gtttcgttat     720
tatacggccg tggattatat gcacgaccgg ggctttttttc gcagcaatga aaacgaatcc     780
cggtacaaaa ccgatccgac ggatgttcgc ttgaacattc gggccaacat cgatgtggac     840
ataacccgtt cgacgcggat gcggctgaac gtgatgggca agatcgctga gacaaaccgt     900
gccaattacg gagatattta caacatcctt tataacacgc cttcggctgc tttttcccata    960 cgatacgatg acgacggcct ttacggcggt acgagtattt acggggccaa taatccggta   1020
gctttgttga tggacagcgg caattaccgg cagaccatcg gaatgctttt gggggatttg   1080
tcgttacggc agaatcttga tgcgctgacc cccggcctct cggcagaggt gtcggtggct   1140
ttcgacaatg tcggctccat gttcgatcag gcgacgaaga cttatcgtta taaggatgcg   1200
caggcctccg tttctacgga cggaacgctg atcacccatc cggccgttta cggcaaggat   1260
tcggaagttg tcggccacag tcagaatttc tactcgttat acatgcggtc cgatttgcag   1320
gctaaaatcg gttatgaccg ttgttggagc caacatcatg tgcaggcggc cgtgatttac   1380
gatcagcagg cctacacggc caacggtcgg aataactcgg ttcgtcggca atcggttctc   1440
gctacagtcg gctacacgtt cgacaatcgc tatacggtga atgtcgtcgg caattattcg   1500
ggttcggcct atctgcccga gggcgatgcg ttccactttt atccggcggt aaacgccgcc   1560
tgggtccttt ccgaagaacc cttcctgcga aacgcaaagc agctcgatct gctcaaatta   1620
tccgcttctt acggcatttc ggggtgggac gggaatctgt cgcacgaact gtggcgtcag   1680
tcgttcggga atacgaatgc gcacggttac tattttttcca acaacgtcgc ggcctattcc   1740
ggtttggcag aagggaatct cgcggccgaa gggcttgtcc ccgaggagtc ccgccgggta   1800
accgtggggc tcgatctgcg ttcgttcggt aatcgtttca cggcttccgt cgagggattt   1860
ttcgagcggc gcagccatat cctgatctct tccggggcca ccgtgtcggg tatcatcggc   1920
atcggcgtgg ggctgcaacc ggccggcgag catgagtacc ggggattcga cgcctcgatt   1980
```

```
gcctggaacg accgccgcaa ggatttctcc tacggagttt acgccaacgc ctcctatctg    2040
gacagcgagg tgatcgtcga cggtcaggag tatcagccct atgattatct ctaccaccgg    2100
ggcaaccggg tggggcaaag ttacgggctg gaggtcgtcg gcattttcca aagccagatg    2160
gagatcaacg aaagtcccgt acagacgttc tcgacggtgc gtcccggcga tttcaaatac    2220
cgtgaccaga acggcgacaa ccggatcgac gatctggata tggtccggat gcacggatcg    2280
agtgttcccc gtttctattt cggcttcggg ttccatgccg gttacaaagg gatcgaactg    2340
tctgccgatt ttcagggcat gacggggcgc acggtcaatc tgctcgactg tccgctctac    2400
aaaccgctga tcggcaacgg taacatttcg caaacgctgc tcgatcacga gatcccgtgg    2460
tcgcccgaac gtgcttcgga ggcgaccatg ccgcgactga caaccctgtc gaatgcgaac    2520
aactaccgga acaattcgta ttggtatcgg gacggttcct tcatcaaact gcgtaacctg    2580
accgttgcct atacgctgcc caaacggatt cttcgcttcg cggatatgaa gatttatctg    2640
caaggtacga acctcttcag tctggacaat ctgaaaaccg ttgatcccga acagttgggg    2700
gctgcgtatc cttcggtgcg gtcgtactgg gcaggcgtga agttcaattt ttaa          2754
```

```
<210> SEQ ID NO 7
<211> LENGTH: 2547
<212> TYPE: DNA
<213> ORGANISM: Alistipes senegalensis

<400> SEQUENCE: 7
```

```
gtgcttcccg gcagcggcat ccgattttac ggtgcgtact gtcgggactt tacccccccc      60
tccattccag acggtgctaa aaatcccggc gtggcgggcg ctttcatcgg cgggatcggc    120
gaccggatcg ttttggccgg cggctcgaac ttcgctcagg gcgcgccctg gaacggcgat    180
gcgaagcaat tcgaagatgc gatttacttg cttactccct ccggaggtac ttataaatgc    240
gaattggttg ccgatgcgaa attgcccgca ggcattgccc acggttgtgc cgcggtggct    300
ggccgtagcc tctactgttt tggtgggctg actgccgaag gggagtcgcg cgcggtctat    360
gtgctgacgc ttgccggaaa ttcggtgtgt gtcgctgcgg cgggagtgtt gccggaggat    420
ttccgacctg cggctgcgct ggcttataag gatgagattt acattcatgg tgtgaaagac    480
ggtgccaacg ctttctggcg gttctcgccc gtgagcggga aatggaccga actcgcggcg    540
tgtcccggtg cggttcgttc ggcaggtcct gcttttgtgg accagcacaa cggacgcgaa    600
aatgccatgt acttgatcgg cggtcgtcac gaaaagggcg gggaattgca gttgtattcc    660
gacgtttggg agtatttgcc ggtgcatgac aggtggcagg ccaagggtga cgtgacgatc    720
ggcggcaagc cggtggtggt gatgtatgcc gctgcggtgc cttacggatc gggtcatgtg    780
ctggtgttcg cggtgacga cggccgggag ttgcagcacc gtgctgcgct tgaacgggcg    840
atcggcgggg cggcgacgtc tcaggaagcg gatagtctgc gcggacagct gcgtgaagcg    900
ttcatggggc atgaagggt ttcgaaagaa ttgctggctt atcacgccat taccaataca    960
tgggtgtcgc tcggtgaggc tcaaacgggc tttccggccg tatcgacggc tgtgattgcg    1020
ggcggcggaa tcgttattcc gtcgggcgag atacgtcccg gcgtgcgtac gcccgacgta    1080
cagatcgtga cgattcacga gccggtggag ttcggctggg gcaactattc cgtaattatt    1140
gcctatctgc tggttatgat gggtatcggc gtctatttcg tccgcaagaa caatacgact    1200
gaccagttct tcaagggcgg agcgaaaata ccttggtggg cggctggtat cagcatcttt    1260
gcgacggcac ttagtgcgat cactttcatc tcgatccctg cgaaggccta cggcgccgac    1320
tggggcatgt tcatgttcaa catgaccatc ctgatgatcg tgccgatcgt catccactac    1380
```

-continued

```
tatctgcctt tctttcgtaa actcaacgtg gcttcggcct atcagtatct ggagcagcgg    1440
ttcagttcgt cggtacgcta tctggcttcg gtgttctttt gtttcttcat gtttgcccga    1500
atagctatcg tgctcttcct gccgtcgctg gcgctgaatg cggtgactgg aattgacgtt    1560
tatgtctgca tcttgctgat ggggctggtg accatcgctt attgtacgat gggaggcatc    1620
gaagcagttg tctgggccga tgttgtgcag agtgtgattc tcgtaggcgg tgcgcttgtg    1680
tcgcttgtat tcctgatcag tggcatagag ggcggattct caggcatgat cgatgttgcc    1740
atgaccgacg acaagttcaa tattctgaac ttcgctttcg acttgacgca gccggtcttt    1800
tgggtgacgt tggtgggtgg tctggctaat cagctgttgg cctacacaag cgatcaatcg    1860
gtgatccagc gctacattac ggtcaaggat acggccggaa cgaaaaaggg gttgtggctc    1920
aacggattcc tgagtatccc gattgccgtg atcttcttca tgatcggtac ggcgctttat    1980
gttttcttca agcagcagcc cgaattgcta agcattggga tgtccaatac ggactcgatt    2040
ttcccgcatt tcatcatgtg ccgtctgccg gtaggtattg cggggctgct gattgctgcg    2100
atcttctcgg cagctatgtc cacccttttcg gctaatatca actctacagc gacggtgctg    2160
acagaggatt tctaccgccg cttccgaaaa ggtgcgacgg acaaacaggc gatgggcttc    2220
gctcgattgt cgggtatcgt cgtgggtggc ttggggttgc tgatggccat cctgctcgct    2280
acgttcgaca ttgcgtcgtt gtgggatcag ttcaactttt ttcttggcct gctgaccagc    2340
ggtttgggcg gcttgttcat gatgggtatc ttcaccgagc ggatcggcac gcggagcgcc    2400
tttgctggat ttatcggcag tatcgtcata ctgctgatca tcaatagcta ttcgactgtt    2460
tcgttcctgc tctacggatt tatcgggttg gcttcgtgtt tcctgatcgg ttatctttca    2520
agttttgttt tcgggcgcgg caaataa    2547
```

```
<210> SEQ ID NO 8
<211> LENGTH: 2475
<212> TYPE: DNA
<213> ORGANISM: Alistipes senegalensis

<400> SEQUENCE: 8
atgtttcata tgattgtaag gaaaattttc agtttattgt ccctcgtcct ctcatgcgca      60
gcgatggggc agacgattac acccgaaata gaaaagcgtg cccttgagtt ggttgcgcaa     120
atgacactcg aagaaaaact tgcctatatc ggtggctaca acggtttttt tattcggccc     180
attccccggt tggggattcc ggagatacgt atggccgatg cccccaagg ggttcgcaac      240 gacactcaca gtacgatgta tccatgcggt atcgcggctg ccgcgacatg gaaccgggaa     300
ttggcccgga cttacggcca ttcactcggt caggacgccc gggcacgggg tgtccatatc     360
atgcttggcc ccggggtgaa tatctatcgc tcgccgcttt gtggacgcaa ttacgaatat     420
tatggcgagg atcccttct gacgtccgaa acggccgtgg cgtatatcga aggtatgcag      480
gcggccggtg taatggcgac gatcaagcat ttttgcggca ataatcagga gtggaaccgt     540
cataacgttt cttccgatat tgatgagcgg acgcttcacg aaatctacct gccggcgttt     600
cgcaaagctg tacagaaagc ccgagtcggc gctgtgatgt cgagctataa tccggttaac     660
agcatacata ccaccgaaag ccgcgaactg attatcggcg tactgcggga aaagtggaat     720
tttaagggta tctacatgtc cgactggact gcgacctatt ctactgtcgg agcagccaat     780
aacggtttgg accttgagat gtcgtggggc cagttcatga tccggataa attgcgtacg      840 gccttggcga cgggaactgt gacggaggag acgatcgatg aaaaatgccg tcatatcgtg     900
```

```
cagacgctca tagctttcgg gttcttcgat cgggagcagc gggattggtc gatccccgaa      960
aaaaatcccg tctcttcgga aacggcgctc gccgtggcgc gcgaagccgt agtattgctt     1020
aaaaacgatg gcgatatgct gcctttctct cgaaagatac ggaatgtggt tgtgatgggg     1080
cccaatgcga ctaatatccc tacgggcgga ggcagcggga ttgttatgcc ctttgaaacc     1140
gtatctgtgg cagaggggat tcgcaatgca gataagcgca tccgcatgaa ggtattggca     1200
cctgaactgt ctgtggattt aacggcttgg gggtgtttct ttacgccgga tggcaaaccc     1260
ggattgcgag gggaattttt cgccaatccg aaacttgaag ggaacgccgt cggaacggtc     1320
gatgccactg caatcgactt tttctggcag aatgctccga tggagggtgt gcctgctacg     1380
cagttctcgg cacgttggac gggaacgttc attccgtcgg ttacggggca ggcagtcttt     1440
cagatcagcg gtgatgacgg ttaccgactt tatatcgacg atcggagat  tattgccgat     1500 tggtacgacc attttatcac aatgaagcgc gcatcggtgg atgtcgaggc gggcaaaagc     1560
tacaaggtgc gtttggaata ttacaatgcc tgggattccg ggactctccg gatgtgcagc     1620
gcttgtcatt cgcctatttt accgcagcag gagatcgaat cggctgatgc cgtcatctat     1680
tgtgccggct tcgactcttc gaccgaaggc gagaattgcg atcgtccgtt ctcgctgccg     1740
caacagcagt tgaaggagat tgccgaagcg gcgatgctca atcctaatct gattgtggtg     1800
gtcaatgccg gcggcggggt tgatttcaca ccaatagtcg ataaggcgcg tgccgtgctt     1860
atggcctggt atccgggaca agaaggcggt cgtgcgattg ccgagatcct gaccggtcgg     1920
atcaatccca gcgggcgtct tccgattacg gtagagcgtc gggcggagga taatccgacg     1980
tttgacagct atcgtgcgaa cgttgctcag gtttacaaca gcccgctacg agtcagttat     2040
gacgaaggcg ttttcgttgg atacagagga tacgatcggg cgggcaccga accgatgtac     2100
ccgttcggct acggactctc ctatacgact ttcgattatg cgaatctgaa gatggaacga     2160
ctggatgacg ggaatgtcgt ggtatcattc gaggtgacga atactggtcg tttcgctggt     2220
tccgaggtgg cgcaacttta tgttggtgat gaggtggcca gtgttcctcg ccctgaaaaa     2280
gagttgaagg gatatgaaaa ggtgcggctc gaacccggtg aaacgaaaag tgtggagatt     2340
cgtctgtcac cggacgcctt tgctttttac gatatgaacc gccatgattt cgtggtcgaa     2400
ccgggtgatt tcacgatttc ggtcggcgct tcatcgcggg atattcgatt gagcgaaaag     2460
attcggatcg actga                                                     2475
```

<210> SEQ ID NO 9
<211> LENGTH: 2412
<212> TYPE: DNA
<213> ORGANISM: Alistipes senegalensis

<400> SEQUENCE: 9

```
atgcgatgga tcgtgacgct gatgatgctg ttgtcggtgc tgtgcgacac gacgcccgcg       60
gcggcccgca agcggcgcgc gacggctccc gaaccgcgta agacggctta cgaacggctt      120
ttcgccggta agaatccccg aacggtgcag ggattgttca ccctgcatct gctcgacggg      180
gatgtctatt tcgaggtgcc cgattcgatg ctcggacgtg acctgctgct gggggttacg      240
gtgctgtcgg tcagcgacgg cgaggagtcg tcggtcggga tgcagccttc gcgtccgcgc      300
catgtcgttt ccagcgaac  cgattcgctt ttgcagattg ccgcactcga cagccgttcg      360
cgcagcgacg atccggcgat cgggcgggcg ctggccgcga gccggcagcc ctccgtgatc      420
gcgtcgtttc ccatcgaggc ggttacgccc gacagcagcg gcgtcgtggt gcgtgcgaca      480
tcgttcttcc ggaacggcga gagttacctt tcgcccaagg acccgaagag ttacagcagc      540
```

-continued

```
cgcgacggat tcgtcctgcg gagttacgaa taccgttctg aagcctcctg gatacgcgat      600
atagcggcct ttagcgacaa tgtctcggtg gtgagcgagc tctcctacga agtctcgtcc      660
tacgctttcg gcgtgatttc tcggggcgat cccgagctct tcacggcggc cgtgcggaca      720
tcgttcctgc tgctgcccga accgatgacg acggtccgtg aagcggatct gcgcgtgggc      780
acctccacgt cgcgttacgt cgaatacagc gccgaccggc agggcgccga agtccgttat      840
tacgcctccc ggtggcgggt ggatgccggg cgtcccatcg tcttctatct cgacgagcgt      900
tttccggcgg cgtggaaacc ctatatcgaa cggggcatac tgctctggaa cgatgccttc      960
gagcggatcg gtcttccgcg ggccatcgag gtgcggcgtg tctcggcgga ggggctgccc     1020
gacgtgaacg acattcgcta ttcggccgta cgctacgttc cttcgccggc ccgcgatctg     1080
cggttcaacg cctggaccga tccgcggacg ggagagattc tgagcgccaa catctacatc     1140
agccataata tcgggccgca gatccagacc gaacggcttc ttcagacggg agccgccgat     1200 cccgggcgc ggcggctgga actcgacgag gcgctttccg gcgagagcct gtcggcgaag     1260
gtggcccgtt atacgggttt ttgcctgggg ctgctgccta acatggggc ttcgcagaca     1320 gtgccgctcg attcgctgcg cagcgcgcat tatacggccg cgaacggact ttcggcctcg     1380
attctcgacg agctgccgtt gaactatgcg gcgcgtcccg aagatttccg gaacggtgtg     1440
aaactctgtc agacatcgct ggggccgtac gattaccgcg ccgtcgagtg gctttacggc     1500
gacggggcgg tgagcgacga tccgtcgtgc cgttttctgc gggaacagcc ggaaaaattc     1560
gcgctcgatc cccgggcccg ggcctcggat ctgggcgacg atccgctgcg ggcggccgat     1620
gccgggctgg cgaatcttgc cgttgttctg cgccatgtct cggagtggat cgacgacgag     1680
gatgtcgatt atgcctaccg ttcggccttc cccgagtcgg tttcgttcta ttgcaatgcg     1740
ttgttcggct ccgtgatcgc ccgcttgggc ggagtgcgga tcaacgaacg ctatgccgga     1800
gatgcgggcc ggagtttcga gccgcttccc gccgggacgc agcgggaggc gatgcggtgg     1860
ctgctgtcgc ggctcgacga tctgcaatgg ctcgacagcc gttcgctgat cgtggggggag     1920 gggctcaacc ccggaatcgc ggatttcatc cgtacggaga ccttcgaccg gattctggga     1980
agcctggacc gcattgcgct ctgcgcttcg ttgaccgacg gggaggctta cacgcgcgcg     2040
gaggcgctgg acgacctctc ggcctatctt tgggacaatg cggacccggc ggacgaactc     2100
gtcaagcagc cgttgcaact gcgattcctg aatcggttgc tggcccttgc cgaacaggct     2160
gcgggccgga aatcgaagct gcgttcggac tatttcgccg aggctgtgac ggcggagaat     2220
tccgcaggct tcgctccgct tgccggggtt tcctacctca cgcggcccga ggacggccat     2280
ctgctctacg gcgtgctgct cgactgccgg gatcggattg cggccgcccg gaatcggagc     2340
gcctcgccgc agatgcgggg acactacgca ttgttgctgc gtcgggtgac gcactttctt     2400
gaaaacaagt ga                                                        2412
```

```
<210> SEQ ID NO 10
<211> LENGTH: 2214
<212> TYPE: DNA
<213> ORGANISM: Alistipes senegalensis

<400> SEQUENCE: 10
atgctttcgg cggcagtgct cttcctcgcc gcctgtgaat cgacggatga gaaggacggc       60
gggagatatt cgctcggaac gacctgccgg attctcgaaa gcagaggcaa tttcaccagc      120
ttcattaagg cgctcgaccg cagcggttac cgcaggcttg tggacggcgg cggactcgtg      180
```

```
acggttttttg cacccgacga cgatgctttc gacagttatc tcgaaggcag gtacggaacg       240
tcggacgtag atcaggttcc cgttgaggag ctcacgctgc tcgtaggctg ccacatgatc       300
cagttcgcct acacgacgga ggatttcctc tctttctcga tgacctcttc ggaggacggg       360
acggatgcgg gcgacggctc ctgttacaag tacaagacgt atgggcgtgc cgccatcgag       420
gattataccg acccggtgac ccggcggaag gtgaagctct tctcccggga gaagtacatg       480
cccgtcttct cgacccggat gttcgccaag cgggggattt ccgatgcgga gggcgactac       540
cgcaaattct ttcccgacgt gaactggcag ggttcggacg accgccttta tgcgggcaac       600
gccgccgtga tcgaaagcgg cattcctacc gacaacggtt atctctacat cgtcgataag       660
gtgatggagc cttcgcgcac catatataaa gagttgtcgg acaattcggg gaccggagcc       720
ggttattcgc tctgcaaggg cctttttcgac cggatcagcc tttacaagta cgacgcgtcc       780
gtgtcgaaga actacgctgc gtcgtcgggc gactcgcttt tctatttcta ccactggaaa       840
gagcccagcc gtacggccga gattccgaaa atcgccagcg aatggaccta tcacgacgag       900
agcggcgtgg tcttcgaccg tccgctgcgt tattcggtca actgtttcct gccggacgac       960
gaggtgctgg aagagtatat gaaggagtat ttcagcgagt acggcacgca gacctcggac      1020
gatttcctga gcctgattcc caaaaacgcc atataccatt tcctgcgggc ccatgtctac      1080
gggagccagg atctgatcct gccttcggag ctcgaccggc gtccggtggc cggcgtgaac      1140
ggcgagcagt tccgtgtttc gtcgtcggag ctgcgcagcg tgacctactg ctcgaacggc      1200
gtcatttacg ggatgaacaa agtgttcgaa ccggctgtct tcacctacct gacggcccccg      1260 ttgttccgct atcctcagtt ttcgttctac gcgcgggctt tcaacacgaa gaacatgtac      1320
aatcagacgg tcgatcccaa caaccgcttc acgctcttca tccagaacga tcaggacctg      1380
gccacggccg gttattcgtc gagcgaggga accgggacga acggcgacta tgcgttccgc      1440
agcaggtccg gtgcgatgaa cgccaaccag gtgtcgaatc tggtgatgtc ccagttcgtc      1500
tacggaactc ttcccgagct ggcggaaacc gacgacctgc gttatttcat cgccaaggac      1560
gagaagacct attttttatat aaaggataag gcgctttacg actattcggg ccgggagctg      1620
gtcgtcaagg cgacgttcga taccgaaaac ggaacggtct accagatcga ccgggtgatt      1680
cccgcccgcg tcggagccta ctccgagacc ggtaagctgc ccgaatacga gcagttcaag      1740
gccctgatga tcacggcggg cctgggcaac aacagcggcg tctggtcac cccgatcgcc      1800 gacggactgg tcttcttccc gaccaacgag gcggttatcg ccgccaaggc ggcgggaatg      1860
atccccgagg tggtcgatgg cgacgtgacg gagctgcgga aatatctcca gtactatttc      1920
gtgccgctga agaaaaacaa gctcaactat tacctgctgc cgggtctcgg tcccgaggga      1980
gcgacggagg agccctattc gggaacctac gtcacgctgt cggagtacca gaacgaggtc      2040
gatgccaaga cgatggctat cgcgtggaat cccgagaatc ccgagtcgct gacgattacc      2100
gacatggccg gcaactccat cacgacggaa cccggggtga tcaatctgcg caccaactgt      2160
gcgacctatt ccatcaccac ctgcttcgat tatcgcacga tgtacggaaa ctaa           2214
```

<210> SEQ ID NO 11
<211> LENGTH: 2034
<212> TYPE: DNA
<213> ORGANISM: Alistipes senegalensis

<400> SEQUENCE: 11

```
atgagtgcgt tacgctggtt tttggacgaa ccgaatcgtt ttacagccca agacttcacc        60
gtaactctat ggaagagtat aaatgatata ggggataaat ggttagatgt gtccaatgat       120
```

-continued

```
gaagaaatac acattgagga ttggtttaat atcgtgccat ctatggatgt gtgggtaaag      180
atagattcat cggaaaaata tcgcgtaata aaccttttgc catctcttac ttggaatggt      240
gaaaaggtag gggccagatt gcgattccaa ccgaaagaag tgaaaaattt gtatgcggca      300
tatataatgg caaaacgaaa tgtaaacgcc attaaggaaa agcatggaaa tgaaagcatt      360
gatatatatc ccaaaaatct gacagatttt atttctcatc gcaataatct acaaacttat      420
tttgaactgg tgtgttacct tcttgacgag aacaagata  tttcagaata taaagagtct      480
gtttatgaaa ttgaaaatcc gtttaagaaa cttattaaaa ttaactgcat agaggctctt      540
cgtgaatttt ccgatcccga tggaaacgga gacaatatta ttgacacttt atccagacag      600
cttcaagaat attataaaaa gcaggtagat ccaagagaaa atatcaggga gaatgattat      660
agtttgctaa aagctattga tgaaaccaat aaggttttg  atgagaattt aatgaaaagt      720
ttcgcctcca ttattgacga gttggaggaa tttaattatc cgggatttca aaatccgaaa      780
atagaaatcc atagttattc aaatccggca tcttcaatag gccatgattc tgccgttcaa      840
tttattatgc cgggagaaga gggattacgc atccctgaga aatataatgg attgggttat      900
cgtaatcttt tatccatgta ttttaagttg attcagttta gagaatcgtg gttacattta      960
agcgatcgtc gtactgatgg caaacaagaa atagaaccta tacatttagt gttgattgaa     1020
gagccggaag ctcatcttca tgcacaagcg caacaaattt ttatccgtaa agcgattgac     1080
ggattgacca atgtgcagtt tctaaaagac aattcgcagt tttctacgca attgatcgtt     1140
tctactcact ctacgcatat ttctaatgag gtgaatatgt gttgtatgag atatttcaaa     1200
cgaatacaaa agactaagga ccatattcct attagcaagg taattaacat gcgtgatacc     1260
tttggagagg acaaggaaac cgaacgtttt gttacaagat acctccaatt aatgcactat     1320
gatgtattct ttgcagatgc cattatactg atagagggtg ccgcggaaaa aatacttttg     1380
ccgcaattcg tacgcaaaat ggaactggga tcgagatttg tgtcgattat agaaattaat     1440
ggaagtcacg catttcggtt caaacctcta atagataggc ttgaagtatt gacattgatt     1500
atctccgata tcgatgccaa aggtaaatat acggatgaag caggaaagcc gaggtcgaaa     1560
gccgaacttc cggaagtcgg taaaaatcaa gaaacgagca caacacatt  gattgactgg     1620 cttcctcaaa ggaaaatgat tgatgaattg ctcacgttgg aatctgacaa gaaagagaac     1680
gcccatatac gcattgctta tccatgcggt atgaaaataa aatataaaga agatacgaaa     1740
gaaattgatg tatatcctta tacatttgaa gacgcattga ttttctcaaa tatcgagttg     1800
tttcgtcagg aaaaattagg aaatatggga gctgttacga caataagtaa tttattgaag     1860
agcaatgcag atttgctgtc attccataaa aagttatttg aaaaactcga aaacaagaaa     1920
attacaaagg cggaacttgc tattaatctg cttttttgctg agcaatttgg aaaatttagtc     1980 gctcctccat atattcaaga aggattaaga tggttaaaat ctaaattgga ctga           2034
```

<210> SEQ ID NO 12
<211> LENGTH: 1911
<212> TYPE: DNA
<213> ORGANISM: Alistipes senegalensis

<400> SEQUENCE: 12

```
gtggattatc tcgacgtggt ccccgacaac attgcgacgc tcgacattgc gttcaacaac       60
cgttccagcg cggaacgtta cctcacgacg tgttattcct acgtaccgct ctacggcgac      120
caggattgga atcctggact caccgcaggg aacgagatct ggtactattc gatggacgac      180
```

-continued

```
aatgtttatg tccagaatct ctgggcattc gggattgcca atggattgca gaacatcgta      240
actccgctca acaactattg ggacggggaa gagcgcggaa tgccgctctt ccaggctata      300
cgcgactgca acatcttcat cgaatacgtt tccgaccgta accgggtggc ggggttgtac      360
gaaaccgaac gccgccggtg gctcgccgaa gcaaaggtgc tcaaggcctt cttccactac      420
tacctgtttc agctttacgg cccgattccg attatcgaca agagcctgcc catcgatgcg      480
tcagtcgaag aggtacgggt gtcgcgcaac aaagtggacg atgtggtaga ctacatcgtc      540
cggacgatcg acgaatgtta taccgacctg ccgaaagtga tacagatgga ggccgtcgaa      600
ctcggccgtc tgacccaggc tgcggcgctg gccatcaaag ccaagacgct ggtgctggcg      660
gcgagcccat tgttcaacgg caataccgat tatgccaact tcctcgacca cgatcacaag      720
ccgtttatca gccaggaaca aagcacggag aaatgggagc gtgcagcgga agcctgccgg      780
gacgcaatcc ggtcggcagt ggacgacgga aagcacgacc tgtacgattt ctcactcgat      840
gcgacgtacc caatgccgga cgaactgctg tacggtatga acacccgcca ggccgttact      900
gaacgattca ataaagaact gatatggagc gtcggtacac agtcgacatt cgacctgcaa      960
atcaatgtga tgccgctgat tacacccggc acgaacaata tcaacgcgtc caatgcgaac     1020
agttattgca aggcaaacta tgcacctacg ctggcagtcg ccgaacgctt ctattcttcg     1080
aacggcgtgc cgatcgaaga ggacaaggtc tggaacgatc cggccaacga ttactacaac     1140
cgccgttacc aaacgcagag cacaaacggt tacagcgaat acctattcaa gcagaattac     1200
gagacggcga tcctgcactt caatcgggaa ccccgtttct acggttcgct cggattcgac     1260
ggctcgacgt ggtacggcaa cggttggaaa aatccggacg atgtggatac gcgcaattac     1320
gtggaggcaa agaagaacca gcgggcaggc cagactaaga tgggcatcta ttcgattacg     1380
ggctattatg cgaagaaact catctattac gacaatactt acggatcttc ggtttcagtc     1440
cgggagtatt ctttcccgat catccggctc gccgatctct acctgctcta cgccgaggcg     1500
atgaacgaag ccaacatcga caagaacgtc cccgacgatg tatatatcta tgtgaacaag     1560
gtacgcgccc gctcggggct gaaaggggtt gtggagtcgt ggcagaacta ttccatgaat     1620
ccttcgaagc ccttgacttc gctcgggatg cgcgagatca tccggcgcga acgttccatc     1680
gaactcgcat tggaaggaca gcattacttc gacgtgagac gctggaaaac ggccgtaaaa     1740
gagttcaaca aacctgtgag cggctggtcg gtggaccagg agaccgtcga agggtattac     1800
aatgtaagga atattttcaa ccaacggttc tatcaacggg attatctctg gccgataaaa     1860
gagtacgatc tggtgattaa ccccaacctg gttcagacca aaggatggta g              1911
```

<210> SEQ ID NO 13
<211> LENGTH: 6441
<212> TYPE: DNA
<213> ORGANISM: Clostridium boltae

<400> SEQUENCE: 13

```
gtgaataaga ataaattagt gaaaagaact ttggccattg tactatcagc agcaatggta       60
tttacaaata ttggccattc cccgactgtt gcgtatgcag ccagcggaaa cagtgtggac      120
ttcatggtat caggaacgga tttttgttgct gctattgaag acatgattca ttcaggagca      180
gagccattaa acaagagga gctggatttt accaatggaa aggcagaaaa gtactatcag      240
tttttctttg atggggagga cccggtatat gagttctatc cggaatttga tggtcaggat      300
atggaggcag aagtaagggt ttttgtccgc cttccggaag cagcggatga tacatattcc      360
cttactggtg aggaagagat tatatttcta tatattaaca atagtgagga taccataagc      420
```

-continued

```
tgctcaacaa caatcttaat gtcagatggc agtgaaaaga ggacaaaaag ggttacagtc      480
aaggactatg aaactgcgtt tggtgataac agaattgagt ataaatccaa tacatctgcc      540
acgggccaga cagaggctga aatacctgaa tccgatgcag cagaaattga gaaacccgga      600
acagatgcac cgatggtgga aacacctgaa accagtatgg aagagtccgg ggtgacagaa      660
ccagagacag gatctgggat tcctgaccag gaaacagagg aaaaggaaaa cgaagctgtt      720
gagacggatg aagtgataga agataccgag ccggaaatcg ttgaaaagtc agagccagag      780
acgcagtctc ctgatgtatc ggaagaggga aaaacacagg ctgatagtcc cgtggcttcc      840
cgtatcaggc atgcagttcc tgtcgtggcg gcagtggata caggagaaga aaattctacg      900
attgaaccca gtgttgataa gcagcaggag gatacagaaa caggtggaac ccatgatgat      960
tcagaaaaac atagtaatga taaggacaat gaaactgtag gcagcgtacc taaggaatcc     1020
tctgcagagg cagagtctga aacggagtca ttgacagagg aaagcgggaa gcagacagaa     1080
gcgtctgccg atgaaaccgg agaagaaaca gctgcagttg agtcatctga acctgcaaca     1140
gatattcaga ccccttcaga ggaaagccgg acagagacat ctgaggagac tcagacagag     1200
acatccgagg agactcagcc agtagaatca gaacccgtcc aggttacgga aacccaggaa     1260
agccagattt cgacagagac ggaaagcatc ccggtgagtt ctattggtaa tggtgatctt     1320
gtggggatgg acggatgcag cactgcaaag gcatatgtaa caacactgaa gaaattgaaa     1380
gtattagatg aggtggacgg ataccgtgtc acatatgaga ttaccccccga agacaaggcg     1440 gcaattgtag ataagtgtga cagggttaaa gcaggagaaa gcgttacctt tggtgtagag     1500
gaacaagagg gttttcgtgt tgggcaggta gaggcaaatg gagatgtggt ggaatccgca     1560
tacagtgagg aaaacatcgt atggtttact ctggagtatg tagaggaaga cttggaaatc     1620
cttataacga tggttccgga tggtacatct atgccttttta acaaaacgat ctcaatggat     1680
gatggtatgg atattaccat atccgctttg ccgggtgttc ttcctgaaaa tacggaggtt     1740
acagccgaaa ttgtaacatc acaagttgag gaggcaatca ggtctgacca gtcagaagag     1800
ggacgggaaa ttatagctgc tcctgcttat gatattaacc tgtgtctgga tggagaaaag     1860
ctggatgatg aaatctggaa caggaatggt gctgttacgg taagttttttc aggccctctt     1920 atggaccaac tgattcagga gtcacagatg gcccaggttc tctgggtaaa ggatgagaac     1980
aacagcacag aagtaatgga aggcagttat aaggatatta cccgggaggg tacaactgaa     2040
gatctaagtt ttgaaaccag tcattttacg acgtttgctg ctgtctttgc tgtagcgccg     2100
gatatatcta atgtatttaa tattgatgaa catggactga tggatgagga ttttcctaaa     2160
cttgttgtcc gggataaaga cgaaaataca cttgatattg agattacaga acaggaagat     2220
ggggccagga gggttacctt gaaagatgga aaacctcttc aaggaacat aagcacctgg     2280 tttgagattt cctacgattt taagaatagt tcagacccctt ttttttgaaac ttacagtgta     2340 cagaagggag accatttttac atatcagttc ccgtcaaata tttttatatga caaaaagcag     2400 actgttgtaa aagatatcaa tggaggagaa gctgtcattg gaacggcatc catcaatgca     2460
gagggttaca tggatgttga ataaacagct gaaaatgtag gccagaatta tcgcggcacg     2520
gcagaagccg gtggtaaact ggatttggaa aaggtttttag aggaaaaaaa tgaaatcact     2580
ctggtgggtg acgaagtgga gtacattatg gaactggtgc cggctccggt gcaggaaaat     2640
tactctgtaa aagtagtcaa aggacccaag agcggaaagt ggacagacca ggatatcagg     2700
tatgatgaga ataggcttcc ttcagctttg cagtaccatg taaccgtgac agctgatgcg     2760
```

-continued

```
cagaacagcg gcccaataac caatgtaaaa gtaagcgata ccttggggaa caccaaaaac  2820
ggaacgattg tatttgacaa gacccaggaa atcaaatttg aatccaataa tcaggatact  2880
gttatagaca atgttacttt cggcggcatg agcaatgggg gaaagaccat aggtatccaa  2940
ctgaatacaa aggatggaat gccggcctct atgatgcctg gagagtctgt tagtttatct  3000
tattgggtaa agcttggagc cggtgcttgg agcggtcaga ataccgggaa ttcttcaaaa  3060
gagatgtccg catccctgtt tttggaactt aagaatacag ttaatgtgac agcggataaa  3120
aaagtatcgg gcagtgacag cactacattt aagaggacca tagaatgcgt taccaagagt  3180
ggaattgtac attataatta tgagatagat ggtaagactg agccggttgt cattgagtat  3240
catgtttttg taaatcccag gctgattaat atgaccggat ggacgattga ggataagctg  3300
gataaaaatc aaaagtatct gggaaatgta gaagttattg cttatactgg caaaaatgga  3360
acctcacttg ggaaagtgga tgacattgaa ccaataattt ctaagaatcc ccaaacatgg  3420
aaatatgtca ttgaaaatcc aggaaaatat tactatgatt tcaaatactt taccactcct  3480
aatgaagcaa cagaaagcaa tctcagtaac gaaataaaga taacatggcc aggcggaggt  3540
tctggaggca taggcggaag taccggtgtc ggattcctgt acaacaccta taccatgaca  3600
aagaagaact taagcagcaa catgaaatcc agcaataaca ttaattccgg cggggtatat  3660
gagcctgtca ataatacagc cggaaatgtt gggtggggggg atgaatttgg cacaatccgc  3720
tggcagagcg tgcttacccc atatgcagac gggcagacga aaggcgccac gattccagcg  3780
ggcactgtct ataaagattc tctcagcgta attaagtggg gaaataaaaa taaggaagat  3840
gctgcccgtg caaatatgca tacattcaag gatgatggca gctttaaggc ttcctttgtt  3900
ctgaaagacg gtaatggcag ggctatatct ccggatgatg ggacctatac attatcattt  3960
gatgaaaaac ttggaaaccg tggattcagc gtagtgtttt caaaagatgt cccaggaccg  4020
gttgtcattg agtatgagtc cttcgtggat ttagagatgt tggaaaatgt gggggttttt  4080
gataaagacg gaacaaaaga taatctgcgg ttcaaaaatg taggtgagat gacaatcaat  4140
gggacaacat ggaagagcgc tacctctcag ccatattaca tcgaagatta tatttcaaag  4200
aactgggtaa aaaatgatac gaaagcaggc accatcacat ggaatctgaa tatcaacaag  4260
ggatatggga atgatgcacc ccaaaatctg gggcgtttca cggttgatgt tattgagtat  4320
ataccggaag gactaactct ggaccatatt aaattccaga gcatgaacta tacgctgaaa  4380
ccagaaaagg gagattacga tatagatgga aataaagtga ccatccacct taacacggtt  4440
gctagaaact tttctggtta caagatgagc aaacatatta acctaaacat cataaccaag  4500
gttacagatc catctataaa gagttttaca aacagcgccc agatggttat tgatggaaat  4560
atgcttcata aagtatcagc tacgactggt tttgataaga gcttcctgaa aaaaggaatg  4620
gcatacagcc gcgacacggc gccgtatgct gaatatacaa ttctggtcaa ccagccaggg  4680
gcagatatca gcaatggtac cctgaccgta attgatacct taggagtacc cgggaaaatg  4740
gcatatgttc cggacagctt taaggtaaca aatgcagaaa acgggacacc tatagaagaa  4800
gcgaatatca gggtgggaaa agacagtttt ggcaatgaca gttttgagat ttccaatctt  4860
ccgaacaaaa cgcccattaa gattttttat aaggtaatga ttacaggagc tataaatgaa  4920
accgttgata cgaagaacac agcatccctg ctctacagca gagaaggtat aattaccgaa  4980
accattgagc gcagcgtcac tattgtaaaa gccgccttta caggaggagg aaaattttct  5040
ataaaactat acaaggtgga tcagaataaa cagccgctga caggagctgc ctttacgctg  5100
agcaaagtat cagaagtggg aagcccggat ttagaatatg tgggagagtt taccccggta  5160
```

```
attgattctg ggaatccgca ggcaggcgca gcagtgctga taacgggact ggagaagggg    5220
cagctgtatt atctggagga gactacggtg ccggaaggat atcagaaggc agaaggggag    5280
tattttatca ttccggatag ggagaatggt attggggtgc cggatggagc gatagccata    5340
gaaaatgccg gaacacctca tgtagtagag aacattaaga attccggtac attaaagctg    5400
accaaagatg taaacggcag ggaatcaggc agtgattttg agaccgattt ctactttaca    5460
gtctatggtg gagaccgata ctacgatagg gatggatcct acgccgacct gaggactgta    5520
aaacttcact atgattccag gattgcggat aacagcctca tactgtcgct gcctattgga    5580
gaatatgtgg tgaaagaagt ggcagacgca gaggggacgc ctattaacgg tgataatttc    5640
tattataatg tacagataaa tggtgaggac aggaatgaag cggtcatagc tattgaaaaa    5700
gaacagcagg cggaatgtct ggtaaagaat ctatatgaag cagatggaaa tctccaattc    5760
actgccatga agacaatgga aggaaggcct ttggaagaag gggaatttac tttccgcata    5820
tacgagggag acacgctgaa agcggaagct caaaatggac taaacggagt tatcctgttt    5880
ccggagatta actacaaagc caatgatgcg ggcagacata cctacacaat catggaacag    5940
aagggtacat tgacaggtgt tgactatgat gatactgttt atactgtgac ggtagaggtt    6000
acggacaatc atgacagaac agtgagtgca gaaatagtaa atatccagag gtctgatggt    6060
gctgaggcag aggtgataca gtttaataat gtttaccatg agaatccaga aaccacaccg    6120
gatccgtctc caaatccaaa cccatctcct tctccgggag ggagtactgg aggaggcggc    6180
ggtacttcca atactggggg tggacggtac cagccttctg atggcggacc aggagttaca    6240
atcagtatta ccccggaaga ggttcctatg gctcagattc ccagccaacc agactctctg    6300
attacgattt tggatgacga tgtaccgctg gcaccactgc caaagacagg tgatatgtca    6360
gttgatcatt atatgctgac tgtgatatca atgttactga cagggattta tctagcgttg    6420
acgaaaagaa aaaaggaatg a                                              6441
```

<210> SEQ ID NO 14
<211> LENGTH: 3714
<212> TYPE: DNA
<213> ORGANISM: Clostridium boltae

<400> SEQUENCE: 14

```
atggatttga ttcgtgattt taaggacccg ggaagggaat acagcgtgct ggccttctgg     60
ttcttaaacg gggaactgaa aaaggaacgt ctggcctggc agattggcca gatggtggaa    120
aaaggcgtgt acgggggctt catgcacccc agggcctacc ttaagactcc ttatctggag    180
gatgagtggt gggacgctgt cggggtttgt gtggaggagt ccaggaaaca gggatttgcc    240
ccctggctct acgacgagta tgcctggccc agcggcaccg caggtagtac ctttgaatat    300
ggattccaaa agccttccag gatactgtcc cggggaaggg acaacatggc aaagggactc    360
tgggcggtga aaaagatgc cggaatagg gaatgcggaa atgaaggtgc cggaaatgag    420
ggcggcggaa gtcagggcgg cggaaatcag ggcgccgcca ccccggatgc cgccaccccg    480
gaggataagg acaaagcggg cgccaatccg tcatcaatgc cgtaccgtgt ggtgaaaaga    540
gatggtttta tctatgagtt ttatgaaaaa gtatttgaaa aggccgtgga ctatctgaat    600
cccgaaacca ttgcttcctt cataaaactg acccatgagg aatacagaaa gcggtgggggg    660 gaggattttg gtaaactgat accgggtatc tttttcgacg aaatctacat gatgggaaat    720
cccctgccct ggacggaccg gctgccagga cggttccggg agacatatgg ttatgacatc    780
```

-continued

```
ctggacgagc ttccctctct tgtggacggc gcgtctgagc gggacaaaca ggtgcgaaag    840
gattatttct ccctcgtaac cgccatgtat gaggaagcat ttttcaggca gatatcagac    900
tggtgcggga aatacggtct taagctgaca ggccacacag aggagttttt gtgggaacat    960
cccagaaggc agggcgatta ttttaagacc atgcgccatc tcatggtgcc gggctctgac   1020
tgtcacgatt accggtaccg gtatcccaga aggattacat actgcgagcc caagtattct   1080
gtgtccgtgg ccagaatata tggaaaagag agggctatgt cggaagccct gggaggcgcg   1140
ggatggaact gcaccatgga ggaatttaaa aagggaatca atactctggc cgccatggga   1200
accggaatgt tcatcctcca tggattctac tacgagtgtg agcaccaggg ttcccagagt   1260
gactggccca ccagtttttt ctatcagaat ccttactggg actattttaa gatatttgcc   1320
gattacataa ggcgtctatc cttcatgaac agccagggaa atcctgtggt ggattatgcc   1380
atcctgtatc ccatagggga catggatgaa aatatggaga acggagagga aaatccctca   1440
ggccaggcca taaacaacgg attccaccag gccctcaact gtatgattga gcaccagctg   1500
gacacggata tggtggacga ggaatccatt ttaaatgctc atatatgtga cggaaagctg   1560
tgcctggggc agcagcgttt taaagtgctc ctccttccgg aagggggaag cctgatggaa   1620
gaaaccgtgg aaaagctgga agcatggaca aagaccggag gcgcgtcct gttttacagg      1680 accggtctgg ctgacgaata ccggtccggc ggggacaggg ctggcgggga caaggctggc   1740
ggggacaagg ctggcgggga ccggtccggc gaaaacaggt ctgacaggaa ctggcctggc   1800
ggggacaggg cgaacggatg cagagtaaac ggatgcagcg taaacggata ctggaacacg   1860
gtcctcaggg aaaatgtaca cagcatcagc cgtattccgg aagcagcagc tgcactggct   1920
gcgccgtccg catccgtgat ttacggaaat cccggagaca tctttttgaa tcatagaatg   1980
gcagggaatg ttgactatta tctggtggcc aacagcagcg atgagaggcg aaacctggtg   2040
ctgtctttca gccatgcttc tacaccggtc cttttggata ttgaaaaagg ggacatggtg   2100
caggctgtat acactcaggc gggcgccgcc caaatgtgcg gaggccgtcc gtccggcagc   2160
ggtgtcctga tttacatgga tttggaaccg ggagaagctg tctacgtact gtttggtttg   2220
gaggaagata caatcagaca ggcaaaaccg gcccttacgg gggatatccg gtgggaggaa   2280
gagtggatta caggaaaatg ggattttctt cccctttccc cgtccggccc gaatcatgga   2340
gataaggcat acaatgaaga gagtacggtt ctggaaatcc caatcgcaga attcacctct   2400
gatgtaacct ccggaacaga gaccatccgg atctgcaacc aatccgggga ggaggggagc   2460
tgcggccgcc atatgagcct ttggaacgga cggtggatta cacgcagacg aagctggaat   2520
gaccagctgg atgcatcgga tctgtatttc agaaagacgg tattcctgga acatgtacca   2580
gaaaaggcgg agtctgcgc ggcagcggtg gattcctttg agtgctttat caacgggaca   2640
atggtttaca aaggaatcag caacggagag ccggtggtat ttggtgataa gagccagctg   2700
acccaggggg agaatattct ggcattccat gtaacaaacc gcaacccgct tcatgatgta   2760
tatgtctgct ccgcagagga gctgcctcca gaccggttca tttcccttct tatggaagga   2820
accatcgttc agggaacaaa cgtggaagtg gtgaaaagcg acagcacctg gattgtaaat   2880
gacagtctga ttaaagggtg ggaacagccg gattcggacg ggcggtttac ggcagccggc   2940
tttgatgtcc gcaaggtcct gaatttcaat tatacggggc tggagcatgt gtggctgaaa   3000
gcctgggaga gggggaaaacc gcctttgaag ccgtggggag accttccgtt atttgggcag   3060
accctgacct atcccagaaa gctctggtat acagtcacaa tacctgccgg agcgtcagtt   3120
atatatgagc ctgttacagc cggagcagcg gtctgtatgc tggacggcaa agaggtgcat   3180
```

-continued

```
tgggaaaatg gcatacacat actcccggac aatgaacgca ttcacatact taccatacag    3240
ataacggcag gcggatgcag cgacgggctg aaacagccaa tccgcgtaac catgaaggca    3300
gtggctgtca atctttcgga ctggcgtatg ctgggacttc cgtggttctc cggaaggtgc    3360
aggtatacta acacatggtc cgtggagcaa ctggagggca cgtacatgct ggagcttggc    3420
ggggtaaacc actgtgccca aatctggatc aacggcaggc tggcagatac aaggctgtgg    3480
cgtccctata gggcggacat cacttccctg ctcaggcccg gggaaaatga gattaccata    3540
ttggtatcca acctggcctc caatgaacgg cgccacatgc tggtggacga aggaatggcc    3600
ctgggatgga accggtactg gaacgaggac aacatggacc gggacagccg gaattatgtg    3660
tcaggccttc tgggaccggt aaggcttctt catatgatat ccccaaaacc ataa         3714
```

```
<210> SEQ ID NO 15
<211> LENGTH: 2895
<212> TYPE: DNA
<213> ORGANISM: Clostridium boltae

<400> SEQUENCE: 15
atgaatatct ctgttatgat aaatgacttt ataaggcaaa atattcagtc tgaggctgaa      60
gtgagaagca aactgattgt tcctttatta gaactattgg agtatcctaa ggatttgaga     120
gcggaggagt tcccagtata tggttatgaa ggaagtaaag cattaaaaac aaaagcagca     180
gattttttac aatttacatc aaatcaattt gataaatata gagggaaaac tgatttagaa     240
gtagactggg tatataaaca tagtttgctt gttttttgagg caaaaaagcc tacagaaaaa     300
gtattggtaa aaggacaacc agtattttat tcagcatgga cgaaatcggt tgcttacatg     360
atttcaaacg gaattaacat agaaggttat atcgtgaatg caaactattc tgatacatgt     420
gtattttcat gcagagttga agagattcct gaaaaatggg aagagataaa tcttttaaac     480
tatgatagaa ttctggaatt aaagaaatca tcagatgaaa aggataaatg gactaataga     540
gatatttatg aaaaatacaa aaatgcgatg cgggtacatt gtacagaaga gttatgcata     600
tgcgtagata gaagcttaaa ggaatttgca tatgatttaa atattttaaa gaatggagaa     660
aataaagatt ttggcgacat attagataat acatcaaaaa taatcacatc agaacctgga     720
ggtggaaaat cgtatctgat gtggatgctg atgcgtgagt atctgacaaa gtgtaatggg     780
gatgaggata aaataccggt aattttagaa ggaaggtatt atggaaaagt atttaattcc     840
atagtagatg gaatttatca agaagttaat ttgctgttgc cttttttaac aaaagaacta     900
attgaaaaac gtctgcgaga aggtggtttt gtaattttat ttgatgctat agacgaagta     960
gaacaagatt atgatgtttt ggtatatagt ttgcatcaac taaggagaaa tacagacaat    1020
acaataatca ttcatcaag aatgcaaaat tataaaggag attttgttc tgagtttgca      1080 cattattctc tggaaccgtt agatgatcat aggattgttg atttgttgaa gcaatactct    1140
caaggggaga tgcagattca aattcatcaa ataccaaaaa gattaatgga aattttaaga    1200
ataccattgt ttttaaagat gtttgtttct atatcaaaga aggaggacaa atatagaatt    1260
ccgtctaatc atgcggcatt atttcaagag tatattaatg agaaaatgaa tgtactttca    1320
tgttctctgt atgataaaac gattattaaa tcagtgctag gtaattatgc aatgtatagt    1380
tttgaaaatg gggacagtac tgaacacttt tttgaaatta tggataatgc ttgcaccgat    1440
ctaaataaaa caaaaatata cgaaaaaata tggaaaacag ggttgatgtc tgagggctta    1500
caaggaatta aatattatca taaagcaatt caagagtttt ttgctgcagt ggaattatct    1560
```

```
acgtgggata gagataagct taccgcctgg ctggatagca atgcattgaa agaaaaatac     1620
aatgagatac tttgttattt gactggtatt atttcaaatc agcaaaaaca aaattatgta     1680
ttggattact tggaaataca caatttaaag ttatttgtaa aggcacttaa atccagaaga     1740
aattttgatg ttgttgagat ggatttgaat tttgaatacg ctcagagtta ttatgcacaa     1800
attttaaaaa cttatgacag tatagttcaa tcctattttt ataaaatatg ccatgttttt     1860
gatgggtaca gtataaaagg aaccggaaaa atctgtatcc gtggctgtat gaattttacg     1920
aaaaaatcta tttctatgat aatttataat ggaacatcgg atgccaaaag tttggatatt     1980
acagtatctg atgaaaacgg tgtatatatg gcagtagcag atggaaccga gataccaata     2040
aattcatcag tatttacggc gggacatttg catgaacggt attacaattt agagttgttg     2100
tcttatgggt ttgattcttc cagggaaatt gcaattgata taataaaaag tcaaatcaca     2160
gaaatgttag agcaaaaaag cgtgtttgat attgagatag atgtattgct agcggagcgc     2220
atagaaaaag aattgaaaaa attgcgaaat aggagagaaa gtcaaaataa cagacaggat     2280
ttaagcttat attctaatga tataaattat gttattgata aagtaaatga actggggata     2340
tataatcaag atgtagatat gattactact ttttgcaaag tattaggact tagaatggat     2400
aatgcggaga gtctcctaga tattaaggag gatttgactt tggctccagg aagacattca     2460
tattggtttg acgaattata ttcagatgag cagttagtaa aaaaagttga aagaatactt     2520
tccttatcga atgaagcaat acaaacgata actacgaata ttattccggt attatcaaca     2580
gtaaaaccca taaccagaaa gataggaatt gttcatcgaa aaggtaaatt ttctggcgtt     2640
agttatatga gagtggaagt cagggagaat gaagatacga ctccaataat tgaatttgga     2700
gaagataata ttgatatata ccctaaatta gatccgtatt atgttaataa attaaaagaa     2760
attggtaaaa gtgaaagtaa tgttcttggg tcaagttcag ctgtttttaga tttatatttt     2820 agggaggacg tatttcatga tcagatttat ggagagataa aagatttgtt taaggagtta     2880
ttaggagaca tatga                                                       2895
```

```
<210> SEQ ID NO 16
<211> LENGTH: 2877
<212> TYPE: DNA
<213> ORGANISM: Clostridium boltae

<400> SEQUENCE: 16
atgcagacaa aggtaaaagg gatgaatggg atattgatga tagccgtgct tctcattgta      60
ttcctgttcc ctctggacgt atccgcagcg gagacggctt ctgccgcgct tgtaggctat     120
tatgaagatg gcgattacat gtatcataat gcgcaggggg agtatgaagg ttataacttc     180
gagttcctcc aggaagtctc aaaactgagt ggactatctt acgaggtagt ggattccccc     240
agctggcagg aagcgttcca gcttttgatt gatggcagga tagacattct gcctgctgta     300
taccgcacgg aaggcagaat ggatcagatg ttatttaccg atgagtccat gtgtacgatt     360
tatactaccc tcaatgtgcg gatggatgat aaccgttaca attatgagga ttttgacgct     420
ttccagggca tgagggtagg cattattaag ggggtgaggg atggcgaaag tttcaaacgc     480
tactgtgcgc agaacggcgt tgcgctcacc atcattgaat atgatgagac gcaggaactg     540
ctggacgcgc ttgggagcgg gaccctggat ggtgtggcaa ttacccacct gggccgcagc     600
agtgtgttcc gcagtgttgc gcggtttgcc ccgaccccaa tgtacattgc ggtctcgaaa     660
cagcgtccgg acctttggc tcagattaac cggtccatta tgacattct tctgcgcaat     720 cctgattatc ggacggacct ttatgacaag tatctctcac caagctccaa tcaggttccg     780
```

```
gtactaacca aggaagaagt tgaatacatc gaggctgcgg atgagccgat acatatttct    840
tacgaccctt cgtttgcccc tttctcatat aaagatgctg aaggcgagtt aaacggtatt    900
atggcagata tttttgcccg gattgcagag aagagcgggc tggacttcca gtttgaagcc    960
tgccctgcag ccacggcctt acgtgcagtg aaactggggg agacggatgc cgtttccgtt   1020
gtggatggag attatctgtg ggatgagcgc aaccatatga acaccacact gcgtttcctg   1080
aatactccca gtgcaatgat tacccaggct gaaagaacgg agatagaggt gctggctctt   1140
ccggaggggt atcagctctc tgaacatgtc gcccaaaaca atccggaaaa ggaaatccaa   1200
tattacgatt ctatacaggc gtgttttgat gcagtcctgg atggaaaagc tcaggcaact   1260
tataccaata cccagacggc aaattacata atcagcgccc ccaaatatga aaagcttcat   1320
gtcactgcgc tgacccagta cccaaacgac ctctgtatcg gcgtatccaa atctgccgac   1380
cccaggttgt tctccatatt ggataaatat atccagtata tgtccaatga agagattgat   1440
accctgctgc tgaacaactc cgtttctgtc cgtcccatta ccatggaagc gtttgtacat   1500
cagaatatct ggttgataac agggcttgtg gcagctgtat ccggcagcat catcctgctg   1560
ctgtgcatca acctgtttaa tatttcccgc agtaagcgcc gtatccagga cctgctctac   1620
cgggatgagc tgacaggtct ggataatata aaccgttttt atgtccgggc ggaggaactc   1680
ctggcgacgg ggaaatatgc ggtggtttat tgtgacattg accgtttcaa gctgataaac   1740
gatacccttg gctttgagga gggggatgaa gtcctgcgcg cattcgggag tatcttacag   1800
aaatcaatgg aggacaggga gtgctgcgcc aggctttcgg ctgataactt cgtgatgctc   1860
aggcattaca acaatgggaa aacgcttgct gctgatttga tgcatatcca ggcggtgctg   1920
aacaagtggc gtggggagag gggaatcata ccttatgaga tcgcggtatc ctttggtgtt   1980
taccaggcgg atgccggcga gactaacgac atgaaacaga tgcttgactt tgcgaactat   2040
gccatgcgta gcgctaagac agcggcaggc ggaagctgct tcctatatga tgagcagatg   2100
cggaataagg ccctgtttga acaggggctg gagggaaggc tggcctccgc gatggaacag   2160
ggggaatttg aggcgtatta ccagccaaag gtggacatgg atacaggcag gattgtgggc   2220
tgcgaagccc tggttcgctg gaatcacccg gaacaggggc ttctgatgcc ggggtccttc   2280
attccatttt ttgaaaagaa gggtcttatt gtccgagtgg accttcatat gtttgagcag   2340
gtatgccgca cagtacgcag atggctggat gagggacgtc ccgctgttac agtctcatgt   2400
aatttctcgc agatgcattt cggacatgac gggtttgccg gccaggtttc tgaaattgct   2460
gatcggttcc aggttcccca tcatctgctg gaagtggaga ttaccgaaag tgcgattgcc   2520
gatgcacctg agagtgtgtc ctccgccctg acggaactga agatgcgcgg atttcagatt   2580
gccatagatg atttcggctc cggatattcc tccttggggc agctgcaaag gctgagggcg   2640
gatgtcctca aactggaccg cagctttgta tgtgccgggc ttcagggacc gcgggagcag   2700
attgtcattg aaaatctggt gaacatggcc tcggagctgg ggatggaggt cgtatgcgaa   2760
ggagtggaaa cccaagtaca ggtaaaagta ctccaggata ttggctgcca catcgcccag   2820
ggctattact attaccgtcc gatgcagaca gcagcgtttg agcagcttct gggctaa      2877
```

<210> SEQ ID NO 17
<211> LENGTH: 2520
<212> TYPE: DNA
<213> ORGANISM: Clostridium boltae

<400> SEQUENCE: 17

-continued

| | | | | |
|---|---|---|---|---|
| atgaaccaat | tgattaaaaa | atataggatg | gttttgtctg | caatatactg | cctgatactg | 60 |
| ccatacagtt | ttgtttccta | tggagcagaa | gcagagtctg | tgattcgggt | gggatttccc | 120 |
| gtgcagtcgg | gtctgaccat | gaaggatgaa | aatggcaatt | atgcgggtta | tacctatgat | 180 |
| tatctgaaag | agattggaca | gtacacagga | tggacctatg | agtttgtgga | accccaagga | 240 |
| tccatggatg | aacagttgat | tcaaatgatg | gatatgctgg | aacggggggga | actggatctt | 300 |
| gttggagcca | tgaataacaa | caagcagact | tcctctgttt | ttgatttttcc | cagtgaaaac | 360 |
| tacggcaacg | cgtacagtgt | gattgcggtc | cgggatgatg | atgaccgcat | tgatgaatat | 420 |
| aatctttctg | atttcaaggg | actgcgcata | gcgcttttga | aacaggcaga | ttaccataac | 480 |
| gaaaagtttt | accagtacgc | gaagctcaat | ggcatccagt | atgagatcgt | ttggtgcgag | 540 |
| agggatgggg | agcaggagga | gagggtttat | tccggtaagg | cggacgcatt | gctgtccgtt | 600 |
| gatgtatccc | tgtcccaggg | attccgtcct | gttgctaaat | tttcgcctac | tcccttttat | 660 |
| tttgccacca | ccaagggtaa | taccaaaata | atcaatgaac | tgaaccgggc | aatctcctat | 720 |
| atcagtgaga | ataatcccac | ccttcaaatg | aacttgtata | ataagtattt | ttcccggtcc | 780 |
| ggaagccaga | tgcacctcaa | cagcaaggag | cgggaataca | tacaggaaca | tccggtactt | 840 |
| aaggtactgg | tccatgacgg | gtttggcccc | atccagtact | acgatggaaa | aggacaggtg | 900 |
| cagggcgtag | ccagagacct | gctcagcagt | atagcccaaa | aggccggatg | gacgctggag | 960 |
| tatgtttacg | cggatgatta | cagtgaattt | gaacaggcgt | taaatgaagg | cagagccgat | 1020 |
| gtgattctgt | ctatcctgta | tgattatgat | gcagtccaac | ggagaaatgt | tctttttaagc | 1080 |
| aatccatatc | tggagacaga | gagtgtgctg | gtggcccgcg | acgggtttga | tatgacaaac | 1140 |
| ctgaagggca | gggtacaggc | tgtgtatatg | ggcatgcgca | aaagcgacga | tgaccggacg | 1200 |
| gatgtgcggt | tctatgattc | tctggaggaa | agtcttaacg | cagttgaaag | gggagagtgc | 1260 |
| gattatacat | acagcaacag | ttacactgcc | tcttattatc | tgagccgcaa | ccagtacgag | 1320 |
| catgtggcta | tctatcccca | ggccggcagt | gacagtgtga | aatacagcat | aggtattttg | 1380 |
| agaaaggatg | ataaacagat | actggctatc | ctgaataaag | gaatccgttc | catagagacg | 1440 |
| ggtgaactgg | aaaaatacat | ctacaacaat | gcgcagcaga | aacaggaagt | gactctcagg | 1500 |
| acctttatca | gggataattc | cgttcccttc | attttgttta | ccctgttggc | tgcttccggc | 1560 |
| ctgctggccc | tgatttatgc | ccattacaga | agccagatga | ggatgaagcg | gcagattgaa | 1620 |
| ctggaaaata | cccgttaccg | ctatctctca | gacatattga | aggaagtgac | ctttacgtat | 1680 |
| gactatggca | gtgatgtgct | gaccctatca | agggagggcg | ttgaaatctt | cggcacggat | 1740 |
| aaaagcatcg | ggcagtattc | gcggtatcag | ggaagcagcg | gacaggagga | gggtctccca | 1800 |
| tctctgtatt | atctgctgga | gcagagacag | gatgtggata | cagagattct | gatggtgctg | 1860 |
| ccgaatgggg | acaccaagtg | gcaccgtgca | gtcataaaag | tgattttcga | cgggaatcag | 1920 |
| gctgattctg | ccatcggacg | cttacagaat | atccatggcg | acaagctgga | aagggagaga | 1980 |
| ctggagcagc | ggagcaaacg | ggacgctctg | acgggattt | acaatatagc | ggcagcaaaa | 2040 |
| atggagatca | cccggatgat | aaacctgcat | accggcgccc | ttgctctggc | tgtcatagac | 2100 |
| ttagacggct | ttaaggaaat | caatgaccgt | tacggccatt | atacgggggga | ccaggtgctg | 2160 |
| attcatacag | caaaagcgct | aagggaatct | ttttgcgggg | aggctgtcac | tgcccgtatg | 2220 |
| ggcggagatg | aatttatcgt | ctgtgtaccc | tatacaggggg | aaaaccatct | ggcaaaatgc | 2280 |
| tgcaatgcac | tgtttgattc | actgcaggct | aaatgcaggg | cgtccggata | ccctgctgcg | 2340 |
| actgtcagca | tcggtatatc | tataagccgc | agggaggacg | actataccac | gctttatcag | 2400 |

```
agggcggata ccctgctcta tgaagttaaa aacagcggta aaaataattt ccggatagaa      2460
gatgaagcgg gaaggacttc ccggccggac acggaacagg aacatcacac ggtacagtaa      2520

<210> SEQ ID NO 18
<211> LENGTH: 2421
<212> TYPE: DNA
<213> ORGANISM: Clostridium boltae

<400> SEQUENCE: 18
atgagagagc gcgggaaaaa tctgataaga tgcggggctg cttttgcggt gtcctgctgt        60
ctgctggcag gaaatgtgtt tcctgcggca gccgacacct ctgtaagcgg agcaaccatg       120
cgtctttctt ccagagaggg cacggtaaat gtgtcaggaa aaggaggaaa ggcggttgcg       180
gcctttgata acatgcggct ccagagcgga tataacctgg aaacagaggc tgcaagctac       240
gcaggccttg cactggatga cgtaaaggcc gtgaagatgg atgaactgag caaaggagag       300
atacggaaga aaggaaagca gctggagctg cttctgtcag aaggaagcct tctctgtgat       360
gtaaccgcgc tccttaaggg ggaggagtcc ctatccatcc gcacctctac catgataacc       420
ggaatccggg gaacggtagt atacgcggaa gtggttgaca gcaatacgag ccgcgtctgc       480
gtcctggagg ggcaggttct tgtaagaccg gtgaatcctg tggagggtga ccggaatggg       540
cagtacatag agaagggccg gcaggcactt attatcggtc ctgaccgcat ggagcggaag       600
ggagagatac agacgcttcc ccttacggaa gcagatattg ccccttatgt gctttgggaa       660
atccatgaga tgaggagct tgccagaagg ctgagagagg caggttggga tgtggactgg       720
atgattgaaa acgcggaacg gcttttaagg gaagaagagg ataaaaactc ccaatgggca       780
gagaaggggc aggaacatc aggctctaag cctggcggga aggatattca caccctctt        840 tataacggag gggattccgg ttctgattcc ggaaccggca cacagccggg cagacctacg       900
gtggagctta ctatgccggt gagtccggaa accatagagg aaaagctgcg gacatctgat       960
gtggttcttc acagcgctgc ggacagcaat ccccttatca ttgataacag cctgaccgta      1020
ccggcaggca gccggctgga attagccggg ggaatggggc tggtggtggg aacgtcggca      1080
gcattgcagg tggacggaac tttgattgtg gacggaaacc tggaaaacag aggaactgta      1140
acgaatacca gtatgaatac cctggatatt aaaggagatt atgtgggaag cggaacactg      1200
aataataaag ggagagtggc ggcaaatggt tcctttatgc aggaaggcgg cagcttccaa      1260
actatcggac agggccggct tgaggtggag agaaaagctg ttattgataa tgcagccttt      1320
gatttcggta ccggaactac attgtttcac ggtgatttga cagtcagaaa cgctgacggg      1380
gaatttggcg ataacctgtg tgtggaaggg atgctttcat tggaagacag cagtattctg      1440
ataacagggg gattttacag cggggggatt accgcagtaa agaaacaaga tggagagaat      1500
atagcatatg aagagctgaa cctggaggga ggaaaggttt tggctgaacg tggggtcaaa      1560
ggggtaatct ttgcagaaaa ttataagctg aatgtacaaa gcggtatctt ggaaaggtca      1620
gatgatggga ttccttttat aaccggcaca ggtattttag aaatggatgg agaggaatat      1680
aaaattgaag agttgacaga gtccatgttt gagagcgaag agacagagac gggctgggtt      1740
ttaactggta ttgtccagga acaaaaaaaa caggcagagg tgcttacttc tatccctctt      1800
caggcagatg ctgaaaaact gccggatgtg aatgaggaag agaaagagct acaggaggga      1860
gagagtttgc cggaggaagg agagccggaa gagggcggaa ccagccgga ggaaggaagt       1920 ccggaagagg gcggaaaccg gccggaagaa ggagaaccgg aagagggcgg aaatcagccg      1980
```

-continued

```
gaagaaggag aaccggaaga gggcggaaac cagccggaag aaggagaacc agatgagggc    2040
ggaaaccggc cggaggaagg agaaccggaa gagggcggaa gccagccgga ggaaggaagt    2100
tcggaagagg gcggaaaccg gacggaagaa ggagaaccgg gagaaggcgg aaaccggccg    2160
gaggaaggaa gtccggaaga aagcggaaac cggccggagg aaggaagtcc ggaagaaggc    2220
gccgcaaacc agccggaaga aggaagtcag gaagaaggcg caaaccagcc agaggaagga    2280
agtccggaag aaggcagaaa ccagccggaa gaaggaagtt ctgaagaagg cgcaaaccgg    2340
ccagtagaag gaattccgga aaagggcaaa aaccagcctg aaacaggaaa accggaagag    2400
tatggaaatc tgccgggata a                                              2421
```

<210> SEQ ID NO 19
<211> LENGTH: 2373
<212> TYPE: DNA
<213> ORGANISM: Clostridium boltae

<400> SEQUENCE: 19

```
gtgaaatatt tcgagcatga gagcgctgcc acctttgatg aggcagtctc cttattaaaa      60
gagtccccaa aagggaaaac agtcgtaatg gcagggggct ccgacctgat tggagtgtta     120
aaggaacaga ttctggagga ttatccggaa aaagtggttg accttaagac cgtcaggggc     180
ggggaataca taaagcagga cggggacacc atagaaatag gcgccctgac aaaactctgc     240
gacatcgtaa agtcggacct gctcaatgaa aaggctccgg ttctctctca ggcggccgc      300 tccgtggcaa caccgttaat ccgcaatgtg gccaccatgg gaggcaacat atgccaggat     360
gtgcgctgct ggttttaccg ctatccccac ggcatcggcg gcaggatgga ctgtatgaga     420
aagggcggaa aagagtgcta tgccgttatg ggagacaacc gttatcattc catattcggg     480
ggcatgaagg tacataccac accgtgttct gtccagtgtc cggccaatac ggacataccg     540
gcttatatgg aacggcttcg ggaaggtgat gtggagggag cggcccatat ccttatggaa     600 gccaaccca ttcccatgat tacatccagg gtctgcgcac atacatgcca ggagcagtgc       660
aaccgctgcg gttccgatga gagcgtgtcc atccacggcg tggagcggta tgtgggggat     720
tacatactgg agcacccgga cacattttac agggcgccgg aaacagagac aggccataag     780
gtggctttag tgggagccgg tccggccggc ctaagcgctg cctattatct gaggaaggcg     840
ggccatgatg tgacggtctt tgataagatg gaggagccgg gcggcatgct gacctatgcc     900
attcccaact acaggctgcc caagtcctat gtgaagcagg tggctgccgc ctatgaaaaa     960
atgggaatcc gcttccgcct gggctgctgt ctgggagagg atatacaggc agaggatctg    1020
gagaaggagt atgacaatgt gttctatgcc accggcgcct ggaaacgtcc tgtgctggga    1080
tttgacggcg aggagttcac ggagttcggc ctccagttcc tgatggaagt caaccagtgg    1140
atgaacaaaa aggaccgccg ccatgtactg gtggtggag gcggaaatgt ggcaatggac     1200
gtggccataa ccgccaggcg cctgggcgca gagagcgtca ccctggcctg cctggagtcc    1260
gagccggaga tgccggccag cagggaagag attgcaaggg ccaggaggga gggcattgaa    1320
atcatgccgt cctacggcgt atcaaaggca atctatgagg gcagccaggt cacgggaatg    1380
gagcttatgc gctgtacctc cgtcaaggat gagaacggc gtttcaatcc ccggtacgac      1440
cgggaggaga ctctcagggt atcggcggac tccattctga tggcagcggg gcagaaggtg    1500
gatttgagtt tcctgggcga caaatacggc cttgccctgg aacggggact gattcaggtg    1560
gacaaggaca cacaggccac cagcaagtcc gggatttatg ccggaggcga cgccaccaca    1620
ggaccggcca ccgtgatcca gggcgtgcgc tccgggcgca acgcggcgga ggccattaac    1680
```

-continued

```
aggggctatg cagtcatgcc tgagcggcgc agggaagata agtttatcca ttttgacacc    1740
gcaggcgtca aggaggagca cgcggtaaag gacaaagagc tgtctgccgc agagcgggcc    1800
ctggataagg aggacagctt caccctgacc ggggaggaag cggccaggga ggccggacgg    1860
tgcatgaact gcggctgcta ctccgtcaac gcctcggaca tttcaccggt gctcatcctg    1920
ttagacgccc ggattgtgac cacaaagaaa accgtaaggg cggcggactt ctttaccacc    1980
cgcctgaaag cagctgacat gctggataca gacgagctgg tgacggctgt ccggttcagg    2040
gtaccggaag gatataccac ggcctatgac aaattcaggg tccgtgaggc agtggatttt    2100
gccattgtca gcctggctta cgcatacagg atgaaggacg gcctcataga ggatgcgcgg    2160
atcgttctgg gcggcgtggc cccggtgccc atggagcgga aaaggtgga ggcgttctta    2220 gccggcagga agccggatga ggcgctggca gaggccgctg ctgaactggc agtggagggg    2280
accgcggcca tggccaataa ttcatataag atacaggagg taagggctct tataaagaag    2340
atgattctgg atatgggggc ggtccaggca taa                                 2373
```

```
<210> SEQ ID NO 20
<211> LENGTH: 1926
<212> TYPE: DNA
<213> ORGANISM: Clostridium boltae

<400> SEQUENCE: 20
atgcctagaa tcatattgaa atgccgttac ctgaagcatg agaaagcaca tctggcgcat     60
ctggtccgtt acattgccac acgggaaggt gtggagatgg caaggggatac ccacgaccat    120 ctgccggcaa ccgccagaca aaaacaactg atcgatgaat tactccgggc ccttcctgat    180
acgcaggagt cttatgaata tcgtgattat caggcgaatc ctaccatggg taacgcatcg    240
gcgttcattg ctatttccat tgagcagaat atggacctgg tagcaaagaa ggaaaattat    300
gtggattata tagccagccg tcccgggggta gagaaaaggg ggacacatgg actgtttacc    360
gatgccggtg tgccggtcat actgtcacga gtacaggaag aagtcgccag acatgaaggg    420
aacgtatgga ccttcatact ttccatacgg agagaggatg cagtgcgatt aggttacgat    480
aatgtaaaaa ggtgggaagc tttgctgcgc ggtaagcgga tgcagatggc ggaggccatg    540
aagatgtcac cagagaatct ggtatggtat gcggctttcc atcaagcagg acatcatcca    600
catgtccata tgattgcgta cagccgcgac cccggtaaag gattcctgac ggaaaagggg    660
attgagcaga tgcgcgccat gtacgcaaaa gaaatattcc atcaggatat gtatgagatg    720
tatcagaatc agacggttca gaggaacgag ctggtaaggg ccagcgcaga cccgctgatg    780
aaattattcg gacaggatca gggaagatgg gaagaaagca gtaaactgga gcagttgatg    840
acacagttgg cagcggatct gaaacagaca aaggggaagaa aagtatatgg ttacctgcct    900
ccaagggtaa agcagcaggt agaccgtatt gtgaatgtat tgtccaccaa ccctgctata    960
gctgaatgtt atcaaaaatg gtatgaatcc agactggaga tttttacacat ctattcagat    1020 cagacgccgg agccgccccc actttccaag cagaaggaat ttaagcaaat caaaaatatg    1080
attatcaggg aggccatgga atgggaagcg tatgggggaat gtatttctga gcagccgatg    1140
gatgatgtga gcctgatgat tgcggaggat atggagatca tggatggaac tgaatttacg    1200
gatgatgttg tggcagatga tgatatgtcc tgtattgtgg aatttataga agatggttat    1260
gccaaatgga cggacgaata caggcagacg aggaatattc tgtatggaac ggatggagaa    1320
aagccggacg taggaacagc caatcagatg atttactccg aagctgaaca gggaaatacg    1380
```

```
tttgcaatgt gtgaccttag acagatgctg cattatggga gaggatgcga accggatccg    1440
gaagtatccc aggcatggta taacagagca ttccgcgttt tcctaaatgc tgaaaccgta    1500
aaggaaactg cttatttgga ataccggctt gggaagctgt attatgacga cctgtatatg    1560
gaaaagaatc tgggagcatc cgtttactgg ctgaacctgg gagcaggtca tgggaatacg    1620
tacgcacagt atctactggg aaagctatac ctgtttgaac caacggtcag ggatgatgag    1680
agcggcatct tctggctgca gaattgcgca gaccagggta tcccatatgc agtatatctt    1740
ctggaacata aggatgagtg gggaaggata cgactccggt caggagttat ccgcttattt    1800
catcatctgt ctgctctgtt taatgaacag gaaaacgaag atcataacaa gatgcatgaa    1860
tggattgacc gcaagagagg acgcaagctt aaggaaaaga agatagcaca gggaatccgg    1920
ggatag                                                               1926

<210> SEQ ID NO 21
<211> LENGTH: 1851
<212> TYPE: DNA
<213> ORGANISM: Clostridium boltae

<400> SEQUENCE: 21
atggacagtt gggcagagat ggaagagcag atcctggaag aactgaatct tcacaggatg      60
aaggctgatg ctgaggtttt cagcagattg gagcgttact ccggttcaga ggccggggaa     120
gcagccgtgg attatctggt tcaggagctg aagcagcgg ggattgaata tgaacggcat      180
tattatgagc ttatgagaag cctgcctgta caggcttctg ttactgtaaa gaaatcagga     240
gagcctgatt tcaccgtgga ggcaatagct gctgtataca gcggtgaagc ctatgggctt     300
acaggagaac tggtctggga tgagatgtgt accaagggcc aattgaacgg tctggaacaa     360
gaggaacggt tccggacatt taagggaaag attgtcctga cctatgatat cagttttcct     420
ttctattatg aagcggcgag ggcaggagca ctgggcattg tggccatatg cccaaggac     480 attcatcacc acgacaccat gggcggtgta tggggaatgc cggaagcag ggacagggat      540 ttgtacccctt atctgcccta tgtgcagata ttggggcagg acggcctgaa gctgattgag    600
atggttaagg cgggcgctgc agccgtggga accgaggcgg ctaagggagt ggaagcagcc     660
atgggaacca aagcagccaa aggtatggct gtgacagctc agatggatgt ggccatggac     720
aaccgcatcg taaggtccag tatgccggtg gccaccattc cgggcaaaag tgagagcttt     780
gtgctcctga gcggccacta cgattcctgg tatgagggga tgacggacaa cggggcagct     840
aacgtgctga tgctggagac agccagggcg ctggaaaagt ttaaggacag gctgaaccgc     900
accgtggtga ttgcctggtg gtccggtcat tcggacgggc gttactccgg ctccacctgg     960
ttctgcgacc atcactatga gtatttgaga aagcactgcg tggctcacat caacatggat    1020
atctgcggat gcaagggaag caatgcagtc cgtttcgata tgagcggtat ggagggagag    1080
gcgtttaacg atgaattcct tgcatcctat aacagccgca aacccctttgc gtacagggct   1140 ctggaccgtt ccagcgacca gaccttctgg ggaaccatga cccctgtatc cattgctccc    1200 cagtttttata tggatgacgg acagacgccc cagcccccaa agagcagcga tatcttaagg    1260
ccagcggtca tgccggcggc ctttggggtg gcggcccct tttactggtg gcataccagg     1320
gaggataccc tggataagat aggggatgat gtgctggccc gggactgtga gatagctgca    1380
aggctggtgc tgcgctatgc catggaaaag ccccttccca ttgatatgag tggtttcatg    1440
agggaaatgc agtcctattt tgaggccttt gcagaggaac tggaccccgga cttcgatgtg    1500 gctccggtac tggcatccat tgccctgacc cgaaaatccg ttgagaagct ctccgatgcc    1560
```

-continued

```
atccgggcat atccaaagca ggatgcggac agcatactca tccggacagc gggagaactg      1620
gtgcgcttaa aatatacgta ttccagcccc tacggacatg actatgcagt ggagcaccag      1680
ccctacgcag tgttttcgtc cctgttagga gtgcacaggg acaatacgcc tgaggaccgg      1740
tatctgatgt cgcagacgga tttcatccgc cagagaaaca ggatgacagg ccagcttcat      1800
gagatatgcg aggccgttga attacagctg taccgctggc aggtacaata g              1851

<210> SEQ ID NO 22
<211> LENGTH: 1836
<212> TYPE: DNA
<213> ORGANISM: Clostridium boltae

<400> SEQUENCE: 22
atgaaaaagg gatttataaa acagaaaagc ctgtccgtca tggaacggct tatgaatcaa        60
agtctgaccg taaaaatcag tgtttttatt tatttaatcg taatcattct attttfattt       120 ctctcccttt tccttttfgg cattgttgga cgcgcatctg aacggcggct gtcagaggag       180
cactccaaat tgctgagggt tgcgattctt atgattaaca gccgccagca gtatatgatc       240
ggtgtggcag actactatgc tctgtctcct gatatcaaga atatgatgga taccagcaat       300
tccggtcttc ctgttacaac catcctggac gagtccaggt tcaaaacccc cacaatcatc       360
attctcagta ctgtgttcta caatgccgaa ggcgaggctg tctattatac tacaaaggat       420
acctcccggg tgccaatcaa tcaaaaaaac aacgatgcct tccagaagct ggcatcagga       480
caagccacct atgtatggga ctatattgac aacaataaca gtgattttat gaagtacgat       540
ttttccccca agctgtgtct ttggagagcg gtccgggaca gcaacgatgt ccatatgatc       600
ggtgccgtag ccgttaccat tgactcccgt tccctgcttg ctttgacga aaccgcaaaa        660 cagctgtctg aaaatctggc aattgtcaac tcaagcaacc aggtggtcta taccgttcc        720 gatatcgatc tgaatgagga tgatatacgg ctgttatcca acaactcctt tggcagcgat       780
gcaggccttt ataccgctga gttaagcagc ggcaggtaca gagtcagtta ccaggcaatt       840
ccttccactg attttgtggc gttcttcctc taccgccata ctccgtttgc ctttgggatt       900
gatgtggtat acagctatat attagccgga ttgtttctgt atattctcag ccttttccca       960
tcaattatat tggtttccaa aatgatcaca aaacccctgg taagcctgac aaaatccatc      1020
cagcagtttg cagaggggca gcagaatgta aaagttcagt ttaaatatac ggatgagatt      1080
ggactgctgg gaaaagcttt taatgacatg gttttggata tgaacgtct tcggatatca       1140 gaatacgatt tgcgtttaaa aaataaggat gcagagcttt ccctgatgca ggcgcaaatc      1200
aatcctcact ttctctacaa tatgctcaat gccattcagt ggcaggctct caaaagcgga      1260
aacaaagaaa tcgccgatat tgcctattcc atggcacagg tattccggat cagcctgagc      1320
cgcggcagga gtattatttc agtgaagcag gaacttgatc tggtcagcta ctatttatcc      1380
ctgcagaaat accggctggg taaaaaaatt gactatcata ttgattttga tgaggatgtc      1440
cttgaccgcc agattccaaa actgattctt cagcctctgg ttgagaactc catcgttcat      1500
ggcatggcaa aggattcttc cctcaatctg gtcatttctc tgtctgttgc cctgtcagag      1560
gatggaaaat tgttacactt tgtaattcag gataatggat gtggaattcc tccggaaatt      1620
ctccggtatt tgcccaatga ggtaatcccg gctgcggcgg aacagggtca aagaccaaat      1680
aaaagcaacc gttttgcggt taaaaacatt tatgaccgcc ttacactggt atatggaagc      1740
gatttcactt tccgcatcca cagtgaacat gggacatcca tcgaaattat tcttcctgta      1800
```

```
aaagagatag atgaaaggag cacctccaat gcttag                        1836

<210> SEQ ID NO 23
<211> LENGTH: 1836
<212> TYPE: DNA
<213> ORGANISM: Clostridium boltae

<400> SEQUENCE: 23
atgaagcatc ctgaactact aagtctgcac agcgtatcgg atctgcggat ctctcccgga     60
acaagccgct gcgcgttcct tgtccacact ccctgtgaag cagaaaataa ttatgaaacc    120
catctgtatg tcagtgattt taccgtgtct tatcccattg ggatgtccgg cattaccagc    180
tttgcctggg tagatgatgc tgcactggcg gttgggcgtc ccagcgcaga tagtacacaa    240
ttcgcgcttt tgtccctgaa ggacggttcg gaaggaaccg tctggaacat ccccttttgac   300 gccagaattg aaggatgggt tttgggacag cttctcatct cagcccgccg cccaattacc    360
gaggaaaagg ctcaggagga tggatcgtgg acaatcctgg atgaacttcc catttgggag    420
gacggcgagg gataccgtgc caaaatccgg cgtcagcttt ttctttgttc ctacggcggc    480
cagcctatac gtatttctcc tgaggagatg gatgtccgta ttgtatcagc acattcaaac    540
ggtctggcct atgccggata tatcctcggg aaccatggga ggatcgtcaa tgagatccgc    600
tattgggccg gagaagaccg gttactccgc aggaactgcg gtgatatcag acatcttgcc    660
ctgggcagca attatgcttt tatctatgct cttgatattg agcgtgagac agactctgct    720
cccgccctga tacaggtttc cctggacacc ggcaaagctg atcccctgta tgtttccgga    780
attgcggttg gcaattacat tgtttccgat atcggcctgc aggggaaaat tctatgcgca    840
gatggtgatg ctctctattt tgccgccaca aaggaaggct cctcccagat ttataaactg    900
tctgcctcag gcgaaccgct atgcctgacc cttgacccag gcagtattga acagctggac    960
gttcgggcag gacggattgt ttttgctggt ttgcgcaggg gctcctgtca ggaggtctac   1020
gtcctggagg atgggggaaca aatgatttca cacctacacg gtaatgacac gcttcctttt   1080
taccctatgg tggaaattcc ctgccatggt attcagggct gggctcttcg ggaagaaaca   1140
gaggaaaaga cttgcccggc ggttatattt cttcatgatg gtcctcagca ggcatttggt   1200
aaagtgtacc actttggtat gcagctgctt gcccaaaacg gctatgttgt gctgtttgcc   1260
aacctgcccg gcagcatggg ctatggcaaa gattttttcca tgctggacgg acacttggga   1320
gacgatgact gcaacggtct tatccgtttc ctggacgctg ctctggatgc ctgccctgag   1380
atcgatccca gccgtctggc tgtgattggc accggctacg gagcttatct ggctgcggct   1440
gccacgggaa aatgtaaccg cttcggagcc gcaatctgtg atggggtcat ttccaactgt   1500
gtttctatgg tatccaccag tgatcatggc attgcctttg ccgaaaaaca gatgaaagcc   1560
tgtgctttta agcaaaccgg ggaactgtgg aaacgttctc ctctcagccg catcgcttcc   1620
atgaaaacgc ccactttgct gcttcacggt gagaacgacc gcagcagcca tctttctcag   1680
ggacagatgc tcttcaccgc gctaaagatt catggcgtgc cggccagatt atgtgtattc   1740
cccggagaaa accacagcct tgcaagcaag ggaacacctc tggcccgtga ccgttatcac   1800
accgaaatcc ttcggtggct gaaaatgtat ctataa                             1836

<210> SEQ ID NO 24
<211> LENGTH: 1755
<212> TYPE: DNA
<213> ORGANISM: Clostridium boltae

<400> SEQUENCE: 24
```

```
atgaaaatag cagtgtggat ggaccgtgga aaaatggtca gggcagctat gggagaaatc        60
ccctgtgacc tgactgtctg caatatacag ctggtcaaca tgtttccgg ggaggtttac        120 ccggcccagg tagatatact ggacggcatc attgtgcggg tgcgcacaga caatgaatgt       180
ccggccctgc cttcggaacg gattttgac gggggaggac gttacctgat accggggttt        240
attgactccc atcttcatgt ggaaagtacc atgatgattc cggagaattt cggaagggcc       300
gtacttccct gggggaccac taccattgtc atggatcctc atgagattgc aaatgtgctg       360
gggattgaag gggtcagctt catgctggac aacgcaaaga aaacacccct gcgccagttt       420
gcgctggctc cctcctgtgt accctctgtg cctggagcgg agaacagcgg ggctgtattc       480
ggcgaggagg aaattgcccg ccttctggaa ctgccggagg tgctgggaat cgcggaaatc       540
atgaattatg tggatgtatg cagggggggat gaaagaatga gccgcatcat atcccaggggg     600 ctgaaacgga atctgtatct gcagggccat gcccccccgcc tggagggaga tgcccttgca      660
gcctacttgc tggcaggacc ggagagcgac catgaatgcc gcagtgcccg ggagtgcagg       720
gagaaagtca ggcagggcat gcatgtaaac cttaagacca gctctctttc caaccatctg       780
ccggatgcac tggagggaat cagggaccat cgctggcatg acagtgtttc cctgtgcaca       840
gatgatgtcc acgcagggggt gatttacaga gaaggacatc tgaaccgggt ggtccaaaag      900
gccataggct atggtgccca tccattagac gccatccgtt atgccagcta taacgctgcc       960
agagagtatg ggtttgatga ccttggagcg attgccccgg gttatgtggc ggatatgcag      1020
ctggtggatg ccctggacgg ccgccggccc agccatgtgt tctgcagggg gaaacttgtg      1080
gctgaagagg gaaggtatct gggaagtccc tacgacggag gactcaagtt caccaatacc      1140
atgaaactgt cctatctgtc cggccccggg gatttcaggc tgaaagcgcc tgcttcccag      1200
ggagagacgc tggtgatata cagcaagtat gacggaccct tcaataaggc cttttatgag      1260
acgctgcctg ttgaggacgg atacatctgc atcaggcaag atccgaatct ggctatggca      1320
tgtgtgtgca accggcacgg actgaaccag aggaccgttg ttcccatccg gaattttgga      1380
attacggaag gagccattgc caccacggta tcccatgact gccataacct gaccatgata      1440
taccgggacc cggaggatgc atggattgcg gcggagacct aaagagaag cggagggggc       1500 atagctgtgg ttctcaatgg aaaggtgctg gcaagcctgg cccttccggc tgccgggctg      1560
atgtcccagc tgtctgttga cagcctggcc ccgcaggtgg aacaggtgga aaaagcagtg      1620
tatgaccttt gcgcgggaaa gagctcgctg cttaagatgt ccacctttgc cctggctgcc      1680
ctgccgggag ccattatgac ggataagggc gtgctggacg gacagtccca gacatttatg      1740
cctgttttcc ggtaa                                                        1755
```

<210> SEQ ID NO 25
<211> LENGTH: 2115
<212> TYPE: DNA
<213> ORGANISM: Clostridium clostridioforme

<400> SEQUENCE: 25

```
atgaagatga tacggcaggt cctcacagtc ctggttctga caggaatgct tttcagtatg        60
acggcctgtg aaaacaaac caaaaccgaa gcacccgaag catcctacat cgcgagcttt       120
tttgatatac cggatacggt ggcggatatc tcaaggctcc tgataaagga taatacagct       180
tatatgtgct gctttgaaga aagtggtatc tcctatctgg cgtccatgac ggttggtgat       240
ggtgaatttc aacaactgcc attagaagtg gaggcatcca cttccctgtt agattttgca       300
```

```
tttgattcca agggcagcac atgggcggtt tgcatggatg ataccgaccg ctatagtctt     360
aagaaattta atcgggacgg gcaggtaatc caaaacattg atttaaacga ggtattggaa     420
accacaaacg cggccggggc cggcagggat ttgttcctga gcatcgatgc ggagggatat     480
atctgtgttg cggaaaaaag aggaaataca tccgcatata tatttgatga taaagggcag     540
tttttattcc cccttacgta tgagggaagt cttctgaaca caataacaac ggctgaaggg     600
aagattggag tctgcgcatc aacagcgaac cggatggatt atgagctgct cacggtggat     660
atgaaaagtc gggactggaa taaggatagg atttacctga aagcaaccgc gggtctgtat     720
ggagggagca gcaatagctt ctaccggttt gattcctcca gcctgtatag ctacgctgca     780
ggctcacagg aaggcaggca tgttttcaac tggtcggacg tgggacttag cgcatcggat     840
gttcacttgg gtgaactttc agatggaaga ttgattgtgg tagctgcttc gcccaatcag     900
actacggcat ttacgtatga gatggcagta ctttctcagg gagtggatga gcgaaccgtc     960
ctgagtatgg tgagcttgac cgcaggacca ggggtcgttc aggcagtttc tgaatttaac    1020
aagacaaaca gccaatacag gattgaacgg acggagtatt ttccatttga gcaaaacgtg    1080
tccgacgagg aatgggacag tgcggttgtc aatctgaata cacggattat ttctggtgat    1140
attccggata ttctggatat gagtaatcta tcggtccaga tttaccatag taaagggctg    1200
ttggaagacc tttatccgta tatagagaag gacccaatgc tccatatgga ggactatttt    1260
gaaaatgttt ttaaggccat aagccttgat gggaaattac cttatatcac agacggggca    1320
gctgtatcaa ccatgctggc tgatgcagac atcatgaagg gaagaaccgg gtggacactg    1380
caggatttgg agaatgtcct gaacgcttcc ggatccaatt ccataagcaa tatgtcgggt    1440
gcaccttttc ttaaagtcat gctccagacg gataacagct ttgttgactg ggcctcgggc    1500
aagtgttcct ttgattcacc tgaattcata aaattactgg aatttgccgg acggatacag    1560
gataacagta aaaacgtctt tggaggagaa aatctaagcg gtacttatgc agcagcatat    1620
gaaaccatcc tcagtatttta ccagattacc cagtataggg actattatca cggaaacctg    1680
gaactgctgg gccttccaag cagcagcggt gagtatcatg ccctcaaacc cgaagtgaaa    1740
atcggaatat cttcggccag cgggcagaaa gacggcgcct gggagtttgt caggacatta    1800
ttgacagaag agcatcagaa gtcctgcagc atgctgccga ttcatcaagg cgcctttgat    1860
acagtcatgc aggcagcgat tgacggaaaa tcaatctgga catggcttta tgaaaatgga    1920
aaggcaacaa cggaggatgc tcaagtgaca aggcagcttc taagcaatgc cgcctatgtg    1980
gtaaatgaca atcagacgct ggaacaaatc atactggaag aagcccggga gtacttttct    2040
ggggcaagga atgcaaagga agcggctgaa cgaatccaga gccgtgccag cctttatatc    2100
aatgagcaaa tgtaa                                                      2115
```

```
<210> SEQ ID NO 26
<211> LENGTH: 1992
<212> TYPE: DNA
<213> ORGANISM: Clostridium clostridioforme

<400> SEQUENCE: 26
atgcgcttac atattgtaga aaaaatgaat atggttttaa aacagcaaaa aagcatgctt      60
gcttctggag agaaatacag gcctctcata gaaaatcgtg tgcagcgcat agctgtacat     120
tctattgttg cgtttttttac actgattttt gtatgcacaa tcatatcccg tatttcccat     180
tcctttacaa ctgccagcat ccatgtagcg accctgacaa gcggggcctt aacggaccgg     240
gctgaagcag aaggaacgat tcaagcagca tctgacaggg gcattacgct gccggagggg     300
```

```
cttaaggtcg tggcggttaa gacaggaaaa ggcagtcagg taaacgcggg tgatgcactg      360
cttgaatttg acgtttcctc cattgaagaa caggctaaga aactggaaga tgaaatccgt      420
atcctgcaat tgaaaataga gctttccgga agtgagggcg gcaatgatgt aatcacggcc      480
caacgtaatc ttgaggatgc caggcaggcg tatcatcgct tatctgaaaa atatgcccgg      540
caaaacacaa gattacagga agattattca aagctggaag agaagctggc ggctgccgag      600
accagagatg aaaaggctgt cgctgcaacc aggcaggacc ttattgataa agcagaggcg      660
gtggttaagg aagcaaaaga aaatctggag gatatcaaag atgcggcaga ggaggctatc      720
tatgacgcca ggagagagcg agatgatgcc tcagaccatc tggatgcctc aagggaggcg      780
tatcaggagt tgttggaggc ttataatcag gcggaacgta atgttaacga tgcgaatcag      840
gcggtgaacg atatcaagga ggcgattgca aatcaggagc ctggagacac ctcggattat      900
accgaggagc taaatgcagc aaaagaggag ctttccaatg caaaggagga attgaaacag      960
gccaaaaagg aactgtcagg agcagactat aaaacttcgt cctatgacag tgctgcagat     1020
aatctggatg ccattgagga gcgctgggat aacaggatag aaagggccag agataccctc     1080
agggatgcaa gagcagcgct gacaaaggca aagaagcgta ccgacttttc tgacgaagcc     1140
gcggtcatag aagcccaggc agcggttgag gccgtaaagg ataccttgac agaggtcagg     1200
cgtgaatcag aagacaattg gtatcagaga gaagaagaac tttatgaggc acaaagggcg     1260
attgaagcag cgcagatagc attggaaaat gcacagaagc agacggatgc gtcacagaaa     1320
gaagatgaaa tcacaaggat tacctgcggg tctgaattgg ctgagaaaga aaaagcatgg     1380
caattgctgc gggaaatgtt ggcccatgat gggcaattgc tggctccggc ttccggaacc     1440
gtattaagta ctgtgaaaag aggcgctaaa acagcagcag atgaggaggt agtcacacta     1500
tcctgtgatg acagaggatt tgttttttgaa ggagtcctgg ataaggaatc tgcacagcac     1560
tttatagccg gagacaaggg ggaactttcg tttcaagcgg atggaagtac gcagaagata     1620
gaggtggcga ttaattctgt cagtacatcg gatgaggagg ataaggtttt tgtatctgca     1680
attttacccg agggaagtta ttcagttggt ctgcccgcac agctgtcatt gagcaggaaa     1740
agcgagacgt atcaaagctg tctgcctatt acagcactta gaacagattc cagaggtgat     1800
cacgtgttgg tgattcgcag acagaattct gtgatgggaa cagagtgggt cactgcaagg     1860
attgatatca atgtaaagga cagagacagt aaaatgatga gcgttgagag cgcgcttact     1920
tactccgacc aggtgataac aagttcaaat aaggcgatag cggaaggaga cagggttcgt     1980
attgaaaact ga                                                         1992
```

```
<210> SEQ ID NO 27
<211> LENGTH: 1956
<212> TYPE: DNA
<213> ORGANISM: Clostridium clostridioforme

<400> SEQUENCE: 27
```

```
atgctattgc ctcgggaaaa aagaattctg gagatactgt atgcaaaaaa gcagggatat       60
acatcttctg aactggctgc agctctgcat atcagcctgc gtacggtaaa aactgatatc      120
aagagaatca gagaggaatt agaaaagacg ggctgtgaga tactcacaaa agcaggaaag      180
ggtatatggc tgtcctatga cagtcaggga aagaagtacc tggacagtct tttgctggga      240
ggtgaatgtg cttcatccat ggatccgaaa accagaaagt attatattgc gcttcaactt      300
ttggacagcg atacatatat atccactgaa tccatatcaa attccatgta tatcagcaaa      360
```

-continued

```
ggaaccgcga ccaacgacat taatgagttg attcctttct ttgagaagca gggtctgaca      420
ctggaaaaaa gggtgaaata tggaatacgc cttcttggaa aagagagtca gttgcgcatt      480
gcaaaggcat ctgtaatccg taagattgtg gtgtaccagg ggagccaagt atcccggaag      540
ctgcagccat tttttgagga tttaaatatt gaccatatta atgctatcct acaggaggca      600
gaggagcatt ttggcttcat cctttcagat gcttcctact cagaactgct gattcattgt      660
tccattattg tgagaagaat ccggaaggga aaagtgtgcg ccatagatga gacggagctt      720
agggcatata gtgaaatgaa ggaatggggc atctgcaggt ttatagcaga tgccctggaa      780
aagagctttt ctgtccatat gacggaagga gaccgctctt atcttatgat gaatctgctg      840
ggtacaagga tgcaggaaca tatcccggca gagacatatt cctggggggga tgatggagcg      900 gactccggac agatactgga gcagtgggag gatatactca gacacgccgg agatatgttt      960
cgtgagaatc tgataggaga tgaaacgctt aaaattgcca tgtttctgca tctgaaagcc     1020
atgtttaaca gattgcagca ccagattcat ctggaaaacc ccatgaagcg tatggtacgg     1080
gaagaactgg tatatgagtt tgaggtagcc acctatgtgg ccaggctcat taaagaggaa     1140
ttccatgcgg atctgggtga agatgaaata tgtgatatcg cgctctatct gggggccagc     1200
ctggaacggg aacgggccat gagaaaccgc caaagtcctg tggttaccat tgtctgcggt     1260
tccggaatcg gtacttcaca gtttttttgag gcaaagctag ccggattttt tccagagata     1320
caggtgagaa agatagtacc tatatcaagg gccaggtatg agattggaaa ggatacgcag     1380
gactttgtgc tggcaacggt tccgctggag ctggagggca tagaggtgct taatgtatct     1440
cccatgctgg gagagaggga cgcccttctg attgaagagc gaattcatcc ggagcgcaga     1500
cagttgctga tatcaggaaa agagaagtat ccggccttgt ttgcactcat gagcgagcgt     1560
atatcaatct ttaagtgtga ctgtcgctcg ctggaagagg taataagcct tatgggtcgc     1620
cgtctgattc acgagaaata cgtaaaagag ggattcattg aatctgtgct taagagggag     1680
gaacttgccc ctacatctat cggcgacaag tttgcggttc cccatgcctt tgagggtat      1740 gtgctgaaaa caggagtcgg tctgatgaca cttaaaaaac caattgtctg gggaaatgaa     1800
aaggtgcaga ttatcatgat gctgtccatt gatataagag agcaggagca attcaggggag     1860 atattttccg aactggcagc aatcacaaaa aataagtggg ccattgaaca gattcttaac     1920
gctgaacgca tcagtgatat taaaataagg aactaa                                1956
```

```
<210> SEQ ID NO 28
<211> LENGTH: 1947
<212> TYPE: DNA
<213> ORGANISM: Clostridium clostridioforme

<400> SEQUENCE: 28
```

```
atgtcggaag tgaatgaagc gacaatgatt gaaaaaacga aaacagaaat atggattgat       60
aaagcggtta tcgtgattgc gattattatg agctgttatc aactactggc ggcaaatttc      120
accatgctgt ctgcagagca gcatatcaac ttacatattg cgtttttctct tgcaatcatt      180 tttttacagg ctattaagtt aacacaaaca aaagataaag cgcgcagtgc ttttatgatt      240
atccttcttg tggcaagtgt agcggctgct acctacatcc actttaatac aacaagattt      300
cagatgagca ttggcagaca gccgtttgat aaagtgttct ctggagcagt attcttagtt      360
gtcattttga ttgccactaa gatgacatgg ggttgggtaa tcccggttat ttccataatc      420
gcgttggcat atggatattt tggaaaatat atgcccggta ttttttatca ctctggttta      480
agcttttccc gtttgatcac atatgtaaca acaaacttta ccggtgtgta cggtatgctt      540
```

-continued

```
gcatcagtat ctgcaaatac gattgtgtta tttaccatct ttggcggctt gatggaggca      600
tttggagcga tcagcacaat catggatgct gctatggtgg catctacaaa aattcgttcc      660
ggcggagcgc aggttgctgt aatttccagt ggtctgattg gttctatcac cggaagcgtg      720
gcagcaaaca ttaccttgac aggcgccgta tcaatccctc tgatgaagaa aagaggatat      780
ccctcggagt ttgcagcagc atgtgaagcg gcagcatcga caggaggtgc gattcttccg      840
cctgtcatga acgcggcagc tttcattatt gcttcatgga caggaattcc ttacatctac      900
atcgttgcag tcggagttgc tcccgcgtta ctgtattatc ttggtattgc gctgagcgta      960
tatattaaag cattaaagct gggagacgag aaagtcaaag cagaactgct cccacagttt     1020
cataaagcat tcggaaagct ggcaatgttt gtcgttccga tcattgttct ggtagtattg     1080
atggtaatga gctattctcc gcagaaagca ttattcattg cagtattcac attaattgct     1140
atggggcttg ctatcgaatt gatggacaag agtaatagaa gtccaatgga ctcctttaag     1200
aaatttatca caaaagttct gtctggattt gaatcgggtg cgaagaccgt tgcaggtatt     1260
gcagtatgta tggcaacgat gggatgcgta gtagaaatcc tcacatccac aggactgccg     1320
tctaaaattt cgcagtttgc tttgtcactt gcaggagata atttatttgt tctggcaatt     1380
ttagttatga ttacctgttt gattttttggt atgggtatgc caagtggttc agcgtacatt     1440
ttggcagcat tattaggtgc tccggcatta actacattcg gaattccgat tattgttgct     1500
cacttcttcg tattttactt tgcggagtta tctgcattaa cacctccggt tgccatcgga     1560
tgtctggttg cttctggtct ggcagatgca aagttcttga agacgtgtat cgtatcaatg     1620
cgtttggcta ttggaggatt tgttcttcct ttcttattcc tgtatagacc ggcattgctt     1680
cttcagggac agtggtatga aacgatttgg gcagttttaa tggtaattag tttcatgttt     1740
tcttttatca ttgcggtcga gggcttcttc ctgcagaaaa caactgcatt tgagagagtt     1800
attgctttag tcggtgcatt gtgctgcctg cttccgattt acgttttaga ttttgtcgga     1860
cttgctctgg tggcagcatt gattgtactg catgtgattc gctttaataa gaataaagta     1920
cttgtcagac agggggcaga ggtataa                                        1947
```

```
<210> SEQ ID NO 29
<211> LENGTH: 1854
<212> TYPE: DNA
<213> ORGANISM: Clostridium clostridioforme

<400> SEQUENCE: 29
```

```
atgcataaga gaaaaattaa tataagaaaa tacaagtatg agattttttt gtatgccgcg       60 tttgtttttaa taaacagcat tccatgcctt tttttgactg tgcctgtttt tagcgatgga      120
ttgaatacaa tcgcggtacc ggcttatata agtggctgtg attggactaa atatctgtat      180
gcagacgggt attattacaa atatggagtg acgatttttat atttgccatt attttatctg      240
ttccgttccc cgattgtgct gtatcgggcc atgctgctgt tgaatgtttt agcggcaggg      300
gtaattcctg tcatcgcata tagaatatcc atggattatt tggatataca aaaaaaggaa      360
aatgcatttc tcatagcagg cgtaaccgcc tttttgccgg cgctaacatt gaatatataaa       420 tacacatggg cggagaccgt tcttctggtc tcgccttgga tgatcctcct tcttcttctg      480
agaatccatg aagataagga tgccgggaaa caggtaaggg acagcatctt aattgcgtgt      540
tcctctgtat ttgcgtatat ggcacatcaa agaggcattg tggtggtttt ggccacgttt      600
ctgaccgttg tatacatacg ttttgtgcgg aaaaaggcaa atctgagaat cggagtttat      660
```

-continued

```
ctgattacag ctatggtttt gctgattgct gacaggttgg tggacgggct ggtaaagcag      720
tatgtattca atgcgggtgt gaacacggta aacagtacat tttccttttg ggatgcaaac      780
atgtgggaga gattgctgtc ctttaccggc cttcaaacca taataaagat tatatacggc      840
tggctattta atgtgtttac cggcagcggc ggtcttgttt gtctggggct gtgtgtcacc      900
ttggtctgct gtttcagata caaatccagt gaaggggggat gctgcatcca tttgattagt      960
gtattttccc ttttatgctt tgttggtgca tttgccttgg gaggtctttt tttcttctct     1020
gatatttatc tgtattatac cggagaaatg gttagaagat gcgacaagct tatttatgga     1080
agatatctgg agtcttccat atcgataccg gtgttaatgg gcatgtattt ttttctggag     1140
aaaggctctc tttttataaa acgcagaaga tatatctttt taatcatggg atcggtatat     1200 ttatttttc ttgttaatat cgcaggcaag gtgaatgggg tggttacatg gcccaataat     1260
acgatgacta ttaatatatt ctgcaatctg gcccagtgca gacatggata cggtgctatc     1320
cgtaatctgt cccagggggct gaccgtctat ggtgcattgg ctatcgtaat tcttatgtca     1380
atattcgtat ttcataaaaa gcagagaatg gcttgtatgg gattgatagc tgtttttatt     1440
tcaatctttg tttggagttc ctataatgtg atttaccgga tggacaaata tgagatagag     1500
aacatggaaa tgacaagaaa cctggtaaaa ggtcttgagc agcttccaga ggattacaaa     1560
gtaatttttt tggacgatga gattaccaga agctcctatc agtatatgtt ccgtgattac     1620
tatattgtga caggcaggga taataatagg acacagataa aagatatgat aatcgtctct     1680
cccaaaggag tgataaatga ggagttggac cagggagact attttgaatt agtggatatg     1740
gaaacagaaa gtccggatta ccatttgtat atcaaggggc gggacatgaa tcaatggatg     1800
aaccaaaatg gaatccggac aaaacagctg atatcagggg gaaggggaca gtga           1854
```

<210> SEQ ID NO 30
<211> LENGTH: 1689
<212> TYPE: DNA
<213> ORGANISM: Clostridium clostridioforme

<400> SEQUENCE: 30

```
atgaaacaga cttttatgaa actgaatctg tcctgccgtc tgtttctgat cattatcgta       60 cttttttctga ttccctatct gtcccttttt tcctgggctt acaggaaagc ggagatcatt      120
atccgtacca aagctcagtc cctggaaaaa gaaaacctaa gccagacaag aaatgacatt      180
gagaaccttt gcttaaacat agccaaggct tctgattacc tgatctccct ggatcattac      240
ggtgtactct atcgtgaatc agaacaaaag ggatatgctt atttaaaatg ctggcagtac      300
gtagatgaac agatccagaa tgcaaataac gccctgttaa actccagtgc agatatcagc      360
gttctttcca aagaccggct tttatactcc acactttctt accagaaatt ccggtatcag      420 gatttttttca gagaacaggt cgtttccact acatattttt caaatgctca caaaagttat      480 cgcaatttg aaaatgacca gactttttatt tcctatatca gagaacttcc atccttctgt      540
tctcagtcat attatctggt gatctccatt ccggcaaaca attttcaaa gcttcttgga      600 actgctgccg gaaccatgga actgacggat ccgcgggca ataccatctg cggagtccgt      660 tcacccaaa ataacgaaag cttccggaaa gaaacctcca tctccctctc cggttggaaa      720
ttggaagata ccattccac agattttctc tacagggaca tttaccagct gcgtctgttt      780
acatttgctg tatccttagt attattaatg gcatgccttc tggtaacatt ttctgctatt      840
tacgctcagt taaggcctct tttaaagctg aaagagcaaa tggagctggt gatgtcaggc      900
aatctgaatg cggaagtggc caccaccaat tccagagacg agatcagcag tctttctcgt      960
```

```
accctttaaca acatggtcaa tgaaatcagc cacctgatca atgaaatcca ggtcactcag     1020
aaaagagaaa gtgagctgcg ttttgaaatg ctcttagcac agatcaatcc ccactttctc     1080
tttaatacct taaactctat taaatggatg tcagtggtat ccggaacaga ccatatcacc     1140
acgaccataa cctctctcgg acgccttctt gagatcagta tgaacaaggt taatgatgta     1200
cttccgcttg gcgaagaact ggaaaatata agaagctata tccagatcca acaggtacgg     1260
tatccgggac gttttgatgt attttaccat atagatgatt cccttttaga ctgccgcacc     1320
ttaaaactga tcttgcagcc tcttgtggaa aattccattc tccacaacat tgagcaccgc     1380
gattatcttt ccattgacat ttccggtaag ctttctgagg atcttattat cctgtgtgta     1440
aaagataacg gaaccggtat gacaaaagaa cagatggaac agatcttaaa gcctaagaca     1500
catgcagaaa aaggctatgt tttctccgga ctgggtgtat gcaatgtaga agaacggatc     1560
cggcttgcat atggccctga ttacggatta gaatataaca gtgacggcta ttcctatacg     1620
gaagtaacga tcacttttcc ccgacaccag aaatcagacc cattattaca gaaagaagca     1680
aaacaatga                                                            1689
```

```
<210> SEQ ID NO 31
<211> LENGTH: 1650
<212> TYPE: DNA
<213> ORGANISM: Clostridium clostridioforme

<400> SEQUENCE: 31
```

```
atggcaggaa gtgcacggga cattcagatg cgtgagctga aggacacgat atcagaactg      60
aataagctga ttaaaacgct gcagcagacg attgaagctg ctaatgcgcg tgaggccgcc     120
ctgtgccagg aacgggataa cctaaaggaa cagatggact atctgacaaa gcgcctcttc     180
ggtgcatcca gtgaaaaggg caaatgcgat attcctgggc agctgaatct gtttaatgaa     240
gcagaaacag cagaagatcc agtggccgcg ctctcagaag aagcgcttcc ctcctgggaa     300
gaaccagaag caaagccccg aaagaagcgc gctgccaacg aggaacgctt aaagggcctg     360
ccagttgagc aggtatttct tgacgtacca gaagaggagc gtatctgcgg tgtctgcggc     420
accctaatgg aaacaatcgg aacggaattc gtacgccggg aactgaagtt cattcctgca     480
aaggtaaagg tcattgagta ttacagcgtg aattatggct gcccgaaatg ccgcaaggag     540
gctgtcctcc ctcagatcaa aaaggggaag ggtggccggg cgcataggat ccatgggatg     600
gcgagtacat ctaccgtggc atggattatg taccagaaat atttcaacgg catgcccttg     660
taccggcagg aacgggattg gaaacagtgc ggtgcaaaca tcagcagaac aaccttcgcc     720
aactggatta tcgcgaatgc acaggatttt ttcactccca tgtatgccta cttccgaaag     780
aaactgcttg cacggtcatt tgcgatggcg gacgaaacgc cagtccaggt gctgcacgaa     840
ccagggcggc gcgcgcagac acagtcctat atgtggctgt ccgcagtgg tgaagatgag     900 ggtccgccaa tcatccttta aaatacgct ccaacgcgcg ctggagacaa tgccgtggaa     960
ttcctggaag ggtacagtgg atacctgatg tgtgacgggt acagcggcta aataaagtg     1020 ccggatgcaa agcggaccgc atgctgggcg cacatacgcc gatacctgat tgatgcgatt     1080
ccaaagggaa agcagcttga ttatacccag ccatcggttc agggagtcat gtatgtcaac     1140
cgtctctttg aaatggaaga taaaatccgg aagaaacatg ccgggactaa tgaagccatc     1200
cgaaaggcaa gactcgaaaa agagaagcct gttatagatg gatttttgtc gtggctggag     1260
cagcagaaac cgacacgcgg ctcccggctg gacaaagcga ttacctatat ccggaacaga     1320
```

```
gaaccgtatc tgtccagata tctggaggat ggaagatgca gcttttcgaa caatctaagt    1380
gagaatgcaa tccgcccatt tgttgtagga cgtaagggat ggctgttcag tgacaccccg    1440
gcaggagccg aaacgagtgc ggtcatctat acgatggtag agaacgcgaa ggcaaatgga    1500
gtaaatgtct accaatacct aaaactatta ctggagaagc agccgaataa ccgaatgtcc    1560
ggtgaggaat tggaacgctt tgcaccgtgg aatccagagg tgaaagccct tctggattct    1620
cgggttaccg atgaacctga aaatggctga                                     1650

<210> SEQ ID NO 32
<211> LENGTH: 1500
<212> TYPE: DNA
<213> ORGANISM: Clostridium clostridioforme

<400> SEQUENCE: 32
gtggaatgta atagaacaaa gctcagcagt gtattgtctt atataatgat tattgtaaac      60
ataacatctg ggcttttttt tacgccgtgg ttaatgcatc gtttgggaac ttctcagtat     120
gctatatata cattaggcat gtcgattatc agctatttga ccattgagct tggaataagt     180
gaaatagtaa ccagaatcag tttaaaatat ataatcgaag gcaaccggca acaggtaaac     240
aggttgatga gtattgcaat tagaaatttat ctgatgattg atatactcat tctgatatta    300
gcaattgtga tgtacttttt tatagattct tttttttacaa atttgacact ttcagagatt     360
gatttatttc gtaatgtttt cattatatgt gctgcaacag taatagtcat tttctgggaa     420
attccattcg aaggtttgta tgccgcatat ggaaaaatat atgtaaatcg cctcgtgggt     480
ttaggatata aattatcata tgtttttagtt actgtcatta gcatttctct ttataattcg     540
gttattattg tcgtactatg ttatgcagtg ttgacaatta gcacaaaagt atttttgtac     600
ctatatataa ccagaaaaaa taatatagta attgacttac atacccatga cagagagatt     660
actaaaaatt tactaggcat gtcaggttgg attattattg caatagtttc aagccgatat     720
ttttatgcaa ttataccgac cctactggga aggttctcaa attcatttga gataacaaca     780
ttttctgttg caagcgctgt tgagggctat ctattccttt tttctaatgc tctaaatgga     840 attttttttgc cacgcattac gcgaatggca atgagtaacg atgatgaagg aattaccgac     900
ttgttaatta gaattggaag aattcaatta atgataattt cttgcataat catcggaatt     960
ataggatttg gacaggagtt tatttctttt tgggttggaa gtgagtataa aaatgcatat    1020
gtttgcctta tttttaattt aataccatgt attgtacatt tgactcagac tgtagcatta    1080
gaggccacat ttgcaaaaaa tcgaattcgg gaaagggcta tagtttatgc tgttgggact    1140
attattagta cagttcttac atgtatttta gcacctgaat tcggagcaat aggagcagca    1200
ataggaatat gcgtggcaga actattatgt tatgaaatag gcatgaactt tgtgtataaa    1260
aaaatgctta atattaatat aagacacttt tttgtacaaa cacatttgaa gctattaccg    1320
ccgttaataa tatcacttat gacggctttt gtggttaatc aattaataga agaatcaaca    1380
attatagtgt ttctaacaga agttggaata tgggcagcga ttcatttgat tttactgtat    1440
accttgggat gcaatacatc agaaaaagat gtgattaaag ccatcctgat gtatagatag    1500

<210> SEQ ID NO 33
<211> LENGTH: 1497
<212> TYPE: DNA
<213> ORGANISM: Clostridium clostridioforme

<400> SEQUENCE: 33
atgaaacaca tcaaaccact attgctggca ggagtagttt cgtttgcggt aatgggctgt      60
```

```
gggaaatcac cggctccgca ggaagaaaca tctgtcaagg aaacaattgc cgccacggaa        120
aaggaatccg tggccgcgaa ggatgaagcc caaacagtta agcttttgaa ggcggacgcg        180
ctgacggatg atatgcagct ggtagacgtc cgtgaagaag aacagtatat tggctggaat        240
atcggggata aaccaggggg acatattgca ggcgccgtgg attttccggc aagctggctc        300
agtcagagcc cggatcccta tgcaatcaga acgacaatgg aaaacgaatt aaagcgccgc        360
ggcattgatt ccgaaaaacc ccttgtcctt tacggagatg atactgtacc ggaggaaaca        420
gcttccatgt atgcggaact gggatttaag gacatctctg ttctggaagg cggcttctca        480
tcctatttgg aaacaggcgg ggaagcggca atgctgccgg gattcagcct ctatgtatat        540
cccgactggg tacaggcact gatagacgga aaaaagccgg atacgtacga gggttccgat        600
tataaaatta ttgaggtctc tttaagcagt gaagagggga aatacgaaag cggtcacatc        660
caaggcgcaa tcaatataaa agacactttc aaccatgttc cggggcttcg tgtactttct        720
gaatatgaga acataccgat ggaggaacaa ctgaaattct ggaattgtcc ggaagattcc        780
gtgattcagg aaaatctgga aaaggccgga atcacgcaga ataccaccgt gattttatat        840
gccacaacac cggccacttc cgccgcgcac cgtgcagggg tcttaatgaa atacgcgggt        900
gttaaggata ttcgtttctt aaacggcgga aaaacacttt ggaaacttca aaacaggcct        960
ctggagacag aatccaatat accggaaaat gtttcctttg aacgaaggt tccgtctaat       1020 cctgacctta tttatgacta tgatgaggaa ctgggatgtg taaacgacaa tcaggcggtc       1080
attgcatcca tccgaagctg gaaagaatat atcggaaatg tcagtggtta tacatacatt       1140
ggcgaggccg gggatattgc caaagcgcgt tttggttatg ccggctcaga cccttacagc       1200
atggaagatt tccggaatat tgacaatact atgtttaact acgaaatgat taaggacaga       1260
tgggtaaaat gggggattgt tccagataaa cgtatttctt tccactgtgg taccgggtgg       1320
agagcaagcg aaacatattg gtattctctg gcattgggat atcctgacat tcatgtgtat       1380
gacggaggct ggtatgaatg gtccaaaatg cctgacagcc cgaagaaaga accaggagtg       1440
cccgcagacg cacctgaaca ggagccggca gaatacttta taccaaagga aaagtaa         1497
```

<210> SEQ ID NO 34
<211> LENGTH: 1392
<212> TYPE: DNA
<213> ORGANISM: Clostridium clostridioforme

<400> SEQUENCE: 34

```
atgccgttaa taggagcagt ggcagatgat ttgaccggag ccaccaccac cggcgtgctg         60
cttgccaggt ccaaggcaag gactgccgtt tttttcaacg aggaggccgc ggagcgggaa        120
ggggaggctg agaccctgga cgccatactg gtgagcagca cagcagggc gctgccggcg        180 gaggaggcat atgaaaaggt aagctccgcc acccaggcat aaaacggat gggggtcagg        240 tatttcagca aacggattga caccacgttg agaggaggta tcggtactga aatcaaggcc        300
atgatggatg tggttggagg ggatgcggtg gcagtggtgg tgccttccat gccccagtcc        360
aggcggattg tggtaggcgg cttctcggtg attgacggca ttgccctgac aaagacaccg        420
gtggcccagg atgtgcgcac cccggtgcat gagagctatg tgccccagct attgagcagg        480
cagacagggg aggagaccgg ccttgtcacg ctgaaaacag tccttttggg gcgggaggag        540
atagcccgcg cccttaagtg gcagagggag agaggaaacc ggatcatagt ggtggacgcc        600
ataaccctgg aggatatcca ggagatagcc catgcctgca tttcgctgga ttggaatgta        660
```

```
ctggcagtgg accccggggc atttacggca aagctggcat actgcagagg gctgaccgag      720
gaagaacggc ccaatgttcc ggaaaagaca ctggacggca cgggcagaac cgtgctggtt      780
gcagccggaa gcgccacacc tgtgacaaag cggcagctgg gaatcctgct ggaggaccag      840
cgccatgtac aggtcagtgt ggaccccatc ccgctgattg acggagcatg ggaggccgca      900
gaggaagcgg agtcggccgt caggcgtatt atggagctga tggaaggagc gtcagcgccc      960
agggctgtag tgattgagac ggcactacac gggccggttc tgaacctggc agaggaagac     1020
gccaaaaggg gatatgcgga cggcatgagc gccaaccgga ttaatgcagg gctggggacc     1080
attgtgcaga aggtgctgga gcgcgctggc cgggaacgga ttgccggatt atacaccacc     1140 ggagggggata ccatggtgaa tgtctgcttc cagctggggg tggagtgtat tgaggtgctg     1200
gattacgtga ttgcccagac cgatgtggga cgcatggtgg ggacatacca ggggcttccc     1260
atcattggga agggaggact gacaggatac gacaccattg ctgttgacat tgtagaccgc     1320
ttgtttagag aggcagccag ggaaatgcag ggggatgccg tgaccggcag accgcaatat     1380
caaatgaaat aa                                                         1392

<210> SEQ ID NO 35
<211> LENGTH: 1383
<212> TYPE: DNA
<213> ORGANISM: Clostridium clostridioforme

<400> SEQUENCE: 35
atgatgaaga caatcatcag acaaggcacg attgtgtcac cgagtgaaat ttatgaggcg       60
gatatactga ttgacggaga aaagattgca tgtataggaa ggaatctgga atcagaagga      120
gcaaaggtca ttgaggccag gggaaaatat gtgattccgg gaggtgtgga tgtacatacc      180
catatggacc ttttggcagg caattcacgg gcggtagatg acttttatga cggtacggtg      240
gcggcggcct gcggaggcac cactgccatt gtggaccaca tgggatttgg gccggatggc      300
tgcaatcttc attaccagct gaatgaatac catcatctgg ctgacggaaa ggccgtgatt      360
gactatggat ttcacgggac tgcccagcat gtgaaccagg atattctgga cgagctggag      420
ggaatgatgg aagatggagt gtccagcgtg aaggtatacc tgacctatga caggcgcctg      480
aatgacgggg aggcccttca ggtcctgaaa cgcatgaaga aactgggagg cgtgactgca      540
tttcactgcg agaaccatga ggtggtggaa tactatcgga gcatgtacag ggaacagggc      600
tgtaccagtc cgtactatca tgccaagagc cgtccaaatc tggcggaggc ggaggctgtg      660
gccaggattc tcagtctggc gcgtctggca ggcgatgcac ctgtttatat cgtacatctg      720
tcctgcaagg aaagcctgga ggcggtactg gatgcccgga agaaggggca gaagaatata      780
tttgtggaga cctgtacaca gtacctgaca ctgacagaag aacggtatat ggataaggac      840
ggcctgaaat atgtcatgtc tccgcccctg cgcaccaggg aagactgtga acggctttgg      900
gaagggctgg cggctggtga tatacaggta gtggcaacag accactgtcc atttaattac      960
ggcatagaga aacagctggg cagggatgac tttaccaagt gtcccaacgg ggcgcccggt     1020
gtggaggaga ggatgtctgt catcttctca gaaggcgtga tgaaaaaacg aatcagctta     1080
aaccgttacg ttgaggctct gtgtacaaat cctgccagga tatatgggtt ttatccggag     1140
aaaggaattt tgcagccagg atcagacgga gatttggtaa tcattgaccc caataaggag     1200
tatgtgctca cccatgaccg tatgcacagc gcggtggatt ataccgcata cgagggtatg     1260
aagctaaagg gacagataga gcttgtgatg cagaggggca gcgttgtggc ggaagggaat     1320
gtatttaagg gaaaaagagg cgcaggacgg tttattcaca gacggccaca tgataatgcg     1380
```

```
taa                                                                          1383

<210> SEQ ID NO 36
<211> LENGTH: 1374
<212> TYPE: DNA
<213> ORGANISM: Clostridium clostridioforme

<400> SEQUENCE: 36
atgaaaatgc gtcgatggaa accagtagta ttttatgttt cgctggcact cgtattgctg        60
gtttcctttt ttggaaaaaa actgattggt gataatcatt atgagattac cttagctgct       120
gttttactgt ttttttcaat acttaactgg attttagaaa cagtatcgat tgcggttact       180
tcattaactt tggtagcact tgtgcccttg agcggtatta tgagcttttc agatgcaatt       240
gcaggaagtt ttggaaattc aatttttgct ttcttcctag gggtgctact tttgtcattt       300
gcatttaaac acacaaatct tggcaggttg atttctgata ttattttttaa aatatttgga       360 agacaaccca agcgggttgt gctggggatt atgctgactg gagcacttct tgccatgtgg       420
gtaacagagg ttgcagctgc agcaattgta tttccgattg cattatctat ttgggataaa       480
gctaaggaac gcgatgacta tgcagcaata ggaaaagcag tgatgctggg agttgcttgg       540
ggatgtgcat ttggaggcgt tgccacaccg atagcaaccg gtgcaaacct gattgcagtt       600
aattacttgg aaacttattg cgggattaag attacatttg gtcattggat gatgattggg       660
attccgattt gtttcagttt gattcttgca ggctggtgga ttttgacgtt acctttaaag       720
agcactgtag aattgggaac ggatagtgaa gcgattgaat ttggaagaaa ggagagaaag       780
ctttcagtga tcttcgccgt tgcaattcta ggttggattt ttggagataa aattggactt       840
ggaagtcatc aggtagcaat tatttcggcg attgcattgt ttttaccggg tattgaagta       900
atcgactgga agacaggaat cacaaatatc agttggaatt cgatctttttt gatttcagca       960 ggtgttttga ttggcgatgt tctgtattcc tccggtttag cggaaaagat ggcaaatata      1020
ttttttgttc catccttact tgaaaatggt attttgataa gagatatcta tattgttatt      1080
tctgtatcta ttttaaaaat attattctca agtaatactg tttcaggagt agtgttggtg      1140
ccgatcatgc tctcggtagc ggctgcaaat agcctttctc cctggggatt ggttgcgccg      1200
tgtatttttt catcagcatt gtccctcatt gtggtttcat ccagcccagt gaatgttatt      1260
ccgtattctt caaaagcatt ttctccgaag gatatggcct tgtatgggat tgttatgaca      1320
attatgactg cgctgattat cggtggatgg ctaacggttt ttggggtgaa ttaa           1374

<210> SEQ ID NO 37
<211> LENGTH: 5229
<212> TYPE: DNA
<213> ORGANISM: Clostridium hathewayi

<400> SEQUENCE: 37
atgaagagag cagccgcatg tctgcttgca ttgtgcctgg tcgtacaggg accggcaagt        60
ctgatgacca gctttgctga tttcgggcag agaggagtgg cgtcaccgtc gaacagcgta       120
tcggcgagtc cttctgatgc atggaaagag agtgacagcg acagtaagaa tgggggaatta       180 aaggtagaaa ttcgtggagt ccttcctgtg cagaaggccg cggaatggga attgtttctg       240
acaaaggacg aggaactgac cgatcagggt tcggtgcagt atgaggccgt ggaatcggcc       300
ggggtctatt cctccggcag ttacacattt acagaccttc cgaaggggaa gtatcagctt       360
caggtgaagg cggtaaatgg cggttatgag gactacatac agaaaaatat ttcaattaac       420
```

-continued

```
ggtgaccggg cgtcgattct gctttttaaac gactacccgg acaaatacgg ctatgccggg      480
gataaaatgc ccggtgtaat ccggatgggt gatgtgaatg gtgacggaac gatcgacagc      540
gatgatatgg aggctttcat tgacgccatt gatgaagcag acggtaattt cgcagattcc      600
aggttcgatt ttaatggaga cgggcagata gatcttgtag accttcagta ttttaccatc      660
ttctataaaa ataagagcaa tacaaaggcg actgtaacga ggcaggccct ggtggatacc      720
gctgctgttg ttgcgtcatc cagcaatgcg tcgttctccg aggagacgct gaaggaagta      780
tttgccggaa atgacagcga ggcgttgacg cttacagcgg agacggcgat cacaccggaa      840
acgccaattg agatcaccgc agacttggga cagagcttaa aggcggaagg atttacaatc      900
cagccggtta caggttccgg aaacaccatc aaagacggct gggtcacggt tgaattggaa      960
ggcgaagaga agcctgtcgt attcaggatt gagaacggcg tggcggaaag acagacaggg     1020
acaaggatgc gcgcggcctt tagaagcgcg cctgaggatt ccgccgctgg taagaccatt     1080
gtcatcgatt tgggcaaaca ggtggcgatc aagaaggtga cgatcaaagt gacggctgca     1140
ttagaaaagg aggccactct ggtcgagata tccaaggtgg aattcttaaa tgatatggag     1200
agcagaattc cggagccgga gatgaacatc ccggaggact taaaggctgt ggcaggcagc     1260
gaatcctttg atttaacctg gaagcgcgcg gtaaatgtaa ccggctatga ggtcgagatt     1320
accggtgagg taaaaggcgg agtcaagtct gaggtgctgt cggtatcgga caaccgttta     1380
agcgtaaagt caataaaaaa tgaggacctg ataaacggaa aagagtatac cgtgcgggtg     1440
cagtctgtaa acggggcgtg gagaagcggt tacagcacgg ctgtgaaggt gacgccggaa     1500
gcctccaaac ggcctgatcc gccggaggga attacggtaa agggcagtta ccgcagcctc     1560
gatgtgtcct ggaaaaagat gaaggatacg gatacgtatt ctctgttta ccgggaatac     1620 gatgatgccg acggtaaata caccagaatc gacaacattg aaaataccag ccagatgatc     1680
cagaatctaa aggatgaaac aaagtacgat atctatctga ccggtacgaa caaaattggg     1740
gaaagtgcgc cttccatgca ctacagcgga acgaccgaga gcgtcaatgc ccccataacg     1800
ccaaactaca aactgatcaa tgtggcaggg gagaatggcg gaaccgaaca tatcaaggcg     1860
gtaaacaatc acggcggaaa tgccgacagt gagtttgcga ttgtggacaa cgatatggta     1920
tctgcgtggg tgcgcaacga ctgggatgcg ggctgcgttt acccgggaga atcaaaatca     1980
ccaacggtga ccctcgacga cagctatacg atggacaccg tggtccttat tccggatccg     2040
gctcagaagt ttgcatatac caatgcgacc ttcttctact ggccggaggg aagcagcaca     2100
caggtgcagg cagcaggcac cttcagcaga aaaaccagct ctaacggaaa agtatattat     2160
gaattccaga cgaaacagcc ggtaacgaca gaccgggttc aggttagact gacggcagga     2220
tacggtgcgg ccaacagaat cagcattgcg gagatgaaat tctatcacta cgatccgatt     2280
gagcatgagg tatacgatct gtttgcagac gatatgcaca tttctttgaa ggaaggggtg     2340
actcaggagc ttattagcag tctgagggcg cgtctggatg agaaggatga ggtaagcggg     2400
gaattccatc cgaagaaaga gattctggag agagaactgg atacggcaga acagctttta     2460
acggatgagg ctctggctgg aattcttacc atagataatc acgtaacgaa aaatgcggac     2520
ggcaatatta ctttttaaagg cggattaaac gcctggcagc cgcttggcat cacagccatg     2580
gccggagaca cggtgctggt ctatgtgggc agcccgtcca ggaagactgg agacagcacg     2640
aatctgcgcc ttatagcgac tcagtatcac ggggaatcca cgcgcatggt cgaacacgatc     2700 ggcacgctga aagcgggaat caatgagata accatccccc agatcactgc cctcgacgtg     2760
gagcagggag gacagcttta catcgaatat accggtgatc aggatatgga gacctacagt     2820
```

-continued

```
gtgagagtca gcggaggaaa tcacattcca acgctggata taacgagagc ttccgattcc   2880
aatgcaaaga gagccctggt gacgaagtat gtggaagatc tggaggccag cacagcggag   2940
ctggaagcaa accatgagaa ccataaaaaa gcgcatgacg gagactggag cgctgcgcgg   3000
aaaaactgta ttctgggcgc cacggatatc gtaacgagat atatgatgta ttccgtttcc   3060
tcccagcaga tactcgccgg attatcaggc ggaactacgg aggaaaaggc ggagcagctg   3120
tatcaggcgc tgacggcggc cgatgagatg gtaaatctct tctaccagca caagggactg   3180
agcagcgatc ctgatgccgg agtgaaaaat aaactgccgg ttagccggct gaatctgcgc   3240
taccagagga tgtttgcagg cgcatttatg tatgcgggcg gactgcatat cggaatcgag   3300
tggggatccg taccgggcct taccaagtcc gtaccggtga agacaacgcc ggaaggcaaa   3360
tacgaaagcg gccagtactt tggctggggc atcgctcatg agatcggcca tgaaattaat   3420
gaaggcgcat atgccatagc cgaaatcacc aataactact tctctgtgct ggcgcaggcc   3480
cgtgatacga atgacagcgt gcggttccag tatccggagg tttataagaa ggtgacgtcg   3540
ggcgtaacgg ggcggtcctc caatgtattt acacagctgg gattatactg gcagcttcat   3600
cttgcatacg atatgggcgg ttataactat aaaacgtacg atacgtataa ggaacagttc   3660
aacaatctgt tctttgccag agtagattcc tacgtaagaa atccgggatc ggcgccgaag   3720
ccgggcaacg tggcgttaag cgtaagcgga gatgtggaca acaagctcat gcgtctggct   3780
tgtgcggcgg ctgaaaagaa tattctggag tttttcgaac gctggggtat ggtgccggat   3840
gagaacacaa ggaagtacgc ggagcagttt gagaaagaga caagagcgat ctggtttgta   3900
aacgatgagg caagggctta cgtgctggag aacggcaaaa atggttctgt ggcagccagc   3960
gccacggtcg aggctgactt aagctacagg ccgaattcca acgaggtgac aattcatctc   4020
ggaagccagt cgaagcagcc ggaggcaatg ctgggatacg aaatctaccg ttccgaaacc   4080
atcaagagcc atgtagagaa gaaaccggtc ggctttgtga ccgcggacca gacagaattt   4140
gtcgattcca tttctactat taacaacaga gttttcacct acgaagtggt aggctacgat   4200
aagtacttaa atgccacaaa accggtggta ctggagccgg ttaaagtctc ccacggcggt   4260
gtgattgata agtcagactg gaccgtgacc acaaacatgg tctcggcaga ggacaaagtg   4320
gatgaggaga taaatccgga tgtggtaacc atggaggcca tcggaaaggt catcgacaac   4380
gatgcaggaa ccacctatac aggaaagacg gtagccggaa gtaacggaaa agtacctgcg   4440
gcctctgtca ccattcactt aaacagagaa gagaccatca ccggtttcac gtataagctg   4500
agtaaggcgg ataacgcggc cggaagtccg atcggcaatt ttaaagtgga gatcagcgat   4560
accggcgcag atggttcctg gacccaggtc aaggccggaa ccttcgccgt agcgcaggga   4620
cagctggcga acggcagtca gaccgtctat tttaacaaga atgacgacac ctggctgtat   4680
gcctatgaca cctcatacgt aaggattacg gcggtggacc agaagggaac cgatatttcc   4740
atttcggaga ttgatctgct ggggcagacc ggagacgaca tcgactttgg tcagacggat   4800
tcgattggcc ttttgaaaga ggattaccat gccggacatg gagagagcgg cgaggccgtt   4860
attccggcgg gctccctcct gttcacagga acgtataaag ggaatccggc gtacaatgtg   4920
gtcctgctgt atgatgagca gggaaagatt gtgggcggta ccgatgcaga aggaaatata   4980
ttggcagcac agatgatctt tgcggaagtg ccggagcacg gagagctggg cgagaccagc   5040 agcgaacgt ggatctatta cattgaaccc gaaaacctta aaaatgccgc tcttccaaaa   5100
cgtgtgagag cggagctcta ccgggtagac aacgcacatg acaacagggg agaacgtctt   5160
```

-continued

---

| | | | | |
|---|---|---|---|---|
| gtcagcaaca | ctctgtttgt | cgatgtgccg | gagacactgc | cggagatcga | gataaaaaca | 5220 | caggactga                                                                              5229

<210> SEQ ID NO 38
<211> LENGTH: 2454
<212> TYPE: DNA
<213> ORGANISM: Clostridium hathewayi

<400> SEQUENCE: 38
atggaattaa cgtatcagat cggatatgat gagacaatca gcagatggaa tgtgacagcc      60
atggggaaag aaccgttcca ttccccgaag aaaacctttg aggccggagt gaacatggag     120
gaatcttatg ttcaggtggt gtatccggtc agggaagcct tttttaaagga agaaaggatc     180 aggaaggcgg tccggtatga cggatcatat gaaagtcttt attttccatt tgagaataac     240
agaattgatt tatccacatt ttttcacaca ccccagtaca tttacgttca tgcgaaggcg     300
ggagtgcgtg tgcaggaaga gggatgctat ccatttgaga tctatacctg cggcggagtc     360
cgggtgtggg tgaacggaga ggaacaggcc tgctatacgc catataccag aaacattgcg     420 ggccatacc cgggtgaatct ttctctgagg aagggactca atgaaattaa ggtttacgca     480
gatgagctcg cggaacggga cgtttttttttc tattttgaac tgcggtataa gggtgtaacg     540
ccagtggaag gcagtgtgga agtgacagag cagcctgaga agatccaaaa agcggagcag     600
attttaaaaa gctgttattt tgagcaggat atgtacacgg aaggagaggt caggctttgt     660
tacgaccgga cgctttttaga cggcgataca actgtgtact tgacttcaac tccctgtgga     720 accgaatgc agctctccga aatagaacat acggtgatga cactgaaaaa agataaggat     780
tacctggtgg ttgcagagac agagaaaagc agtatcaggc tttcgcgaat ctccgtctgt     840
ttgacagtag ggggctatgt aataccgcgc aatttatttg tcggtgtgat cccgaaaaaa     900
cggattgtac tggaaccggc tggaacgatt ggggagagga agcagcaggc tctggaattc     960
ctggtaaaga acggtgagat cggttttcag tctgtgatta cttcgctgga actcttaaag    1020
ggctggaatg acaatgcaga aaaagggttt gatatggcat gtaaaaagat cgagcgccat    1080
gatgactgtg ccgatttcag cctcgccccc tttagccttt tgatgacccg ctataagcat    1140
ctcctgacac cggaaaagtt ggaacggatc agagatatgg tgctgaactt ccggtactgg    1200
attgatgaac cggaaatga tgtgatgtgg tatttcagcg aaaatcatgc ctttctgttc    1260
catgtttccc agtatctctg gggatctgtt ttcgagaaag aactatttac cgtcagcggc    1320
aggacgggag cagagcagta cgaaatcgga aggaaaaggg tgttggaatg gtttgacagc    1380
tttttcagct atgggtatgc ggagtggaat tcagcaacct acattcctat cgatctgatt    1440
ggctttttca gcctgtactt aagcgctcct gatggggaaa tccggcagaa agcagaaaaa    1500
gcactggatt ttaccatgca gatcatcgga tataactctt ttgaaggtgt gatgaatacc    1560
acctatggaa gaatttacga agaaactatc aagacgcggc tccaggttga accgaatttt    1620
gtgagctggg tgtctgccgg gcggggcttc tgtacctatt acggcaatgc cacatgtctg    1680
tacgcgatca gcgattacga gccggaggac tatgaaatgg agtgcaggcc ccagccgggc    1740
cagggtgtgg tgatggaaat ggatcaggga atcgcgggag taaagattca tacttaccgg    1800
acaggagagt acttaacggc aggagtcaga aggtttaaac cattccgcca tggccatcag    1860
cagcatctga tgaatgtggt attcggaaaa gaacgtccgg cgatttttcta tgttaatcat    1920 cccgagagc gggtttttcag cggagaaaac cgtcccagct attgggcggg caacggaacg    1980
atgccgtgga ttgagcggta ctgcaatgta acggttatgc tgttcgctat cgatcctgat    2040

-continued

```
gaactggtgc attatattca tgcctatacg ccggtctatg agtatgaagc gtatgtctgc    2100
ggcggaaact ggtttttttgc caaatccggt gacggatatc tgggctgctg gtttttccaac   2160 gggtacgaga tggctgcata tggtgccaac acgaaaaaag agctgatatc agaaggattg    2220
aaccatgctg tgatcgtaaa atgcgggtcg aaggaggaat ttggaagctt cgaggtgttt    2280
caggagaatt taaaagagat ggatatcgaa tgggacgggg accgcagcat tgcattcgca    2340
gatgtgcagt acggtgaaat gcgggtaagg gatgcggagg aatttctggt gaatggtacg    2400
gcagttggtg tggaaccggt tgagggagtt cggttccttc gaagggagct gtag          2454

<210> SEQ ID NO 39
<211> LENGTH: 2424
<212> TYPE: DNA
<213> ORGANISM: Clostridium hathewayi

<400> SEQUENCE: 39
atgaaaagaa acagcgatat tttcaatcag gtgattcgtt ttattgtgta tcacgggaag     60
atcattgaga agattttcct ggtaaccaca attctctgtg ccgtttgttt cccgtttgtg    120
ggggtgaatt acgatctgag caaatatctg ccggattttg caccgacaaa gcaggcgctg    180
gatgtgatgg aggcggagtt tggttatccc ggcatggcgc gtgttatggt aaaagacgta    240
tctctgcagg aggcgaaacg catccgggaa gagatatctg cggttgacgg ggtagatctg    300
gttctcggtt ctgacgtctc gaccgatgtc tacatgggaa caccgtttct gagtgaaagc    360
atgacggaat tcatcggcgt cgatttgctt gcaatcgacg attactataa agacgggaac    420
gccctgatgg acattgtctt tgaagataaa gacggggagc cgcgtaccaa tgcggccatc    480
gaggaaatct accggatcgt cggtaaggac cgggggatgct tttccggaag cgccatatcc   540
agcaaggaac gggaggcttc gatcacaaga gagatcgcca tggcgattgc catgtcaatc    600
gtgattatat ggctgatcct gacgctgacc accacgtcgt ggatggagcc gtttctcttt    660
attttcgtga tgatcgtggc gattgtactg aatatggggt cgaatattat ttttggaacg    720
atatccttct ttactttctc cacagcggct attttgcagc tggcggtatc gatggactat    780
tctattttcc tgcttcatac ctttacagca ttgaaaaaca ggggcatgga aatccatgag    840
gcgatggtgg aggcgatcag ggaatcctgc agttcgattc tcgccagcgg ggtgaccacc    900
attgtgggat ttatcgttat cgcgtttatg cggtttacca taggaaagga cgtgggattt    960
gtactcgcaa agggaatcat atgcagcctt ttaacggtgc ttctgctgat gcccacactg   1020
attctccggt ttgacgataa gattgtgaaa acggcgcata agccgcttat cgcttctttc    1080
gatggatttg cacgggccat gtaccggatc aggattccgg tgttccttttt ggcggcgctc   1140 ttagcagtgc cctgttattt cgggcagggt atgaatcact tcctgtacgg cgacgatgcg    1200
atcggtgcgg gaccgggaac gcgggtttac gaagacacgc aggagattga ccgtctgtttt   1260 aaaaagtcca acatgacgat ctgcatcgtg ccgaacggtt ccggcgtgac ggaaaaggaa    1320
ctgtcaaagg aactggagaa cctggatttt gtcaattatg tgatttccat gtcaggaacc    1380
atgcctgacg gaataccgga aagcttcctt cctgatgatt tgacgagcca gctgcggggc   1440
gatgtttatg ccagaatgct gatttccatg aataccttac aggagagcga ctatgcgtttt   1500 gagtgcagtg ccagactgga ggagattgta cataagtatt atcctgacaa ttcctacgtg    1560
atcgggatga cgcccacaac cattgacatc agggatattc tgcacagagga ttacaatcat   1620 gtatctctgc tgtctctggc tggtgtggca cttgtcgtat ttctgacatt ccgctcggtc    1680
```

-continued

```
ctggtgccga ttctggtgat tgtgccgatc gaagttgcca tctatttaaa catgacgctg    1740
ccctatgtga tggggacac catgatctat atcggctata tcatcgtcag ctgtctgcag      1800
ctgggggcta ccatcgatta ctcgattctg atgacaaaca actacctggc gtttcgaaag    1860
gaaaagggac gccgcgaggc tgccgttgcc gctgtcaata agagtacgct ttcaatcatg    1920
acatcgggcg gtattctgat ggtggtagga tatctgctgt attttacttc gtccatacag    1980
gcgatttccc aggtagggcg tctggtggga cgcggggctt tcctgagcgt gacactggta    2040
ctgtctctgc ttccggcgct cttatccgca tttgataagc agatcaaacg gcagcaggag    2100
cgggcggatg cacggaaaga gagaaggcgg aaccgtctgg cggcagcaaa aaacctgaca    2160
acagggaaaa gtctgccggg agcgaagcgt gtgacggaag agaaggaact gacggaagag    2220
aaggagttat cggaagagaa ggagttatcg gaagagaagg agttatcgga agagaaggag    2280
ttaccggaag aggcaggtct tacgacagat gtgagcccga catttgcaga tggaaaatgc    2340
gggcagaaag aaggttccgc gcaggcggag gcagaagagc cggagcagaa ggaaaaggga    2400
gatgacagcc atgagaaaga gtaa                                           2424
```

```
<210> SEQ ID NO 40
<211> LENGTH: 2247
<212> TYPE: DNA
<213> ORGANISM: Clostridium hathewayi

<400> SEQUENCE: 40
atgccaacga tcaaagatat tgccgccaaa gcagggggtat cccacggcac agtttccaat     60
gtgttgaaca agaggggaaa cgtcagcgcc gaaaaaatcc agctggtaga gcggattgcc    120
aaagagatgg gatataaaat gaatgtccag gcccagcagc tgcgggccgg tacggcacgg    180
agagtctgcg tcattgtgcc taagatcagc ttaaaatgct acaacgattt atataacggg    240
ctggaacagt acctgcggga gtacgagatc agcatagaac tcatatccac caataacctg    300
gagtgcgacg aggaaaaagc agtaaagaag gctctctcct aaaatcccat ggcggtggtg    360
gtggtcagct cgcttcttaa gaacagggga ttatacactt cagataccag gttttttcttt    420 gccgaaagaa aggtaaaggg aatgccggac gcgtctgtct acgtatcctt tggatttgag    480
caggcgggac gggatatcgc ggttaagtgt atcgaggatg gccatcagaa tgtggctttg    540
ctctgtgaga acagcatcta ttccaacaat aaaagcttta ttaatggtgt ggtggatgtg    600
ctggaggacg ataattgctc ctgcaaaata tttcccagcg acgacagcat gtggtttaac    660
aaggcctttg tatcctgggg atcgaaagag gattttgacg cggtgattgc catgagccag    720
gaggacgccg attatttgag ggtggcccat cagtataatc cggataagaa aatgccggtt    780
atatatgcgc tgaccagcaa gagcatcgga atcgatccgg ccgtgtgccg atatgagctg    840
aattataagc tgatgggaag aaacatagcg gaacagatcg taaatgccgg cggggaagag    900
gcggagacgg cgcctgcgca gaaacagcag atcatcatgg aaaatgacgg attctacgat    960
aatccccttc cggccgcagg gaagaaagac agcatctgtt ttttgaccat tcagaatctg   1020
accagcaagg ccatcggcat gctgcttcct tcctttacca gggagaccgg tatcaaggtc   1080
aatatgatcg aggtttccta cgatgagcat tacaagatgg cgcaggcctg cgtgcagaac   1140
agcccctatg atctggtccg catcgatatg gcgtggatga cggagctggg cgataagatt   1200
tatcagccct tcgacagctc cagctcttcg gtcaggtggc tgcggcagca gattcttccc   1260
tcactctcgg aaaactattc catggttcat ggtgtccagt acgcgtttcc gttggatgcc   1320
tgcgtgcaga tgctgttcta ccggaaggat ctattcgagg atgagctgat caagagggaa   1380
```

-continued

```
tttttcgaaa aatacaaacg gcgtctggag attcctaaga cgtttgaaga atacaatgaa    1440
gtggccagat tctttacgag aaaagagaat cccgattcca ggacgaggta tggagccgtt    1500
accgcttatg gaagaacatt cctggcggcg tgcgattttc tgccgcgttt tagggaactg    1560
aagaaggata tcttcgatgc acggggaaat gtaaatatcc tgatccccga gatgaaacag    1620
gcgatccgca attatctgga tacctgcaag tatgcgggca gtgatatcta tcagtggtgg    1680
ggggaaccca cccgccagtt ctcggagggg aatacggcga tgcatatcgt gttttccaac    1740
tatgcctccg agatgataca caatccggaa tcgaaggtgc tggggcgaat cgcctgcgac    1800
accgttccgg gcgggcagcc attgtcgggc ggaggctcgg tgggaatctc cagattcagc    1860
aaaaagtatg acgcgtgcat gagcttctta aagtggctgt accggaagga tatcgcggag    1920
accatcacgt atcttggcgg atacgtctgc aaccgccaga tcagcaggaa catggatatc    1980
ctggaacgct atccgtggct cgagaacatg gaaaaatcct tcgaacccgg ctggaggctt    2040
tataaacatg acagaaatcc tgatttcaat gagttcctgt ttgaggatat tctgggtaag    2100
gcgatccggt ccatcgcatc gggaatcgaa gagatggatg acgcgctgga gaaggcgcag    2160
gaggaatgtg atcgggcatt taacgaaaca agcgggaatt cttccatctc aataggcgga    2220
gggctgaatc gccaaaaaca agtttag                                        2247
```

<210> SEQ ID NO 41
<211> LENGTH: 2127
<212> TYPE: DNA
<213> ORGANISM: Clostridium hathewayi

<400> SEQUENCE: 41

```
atgagaaata gaagaaaaat cagatataaa attaccgccg ccgcattgat cagctcgatg      60
ctcggcatgt ccatggcagg cagcgccctt gcgggaccgc ccgcggttgc cacgatgag     120 gcgctgtatg tgaacctgga ttattacgga aatcaggtgg acagcagtgt ggtgaaggga     180
gtttccttaa acggccttcg aacatttacg gattatggaa cttatacaga tgtaacaaat     240
atgtctaatt acgcggaacc ggtgatcagc ggggacggag tcacctggca gctgccggag     300
gactcaaagg agcggtttta ctacgagtgc cagctgaaca cgacgaggt ggttctcccg      360 tggaattttg acgtgtccta taaactaaat ggtattccaa aggaagcaaa ggacctggtc     420
catgccaatg gactggtgga atggaggtc cactgcattc cgaatgagaa tgcaaaggag      480
tactaccgca acaacatgct tcttcaggtg gcgaccatgg ttaatatgga agacgtaaac     540
gctgtggagg cgccaggctc tcagacacag gcattaggaa cgtataaggt tgtgattttt     600
gccgcggtcc caggggagga gaagaccttt cacatcggga tcagcacgac gaatttcgag     660
tccatgggcc tgatcatgat gatgattccc ggaacgctgg accagatgag cgagatcacc     720
gatatcaaag aggtaaagga cacagtgggg gattccaccg ataagctgct ggatggtatg     780
aatgaaatcc tggatacct ggaccggatc agcggcggta tgaatgtggc acaggcgggc     840
ctggaggatc tgcagaaggc gagatcgggt ctggacgcgt caaaggacga aatcatagcc     900
aacgcggata acagcctgga cagtctggaa gctgtcaatg aaaaaatcag ccagctggct     960
ccggatatca atacgaataa gcagtctctg gatgaaatca cacgagaat caacgccatc    1020 gtgaagactc tgagaagctc cggcaatgac ttctttgatc tggcaggaaa actcagtgat    1080
ctggaggact ctctggggga tttgcgggat gatttgaata attccaacag ggacgagatt    1140
ctggatcatc tgcagattgt agatgaccag ctggaacaga tcaatgaagt gcttcagaat    1200
```

-continued

```
atcatacaga cggccggagg tatccctgcg gaactggatg aggaagatct ggcggagcag    1260
caggagacgc tgagcaattt gctggaggag acgtatggta ttctggatga catggagtcc    1320
gttgtcggct ccgatgccgt ggaccgcctg cgcagccagc tggatgcgat taacggaaat    1380
ggcctgggag acgcggccag cctttcgaag ctggcggcag cggccaaggc gcttctccct    1440
gtggtttccg gccttcaggg catggtgagc gatctggagc gcacactgtc tggaatccgc    1500
ctggatgacg gccttgagag cggccaggac gcggccgggg agatcagctc catcatgggc    1560
cggatcgaga ccttgatcgg cgacgtcaat gatttaaaca ggactgtcaa tgaagataaa    1620
gccggttttg acctgatgct tgatgacatg gccgcctccc tcgatcagat gagttccggc    1680
acaagtcagg tgattgctct cttgagaagt gtgcagaaca cggccaggac caaccggagc    1740
gcggtggaaa acggtacgaa gcagaccctt gacggcctga tcgatattct ggaaaaggct    1800
gcggatacca agggcaccag cgacaaatta aaggatgcca cgaggactt gagagccagt     1860 gtaaaggatg agctggataa gatcgaggac gatacgaatc tgctggaaat ggacccgtct    1920
cagtccatga tttccttcac ctcggataag aatccgtctc cggccagcat tcagattatt    1980
ctgcgcacag aggagatcag cgaagaagat gtgaatacga acgcggttga tatcgaaccg    2040
gttccgcaga atgtcgggct gtggcagaga attgtaaatg tgtttgtgaa gatatgggat    2100
acggtaacgg gattttttaa gaaatag                                       2127
```

<210> SEQ ID NO 42
<211> LENGTH: 2076
<212> TYPE: DNA
<213> ORGANISM: Clostridium hathewayi

<400> SEQUENCE: 42

```
gtgtatacaa aaaagaaaac agctgagagg cgggagaggg gaattacgat gaagtttaca      60
gtagaaaatc cggatgagaa acggagtccc tatacgggaa tgacaagaga acactggatc     120
agtatcagtc attttttcct ggaaggaatt tttgagcatg tggagaagat cgaggatccg     180
atcgtagtcg gacgccatga gacaaaggtc agctatccac agccggatgg gccgaaatgg     240
agaattgcgg cggagcggtt tgagggactt gccaggagct ttctgattgc ggcaccgctg     300
cttcataatg agccggaggc agcggcgggt ggctactctc ttaaggagta ttattcaaaa     360
cagatcctgc tctccgtcac acccgggacg cccaattatc tgcttcgggt ggaggagata     420
tttccggagg cgcaggaagg ggagatggcg tttcagcaca cgtgtgagtg cgcttctctt     480
gttatcggcc tgtccatgtg ccgggaggtg atctgggaga attatgcgaa ggaggagcgg     540
gaccgcattg cagattacct gtcgaatttt ggccattcct atacgggcca ccacaactgg     600
cgcctgttta atatgctgat tctggccttt ctggaccggg agggataccc ggtggatcat     660
gggatgatgc gggatcacgc ggccgccatt ctctcctatt acgcagggga cggctggtac     720
cgcgacgggc atttgtttga ttactactgc ccttgggcct tccatgtgta cggacctctc     780
tggaaccagt ggtacggcta tgaaaaggag ccgtacatgg ccgcaaagat cgaagaatac     840
tccaaccgtc tggtggagac attccatcgc atgttcgatg aagagggcca tgtgaccatg     900
tgggggagaa gcggtatcta cagaagcgcg gcttccgctc cgctggcggc taattttctg     960
ttaaagaatc cggctgcgga cccggggctg gccagaagaa tcgcctcagg tgccgtactc    1020
cagtttgcga cccgggaaga gtgtttctat gagggagtgc cgtgccttgg cttctacgga    1080
ccgtttcagc cgttaattca gacctacagc tgcgcggcca gcccattctg gattgccaac    1140
gcatttgtct gtctcgccct tccgaaggat catccgttct ggaccgatac ggagagaaac    1200
```

-continued

```
ggggtctggg aggagatgaa ggaaagggaa gtaaggacta cggtgctcga tggtccgggg      1260
atcgtggtgg ataaccacaa agatacggga attacagaat tcaggacggc aaaggtcctg      1320
atgaagaaag ataatccctc cctcaatacc tattccagac tgtcctttaa cagccagttt      1380
ctatgggagg acttcgattt taaggggatt gaggccatgc agtacagtgt gacctatgac      1440
ggcagaccga agagcctgat cccgaatatc ctgatgtacg gcggcgtgaa ggacggagtg      1500
ctctaccgga aggaatactt tgaatttgaa tttaccttcc agaaccaggc gtcgatcgat      1560
ctggccgatt tcccggtggc ggacggcatc gtgcgcgtgg acaggaccag aattccggat      1620
aagccatata ccctgacact gggttcctat ggaatgccgg acgtggaccg ctcgggtgtg      1680
gacgtgagaa tccgcacgga tcaggtgacg ggggccaagg caatcctttt gaagtcttcc      1740
gagggacaga tggcgatggt catctacggc ggcttcgatg atattgaaat catgtcgaga      1800
cagggcgtga gcgctgtgac gaagcagagc tgtattatgt atggcgtcag ccgcaggagg      1860
aaatactatg aataccttcc gtatgcgatg atcagcgtga ttctgacaaa gaaaagccag      1920
gaagagtggc gggacgagga ccttttcccg atccggagca tctcctatgc ggataaagaa      1980
aaatgcgggg catacggtcc cattgttctg gagatgaagg atggcaggac ggtcacggtg      2040
gattatgagg gactggaagg aaggctccat atttaa      2076
```

```
<210> SEQ ID NO 43
<211> LENGTH: 1956
<212> TYPE: DNA
<213> ORGANISM: Clostridium hathewayi

<400> SEQUENCE: 43
```

```
atggcgcttt atgactattc aggtgctttg aaaaaaggaa gaaaacagta tcaggtttcc       60
gtggcaaagg gagagtatcc ttatcttcct gtgctggacg atatcctttc ctacacggat      120
atcatttcag aagtgaatct gggactgatg gatgtcccgc tggataagat cgttggaaca      180
aaaacaaaag gcagaacgag tgcctttgcc aataatttta tgcctctgct ggcagagaag      240
tcagagtttg gggcgaaatg ggcgtattta tacgaccatc agatagaaga ggggatccat      300
gatcccatcg ttgcgtatga atttatgaat caatattacg tgcaggaggg caataagcgt      360
gtcagcgtgc tcaaatatgt gggtgcattc agcatcacgg cctcggtgac ccgtctgatc      420
ccgaagagaa cggatgatct cgacaatcgc ctctattatg aattcctgga gttttaccag      480
gtgtccttta actgtgatgt ctggttcagc caggagggct gctacgaccg cctgttaaag      540
gctatgggaa aggccccgga gaggtgtgg agcgaggacg acaggatcta tttcaaatcc      600
gcctacgacc agttttccaa ggcgttccgc gcatttggag ggagttccta tgagatgacg      660
tgctctgacg ccttccttgt ctatgtcgaa ctgttcggct atgatgtggt gaagttaaag      720
actgaagggg agatcacaaa ggatctggcg aagattaagg atgaacccct gctggcatcc      780
agaggcagca agattgccct ggtagagcag ccggaagagg tggaagagca ggataacggc      840
ccgttaaaga tcattaactg gctccgccca tcccagaaca tcgaacctga gatgctgaag      900
attgcattta tccatgcgaa gaccgctgag acgtccagct ggacctacgg ccatgagctg      960
ggacgcatgt atctggagca ggcctttgag ggccggttaa agacggttgc gttcttcgag     1020
gccgacacgg atgcagagat tgcgaacgcc atcgacctgg cgatagcggc caggtgcaac     1080
atgatcttta cgacggcctc ccagatgatc ggtttaagcg tcaaggctgc catcgagcat     1140
ccagaggtga agattttcaa ctgttccgtc aacatgtcgt attcatctgt ctgcacctat     1200
```

-continued

```
tatgccagaa tgtatgagtc gaaattcctg atgggcgcgc tggccgcttc catggcgcag    1260
tgtgataagc tgggatatat tgcggattat ccgatctacg gaaccatcgc caatatcaac    1320
gcatttgccc tgggcgcgcg tatgatcaac ccatacgtca aggttcattt ggagtgggcg    1380
agggtaaaag gcaggaatgc ccgggaggaa ctggagaagg aaggaatcgc gtttatctcc    1440
ggagaagaca tgatcacgcc gaagaccgcg tcgagagagt acggtttata taaaatagag    1500
tctgacggag aattccggaa tctggcgacg ccgatctggc actggggaaa attctacgag    1560
agaatcgtga atatcacctg ccgcggcggc tccgatgtga aggagatgaa gggaaagcag    1620
gccatcaact actggtgggg aatgtcggcg gatgtgatcg atgtcatctg ttcccagaat    1680
ctgcctcacg gcaccaaccg gctgattacg ttcctgaaga attcgatccg aagcggaagc    1740
ttccagccgt ttgtaggaac catctactca caggatggga cgattcagtg tgaggaggaa    1800
cagaggcttt ctccggaaga gatcatcacg atgaactggc tggctgacaa cgtggtggga    1860
aagcttcctg aatttgatga actgacagag gaggcacagt cgctggtaag gcttcaggga    1920
ctgacgatat acgacaatgc ggtgatggag gaataa                               1956
```

```
<210> SEQ ID NO 44
<211> LENGTH: 1947
<212> TYPE: DNA
<213> ORGANISM: Clostridium hathewayi

<400> SEQUENCE: 44
```

```
atggttgagg caagaaccag atatgttatc atgataaaaa caatgttagg caggaaaacg     60
tacgtgacct cggctgctct cgcagaagca gccggggttt ctgtgcgcac ggtaaagtat    120
gacttaaagg agcttcagag cttcttaaag gagtatggcg tggagatcga atcgaaacgt    180
tcttacggct accgcctgct ggtgggagac ggctccgaca tggaggggct gtcgaaggcg    240
cttcgggcca atctgcggaa acataaggga gaggtgttcc gctataattt tcagagggtg    300
atctatatca tcaacaagct gctgatcgga aagccgtact ataaggcgga ggagctgatg    360
gatacgtttt acatcagccg ttcgacgctc acccaggact taaaccgcgc ccggaccctt    420
cttgcaaagt tccgcctgga aattgacgtg aacctgcgcc ggggaatcgg cgtcaccggt    480
gatgagctgg ataagcgcct ctgtatagca gaatacttct tccggtacga tgataagctg    540
caggttatgg tgcagaggcg ggctgacggc gggaagtatg actgggatgc ccagagggac    600
actcttgtcc gtatcgtctg ggaggcatgc cgtgccaata agatccggct gtcgccgttt    660
ctggccgtgg atcggccag tcacatgtat gtcagtgtgc tgcgcatgaa ggcaggctgc    720
ggcatcgggg agctgccggg ccataccatg acagtggaat atgtgaggga gcggtacgcg    780
gcaggggagg tcgcggatca gctggaaaaa ctctattccg tatcgatttc agagaaagag    840
cgggagtatt ttgccctcca tatactgagt aagaaaatgc cggacagcgg gcctgtgggc    900
tccggagagc acgccacgtt aaagcagtgt gtgacggaaa tcatgcggga ggtaaaggat    960
aactttgaac tggattttac caatgatccc gtgtttctcg attttttata ttccagcatt   1020
gaacctatgg tcttaaggct cagaacgcat ctgattgtca gaaatccgct tctgtttgag   1080
aatctgcgcc gttatttatt tgccaccaag gtggcccact cggccagcgg aatcatagaa   1140
aagctgtttg gcgttcagat ggacaataat gagtttgcct atctggtgcc tgcattcaac   1200
atgatcatca gtacccatga gaagcggaag aagtttaaga tcggattctg cggtgacttg   1260
gggctctcgg aggctctgat ctactataat gagctttcgg agagtcttcc cagggatggc   1320
tatgaactgg tgtggctgga cagataccac aataccggtt atttaaacca gctccagtat   1380
```

-continued

```
ctgatctacg tcagtgacta ccgtcttccg tcagagctgc cgtattatga gatacaggac    1440 gggattcca  ccagtgaggt ctgcagtgca attgcggaat ataagctgga gcaggtacag    1500
atagaacagt atttaaagcc ggaattcggc atattcggtc tggaggggaa aagccgggaa    1560
gaggtcatgg agaacttata ccgctgtctg gccgcccgcg gcctgattgc cacggagctg    1620
gactggaaaa atgcattccg ggccaatgag gtgggcaatg ggatcgccca tattcaggac    1680
ctgggaagga ttcttaagaa tgccggctgt tacgtctgca tcttaaaaac acctatcctg    1740
tgggagcagg atatcataaa agtactggtg atgatcaaga caaagcggga tggagacaag    1800
aatttgtccc tgctctgccg catcgtctcc aattgggcat catcgccgga aaaggtggaa    1860
cattttctga aatcgcagag ctatgatgtg ttctgcgggg atattaagtc ggaatgcctg    1920
aacatatgct tccattccat catctga                                       1947
```

```
<210> SEQ ID NO 45
<211> LENGTH: 1944
<212> TYPE: DNA
<213> ORGANISM: Clostridium hathewayi

<400> SEQUENCE: 45
atgaaggcat atgggaaacg gctggggaag attgtgattc tggcagctgt tttaaatttt      60
ttgatcgagt ttatcagcag gaagtcgctt gcagtgcttt tggcctacgt gttggaaagt     120
ccgctggtct tccttttgaa tacatgcatt atcgctctgc cgtttacggt gctgtttctt     180
acgaggcgca gggtgtttgg ggcaatcgtg ctgtcgattg tctggctggg aatgggagtc     240
gtgaatggga tactcctgat tttccggacg actccgttta cggcggcgga tttcaggctg     300
atcaagtacg cggccaatat tgcgaccacg tatttcacct ggatgcagct ggttatgata     360
gcagcggctc tggtggtggt ggcggtcttc tgcgtgtttg tgtggcggat tgcgccggtg     420
agccgggaaa aggtcaatta cgtcaagggc acggcggttg tggggatcag cgcggcggtg     480
gtcctgggac tgacgacagc tgccatgaac accgggctgg tggcggtgcg tttcggcaat     540
atcggagcgg cgttttttagc gtacgggttc ccctactgct ttgccaattc catgttcaac     600
acgggaatct ccaagccgga ggactatggt acggagacga tcgaggtgat taaggcggag     660
gagctggttc cggaaaatac atatgcggtc tcggccagta cgaagccgaa tgtcattatg     720
atccagctgg agtcctttt cgacccgctc ctgtggaaga agaatccggt gatgggcaat     780
ccggaatccg gtgggacgga aaactatgat cccatcccat ttttccacca gctgcagaaa     840
aattatcccc atggatattt gaatgtgcct tccgtgggcg cggggacggc caatacggaa     900
tttgaagcca tcacgggcat gaatctggat ttcttcggac cgggcgagta tccttataaa     960
accgtgctga aaaagacctc ctgcgagagt gtggcctttg atttaaagaa tctgggctac    1020
tcggcccacg ccatccacaa caacgaggcg accttctatg acaggaacaa tgtattcgcg    1080
cagatcgggt tcgatacgtt tacgcccatt gaatatatga acaatattga gagaaatccg    1140
gccggatggt gcaaggacaa gatcctggtg aaggagatta tagggacgct ggattccaca    1200
gaggggcctg attttatcta taccatatcg gtgcagggcc atggaaagta tccggatttt    1260
aagtattact gtgaacagat cggtgagatg gatgatttca tccgttcgct tgtcaatact    1320
cttcgcacga gggaggagcc catcgtactt gtaatgtacg agaccacct tcccagcttt     1380 gaatggacgg aggatgagat gatcaacaaa tccctgtacc agacggagta tgtggtctgg    1440
aacaatatga atcttccgaa gaagaaggtg gatgtggagg cgtatcagct ggccgcccac    1500
```

-continued

```
gtgctggata tgctggggat tcatgaggga accatgatgc ggttccatca gaactatctg    1560
gatggcggca tggaggatga ggagacgtat ctggccgata tgaaggcgct ggaatacgat    1620
atcctgtacg gagacaggga ggtctacggc ggggaaaatc cctaccagac cacggattta    1680
cagatgggaa tcgatcccat caccattgat gatattgtgt ataacgattc taatattctg    1740
gtgtatggtg agaattttac accatattcc aaaatctgcc tggacggaaa ggcggtggag    1800
accacatttg tgtggccgga actgatcatt gccaggaata ttccggagaa aaaggtcacg    1860
gatgccgata ttacggtgtg gcagatcgga agggacaaga ttccgctggg agagggagtc    1920
agagaaaagg ggaaaggatc atga                                           1944
```

```
<210> SEQ ID NO 46
<211> LENGTH: 1845
<212> TYPE: DNA
<213> ORGANISM: Clostridium hathewayi

<400> SEQUENCE: 46
gtggagcgtc agtatcagaa cgaagaagct atgagaaagg agcttgaacg cgggaactat      60
acctcagagc atccttatat cgtggtaaat ccttatctcg taaatccgct gacggccatg     120
attttattta aaacagaaaa agaagaggca gtgactctga ctgtaaaggg gaaagaagct     180
gccggtgata ttacccatac atttccgaag gcaaaggagc agatccttcc ggtgcttggg     240
ctctatccgg agtatgataa tacggttgtg attgcgctgg aggacggaac ggcttacgaa     300
gtaactgtga ccacggaaca gattgaaaat atgccgtacc aggcggatta tatcaacaca     360
acaagtgatt atatgaatgg gcagctgatg ttcgtgacac ctgccgggga ttcactggcc     420
ggaggctatg actatcgggg agactgccgc tggcatctgg tggagccgtt tatatttgac     480
atgaagcctg ccgcaaacgg ccgcattctc attggctcca accggctttt aaacatgcct     540
tactacacgg cgggcgtctg tgaaatggac ctggtgggaa aaatatatac ggagtactgc     600
attccgggcg gctaccatca cgaccagttc gagatggagg acggaaatct gctgatcctg     660
actcaggaga aaaatgcagc cacagcagag gacatgtgcg tgctggtgga ccggaaaagc     720
ggaaaaatca tcaaatcatg ggattacaaa aaggttcttc cccagcaggc ggcgaagtcc     780
gggagctggt cggaacacga ctggttccac aacaacgcgg tgtggtatga caggcggacg     840
aattccctga cgctctcagg cagacatcag gatgcggtca tcaatatcga tttttgagacg     900 ggagaactca actggatcat cggagacccg gaggggtggc cggaagatct ggtaagccgt     960
tatttcttta cccccggcagg cggcggtgac tttgactggc agtatgaaca gcacgcctgc    1020
atgatgcttc cggatggcga tattatgatg tttgacaacg gccactggag ggcaaagaat    1080
aaggagcagt acaggctcaa ccgggataat ttctccagag agtccgctca ccacattgat    1140
acggagagga tgacgattga gcaggtatgg cagtttggaa aagagcggaa gaatgacttc    1200
ttctcatcct atatttccaa gtgtggaatat tatcgtgacg ctactatct ggtacattcc    1260 ggcggaatgg ggtataatca tggtgttact tgtgaggaac ttccggtcta tatgaatctg    1320
gaggatccgg aatgcgtatt aaagagcatt accgtagaaa tcatggacgg agaactggtg    1380
tatgagatgc atctgccatc caattattac cgtgccgaga agatgagcct gtaccgggaa    1440
ggagccaatt tagacctggg aaagggcaga gtcgtaggaa atctgggagt gacaggcgag    1500
tttgatacgg aggttccggc agagaacaca ggggaactgc ttccggaagc ctgtgaggcg    1560
gtgctgacga agaggacga ccgcatcatt tttaaggcga agtttaagaa gggacagctg    1620
gtaatgttcc agctggaaaa ggaagatgat ccggaggaga tccatcggta tttcatctcc    1680
```

-continued

```
accagtgcac agaagtttct ggcgatgtgt tccggcacct tcctgcccaa ggatgacagg      1740
gaagtgacgt taaacgtcga caaagagggc ctgaacggca cctttgatgt gcgtgtcatc      1800
attgacgaca gcaagtatga gaccgggctg aagctgaagt tctaa                      1845
```

```
<210> SEQ ID NO 47
<211> LENGTH: 1746
<212> TYPE: DNA
<213> ORGANISM: Clostridium hathewayi

<400> SEQUENCE: 47
atgaaagaaa tgagtcggaa ttttatgaaa aagatctgga aaatggggcg ctatcgtgac        60
gcgtccattc agaaaaaact tacgctgtcg acatgggtgg tggcaattat accgattatg       120
attatatttg ccattgtttt tttcgtgttc acaaatgtca gtgtggagaa ttcaaaacgc       180
cagtcacaga tgctttttaga taagacagtg gaggaactgg atgcgtattt cgcgcaggcg       240
caggaaggca tgaatctgat ggtgacggat attaatgtgc agaatgccat cgataattac       300
gtgaccggga cctataagga aaaactggat ttaagggatt ttatcagaaa ccgtctgacc       360
aatatgagta cggtgggcag acgaacaggt acgatatcca tttatatcaa ggatgccaat       420
cagacctttt ccagagactt ttccgaccag gatttagggc tggcctgctc cggtgctccc       480
tggtttgaag cgctgctgtc aggggaggcg tcctttgtcc gcgaggatgg gaactccctg       540
caggacgggc ggcctgtctg gattctggcg tccaatattg tcagcgtcaa aaacggagag       600 gtccagggggc tggtctatgt ggagctggat aaaaagaaga tgattcagcc gttttacgat       660
ctggtggagg gcagcggaga tgagatcatc tgtaatggac aggagattgt atccgatgcc       720 tgcaggagg gcggccattt tgttccgctg tactcttatt ccacggcgct ggggcagaat       780
gtggagttca gactgcagtt aaaggaactg cagagaggct atggcgcagc cctggtttac       840
tttctgatcg gtatggtggt tctcattatc ctgatctatc tcattgacaa gctgctggca       900
gactggtttt ccaggagaat catcacgctg cgtgatgcga cgagggagat cgccaagggg       960
aatttagacg tggttgtctg tgatgaccat cccgatgaga tcgggggaact ggtacagagc      1020 ttaaatacca tggtaaagga tatgaagcgt ctgattgaaa gcgaatatct ggttaaaatc      1080
gagagccagc aggccacctt aagggcgctt cagagtcaga ttaaccctca ttttatctac      1140
aatacgctgg aaagcatctc catgctggcc ctgattcggg atcattatga gattgtagat      1200
atggcacagg cgtttttccct gatgatgcgg tattccatgg agccgtccac tcttgtggcg      1260
gtcagagaag aggtcgagaa tgtgcggaat tttgtgacca tacagaaaat ccgtttcccg      1320
gaccgttttc tggtggagta cgccatcgat gaggagtgca tggcggaaaa gataccgagg      1380
ctgaccatgc agccgctggt ggaaaatgca tttaagcatg gattcgagga cacgccggag      1440
cacaagcgtc tcctggtttc tgttctgaaa cggcggggat ttctcgttat cagaattttt      1500
aacgatggta tggcggttcc ggcggagcga attgccagaa tacgggagct gctgatgccg      1560
gataaccagg aggagacgct ggactgtttt gctctcagga acttaagcag gcgtcttaag      1620
cttctgtttg gggaaaacag ccgggtgacg ctgcgctcgg aaaaggcat tggaacgatt      1680 gtttcattga gaattccact gcgagaagag gggaagagg acgatgagaa agatttttgat      1740 ctgtga                                                                  1746
```

```
<210> SEQ ID NO 48
<211> LENGTH: 1740
<212> TYPE: DNA
```

<213> ORGANISM: Clostridium hathewayi

<400> SEQUENCE: 48

```
atggaaagag aaaaaccacg cagcagaaag aaaaagcggc tgggcgtaaa gttctgggca     60
gctgtctgcg gcggtatcgc agtggcggcg gctgccacgg ttaccgtgtt gtacatacag    120
acgggaaagc agtatcgtac tgtgtttttc ccaaatacga ctattaacgg cattgatgcg    180
tcgaagaaga ctgtggatga agtgaagcag ctgatcgctt cggcatcga cggatatacg     240 ttgaccatca aggagcgggg cggcgcagag gaagtgatat cgggcgatga gatcggcctg    300
gaatcggtgt ttgacggcag ccttgagagg cttctggagg aacaggagcc caacgactgg    360
ttccgccatc ggaaggcgac tcagactttt gagatcgata ctatgatcca gtttagtgat    420
gagaagctta cgggcgtggt ggatgcgctg aactgctttg atgagacgca ggtggtgaaa    480
ccacaggatg cggtgatgtc agagtatgtg tcaggccagg atatagtgt gattcctgca     540 gtagagggaa gcgaactgga tagagagaag gtgatggccg gtatcgcgga ggcggtaaac    600
ggcttacaga gagagctgtc cctggaggaa ctggaggcct acgtgaagcc gggagttccc    660
agtgacgacg cagagctcct cgcccgcgtg caggcgctta ataaatttgt gaatgtcaga    720
gtgacatata cctttggaga cagtcgggag gtgctgagcg gcgatactat caaggactgg    780
atcggcatcg gtgacgatgg aaacgcttat gtcagcagcg gagcggtcac ggagtatgtg    840
aagagtctgg cctccaaata cgatacctat aataaggcaa aaactcttaa tacctcctac    900
ggaaagaccg ttaggattac gggtggaagc tatggctgga gaatcgacca gtccgcggag    960
gcggatgaac tggcagctat aatccgttca ggcgagagtc agacgagaga accggtctac   1020
aagcagaagg cggtcagcca tggggccaat gattatggca gcacctatgt ggagatcaac   1080
ttgacggcgc agcacctttt ctattataag gacggcagtc ttgtggtgga atctgacttt   1140
gtgtcgggta atgaagccaa gggctgggcg actccggcgg gagtttatcc cctgacctat   1200
aagcagaagg acgcggtttt aaagggcgaa gattataaga ctccggtgga ttactggatg   1260
ccgtttaacg gcgggatcgg tctccatgat gcgacatggc gttccagctt ggaggcacg    1320 ctgtataaga acgcggatc tcacggctgc gtcaacctgc cgcattccgt agcacagaag   1380
atatttgaga acatctcggc gggtactccg gtactctgtt accatctgga gggaaccgag   1440
tcaaagacca cctcaacacc ggcgggcaag ccaatacagc cgacgaccgc ggcaccggag   1500
acaacggcgg ccaccactcc ggcggctact gccccggcag ctacaacggc gtctcccgag   1560
accacggccc cgtctgaagc tcctgcgccc aagccaacag agagccagac tgcggcccct   1620
acaaaggccc cggagacgga agcctcgact acggcggctt caccggagag cggagagaag   1680
ggacctggag taccaactgg gagttcaggg aataaagaga ttggaccggg cgtctcatga   1740
```

<210> SEQ ID NO 49
<211> LENGTH: 2154
<212> TYPE: DNA
<213> ORGANISM: Dorea longicatena

<400> SEQUENCE: 49

```
atggatttta aggaagaatg gaattggttg aattcctatc agatggaagc agtgacagat     60
gaaaatgatg catgtattgt aaatgccaat gtaggaagtg ggaagacgac cgtactgatc    120
gcgaaaattt tatatttgca ttatgaaaag aagattccgc ttgagaagat ggtggtgctg    180
acatttacga ataaggcagc aggagagatt attgaacgtc tgaagaaaaa agaaccggga    240
cttacggaag aacaggtgca gttttttgga acattccaca gtgttgccat gcggatgctg    300
```

-continued

```
aaaaatacac tgttacagac aaaagcagag aatggagaaa tagctcatac agtggaaaat      360
agcagcatgg caccggaaga atggacttcg gagtttgaaa ttatagatcc ggacgaggaa      420
caggaactgg cgctttatct gattgcagaa tatagtctga aagtaaagta taaaaaccgt      480
ttgaaaaaaa gactggagca ggaatatcca aattataagg ctggaaaagt aaccagccgc      540
tataaggatg aactgtttcg gttatatcct cttttaaaga aggaaaagaa gaaagagaat      600
aaaatgagct tttccgatct gctggaagag gggacaagac ttctgaaaat ggggaaaaat      660
tctcggccag aatggattat tgtggatgaa gtacaggaca gtgaccggtc acagctggaa      720
tttctggaag cattaaaagg accggagacg aaaatctttg cagtaggaga tccaaatcag      780
gtgatctata gtttccgcgg gacaactcag aatatgtttt tcctgttaaa gaacaggttt      840
caggcaaaag aactttcact tccggttaat taccgatcga atgcatccat tctggaggcg      900
gcaaaccgtt tccttcaatt tggcggaaag attcaaggca gtaatgaatg cggggagaag      960
attcagataa ggaatcatta tgatccgttt caggaagcaa tgtatctggc agacaagatc     1020
tggacacttc atcaggaagg gaaggaatac agggatattg cagtatttta caggctgcaa     1080
aaacaggcag aaatcctgga aaagatgttt gcagaacaga atattccata tgaagtatcg     1140
gtgaaaaagt cgtggaaaga tattcctgta ttgaactggc ttatgtatgt cttaagattt     1200
gcgacgcatc cggacgatat acaggcggga atgcaggtat tgatggataa aaggttcgga     1260
gacaaatgca caaaaaagaa agcagaagac attataaaga atcacaagac agagaaatct     1320
gatatatata agaatatgat gctgttttat acagagaaag aagtattgtc aggagaagat     1380
atatttgatt cgcttggatt gaaagaagca ctgcacccta cctctgcaga ttatcagcaa     1440
gatgcaaagc aggtattgga ttttctgaat cagatctgta catatagcag ggaaaagaag     1500
ctgaatatgt cagacggaat ccgggaattc ctaaatggga tggcactcgg aacaatagaa     1560
agtccagagg atacgcaaga gtctgcggag aaggaagaag caggcggcag agtaaaactc     1620
atgacattac atgcatcgaa ggggctggaa tttgatacgg tattcattat cggagtaaat     1680
ccgggactgc tgccgatcag atgcagtagc tttgatcagg aagaggaaga acggagatta     1740
ttctttgtag ggatcacgcg tgcaagaaat cacctggaac tttcttatta cacgaatccg     1800
ggagaaccgg gggtattggg cagttacagt aattatctga aaatgatccc ggaggaatta     1860
cttgagtgga aagaaatacg cagtgatgaa gaaaagcgga caaatcttaa agaactaacg     1920
agaagggcaa aagaagaaat ccgaaaagca gaagcacaga agcagaaaa tgttcaggaa      1980 caaaaaacgg aatccgagaa aacagaaaat gttcaggaac aaaaagcgat acatcccaaa     2040
tatggaaccg gtattgtgac atcggaagac gatatgatgg tagaagtaga atttccaaat     2100
tacgaaagaa aacaatttat caaggcattt caggaggtcg agatgatcag gtaa           2154
```

<210> SEQ ID NO 50
<211> LENGTH: 2112
<212> TYPE: DNA
<213> ORGANISM: Dorea longicatena

<400> SEQUENCE: 50

```
atgggtagga agataaaaaa agtaataatg atagcagcgt ttggtatggt gaccggagga       60
cagattgctg atctgttacc ggaaggaaat gtgatgcagg tagaagcggg aagtcgaaag      120
cagattataa aagtaaaaaa taaagtaaaa gacagtaaga agaatttga caaggacaaa       180 gataacgcca aagataatga aaaggatctg gtagaagagg gagaaaaaga ggacagaaaa      240
```

-continued

```
gattcggagg aagatagaga gaaagacgat aagaaagatg acgggaaaga tccggagaag      300
gatgatgaaa aagatgacgg gaaagactca gagaaggatg acgagaaaga ggatggaaaa      360
gatccggaga aggatgacga gaaagaggat gggaaagact cggagaaaga tgacgagaaa      420
gatgacgaga aagatgacgg gaaagactta gagaaagacg atgaaaaaga gaatggaaaa      480
gatccggagg aagaagagat aaaaatgtat catgcggaat atgaggatcc ggatggtcag      540
aatggctatt atatcagtgc tccgaccgga aagatcacac atctgagtaa gaatggcgtg      600
accagatacc tttttgagaa tggagatggg gaaaggcagg aaggtacgct ggaaaaatta      660
aatgaatcct gccggttgaa acaattgaat tttgcagatg gaaggaatga actggaagta      720
tggatggaag atgaagaaca tcatcagatt gaaaattcag aaagcagaaa ggaattctgg      780
atagacagtg taagaccggt gatcggtctg gaagtgtccg gaggagcaga tatttggcac      840
aaagaggcag cagaggtagt ggtagaagct tctgacggga gcaatggaag ccagatcgcg      900
gaaattatct gtaaaacagg agaaaaaata gttgggaaaa gcagtaaagg agcagaaaaa      960
tttgtcatta cagaaagttc acagaatggg gaaagtaccc cggtaacaat tattgctaca     1020
gactatgcgg gaaatcagac ggtggtaacg gatcgggttt ttgttgacag agatgcaccg     1080
aaagcattga tacaaggagt ggaggattat acgattacca gtaaacctgt acaagtcagc     1140
tatctggcag aagaagagaa tgtaattcag acggtgcggg caaatatttt aaaagaagat     1200
atcgatggga aaaaggaaga aacagaaatc acagaatgaa aaacaaaaag caggaatgag     1260
tctggtgata caaaaaaaga aagtgtgcag acacttgcag aggacgggct gtataaactc     1320
cgaatgaatg taacagatat ggcagggaat gtcagtcatg ccgagagaca gctgattata     1380
gataaagaaa atcccgttat tgcacatgta gatgagttgg atggaaagta tttaaagaag     1440
tttagctgga attattctat cgaggaatcg attaaggatt ttacgaatta tacatatgta     1500
atgaaagtgg acgatgcatt ttatcggcca ggagaaaaaa ttgaaaaaga aggggtacat     1560
gtactgacaa ttgaagcttt tgattcagca ggaaataaag gagaagcaaa agcgaggttt     1620
accatcgatc atacaccgcc ggtgatcgag tttgagggga tagaagatgg agaaaaatat     1680
gaaaaagaaa aaacatttta tgtcagaaca gagaatctgg aagatcagat tgaatacatt     1740
aaaattaatg ggaaaaaaca aaacaggaaa aaacagaaga agggatatga aattcagcta     1800
aatgaggcaa aaaattatga aatagaggta aaagcaaaag attttgcggg aaaatgaaaaa     1860 gtttcacaga taggatttga aatatacgag gaaaagagtt tgtggcagaa aattgtggaa     1920
ccggtcagaa aatatatttt ttatggaaat gaaaaggtaa tacaggatga aaaaatggtc     1980
aaggaagata aaaggaagg aaaaaagaag aacataattt tatgggagag agctgtttta     2040
tttggcgcat tgattgttgt aggaatatgg aaacgggaaa aagtgaaaga aatctggaaa     2100
aatctttcat aa                                                          2112
```

```
<210> SEQ ID NO 51
<211> LENGTH: 1995
<212> TYPE: DNA
<213> ORGANISM: Dorea longicatena

<400> SEQUENCE: 51
```

```
atgaaaagta tgttgaaaaa aatatttttt aaactgctgg gagaaaggaa aaaggattac       60
ataagagtta ttttaagtgg aatcttctgt atatcggtcg tatttttttc tacgtctgtt      120
ggcagcagtc ttgtttatat atcaacggga cgacgggcac ctatgacaga attagtaatg      180
gaagttgaaa agaattttat tttgccgtat gtgttactga tctttctcat gattttaatt      240
```

-continued

```
atactcggat atattcgtaa acgatccagc gattatgcaa tgctcaatat actgggaatc       300
aaaaggaaac acagatatat gtatattggc tgtgaatatc tcggaatcat tttaggatca       360
attgcaggag gattgattct tggaatattg gaagcaatga tcgtaaaaaa gatactggaa       420
aatatttttc agaattatgt aagcaatata tatttgggaa tatcaccgtt aattctcaca       480
ctaattatca gcgtaatcat gtttggaatc ggcttcgcct tttgtgatca gtatattgcc       540
tgtatcggaa ttgaccatat agtatcggga ggaagtaatc ataacagaac aagtaagaat       600
acattgctat tttgtcttat aggagttgca gtatttattc ttacattagt ttctattgtt       660
acatattggg gacaaatcgg atatacgatt ccgacagctc tgggaatcat aacggcagtt       720
atttttactt tatttggctg tagattatat cttgaaaaat taagaaaaca aaagaataaa       780
tattataaaa aaatcctttg gctcgataac tggtacgatc agttttttcag tcatgctaat       840 atcagttata ttgtcagtgc ttttctgatt gttattctgt ttggatttaa tattgtattg       900
gtagacaatc ttcctgtaaa gcagccggaa aattatccgt atgacatagt ctggggtgcc       960
aatacaaaag ataaagcatt tatcgaaaag ttaaaagaaa agtataatgt tcagacagaa      1020
ttcattccat ctatcagagt gacttcagga aactgtgcag aacatactgg aatttctgca      1080
acagaatata aacgccttac aggaaagcag gttcatttaa aaaataatga aatatacgtt      1140
atataccaat gggaccgaag cgaatatgga acaattggtc tggatttcgg aaagctgaaa      1200
ccaagattat acaccggatg cgctactgca gatatctgga tttatactgc gagaacatta      1260
ccaggtaata aatttacaag aaaatataca attaagggaa atgacagaag aatcattacc      1320
gggaatttta aaacaagggt tttgagtacc agcaatatga atacggatgt gtttgaagat      1380
ataattgtat tttcggatca tgaatatgat aagatcagtc aaaaagccaa agggtcaaac      1440
cttacagtat taatgaacgt agcacagaat tatgatgctg ttgtaaataa aatagctaat      1500
tatgcagcaa acattcaca gattaatttc tttgattatc atgacggaaa tctgatttat      1560
gataaaaaac cgtgcacaat agaaaatcag gaaaaccgaa tgttaaatgt aagtgcgatg      1620
ttgattgata tgcttgtgtt atttatcagc ataatctttta tcttactaga gaaaatatcc      1680
agtgattacg aagcactgga atggaagtat ttattctatt accgtacagg aatgccggag      1740
aaaaaacgaa gagaaagtat ttataaagaa ataaccatga catccaaagt tgccttgata      1800
acaggaatat ttatagcagc agtaatgata ttggtgaaaa tattatataa gaaaatgccg      1860
gtatattgga caaagattta tctggcagaa gccgcagtaa tgattatagg tatgaccgct      1920
attatcatag taatcgtaag aattgcagca tggcgttcat ttaagcgcag tgagaggaga      1980
aataaggatg aataa                                                       1995
```

<210> SEQ ID NO 52
<211> LENGTH: 1974
<212> TYPE: DNA
<213> ORGANISM: Dorea longicatena

<400> SEQUENCE: 52

```
atgctgcata aataattta caaaaatttt aaaagcaata tacggaaata tattttattt        60
tttgtcagta acattatagc cgtagcagaa ttatttatct tttgggggatt gaatgatgtt       120 gtagtgcggg cagttacaga accttcgatt atgatgggaa taaaaagtga ttttatgata       180
gcggttggat taataactgt tgttacaata cttttgatgg tattttctat gcgctattat       240
attaaactcc gggcaaaaga ttatggaact tttattatgc ttgggatgaa aaagaagatg        300
```

-continued

```
tcttatatgc ttctttttgc ggaatacatt ataggatgta taggttcact tttaattggt      360
attttgttag gaaatctgct cctatatgga attttatatt gcttaaatca atacaatcct      420
cagattatta cattacaaaa agtggatccg gtcgtatata aaaatacaat tcttttgtgt      480
ctgggagtta tgcttggaat ctttataatt ctcctggtgt ggatggacgg aagaaattta      540
agctctttaa tgatgaaaga ggaaataaag gaaaaacgtc ccgtcagttc aaaatggctg      600
ttgtttacag tgttagggat tgtatttata atacttgcaa ttaaacaata taagccagga      660
acatggggat attattttgc acatatatat tttctgatag gcggaattct tattatcact      720
ttcagtggtg catttattct tgaacaggcg aaaaaagaac ctttttactt tcggtatgca      780
ttgaaaatca atcaacttga tagtaaatat caaagtaata tattaattat tctgatgtta      840
tttgtaatac atttttttgt tctttcttat atcggtacac aaatagtaga gattctgcct      900
cttgacaaga caaatagtaa ttatccttat gatataatct ggatggcacg ccagaacgat      960
gaaaaataca gtgaaaaaat agctgaaaaa tataatggga cagttaaaca tattccgatg     1020
atccgggcaa caatgtttta ttcacaggaa gaaattggaa tatctgaatc cacatataaa     1080
gaactaacag ggaaggctta tggtttgtct gggaaagaaa ttgttatagg aattgaggac     1140
cagaattatc aaagggaaga aaagtaact gataaggttc tttatgattt atttggatgg     1200
ctgtatattg gtaaatttaa tccgaataaa aaggaatttg aatcttccaa tatttttaaaa     1260 gatgcgaatt atcagtatag gataaaagaa attcatacac aaaacgtatt tggaaaattc     1320
gtaccagaag atgccggtga aggttgtgaa gatacagtta tattttcgga tgaatatttt     1380
gataaacaat gggaaaaaca ggcagcagat gatgaagaag tttcaatgtt agaagcattt     1440
tcttttccaa aaacaaaaga gcagatggcc tggaaagaga taaaagatca tgcagataaa     1500
gagggaatta ctgtatttca accagatgac agtcattcgc cacatgctat atgctatgat     1560
aagactgtgt ttttaaaaga gcagaaagca agtaatatat ttttactttt tagcaagctg     1620
tttattctga taacacttt gattagtggt actttttatta tggttgttaa aaatctggcc     1680
gaaatgtctt cttatcaaag acgttatgaa ttttttcatt ctatgggcat gaaacaaaaa     1740
gagcaaaaga agatcttaag ttttgagatt tgcagcgtag caaatatagc attaggtaca     1800
ggtatttgtt tagctcttt atatgtaatg acttatttac attggtatga tgcgatgggt     1860
gaaaaaatat caaccacttt ttggagctac tggcttaagc tcgttggaat ttatataatt     1920
attcagatag ttgtgcagaa attatttgta aggtatgtga acaaaagaat ttag           1974
```

<210> SEQ ID NO 53
<211> LENGTH: 1917
<212> TYPE: DNA
<213> ORGANISM: Dorea longicatena

<400> SEQUENCE: 53

```
atgcttattt cgtataataa aatatggaaa gataaagtac aatcgccatg ggctgttatg       60
aaggtagagg attcaccgaa ttatttgggg agtaaagaca ttattgaatt gcaaaatgga      120
aaagatgttt ctcaaaaaat acaaatggtt agtgaaaact taactggtgt agcaataaaa      180
ttcgcaaatg tggataaaaa agcaacaggt attattgaga ttgaattatt ggatccgaat      240
agtaaattag ttgaaagatg gaagttggat tgtgcgatcc ttcaaacaga cggatattgt      300
aatgtacaat tgaaaaaaga tataaaggtc aaagtcggcg aaaaatatga gttaattatt      360
agacctagat tacaagatgg aaaaggatta gcacttgaat tatcaagacc atcagtgata      420
acaggtcatg ccaatgtaaa aggtgaaaaa aatatatcgt tgtctttggc gtataagttg      480
```

-continued

```
tacgatggcg acggaagtgc attaaaatat ttaattgtcg caattattat tacagcactt      540
gtagcaatgc ttggaagctt tttgatgatg aaaaagggaa aaatcgcaag tacatttgtc      600
gtaatgacat ttttattgg atgcatttat attttgtat taccaccgtt tgctgtaccg       660
gatgaaagtg cccatttgt tacggtatat tctaaaagta ataaattgct aggaaaagaa      720
gttgctgata aagagggaaa agtaattgct gattctaata tgggattata ttttattaga     780
gaagagtatc ctacaaaaga gtcttatatt agatttgtaa aaggagcatt aggaaaaaat     840
tcagatacta ttactactaa agaaggattg gcgaatcctt taaatgtaaa agcgataggt     900
tatattcctc agattatagg agtgagtatt gcaagaatac tgggaggatc tggagaacaa     960
attttattga taggaagatt atttgctctt ttgtggtatt gttttgttat gtattttgca    1020
atacgaatat ttccgtttaa taaaatgatt attttttgcag taggattatt gccaatgaca   1080
atacaacaag tgtgttcgtt tagttatgat tcgatttat taggtttatg cttttttctta    1140 atatcataca ttttatggtt aatttatact aaggagagtg tggagataaa ggatgttcta    1200
atattagttt gtgctattag tggaattgta atgattaaat atatatatat accaataata    1260
gggctgcttt tatttgtccc aaaacaaaag tttaattta gagttaacag aaaaaaaata    1320
gcattgtata tgtttggaat gctttcaata gttgaaatag tttcaaaagt gacattgatt   1380
acagaagcag cagaaaaaaa tatgcaaatt agatcggatg gattatacaa atattcaata   1440
ggatatataa tgagtaattt gggtgataca ttggtagtag ttgttcgaac aattttttgaa  1500 aagctctctt ttttttgttga gtcgatgatt gccaatccat taggttgggt agatatacag   1560
gtcccgaaca ttattgttat ggggttcgct attgtttga tttttagtgc aattccaaat    1620
catatatcaa aaaaaacgac taaaaagcta atgataatgt caggggttat agttatatta    1680
gttagtggat tggtcttggc tgcgatgtta attagttata cctatgttgg atcagatatt   1740
attcttgggg tacaaggaag atatttcctt cccgtttttac cgttgatatt gttaattatt   1800
caaggaagta agaatattgt tgtaaaagat agtatagaga cagaattgat acttgctatt   1860
acgggattgc agttatatac aatttggtca atagtatcag ttgtgattac aagatag      1917
```

<210> SEQ ID NO 54
<211> LENGTH: 1752
<212> TYPE: DNA
<213> ORGANISM: Dorea longicatena

<400> SEQUENCE: 54

```
atggacaaag aaaaagtgat caaaaaaata aaacagggtg caccggctac ctcggcgatt       60
gtagttgcag cctgtatcgg ggtgtcatta agcggctatc aggcaccggt ttatgaagct      120
caggcacaga cgaaagagac aaagacaacg gatgccgagg aagcgaagaa gacagaaagc      180
aaggcaaaag gttctttga tctggcggac ggaatctata aggaacagg aaccggttat       240 gccggcgagg tgactgttgc ggtaacgatc aaagataaac agattacggc aatcgatatc      300
ttaagttctt cggacgatgc agcgttcttt aaccgtgcaa aagcagtgat agacaggatc     360
attgcaggac agacgctgga tgtggatgtg gtgtctggcg caacatttag ctctaatggc    420
attatcagtg cggtgaagaa tgcattgaca ggagaaaaag acagtggaga gacgggagag    480
tcccagtccg gaaatgcagc ggcacaggga agtgcactgt cactggctga tgtacaggat    540
gcggcagcgt ataaagatgg aacctattat ggaacaggaa ccggattcgg gggaactttg    600
aaagtcaagg ttgtgatcag cggaggaaag attgcgtcta ttgaggttgt ggagaatcat   660
```

-continued

```
gatgacagca gttatctgaa tcgtgcaaaa gcattgatcg gcaatattat ttcgtcgcag    720
agtacaaatg tagatgtaat ctccggggcg acttacagtt cgaacggaat taagagtgca    780
gtaagagatg cactccgtca ggctgcagta agcggtaatt cacagtctgt gaatgcgaag    840
acggaagata cttctaagac agaagacaat acgactgtca aaggcaattt cccgtataaa    900
gaaggtattt attacggaac ggcagaaggg tataacggtg agatagaagt agcggtggtt    960
cttcaggata aatcaatcaa ggcagtactc gtaacaaaga atcatgatga tgaaaaattc   1020
tttaaccgtg caatggatgt agtaaaaaat attatgaaaa aacagagtac ggatgtggac   1080
gtagtatccg gagcaactta cagttcaaat ggtctcataa atgcagtgaa gaatgcatta   1140
aaagaagcag aaaaggtaac aaacggacag acaacggagc cggataagga agaagctgat   1200
acttcagaac ttgaaaaagc gatgaaagaa gcagaagaac tgaaacaaga ggattataca   1260
gaagcaacct atgcggttct taagaccaga atggaagacg cacagaagct gcttgatgca   1320
gataagacag agatcagtca ggaagatgtg gatcaggctc ttgagaatct gaaccaggca   1380
ctggcactgc tggagaaaaa agatgatggc gaagatgata ctacagtata taaaaatggt   1440
atctatgaag gacgtgcgct gtgcagacca gatgaagatg aagatttcac ggcttataat   1500
ctgacattga aagtgacagt gcgggatgac aagattgttg ctgttactga tgtaaaaggg   1560
gacggagatt catcgaatga cagatatatc cttcgcgctg caaacggaac accgaataaa   1620
aaaggtgtga caagccagct gatcgagaaa ggtaatacag aaggaattga tgcagtatcg   1680
ggtgcaacct gtacttcaaa agcaatcctg gatgcatgtg agaacgcctt gctttctgca   1740
aaaagacagt aa                                                        1752
```

<210> SEQ ID NO 55
<211> LENGTH: 1671
<212> TYPE: DNA
<213> ORGANISM: Dorea longicatena

<400> SEQUENCE: 55

```
atgtctgaac aacgtaaaaa aaatgagaag aatttcctcg tacagggatc gattctggcg     60
atagcaggag ttatcacaaa gctgatcgga gcattttacc gcattccgct gcttaatatt    120
atcggaacgg aaggaaacgg atactattcc gtagcgttct caatctattc cgtggctttg    180
atgttgactt cttacagcct cccttttggca gtatcaaaac tggtatccgc aagagtcgcc    240
gtaggagaat acaaaaatgc acataagatt tttcgtggag ccataacatt tgcattgctc    300
gccggtggtt ttgtagctct gcttgtattc tttggagctg attttattgc aacgacgatc    360
atgcatctgg atatgagtgc atatgcgctc cgtgtattgg caccgtgtat tctgatcgtt    420
gcattacttg gagtttttga gaggatttttt cagggaatcg gttccatggt cccgactgca    480
atttcacagg ttattgaaca gatcataaat gcagttgtat ctattgcggg agcctatgta    540
ttattaaatg caggaaaagc cgtaggaaaa acgagaggtg acaaatcttt cggtccggca    600
tttgccgcag ccggaggaac acttggtact gttcttggag cattcagtgc attagtattt    660
gttggtcttg tatttcttgc atataacaaa gtcttcaaac gcaaaatgag acgtgaccat    720
tcgaaaaaac gcgaaagcta taagacggta tacaaagttc tgtttgtaac gatcgcaccg    780 gttatttttaa gtgcaactgt atataatatc agtgacttcg tagatacggc gctttttaat    840
aacgtaatgg ctgcacaggg gttcagtaaa aaagaatatg caagtctttt gggaatcttt    900
cagggacagt acagtacaat gatcaatgta ccgctttcta tttccagtgc actggcggca    960
tctctggtgc caagtctggt tgcaacagta cagactggta gcagaaaaca ggtacataat   1020
```

-continued

```
aagatcaata cggtaagccg ttttaatatg gtgatcgcaa ttccatgtgc ggttggtttt      1080
attacgctgg caaaaccaat cctgaatatg ttatattttta ctcaggataa tacaacggct     1140
gcactgatgc ttcagatggg agctctttcg gttgtattct tctgtctgtc aactgttacc      1200
aactctgtat tacagggcct tgatgacatg atgactccgg taaagaatgc tgcaatttcc      1260
ctggtgatcc atattgtgac attgttcctg atgctggtag tattgaaatg gaatatctat       1320
gccgtagtat taagtaagat tattttctcc ggagcaatct gtgtattgaa cgcaaaagca      1380
ctgcgtgaca ggattggata tgtgcaggaa aagaagaaga cttttgtaat ccctgcactg       1440
gcttcactga tcatgggtgt gatcgctgtt ttggtccacc tgattttcga attgttcgca      1500
ggcccatata ttgcgacgat catcgcactt cttgcagcag tggtaactta tggtgtggct       1560
attgttgtac ttggaggaat tacagaagaa gaattacttg gcatgccaaa aggagctacc      1620
cttgtgacat tatgccgtag attacatttg ataaaagggg aatacaggta a               1671
```

```
<210> SEQ ID NO 56
<211> LENGTH: 1659
<212> TYPE: DNA
<213> ORGANISM: Dorea longicatena

<400> SEQUENCE: 56
```

```
atgactgcag gaatgttggc tatgatactt gcgatgggaa tgacagcgtg tgcaaatgca        60
gacacgaaag agaagagcac aacgaagaaa gaacaggttt cagagtctga tgaaaaaaaa       120
gaacagaaaa tgtcagataa tgaagcaaat gtaatgaatg aaaaacagaa aaaaatctat       180
gagaagatca aaaaaacata caatgcagaa gagcagcaga aaatagcgga cgaactggaa       240
aagaaaaaag aatctcagga gtatacactg agtaatatgc tgatcgaata caatcctttt       300
ggaaccaata cacagtcatt gtatgtttat tttgagacag attcggcggt gaaagtttct       360
tatacgattc atgtaaagga ggatgatatt gccgacttta gcagaaatgt atatcaggat       420
gaagagtatc agaaagagca tgaatttcag gtgatcggtc tgatcccgga tacggagaat       480
acgattacat tctatataac gaatgaagac ggttctacgg atacgaagga aatcgtatat       540
gagatgggaa gtctgtatgg agaagaggca gtacagcttg tacggatgt aaaacaaagt        600 gcggacaagt tagaagacgg gctgtatgtg gtacttggaa atgacagtcc ttctatggat       660
tttatgtatt attatgacaa taacggagtc ttaagaggag aagttcctct tctgggatac      720
cgaagtcaca ggcttatctt tgacgagaat tcgatgtatt acagtatttc cgaaaagaag      780
atggcacagg tgaaccgtct tgggcaggta acaaaggtat atgatcttgg caattacaaa      840
ttgcaccatg attatgtgtt tgatgaaaat ggaaatatgt tgattcttgc aactgatacg      900
acgcaggaca gcgtggaaga tatcgtgttg aaactggatg taaattccgg tgaggtgaca      960
gaggtactgg atctgggaga tctgtttggc gaatataaaa agacctgtgt gaaaaattct     1020
tccgatgaac tggactggat gcatatcaac acgattcagt atataggaaa tgggtcagta     1080
cttttaagtt caagagagac gtcaacaatc atcaaagtag ataatatcta tgacgggccg     1140
gtggtttctt atatgatcgg tgaaaaagat ttctggaaag atacttctta tgtaagtctt     1200
ctgctgaata agaaaggaga ttttacaata caggtggcc agcatacgat cacatatgag      1260
acagatgaaa gccttgcgga cgggcagtat tatctgtata tgtttgataa taatattgga     1320
atcagtgaga caagaccgga ttatgactgg tcgtcgatag gtctgaaagt aagttctgcg      1380
gttgacggaa agaattccaa gtattacaaa tatctggtgg atgaaaatga aggtacattt     1440
```

-continued

```
gaacttgtag attcgtttaa agtaccttat tccggatatg tcagcagtgc gcaggaaaca    1500
ggagataatg tacttgtaga ttcgggatta aaggggactt ttacagagta tgatgcagat    1560
cataaagcaa ttgtaactta taagatggat tatgagaaat ttatttatcg tgtattcaaa    1620
tacaagtttg atggattta ttttgaaaaa agtgaataa                           1659

<210> SEQ ID NO 57
<211> LENGTH: 1632
<212> TYPE: DNA
<213> ORGANISM: Dorea longicatena

<400> SEQUENCE: 57
atgagaaagg ggctttctg gcattatctg gagaaaagtg aattaagacc ggtggtaagg      60
gaagaatata aagaaccttg cagcagcctg tatgtacggg ataaaaagac actttatt    120 gaagtgacat attataaaaa acggatcaat tttgaagtat tccatgcgct gacagatgga    180
accggtgcaa cagaattcct aagagaactg gtgaagaatt atctgtatct gatccacgaa    240
gaagatctgg agccggtgga gctgtcaaac cagtatctga cggtaaaaga tcaggaagat    300
gacagtttca gccgatatta tgatccggat tttccaagaa agaaaaagaa aaagatcagg    360
gcggttcaga tcaaaaaggg tggaaaagga tatgaagagc tacagatcaa tgaagcttcc    420
atgtcggtaa aagaactgct ggggattgcc agagaaaaga aagtttccat gtcggtgctc    480
ctgacggctg catttatctg tgcaatccat gaagaaatga gccggatgca ggagaagaag    540
ccggttatcc tgatggttcc ggtgaattta agaaagattt ttccatcgga ttcgatgctg    600
aatttcttcg gttatataga gccggggtat cagttcggag ggggaaaaga ttcttttgaa    660
gatgtactgg aggcagtaaa gttatatttt caggagaatc tgtccaaaga gcatatggca    720
ggacggatga atgaactgat tgcaatagaa aagcataaga tcttaaaatg ggcaccgctg    780
gaactgaaaa accgctgtat ccgtgcgggt gccaagatgg cggagcagga agtaaccgcc    840
gtgctttcga acatgagtgt ggtaaagatg ccggaagatt atgcgcaata tattgaaaag    900
tttggcgtgt atacaagtac gaaccgaaca gaattatgta tctgttcttt tcaagatacg    960
ttatcacttg gctttacatc gagatacgac agcacgaata tccagcggaa tttctaccgg   1020
atattgaaag aactgggggc ttcggtcaaa gtggcagaac cggatttccc ggaggatgca   1080
agaccaaatt atgaaggaaa gaaagtatta cagatctta cattttgctg tattgcagcg   1140
atcgtgatca gtatgatgac ggatatcatt atatcgcccg gcgtgcactg gtcggtgttc   1200
gtggcagctg ggtgtgcgac gatgtggctt acaatggcag tcggttatgt gaaacggttc   1260
aatctgctga agaatgcggc atggcagctt ctgatcatgt cagggatctg tgtattgtgg   1320
gatctcggaa ccggatggag aggctggtct gtgaatatcg gaattccgga tatctgcctg   1380
ctgatccagg ttgtaatgtt gatcatatca ggaatacgtt ccctgtcacc gagagaatat   1440
atgatctatt atgtgatggc cgctgtctat tcgatgattc ttccattgat tcttttagtg   1500
acaggagtaa tccattacaa gactccatcg gttatctgta tcgggtgcag ttttctgctg   1560
ttgatcggat taattttatt caaacgaaaa gaatttaaag aagaaatgca taaaaaattc   1620
cacgttggct ga                                                       1632

<210> SEQ ID NO 58
<211> LENGTH: 1623
<212> TYPE: DNA
<213> ORGANISM: Dorea longicatena

<400> SEQUENCE: 58
```

```
atggtattaa taaaaggtat gaggtgtact atggggttgt taaaactggt gatcgtagat       60
gatgagccga tcctgctgga gggtctggta aagacgtatg actggaacgg tatgggatat      120
gaggtggttg gttttgcgca gagcggagag caggcgttaa aggtaatacg tgaaaaaaaa      180
ccacacgtag tgctgacaga catcaggatg aaacagattt ccggacttat ggtaatggaa      240
gaaatcaaga aagagaaccc ggaatgtcag ttcgtggtat taagtgcata cagggatttt      300
gaatatgcga agaaggcatg tgatctgggg gcattcgcat atcttctgaa gccgattgaa      360
gatgaaaaat tacaggcgac gatgacagat gtcggtaaaa tctgtgaaga tcagatcaga      420
aatgaggaaa agtatgaccg ctgggagaga cttctgaaaa aggacggaga tggatttttg      480
caggttgtcg tgcaaaaata tgtccagaac cggctgccgg aagaaaaagt agatgaagtc      540
ttccatacgc tgcaggatgt catgaaggaa ggagaccggt ttattacagt atatgcagat      600
cttgatctgg cctataagat taccaatgaa ctggaatatg aagcctcgag attttccatg      660
gtcagaatga ttgaagaaaa gatcgcagag agattcacat actggaaatt cgaaagtgaa      720
gaaggacatc gtacatttat tgtaaagacg caggagaaca cagcggtaca tgagctgaaa      780
gaactactgg aagaggtaaa aaaagaagag aacagcccgg ttattgcagc aatatccaaa      840
ccatataaag ggatccgcgg aatcagaaga agtttcgaag aagcgcagag attgttcgct      900
gttacaaatg catccggagc gggagtattt acaatcccgg agactgttga agaaaaagag      960
gaaagcccat atccggcgga ggcagagatg atggtggtca acagcgtgcg gaagaacgac     1020
gccgtacagt taaagcaggc atttgtacat tttatttacc aactgccaca cagagaagaa     1080
ctgcaatgcc agtatatgca caagatcatg gtaaagacag aattcatgtt aaaagacagt     1140
tacgggatgg acgaatcact gaatcagcaa tttgaaaatt attattcgaa tatgagaaac     1200
ttaaaggcgg caaaagcagt ggatgtctgt tacaagattc tgggaactgc tattgaaaaa     1260
agactggaaa atgcagaaaa gaaagagaat aagggatcaa aagaatacat tgcagcggct     1320
gtggcatata tagatgaaca tctggataat gaagatcttt cgattgtatc agtggcgaca     1380
catgtatatc tgaatccggt atattttgga cgggtattca agaataccct tcatatgaca     1440
ttcaaacaat atctgctgca gcgtagaatg gagctggcaa agagactgct ggaagacgga     1500
agaaccagca tcggtaatat ctgcgagcag gtcggaatca gtaatccatc ctattttcg     1560 catttgttta aagaatatac aggacagctt ccgagagatt acaaaaggga atatgaagta     1620
tga                                                                   1623
```

<210> SEQ ID NO 59
<211> LENGTH: 1542
<212> TYPE: DNA
<213> ORGANISM: Dorea longicatena

<400> SEQUENCE: 59

```
atggatagtc gttcacgtac agaatattcg atactaaata taatagcagg agttggggga       60
tatattgtaa atactattct tggttttata tgcagaatgg tgtttgtaaa gtgtttggca      120
gcggattatt taggagtaaa cgggttgttt acaaatattc ttacaatgct ttctttggca      180
gagctaggaa taggcggtgc aatagtttat gcactgtata aaccattagc agaaaatgat      240
gaaagaaaaa tagcatcatt ggtaaaggta tatggaacgg catataaagt tataggttgt      300
gttattggga ataggaat   atgtctaatg ccgtttttaa atataattat tacggaacag      360
ccaaatattt ctgaaagtat ttatttattg tatattttta atttgttcaa cacagtaata      420
```

-continued

```
acatatttct atagttatag aagttcgttg ctaatagctg ctcaacaaaa ttatattgtg       480
gttgcaacga attatatagt aactattta caaagcattt tgcaaatggt ggcattatta       540
gcgacgcata attatttggt gtatcttact attcagacga taggaacatt ggcatacaat       600
tttggggtgt cgcatatagc aacaaagcgt ttcccatgta ttatgtcaaa agatattgaa       660
ccgttgccag ttgatgaaaa aaaggcatta tttaaaaata taaaggatct tacatattac       720
aagatttctg gattattagt taatagcact gataatatat taattacttt ttttaaggga       780
ttggctacaa ctggagtcgc atcaaattac acattgttaa caaatacaat aaattcctta       840
ttaggtcaaa ttttttaatag tttaactgca agtattggaa accataatgc aactgaaacg       900
gagaaaaaaa aatatgagat gttcagcttc atgaatttaa tgaatttctg gattttttggc       960 tgggcgacat taggaattat tttttgttct tcagatgttg taagattgtg ctttggcgag      1020
aaatacgttt tgtcaaaaga aattccattt gtattagcat taaatttta tactgtaggg      1080 atgatgaatg ccgtatggac gtataaacat acaatgggct tatttagata tggaagattt      1140
ttgcagatta ttacaggagt gcttaatatt attttctcaa tagtattagg acactattgg      1200
ggattgtttg gaattttatt tgccacattt atagcgcgag ctatgacaaa tttatggtat      1260
gatccgtatg caatatttat tcatggattt cataaatcac cattacagta tttaaaaaag      1320
tatatttatt ttattattgt gttattaata tctgcgggtg gatgttggct ttcatttaaa      1380
cttattaaag gtggaattct agcacgtgta atggaagaaa tagtattgtg tagtgtagtt      1440
acgaatttag ttttttatat atttttttaga aaatcagaag aatttattac attaagaaag      1500
attattaaaa atataataaa tttgataatt aaaaaatcgt ga                         1542
```

<210> SEQ ID NO 60
<211> LENGTH: 1542
<212> TYPE: DNA
<213> ORGANISM: Dorea longicatena

<400> SEQUENCE: 60

```
atgttgcaac aaaaagaaag ttatgatgtg ttgcggctga ttgagcatgg acaattatgc        60
tatatcagtt ccgaaaatgt gcaggggaaa accctggaca gatacttaaa atatcatccg       120
gtaataaaaa aacgggagat attttttatta ttaaaagaga tagcaggaca actggcgtca       180
tttcacaggt gcaggggaaa tccttgttat caatatgtaa atccatatag tattgtcagg       240
tctgaagatg gaagaattta ttttctggat atgcagtcgg aagcaaacag aagcaagatg       300
atatttatgc aaagaagaga tatccgtgaa tatttttcttc cgccggacga aaagtattat       360
caacatgcca gtaaggaact ggatatgtat gggctgggaa aaacatttca atatattctg       420
gcatctgtgg aggcagaacc acgttttaac agacgagaag aatatcgtct tcagagaatt       480
atttcaaaag caatggggat aagatcaccc cattatctaa atgtatcaga aatccaaaag       540
caaatcccaa ggtatgaaga aaaagacaga gataaaattt tgaataataa ggggaaaaga       600
agaaaaaaag tgtgtataac agtagttttg tctattgttt tcggggggata tttgttcata       660 aatgcatggg aaaatgctga aaaagcaaac cagagagaga tgaaaagaac ggaatcttcc       720
aaatcagaag agaaaaaaag tgaaaaatcg gatgaccgga taaaaaagaa aatatatgaa       780
agagatgaag agtatctgga attggcactg gcatatttcc tgaatgtggg agatatgaaa       840
aaaagtctga aatgtctgaa tcaaatggag aatcagacgc tggcagttaa tctgaaaagg       900
cttatcaaag cgtatgaaaa acaaaaagtg ccggaagagg cagaaaaatt tgcagcaagt       960
cttgcttacc tggagaatga atggaaagaa agaagtatgc agtcggaaga gaagaaaaaa      1020
```

-continued

```
caggcaatac agtgcctgat aagagggtat ggattactgg atgataaaga aagttcagaa    1080 aaaagtgttga atctggtaga agaaggatta aagacagatt atctgaatga ttctgcgaag    1140
agagaactat tgcagtatca ggcgtctgca ttggaaaaag aagaaaagaa agaggaggca    1200
gcaaacatat atgcagagat attggaggat gagacggaac cgggtaagag agaagagctg    1260
tataaaaaga tggtacagtt gtatgaaact gcaggaagac gggatatggc aagcgataca    1320
tgcattcagg ggataaaaga gcttggagaa tcagaagagt tgaaattaac acatataaga    1380
ctgatatgtg cagatccggt tgtcaataga gatacgtgtg cactcaagat taaagaatat    1440
gtaacagaag atactgaact tttggaaaat gcagaattta agaaattaca aaaagaatat    1500
ggaattaagg cagaaggagg aaatatatgg gtaggaagat aa                       1542
```

<210> SEQ ID NO 61
<211> LENGTH: 4359
<212> TYPE: DNA
<213> ORGANISM: Eubacterium siraeum

<400> SEQUENCE: 61

```
atgacaaatg taaagaaatt tacagcaaaa gtgacagctt tactgctggc gctttcactg      60
gcactgctgt cagtaccgca ggtgagcttt actgtatttg ccgatgatga cctcggaagc     120
gtccgtgtta ttgtagaaaa cacaacgttt accgaagcgg tcagcggcgg taacgctcct     180
gcgtggacag gtaccaaggt cgacaagtgg gtatcgcttg acaagacctc aagtgcaatg     240
acctgcataa aggacgctat cgaaagctcc ggctttactc agaagggcgc agacgatggc     300
tacataagcg agatcgcagg ccttgcggcg tttgacggcg gctcgatgag cggctggatg     360
ggtacgctca acgactggtt tacaaacgaa ggcttcacag cctataccgt tgctaacggc     420
aagcttgcaa gcggcgatga gatccgtatg cagtacacta tggactgggg tgctgacctc     480
ggcagtgact ggagcggtac agatacatcg cttaaagcga taagcagcga ttacggcaca     540
ctttcccccg aattcagtgc aaagacctat aattatactc ttacagttcc tttcggcaca     600
aagagcatca atttccgtcc taccgcactg aacaagaatt tcaagacggt aagcaaaatc     660
ggcgacaaga cgctgagcct tacaaaaccg actgaaataa aggacggcga tattatcacc     720
gttactgtag gcgagggtgc aacagcaagc acttataagg taacaataaa ggagggtgca     780
agacccgccg cacgttttga cagctttgca cttttcggctt tctcgcttga cggctgggac     840
aatgacgctt tcgaccctga aaagctcgaa tatgatgtaa agataaagtc ttacagcaca     900
tcatctttct atatcaacag cggaaccaag ttcaacaagg acctgctgaa gtgctatgcg     960
gtatacaccg atataaacgg agttgcacag agaaacgaga taaagtccgg cagcttcaac    1020
agcatttcta atattccttt cggcttgact aagctgattt tagagctttg ctacattgac    1080
gatgaaagca taaagacgca gtatgtgttc aacataacac gtccctatga ctacactgcg    1140
gaaatcgcaa gcacaagcgg catcacgctt gttcctgccg gcagagagct gtatgcgaca    1200
aagtacaacg gctttgcaga gggaacggtt ttcagaaatg acgaaaatga caatgtgacc    1260
gatacgacag gcacaaacgc agaatgccac agctacacag cctatgtttt gggaggcacc    1320
gacagcgttg cacttactct caagggcaaa accgcaaacg ttcatttcag agcgaaggct    1380
gacggcgaat atacagagct taaagcggc gaaacaactc ccgcatattc cttcggcaag    1440
gacggcactg ttacagtatc aatagatgct gtttcggacg gcgattatct tacagacaag    1500
tttgatgatg cagacaagat aacaagctac aaaataaagc ttgtaaaggc tgacgtttct    1560
```

-continued

```
ataaagaacg tacactttac agagcttaaa agcgaacacg gcgatatgta tcccgcattc    1620
gacccgtcac ttctcagcta taatatagtt atagcaaatg acgcagaatt ccccacagta    1680
tatttcaagg ttgccaacgg ttgcacagtt aagataggca acgatgccgc aacagcagac    1740
gaaaacggcg tttacagcct tgttaccaag agcgcaaaca ctactgtaac ggtaacagac    1800
ggcactcttt cagaaagcta tactgtcaag gctacaaaga gaagcaagta tgacgtaccc    1860
gacaaggtcg ttgattatct ttgcatcaac agccagtaca ccaacgtttc ctacggtgta    1920
ggccccgagc agacgctcgc aggcactata aaatcactcg gtaacttcgg cggttatatc    1980
acatattact atgaaaaccc cgtaacagac gaccctcaa accccacggg ccttgacttc    2040
tacgcttacg gcaacagctt tgtaagcggc ggaagtgcgg ctgaaagcgg acaggtatat    2100
gtttctgagg acggcaaaac atggtatgcg ctcgcaggaa gtgagcattt tgaagatacg    2160
accatcaccg attacgaagt gacatacaaa aagacagccg acggtaaaac aagctggaca    2220
gacaatcagg gcaactcaaa cgacggctca aagcagacag gcagatgggt ttcacccagc    2280
gtttattata tgaacgatct tgcaaagggc gatactgtca cactcagagg cgttgttatc    2340
cccggtgttc agggcagtat acagggcgac agctctacag cttcctttgt aggcacgaca    2400
aggttcggct atgttgacta cttcaagaac ggcacgatag gcactaatgt aaacgcatac    2460
agcgaaaatg ccgaatcaaa cggtttcgac ttaaagtggg cggtagatga aaacggcaac    2520
cccgttacat tcaaaaacgg cgttcactat ataaagatac agacggcaag caacatctgg    2580
gcaggcatat tcaacgagaa atcgacagag gtttcttatg ttgtaagaac agctgcaaac    2640
gagcaagagg tcggcacgac agcgcttccc ggaaaaatag tcttaacaga cgcaaacggc    2700
aagacaataa aggaaatcac tcccgatgat aacggtgttt acgagataag cacaggcatc    2760
gaggaaagcg tgaacgtttc cgtatccggc gctgacgatg ataacatta tatcaacaat    2820 cagcgtgtag catccggcac agaggctaaa atcgcactta atcagtctga aataaaggtt    2880
gtcagaataa tcgttcagaa cggtgaaaaa cagcccgtat acgcttactt aaagctcgtt    2940
cccgatgatg taaaggcggc tgagcaggtc gaagaactta ttgacgctat aggcgatgta    3000
acgctcgaca gttatgacag catcacagcg gcaagagcgg cttatgacaa gctcagcgac    3060
aacgcaaaga cgcttgtagg aaactacgaa accttaacag ccgcagaaga agctctcgct    3120
aaggctgagg ctgacgttat aagcaatgcg ataaaggcaa tagacgcaat cggcaaggtg    3180
accgctgaca gcaaggataa gattgaaaat gcaaaggacg cttactcggc agttcccgag    3240
cgtttaagag ataaagtcac aaattcggat actcttgaca aggcaacaga aagatttgcc    3300
gttattaaca cgataaagca ggcaggcaca aagagtaagg agcacttcga cactgttctc    3360
ggtactcttg cggataacaa tatctacccc gttcagtcta tcggcggtga atggtcggtt    3420
atcgcactcg caagagcagg aaagctctct gccgacaagg cggcaaaata ctacagcgag    3480
ctttgtgaag cagtaaaggc taacggttca gacagacttt cggacagaaa gcctacggag    3540
aacgcaagag ttataatcgc tctgtcctca ctcggaaaga attccgcaga catcgcaggc    3600
cataacctgc tgagcggtct tgacgatatg gactatatca catcgcaggg tatcaatgcg    3660
gttatattct cactcatagc attcgacact acagattaca gcgcaaagac gcacgatgag    3720
cttatcgctt atattgttga caatatgacg ggcaagggct gggcgctcgc cggcgatacc    3780
gcagatgttg accttacggc tatggctata caggctctcg ctccctatgc ggctgacgag    3840
aaggtaaatg cggctataga cagcggtctt gagttccttg cagaatctct tgacgagaac    3900
gcaagatatg caaacggcag tgaaagcacc tcgcaggtac ttatcgcact tgccgctctc    3960
```

-continued

```
ggcatcgacc cgcttacaga ttcaagattc atcgttgacg gcatcacgct tatcgacgca    4020
cttgaaagct acgctacaga aaacggctac agccacacac tcggcggcga agaaaactat    4080
atggctaccg agcaggcggc actcgctctt acagcttatg agctttcaaa ggacggctct    4140
tcactttacg aaatgtctgc gaaggctgag ccgacagaac ccgaaaatcc cgatacgccc    4200
gcacagcccg gcgattctgt aaagcccggc gactgctcgg gcaagcccga agataaaaac    4260
gatcccataa atcccggtac aggcgtactt gtaacaggcg gtatggcagt tctcatctca    4320
ggcgcagtta tgcttatttc gaagaaaaag cgcaaataa                           4359
```

```
<210> SEQ ID NO 62
<211> LENGTH: 3681
<212> TYPE: DNA
<213> ORGANISM: Eubacterium siraeum

<400> SEQUENCE: 62
atgaacttca tgcaacttcg tgaaagacag ccgaaattcc ccgttaccgt aaagacggga     60
gagggagtag tagagcttat ctggaataaa attgaatatg ctgacggcta ccgtgtgttt    120
gcgtcgcctg tcggcaagaa tcattttgtc ggtgtaatta acgtcaaagg cactactgcc    180
gttatgaaaa aacgtgcaaa cggcgttcct atgcagtata aggtcaaggc gttcagaatt    240
gcggacggtc cggataattt tttcggagag tccgaaattg tcatagcgtg tccgcttgaa    300
actccacgca gacttaccgc aatagtcgga agcgacggta tatgcacatt gtcatggaga    360
tacaactcgc agtgtgacgg attcaagatc tatgccgatt cgaatgaaag cggaaaatac    420
tcttttgtgt gctacagcgg aaagaattcc tgcaggcttg acagcttcac aaaaagcggt    480
aaggtttcgt ttgttgtacg cagtttttata atgaccgggc atatggaaaa gctgggcgtt    540
tcttctgctc ccgccgaagc cgttattccc aaatccaaag gcgctaaggc ggtgcagttc    600
gaccattcga tgataagaaa aacggcaggt gattacaatg caaggcgctt tgccggcaag    660
gacggaaggc tttgcaacga tcaccataaa tgcaccgtga tgataggcgg cgatattacc    720
gtttcggctg aaatgcagaa aaatgcggca aagggaatgc ctgtttttga cgagactttt    780
tcatcgctcg gcggaatatt cggttcgttt gattttttccg ttgcgatgct tgatacggat    840
attaacgata aaaaggcgta tacattcgag gacagccgtg tcatcaactg cccgtcaacg    900
atcgccgacg ctgtatgcaa gagcggaata gacgcacttg ctgtcaacgc aggacttctg    960
cagagagcgc cgcagtcgct cgaaaagtat ccgcttacgg ttataaccga gaacgactgc   1020
acacagggcg gagaaaagtt cagcattgta aatatcaaca atataaatgt cggattcatt   1080
tctgcgacag tgaacaagga tatatcgcag tatgtgtcac agctcagaaa agcgggggca   1140
gagtacatat tcttcttctg ctcgtggaat gaacgtcata cgcctgcggt aaagcctaag   1200
tggagaaatc aggcggtaaa ggctgcggag agcggagcgg atataattat cggcaacgga   1260
cttaacgcca ttgccgaata tgatgttata gagtgcgcag acggaagacg tgttcctgtg   1320
gcttattcgc tcggctcgct tattcctgcc gatcctgcga cacgctttga aaagatagga   1380
gcgttacttt gcgtaaggct caagcgtgat accgcaacgg gcaaggtgaa taccgacctt   1440
tgcggataca ttccttatgc gttcaaggat tacggcacga aacacagagc ggtgcttttg   1500
tccgatgata atgcacgtta tttcgggctg tcggtatacg atacgcttaa aaagcaggtg   1560
gcaacggcac tcggcagtaa aatagagctt gcgagatatg cagagaagcc cgaacagcaa   1620
tcgtttgcac ttctcggctc ggcactgatt tcggagcttt tcaaggacga taacgatgta   1680
```

```
gaaaccgacc gttcacatct gttcatatca cagcttacta tgaacggaac acactgcgat    1740
gttgatgaga aatacttccg tgacggtgtt gtgcctcttt actacaacct ttccaaaggc    1800
tatgacgaat accttgcaga aaacaaggct gatgcgctta taacggacct ttattacgct    1860
gtttccacgc ctgtttacag gctaggagat tcgctttatt cgggcggaaa agcgtttata    1920
caatcacgtt tctacgagga aaacaaaagt cggctgaaac ggctcgatat aaaggatgaa    1980
gcggtgtgga agcctctgct tgacaagttc attgattcgg ttaccgctgt gtacgacagg    2040
gagaagatta tacttgtacg cataacggat cccaagctgt actatgtcaa cggacgatat    2100
gtacgctcga cagaccgctc gtgcaacttc aggctgcttc ttgatatgga gaactacttt    2160
ataagacgtg tttctccgaa ggtcatcgac atatcacggt tctatcccgg tgtgataaac    2220
aaaaggggaa gaagctatgc ggtatgccgt gacgagcatt tccgcaataa catttcgttg    2280
attgccaaaa gtatatgctc cggcaagaag gcaaactatg tcaactcgct tgcttacgac    2340
cctgaaatat ggctcacgga agtggctgaa aactttgata taataaaggc aggcaaggcg    2400
gacagcttct tcttcggcac aaacaatgcc gtagactact ttataagcag gctgagccgt    2460
gactttatct gtgcggaatt caaggatatt ctcaggctga aaaccagtga gcttatcacg    2520
ttcaatgaga taagggcttg ctatgatttc ggcagaaacg cagtgctgaa gcgggtttat    2580
aacggcatct gcgctatacg caagggcgat attacgaatg cggatattga tgagatcata    2640
aggctcggat tatatgcaca aagcgatctt gctaagacgt tggaatcatt ttacaacaaa    2700
aacgggatta tcagaaactg tgtgctttcg actaagaatc ttagcttcta tctcaagtgt    2760
gcaaggctgt ggatggcagg cacagacaag gatgcggtgg cacagcttgc ccgtagatat    2820
tacgaaaaac acagacctgt gattcttgat gtttttggca gggcagacgg cggtgacatt    2880
tcagagcttg cggacggtac ggtaaagggc agtgtgataa gcggttattc ggctctgacg    2940
gtgtgttcgg agaaacctgc ggatattgat ttgagctata ttgacgataa gtcggctgtt    3000
tttaccgagc ttacacgctc atactttgcg aatgcgcacg gcgactggct tttagtcgat    3060
ttttcggata ttgtaaagcc gatttacagg cataggtcgg cgtatgtcgc atcaattgat    3120
gaattatgct gttctatggc ttacagagca tttatgacgg acgatgaggt tttcgagccg    3180
ttcaaggaaa atgctgacag caaatttatc gaaaaagcga tttccgattt tgcaagaacc    3240
gtaaaagcaa aatatgggaa aaatataata ttaaggaaaa catatcttcc gcttaacaga    3300
ttggatatta caggaagaat ccgtcctttt gacgatacgg aatttatatc cgagaaagaa    3360
aatctgataa gcagagcaga ggagatattt gtaaatgcca cagactgcta tataattgac    3420
tatgaaagcc ggtatctgcc tgtgtgcgcc gataaaaacg ccgatatttc cgagcgtatg    3480
cttgaaagcg acttctataa ggaggcggca gctgccgttg accgcataat ttcgggaaca    3540
agcaaaaaga cggtaaacaa tgtggatata gtcggctatc ttgagcggtg cgagcgtatc    3600
agaaaggata accccgatat gtctgccgag ctttcccgtg agatattcgg cggtgcgtcg    3660
gagatattca tgacagaatg a                                              3681
```

```
<210> SEQ ID NO 63
<211> LENGTH: 3456
<212> TYPE: DNA
<213> ORGANISM: Eubacterium siraeum

<400> SEQUENCE: 63
atgctgaaag ctccgcaaaa cttgttcgct accgcttatg acggatctgt gcgatccgac      60
tggcagacgg tagagggcgc agacggctat atattgcagt tctataatgc agatgaaccg     120
```

```
gaaaagtgca ttaaaacacg ctatgcacag aataattcaa agctgatact tgggtttcgc        180
aacggcagaa agtatgttgt acgggtaaaa gcgttcagct atcgtgacgg gaaagaggta        240
tgcggtgaac tgtcacagcc ggcagaattt acgccgatgt gccatcacct taaagctcag        300
aatgtaatta cgatgaacaa gggtgaaacg tcgcagatag tatgggaatg cagaaataaa        360
gtgcctgccg ttacttttga atgcgatgac agcgatgtgg cgaccgtaac aaagggcgga        420
caggttaccg ctgtttcgga cggcgcggct gagataaagc tgacggctga tgacggtcag        480
acttttactg ttaagatagt tgtcggcagg gatatgtcac gttatccggc tacgggaaga        540
atcatgctct gcggcgatat aatgtgttcg cttgagcatc agcggaaagc cgctttgcgt        600
tcgcttgatt ttacagacgc attcggaacg cttaaagata cggtcagttc agccgattat        660
gctgtagcgg tgcttgaaac cacctgcttt gacggagcac cgtttgaata tgaaaagata        720
cgcacagaca gcggaagccc caattgcaat tctccgtcca ccttcataga cgcagtgaaa        780
aactgcggat tcaatgcact ggtaaccgct aataatcata actgtgatac agggcttgaa        840
gggcttcacg ctaccgtaca acgtatcaga aacagcggta tggcaaatat cggtacgctt        900
gacgatgaaa ctcatattgc cgatataaac ggcataaagg taggatttgt cgcagtaaat        960
tcaatatcaa acgggcttga gaaaaatata ccgcccgaaa ttatcgggaa atatgagcct       1020
gagcatttca gacagcttgt tgaaacgcta aaaaatgaag gtgcagagta tataatcgca       1080
tatcagcact ggggtgttat gaattccgtc actgtccgca attctcagat aaagacagct       1140
gaatatatgg cacagtgcgg cgtggatctt attatcggtt ctcatccgca cgttatgcag       1200
agggtcggta aaatacacac atccgccggc agagatgtga cgtgcttcta ttctttaggc       1260 aatctttttgt catcaatgaa agagcttcgt gaaaaccgtg agagtgtaat tgtaaatctg       1320
attctcacaa ggaccgaaag cggagtaaag tctgatatat cgtgcattcc gacgctttgc       1380
aaggatacat ccgacggata tacggtaagc gttcttgacg ggttgctgac acaaacagaa       1440
cagatttccg aagatcgcat aagagatata ctcggcaagg agggcgttat acgaaaacac       1500
cctaaattct tgctgcaagg ctcagccgtg ctgagaaata ttttccgtga cagcggcttt       1560
tcttatgacg ataccgctct tattctgtcg cccttatcgc ttgtaagcaa aaaaagtaat       1620
ctttcgggaa aagccggcag ccaaagaaat aaaattgata taaataaaaa tttcaaatcg       1680
tttttagacg gctcagacag cgattatatc gtaatcgacc tttatacagc ggcggctgtt       1740
tcgtgctaca agtacggcga cagcttctat acggcatcag gcagttttat ttcttccgat       1800
ttttacaatt ccaataaaga caggcttgaa aaaatttctc cgccttttga cgaaaaaaca       1860
gtaaaatctg cacttaaaga atatgcgaaa attgtcttgt caaaatatga taaggataaa       1920
atcatattag tgcgtttaaa attcagcaat atctgcgtaa aagaaaatca gctcagaaac       1980
ggtaaaagca gaaatgcgtt gaataagcgg ttgaggctgt atgaggatta tctgatttcg       2040
cttttacagc cggtggttat tgatgtttcc tgcaattatt ttatggcgtc aaaaagtgac       2100
aatatgatgt cctttgagcc gctttttctac gatgatgtaa gaatcaagct gaactcagcg       2160
gtaaaacgta tccgcaagga tacatatttt tctgcaccgg aaataaggct gcagcttatg       2220
cgtgtcataa aatattatga taatatgacg gcaagagcct atcaacctga actgcttgac       2280
agaaattttg tatcggacag aatggcagag cttacatcaa agcggtttgt cgcagagaat       2340
ttcgagtatt ttgtatatct gcgtgaaaat gagatccgta cctatgatga tgcaaaaatc       2400
ctgctttccg ctaaagccgg tgcagaaagg cttgtttcgg cgataaaagc cgctgagtgt       2460
```

-continued

```
attgacggcg accttggcga ttgcagttac gataatataa ggattgtttt cgatgagaac    2520
ttccttatga aaaaacaact atcccgtaaa ctttctgagg tttacaaata tactgttccc    2580
gataactgcg aacatatttt ccttatcaga aacgaccgca aattgcttga agactacaaa    2640
gcacagcaca aacctgtatt ggttgacatc tggggcagct gtatttcccg tgaatccgtt    2700
aaccgtaatt catcaggtat ctatgtcgat aagtacattt tcaagcagcc gttttttgctt   2760 gcggacgagc ctgaaatatc gtttgacaac gatttgtcgg ctgataaatt ctgcggcagt    2820
aagtggcgaa ggcgcactgt taaagaggcg ttttttgcacg aaggaaaacg cattctatct   2880
gatagtaatg ccgaatggct gattattgat atgtacgacc ttatctgcaa tatgcgtaag    2940
tgcggcgatt cgcttttcga ggtggatgat ttcatacttc gcaccgcttt ttacaaatcg    3000
atttccgata aatgtgaaag cacatattta tttaacgaaa gaagccgtga atatctcgaa    3060
agagtgcttg aaaatttctg caaatttgtc actgagcgct atggaaaaaa cattatttta    3120
attaaagccg atcttaaaga ccgttatatt tcgcttgaca atcggttaga aatgttatct    3180
gacagcgata acacattcaa aaccaaaaaa gcatttataa acggatttga agaagaattc    3240
gcacgtctta ccgattgctg tgtaattgat atttctaaaa ggtttttatgc cgatgaccgc   3300 tttgcacttg gcggtgcgca tatcgtccat tatgaagatg agttctacag tcaatgctgt    3360
aagcatataa cggctttcct cggcggttcg gagagccgct ataccgataa agtcgatgag    3420
gagtatatcg ctctgagaga tatgaaaatt aaataa                              3456
```

<210> SEQ ID NO 64
<211> LENGTH: 3345
<212> TYPE: DNA
<213> ORGANISM: Eubacterium siraeum
<400> SEQUENCE: 64

```
atgaagataa gtaaggcgat tgttgccgct gtaggtgcgg cggctgccgt aggtgcggct      60
gtatacgcca agaaaaagct ggaggaaaca cagactccgc tcagaaagaa aagcctgacc     120
gtatggaaaa acggcggggt aactcataag gagataatca gaaagcctat aagcgaggaa     180
gaacagaccg atgcgataaa cagccgcatt gatgaggctg tacgccggta taagcctatg     240
tccgaaaggg atagcggcga aaccgaaacc gagcctgaaa tatcgcctgt caattttaca     300
tttactcaga gtgaagatga cgacgatacc ggtgtgagct ttgagcgtgt attcgaccat     360
ttcaacaggc ttgaatcgtc cgtcggtaat gaaggcgagg atgtaggcga aagcggcaaa     420
aaagctgagg atacagccga agaagcctta tccgcagtaa cggcaacggc agttgaggaa     480
aattttgacg agcaagccgg aatgccgaag cagatgctgc ttgaaaatgg gataatggca     540
tccgctccga tagcaaatgc ggttcaggag cttgcagaaa tgccgtctgt tatacaggat     600
aatgaagaaa ttgaagacgt aagactgcct gttgatgaga gcattttcga tttatatgca     660
agcgagcctg tcgaggacgc agtaaaggct tttgaagaaa tagccgagca ggaagaaacc     720
gccgacagcg aaactgaaat tgacagcgaa caaaatgaca ttgctaccga agaagccgta     780
agcgagcctg tcgaggacgc agtaaaggct tttgaggaaa tcgcagagca gaaagaaact     840
gccgacattg aaactgaaat tgacagcgaa caaaatgaaa ccgccaccga agaagccgta     900
agcgagcctg tcgaggatgc ggtaaaggct tttgaggaaa tagcacagca ggacgaaacc     960
gccgacagcg aagctgaaag cgaacaaaat gaaactgcta ccgaagaagc cgtaagcgag    1020
cctgtcgagg acgcagtaaa ggcatttgaa gaaatcgccg agcaggaaga aactgctgac   1080
atcgaaactg aaaattgacga tgaacaaaat gacactgcta ccgaagaagc cgtaagcgag   1140
```

-continued

```
cctgttgagg aggcagtaaa ggcttttgaa gaaatagccg agcaggaaga aaccgccgac   1200
attgaaactg aaagcgaaca aaacgacacc gctaccgaag aaccggtaag cgagccagtc   1260
gaggacgcag taaaggcttt tgaagaaatc gccgagcagg aagaaaccgc cgacagcaaa   1320
actgaaattg acagcgaaca aaatgacact gccgtcgaag aagccgcaag cgagcctgtc   1380
gaggacgcag taaaggctct tgaagaaatc gccgagcagg aagaaaccgc cgacagcgaa   1440
gctgaaagcg aacaaaatga cattgccgcc gaagaagctg taagcgagcc tgttgaggac   1500
gcagtaaagg cttttgaaga aatagccgag caggaagaaa ccgccgacag cgaaactgaa   1560
agcaaacaaa atgacactgc cgccgaagaa ccgataagcg agcctgtcga ggatgcggta   1620
aaggcttttg aagaaatcgc cgagcaggaa gaaactgccg acagcgaaac tgaaatcgac   1680
agcgaacaaa atgacactgc taccgaagaa gccgcaagcg agcctgtcga ggacgcagta   1740
aaggcttttg aagaaatagc tgagcaggaa gaaactgctg acagtgaagc tgtaattgac   1800
gatgaacaaa atgacactgc caccgaagaa gccgtaagcg agcctgtcga ggatgcggta   1860
aaggctttcg aagaaatcgc cgagcaggaa gaaactgccg acagcgaaac tgaaatcgac   1920
agcgaacaaa atgacactgc caccgaagaa gccgtaagcg agcctgtcga ggacgcagta   1980
aaggcttttg aagaaatagc cgagcaggaa gaaaccgccg acagcgaaga aaagtcgctc   2040
gaagaacagt tccacgctat aatggaggag gaaaccgcaa gcgagcctgt ttcttctatt   2100
cgtacagccg agtctgtaga ggatgcattg aaagaattcg gcgactttat aggattatcc   2160
gaaaccgctg acagcaccgg tagcatcggt agctccgaag atatttcgga tgacgatctt   2220
gaacagacaa gcggtatttt tgaggaaagt acattatccg atgagctgtc cgaaactccg   2280
gacgagccga ttgacgctga cgaaaagccg agaactatgg acttttctcga tttgccggac   2340 gaagtatata cgcctgtaca gcttaccgaa gaaaagcaca ctgagaatgt tgccgaggta   2400
gaggatctgt tcggaaatct gcttatggat gacgagcctg aggtaaagaa aacatttaac   2460
gatccctcag aggtattttc actgttcgat acggctgacg gcggacagga cgatttcgac   2520
aagtacagcg atgaaaagat tgaggaagaa agcgagaaaa agaagaccag cgatacaaga   2580
aagtacatag cgcaggatat tgcggataat atcgcatcgt ttgcacagct gcttgaaccg   2640
ctcaatgcca tcaaggagaa caagatacgc agtaagagcg gtatactgtt cgactgggaa   2700
atgagaatac aggcgcttat aggcgatttg ccgataaaga cgtactggag aaacaacttc   2760
cgcaattatg agatatggag cgatgaaaag tgcatggaaa aggcaggcga gctgctctct   2820
atgcttgagc ttgtcggaat agtgcgtgat aaggcaaaag aggtcgtgat agacaaggat   2880
acgcttgatt tctattcggc acagagcgag catctcaaca cgatttccat ataggtgaa   2940 actgtcgttg ttacacggcc gtgctggaaa ataaacggac accctgcaag aaagggcgaa   3000
attgccaaga aagcaccgtt tgcggaattc agccgtaaga aagtatcacc gcttgaaact   3060
atgctgagag aaaacagctg ttctgacggg gatgttaata ttcccgttac ggaggacaat   3120
ttctgtacat acgaccgtga tataccttat gtaaagaggg caatcgccga aggcttctgc   3180
aagtgcgcag taagacgtat ggaggacgga ggcgctctgg cattcttcta tgaggttatt   3240
gcggagggcg aaaatgttca ctattcgccg tgtacgctga gattcgaggt aaacattgac   3300
aagaatgcaa atgttgtcgg aagattcaga agcgaaaaag tgtaa                  3345
```

<210> SEQ ID NO 65
<211> LENGTH: 3141
<212> TYPE: DNA

-continued

```
<213> ORGANISM: Eubacterium siraeum

<400> SEQUENCE: 65
atggcggcaa cggcaaaaag cagatatatg acggcggtaa aatggtttac ggcatttgta      60
tgcgctctgc tttgtgcggc tgccgtctgc tgttttacgg gaagcagtgc agacgctgcg     120
gcggtaacaa actgcaaggt ttcggggctg acaacaaaga cctatacggg taaggcacag     180
acgcagtcga tcacggtaaa atacgggaat aaaacgctga aaaacggcaa ggattacacg     240
gtaagttatc agaataatat aaacgcagga acagcttatg ttattataaa aggcaagggc     300
agttacagcg gaacagtaaa gcgttcgttc aagataaacc ctgcgttgat atacaagcag     360
tgtacttttt ataaaatcgc ctcgcagtat tataccggct cacagataaa gcctgttccg     420
aaaatcaaga acggaacaac gacactgaaa aacggaacgg acttcacgct tacatatcag     480
aataacgtaa acaagggtac tgcgaaggta tatataaaag gtaagggcaa ctacatcgga     540
agctgttcgc tgacattcag cataacggca aggcctgttt ctacgctgaa aatcaccgtg     600
ccgtcagtga cttataacgg gaaggcacaa aagcctgccg ttacggtaaa gtataataac     660
tatacgttta aaaacggtac tgattatacg ctgagttata aaaataacac gaaaatcggt     720
acagcaaccg ttacggttaa gggcaaggga aagctcagcg gaacaagaag cgttacattc     780
aagataaacg caaagccgat aaaaaacgca gttattacat ataacaactc gctcacatac     840
aacggctcgg cgctaagccc tgcgttact gtaaaatacg gaaacgcaac gcttaaaaag      900
aataccgact ataccgtcgc ctactcgaat aacgtaaatg ccggcacggg aacaatcacg     960
ataacaggaa aaggcatata cggcggaagt gtaaaaaga cctttacaat aaagaagctc    1020
ggaatatcgg ccacagccgt atcgggaaca ggaaacaagg tctatacggg aagtgcgata    1080
aagcctgtac ctgcggttaa agtcggcggc aggatgctga aaaacggaac ggactttacc    1140
gtaagctata aaacaacac cgagccggga acggcaactc tcaaagtgac aggcaaggga    1200
aactattcgg gcagtgtatc aaagaccttc aaaatcaccg caagagcgat aaacgatgtt    1260
gaggtaaccg tacccgatac ggtatttacc ggtgaacagg taagacccga tgttgttgta    1320
agctacggca actatcaatt tataaataac agcgactata ccctgtcatt caaggacaac    1380
gtcaatatcg gtacggcaag cgtggtggtc acaggcaaaa aacatctcag cggaagcagg    1440
acggtaacat tccctataga aaaggcggat atttcaagtg cggagatagc cgtgaagaac    1500
gcaacattta cgggaagtgc ggtaaaatcc gacgttgatg taaggctcgg taatgtgacg    1560
cttaaggaag gcactcacta cacgctttcc tataaaaaca acgtcaatgc aggtacggct    1620
caggtgacag tcagcggcaa gggaagcctt gagggcgctg taacaaagga tttcactatt    1680
gcaaaggcgg atatttcgaa agcctcgatt tctgcaagcg gaacgtatgc tccggacggt    1740
gtaaagatcg gcataaacgc taaactcggc aattacacgc ttaaaagcag tgactacagt    1800
tttaccgctc cgaccgctgc gggagagcag acgctcacaa taagcggaaa cgacaacttc    1860
agcggcaagg ccacagtgaa atgcaatgtg gcaaaagcgg atatagcaaa tgccaaatcg    1920
tctttatcgc tgtcaaccga cggcaagggc tataccgtaa cggtaattta tgacggtgtg    1980
cttttaacgc agaacaaaga ttataaggta gctgtaacag aatcaggcac aggcgtcagt    2040
gcggttatta caggcatcgg caattacggc ggaacagcga ctctcagcgg cataagcaac    2100
gagcttgaag cgtttgaaaa tgctgttgtc acaataggta aagtcacata caacggcacg    2160
gcacagcttc cctcggtaac agtgaagata ggctctgtca cgctgaaaag cggaacggac    2220
tatattctga gcgcttatga taacactaat gcaggaacag ctacggcagt tatcacaggc    2280
```

-continued

```
aagggaaaat atgccggtgc ggaaaagaaa acgcagttca cgatagcgcc tgccgccata    2340
tcatctgcaa gcataagctg tgaggatcag atatatacgg gacatggcgt caccgcacag    2400
cccattgtta cattcaacgg caaaacgctt gctctcggta ttgactacta tatatcggga    2460
tattcaaaca tagtgaatgt cggaacagct accgttactg taaagggcaa aggcaatttc    2520
acaggcactg caaaaggcac tttcagaatc gtcaagcagg acaatatgga agcgcttgtc    2580
aagaagcgcc ttgatgagat gatggaaggc aagtgggaca ggaagatata tgactactgg    2640
cacagctatc agattggcaa gtattacaac acgctcctta cctctccttg tacctgccac    2700
tcctactgtg aaacgggcaa cgaggcaggc tgtacctgtc ttataggaag aagtcacgtt    2760
ctgaataatt ccggcataca gtgtgcggga tttaccatcg aggtgttcga gtatctttc     2820 ggcaaaacaa acgaacggg cgaaaatacc ctcacgataa ggaatcgttc cgacggaaac     2880
tggacagagg cggcactgaa gaagtggatg accgatacgt tccgtccggg cgactatctc    2940
gcatatgaca acataaagta cggctatccg cactatgtca cgatatactc tgttgatacc    3000
gacggtatat gggtgtacga ggcaaattac ggcggaaggt gcaaaatcaa tttccgtaag    3060
tttacgttta aggagattta cgaagaaacg gacggtttat ggcacaggac accgaacaat    3120
tatgagttgt cggagtattg a                                                3141
```

```
<210> SEQ ID NO 66
<211> LENGTH: 2898
<212> TYPE: DNA
<213> ORGANISM: Eubacterium siraeum

<400> SEQUENCE: 66
```

```
atgaaaataa aatttaaacg cattacagct ttgtttgcgg cacttgctat tatgataacc      60
gcactgcctc tgacaatcat acctatcagt gccgcaggca ccgatggtga aagcacagag     120
tatgcaagtg acggatacct tatcgtccgt agttaccggc agctgagatt ggcatacaac     180
ggcagtgagg agtctaagat aaggcttggc gcagatattg actgcgaccc tgaggaatat     240
aagcctaact atctgacgag attgtgtccg cctatagaaa gtgacaagac gctggacctt     300
gccggatata cgcttaaaaa gacaggtaac agtattgact cgaaggatca tctgttaagc     360
gtcgaataca gtaagctgac cattgaggat tcggtgggaa cgggtaaaat gtatttctat     420
gccaaggatg tagcccagaa tctgtttttg gctgagaaca gaagtacgat cgttataaac     480
ggaggtacat tctgctacac gggtaccaat gcgatgtatt gtgaaatgat caagctgagt     540
gcatcggatc ttgtaatcaa cgatggttat tttgacgcac agatcggtac tccgataaag     600
ctggataacg gttttgccgg caaacaaaga acgcttaatt ctactgctct gataaacgga     660
ggtactatag taactacctc cagtatagcg ctctcctcga tagacggttg tgattattac     720
gcatcgctgg ttatgacggg cggaaccatc acaaacaaga gcaagggcag agtgaccgat     780
aaaacgggaa cgataatttc cgatccgtat tttgtccgtg ttacaagtga cgaggcgtta     840
cagaaaaagt attacaacat aacgctcctg ggcggaacca tgccgcttag cctaaatgat     900
atagaggtat attatcctgc cgagaaggcg gtacttactt ctaaagcagg tacgatcaca     960
aattctgcag aaaaggtaga gtacacgact ctgcttaccg caccgcaggc cggcattgac    1020
gaaaagaagg ctatggcagc aagaggcgca gacgaaatct gcaggctgaa gacagacaga    1080
aataattatg tgctgagcaa taacaaacgc acacgtttta ccgtcaacag caacagcgta    1140
ggtaagattg acctgctcac tcaggctccc aatccgtaca cacgggcga tccgataaaa     1200
```

-continued

```
acggtagatt ggtatgtgtc caagaatttc ggctcgttca catcaattcc cgaagctata    1260
aacgatctgt cgtatacgcc gccggaggtt acggaaaaat gcacaatgct gtataaggct    1320
gttataaatt acggcaatgt gctgagaatc aacgagataa taataattga ttatgatttt    1380
gaagccgtaa cggaaatcaa ggcggtcgtg tcaggctttc acggaggttc gacgttaagc    1440
gacgtcagcg ttgcgtcggg tgaacccgaa aaatacagtc tgacgataaa caatatccgt    1500
gatgtttacg gaaacaatat agtaaacgat cgtcagctgt gcaaaggctt caaatacaac    1560
atatttgtaa aagtaaagct gaaaagcgga tacgttgcag cgtatacaac aggcacagta    1620
aagatgcgca ggtttgagga tcccgcaaat gaatggcaag cggcagacca tatttacatc    1680
ggccttaacg agattgcatt taagagcgtt cttgtttgcg acgaaggaat caggacggtc    1740
ggggtcgaaa tcagcaactt cctgccttac agaaaggtaa acgatctgca gcttactgaa    1800
tcggaacctg ataaatatac ggtaactctt gtcacgccgc tttttaaacac atgggaatat    1860 aacgaagagg tttacgacga tgacgagctt atagtagata actgttatgc ggtcaaattc    1920
aaggtaacgc ctaagtcggg atatgcgctt tctcccggtt atatattccg atgcaggctt    1980
gatacttaca aagaaggatt ctggctgaca tccgaagaca aggaactgtt cacggtttcc    2040
aatgacggaa cggtagtgat taacagtctg aggggtgccgt ttgaagaata tgatcagaat    2100
atatatgtac agataacacc tccgaaggca ggaggaactc cggcaaagag tttaatctca    2160
cataatcttc ctgagcatat gagccttata agtattgact ggtatgacga tgaagagcgg    2220
aaaacaccga ctgtatttga gaagggcaag acgtactggt gctatatata catcaatgcc    2280
gactgctatg agtataatct caaaaaagca aaattctatc tgaacggaac tcaggtcaga    2340
caggattaca gttacaattc aaaagagaac tactactata ttctcggtta tacggaaatc    2400
aagatcgaca atgatgttgc aactcctaca ggctttgcgg ctggatcggc gacttcatcg    2460
agtgtttcgc tgaagtggga taagaacgca aatgcgagcg gctatgagat agagcagtac    2520
aaaggcggaa agtggacaca gattgcaaag ataaataaca actccacggt ttcggacaaa    2580
gtaagcagac ttgccgccga tacaacgtac acgttcagga tgagggcata taagacttta    2640
tcgtcgggta cggcatacag cgactatgta aggcttgcgg caaaaacgca gcttacaaat    2700
accgacaaat ttgtcggcac cgcaatatct cctacagctg taaagctgga ctggaacagg    2760
aatgataagg ttacaggcta cataatcgaa cagtacaagg gcggaaagtg gacgcagata    2820
gcggtaacaa agaacaacac aacgcttacc tttacggtaa aggggctggc ggacgcaaca    2880
ccttattcat ccgcataa                                                 2898
```

```
<210> SEQ ID NO 67
<211> LENGTH: 2556
<212> TYPE: DNA
<213> ORGANISM: Eubacterium siraeum

<400> SEQUENCE: 67
gtgcagttaa acaccaacgg tcagaagttt ataaatataa taatcggctt ttcacgggat      60 tttccctta ccgtaaatcc gggcgaacat tccgagaaaa cctacccttc tcttttagag     120
ctgataaatc ccgatgatat tcctccgata accgaaatgt tcaccgatgt atcacaggac     180
gaggaaaagc gttttgaggc gcattgtcgt tttatggtga cgatgaata tcactggttt     240 ttcctttcgt gcaaggcggt atatgcagag tacggcaggc ctgtgcgttt tgagggaacg     300
atgtgcgatg tatcgaccta ccttgaaaca gcgggtgacg accttgtata taacgaattc     360
cgcaaaaagc acaatataaa gctgtccgaa cttaaaaaag gcgcaccggg tcttgccgat     420
```

-continued

```
gtgcttgatg tcgactacct cacaagcata cagcgtcctt ttgccgtgcc acagctttat      480
tccgccatat ttgacgaaaa aggaaagctg atatgtgcgc cgaaaacaca gcataaatct      540
ctttctcccg atgattttgc atatcagaag aaaaagaata tccgcataaa tcaccttgtc      600
agcggaacgt ggatactggg agcgaaaacg caggaattgc tcgatgacaa cattcagctg      660
tgggaaacgc ttgtacagac agtttcccgt atggcaaacg catttgttgt agttctttcg      720
gagatggaca attcgcagaa tgcaaacaaa ctgctcggtc agaatgtcga ggagcagata      780
ctgctgaata atatctacgc tatcataatg cagagcaaaa gcgcagatat tgcgttaaac      840
tccgttacag agcttatagg cgattatttt caccttgaca ggataaccat aatcgaccgt      900 gatgattta ctcaggagct gtgctggtgc aaggattaca agtaccgcca cctccctctt      960
gaaatagacg gcgataccgc acttgactgc gcctcgatac gtgaggatct gagccttacg     1020
tcatcggctt tttcggatac ggataccaac gaccttgcaa agttcggtat caagtcgtat     1080
gctatcttca agctgataaa ttctggcact tttgacagcc ttataatgtt ccagacgatt     1140
gaaaaggaac ataactggac acagcgtgag cgtaaacagc tccgcaacat ttcacagata     1200
atctcctcgc ttatgatgcg taaggaaacg caggataagc tggagcagtc gcagaagcgt     1260
atgcgtcagc ttgcctttta tgacgctatc tacaatattc cgaaccgtgc aaggctgaac     1320
aaggatcttg acaagataat gaagcgtaat acaaaaggct cgcttatcgc tttcaaagtc     1380
accaacacac gcactctgtc cgcagtttac ggtcacacct attcggatat gctgctgcgc     1440
agtatcgctc agtatcttaa ggacctgccc gtaaaggata ttggtgtata ttatttcaca     1500
aatgcgattt ttatgcttaa tctaccggat tgtaccgaca atgaagctaa aaatcttgtc     1560
gaaatgctga tacaccgttt ttcaaagccg tggaaattcg gtgaggatga gcattcaatc     1620
cattgcagtc tcggcatagc gttctatccc gaaaacggcg aggatgcaga ggagctttgc     1680
aaggcggcaa gcacggcaat gtaccgtgca agagaattca aacagaacag ttatgctttc     1740
tattcaggct cgcttgagcg tacaagaatg tttgcggcaa gccttgaaca gcatataaga     1800
gaatgtataa acgacggtat gaggggcttt tcactgcgtt ttcagccgtc attcagtgcg     1860
gtcgacggca gtataatcgg ctgtgaaagc tttgtacgct ggcacgacga gcagtacggc     1920
aatattccta actcaacttt gttccctatg gctgaaaatc tcggcttatc ccacgtcata     1980
gacggctggg taatggaacg ttcgtgcgaa ttctgcaagg agatacagga cgcaggcttt     2040
gagaatttta ccgtcagcgt aaatcttacc gcaggcgaac cgcaatctgc cgaaatcgta     2100
actcaggtac gtcacgctct tgaagaaagc gcactccctc cgtcctcgct gatactcgaa     2160
attcctgtaa aggccaacat tttctacagc gacagcaccc atatcctgca cgatctgcgt     2220
actctcggtg taaatattgc catagataaa tacggcacgg ggaatatttc gttaaaggtc     2280
ctcaaaaact catacgtcaa ccttgtgaat cttccggcaa agctgtttat gaatcacgag     2340
gacgaatttg acactgagct tgtaagctct gtcatccatc tggcaaaatg ccgtaagctt     2400
accgtatgtg taaagggcat tgaggacaag gaacagcttg ataccgtgca gaagttcgat     2460
attgacagga tacagggcta ctactgttca cgtccgctgt cgctgtcgga agcaaagaca     2520
gtatttaccg aaagtataag aataaaggga tactga                                2556
```

```
<210> SEQ ID NO 68
<211> LENGTH: 2256
<212> TYPE: DNA
<213> ORGANISM: Eubacterium siraeum
```

-continued

```
<400> SEQUENCE: 68
atggacttaa agctcacgca aggcatgaaa aaacgcatac tggttattct ggtggcattg      60
tgtataggtg tcaccggcat tgtcagtggt gtgctgttca aggtttcggt cattgacagc     120
aaggaactgt ctgcaatggc taccgatcag caacagagca gctttgacat aaaggcaaag     180
cgtggaacga tatacgaccg caacaacaag gtgctggcgc aaagcgctac cgtgtgggat     240
gttatcattt cgccgggcga cattgaaaaa aacgagcctg agaaccgtga gtttatatgc     300
aagggaataa gcgggatact cggcactaaa tatgaaacgc tgacggaagc gtgcaaggac     360
acttcttcac gctattatgt ggtcaagaag aaggtggacc gcagtacagt tgaaaaaatc     420
aacaacttcg tactgaagaa caaccttaac cgttattccg tttacactgt tgaaaacagt     480
gagaggagct atcctaacgg aactcttgcg gcaagcgttc tgggatttgt aaacgagaat     540
gaagagggct acggcatcga ggcatactac aattcgtatc ttaagggtac ggacggcaga     600
gttatcacaa caacagacgc tcacggaaac gcaatgcctt atgactattc cgcacgctat     660
tcggcaaagg acggcaacag ccttgtgctg actattgacg aaacgcttca gtattatctt     720
gaaaagaatc ttgaaatcac ggtttcacag cataagctgg cgaaccgcag tacgggaatt     780
attatgaatg cgaaaacggg cgctattgtg gcaatggcga catcacccgg attcgatccg     840
aacgatccgt catatgttta ctttgaaagc gacaggctga cgcttgccaa gatgtcggcg     900
gacaagaaga ccgaagagga aatacttgct aaaaagcagg agatatgggg aaagcagtgg     960
cagaacaagg cagtaagcga actgtatatc ccgggttctg tattcaagat gttcacctgc    1020
gcttcggcac ttgaggagga agtcgtatcg cttgacagca cattcgaatg ctcgggcatt    1080
gcagatgttg cgggaacgaa gataagatgc tggaacatag gcggtcacgg tgtatcgaat    1140
cttacagaag cgatgatccg ctcgtgcaac cctgcattta taaagatagg tcagcttctc    1200
ggtgtggaga agttcagcaa atatttcgag gcattcggct ttaccgaaaa gacgggaata    1260
gatctgccgg gcgaagcgga ttcgctgtat gtgaaagaat cggacatggg aatagttgag    1320
ctttccagct cgtccttcgg tcagacgaca aaggttacgc ccatacagat ggttacagcg    1380
gcggctgctg tcgtaaacgg cggtaagctt gtcacaccct atgttgtgga taagataata    1440
gacagtgacg gaaatgtcgt gaagtctgca cagacggtgg taagacgtca ggtaataagc    1500
gaagaaacaa gcgcaacgat gcgtaagata cttgaggacg ttgtaaccgc aaacggcggc    1560
ggtaacgcat atatgagcgg ctatcgcata ggcggcaaga gcggtacttc ggagaagata    1620
gacgactaca acagcggaaa gacaccggaa ctcagatatg ttgcgacatt ctgcgccata    1680
gtgccgatag atgaccccga atatgttatg cttgtcgtat gcgacgagcc tacatcggga    1740
tatatctacg gcagtgctat tgcggcgccc gtagtatcgg ctgtgttcaa ggaaggcctt    1800
gaatatatgg gaatatatcc tcagtatacg gctgacgagc ttgcacagca ggatgttact    1860
gttccgtggg tcggaggata taacagtata agagcggagg cacagcttac agccgcagga    1920
cttaaagcag agtacatagg cagtacggac ggtacagagg taacaggtca ggtgccgtcg    1980
gcaggtacgg ttatgccgag cggaagcacg gtaatgctgt atatgggaga cattccgtta    2040
tcggattaca gaatgtctac tgtgccgaat gtaataggaa tgacggtcga agaagcaaac    2100
aaggcactga gcgaggcagg actcaacata agtattaccg gtgcggcaac gggaagcgaa    2160
gcaaaggcgg taagccagag cgttaattcc ggactggtgg tatacagagg atctgttata    2220
gaggtcaatt tccttgtaaa caacgaaacg ggctga                              2256
```

-continued

```
<210> SEQ ID NO 69
<211> LENGTH: 2205
<212> TYPE: DNA
<213> ORGANISM: Eubacterium siraeum

<400> SEQUENCE: 69
atgtcagaag tcagagctgt tcagaaaacc gaaatgcccg agataaatgc tcaggcggca      60
atcgttgtta ctcagcatga gggtcgcata ctgcttgaaa agaatgccag aatgaaactg     120
tcgcctgctt ttcttattaa aataatggca tctataatag ctctggaaaa atgtaatcct     180
aatgataccg taacagtatc ggacagcgtc ataaagcaga tttcgaactg gaaaggctcg     240
gcgtctatca atcttgaagc aggagaaaaa atatctgtac ttgatttaat ttattcgatg     300
atgctggttt cagccaatga ctctttattt gctcttgcgg aattcatatg cggaagcctt     360
gacaagtttg ccgcaatgat gcaggagaag gctaaatcta tcggtgcggc ggatacaact     420
gtgactaccg ctgacggcag atttacagcg gagcagtatt caaacgcata cgaccttgcc     480
atcatctgcc gctactgcat gaccaacaga atgttcagaa caatagcggc taccgataaa     540
tatacaatcc cggcaacgaa taaaaacggc tcaagggatc tgcagaatac gaatcttctt     600
attaacagcg gtaacagaag atacagatat gaaacggcta tcggcataaa aagcggatat     660
acggctcgct caaaatcgtg ccttgcctgc tctgccctgc cgcccgcaaa caaattcgga     720
gaagaagtgc ttgcaataat actcggagca gaaaacacaa agcagatgaa atacgttttc     780
tatgacgcaa taacactgct cgacttcacg ttcaacaatt atgaagcgct cagcggtaaa     840
aaaccggaac agcagaattc cgaagcgaaa aaatccatta ccacagtagg aaagctgtgt     900
gaaattctta atgctgagct tcgcaatgcc gcagacgttc caattacatc atttgccttc     960
ggtaaacaga aaataaaacc cggatgtgca tattttgccg ccgataagga aacggctgtc    1020
acggcatttg aaaagggtgc ggctgttatt atcacaactc agccgataga gaagattccg    1080
aatatcgttg tggcaaatct tgataccgct ctcagcagga ccgcagtatt tataaagtcg    1140
gcactgggaa tgtggactgt agctgttatg gacagtcccg aaaagataaa tcccctttcg    1200
atgatagaac aaatgctttc gagcaagatg gaaaccgtgc attcaatttc cgttacaaac    1260
aactacaatt caatgctcca tgcaatgttt gcttctacac ctaaaaccga gacggctgtc    1320
atcaatgttt cgtgcgtaaa cggaggaaac gttgaacgtg tttcgcagac agccaacttt    1380
gatgttgcga tacttacaag cacggtcgta tccaaaaatc cgagggaact gacaaagcct    1440
gagcttattg aagaaaaact caaggtatgc ggcggaatga acgaatcggg tgcggtcatc    1500
ataaatattg acgataagaa tctcgcaggc atattcacca taccgcagga tattatcacc    1560
atcggcgttg ataacagaat ggctgattat tttgccgata acatagagct ttcccataat    1620
aaaatctcgt ttgatataat acacggtgcg gataattatc atatcgagct ttattccgat    1680
gataagcaca gcgtatatca ggctctggca acatttgcac tgggcgagat tatgggcata    1740
ccgccaaagc agattatacc ggcaatcgaa aaataccgcc cgtcaacagg acttacaaca    1800
gtacgcaacg aaagaggtat ttatgtaata tccgattttg aaaacgaggc tgttgaaagc    1860
gtaggtgcgg ctcttaagga actctgcacc atgcagcttc ctcccgattc aagaagaata    1920
gcggtattgt ctgaagtagg tgacggtgac gagcatgaac ttgaaatata caggaaggtc    1980
ggcaatatcg tcaataaagc aagcgtaaat attacggttt gctacggtga aaccgccgca    2040
gaactgatga aaaccgccga tttaaaaagc aaattcgtaa taaagctgaa cacaagacag    2100
gctcttacag aatttttaaa gctgaatctg cgtgataatg acgctgtact tttcaaaggc    2160
```

-continued

```
tcgacggtga ccgagcttga cgaaattatg acggacgtca cataa                2205

<210> SEQ ID NO 70
<211> LENGTH: 2019
<212> TYPE: DNA
<213> ORGANISM: Eubacterium siraeum

<400> SEQUENCE: 70
atgaaaaaat ggcttgtcag aaatacggac aatgcacttg caatgaaact caagaccgac      60
acgggactgc cgatgctttt gtgcagtctg cttgtcagca gaggaatata cacagccgag     120
caggcacagc agtatttcaa cggtacggag ctttccgacc ccttgcttat tgcggatatg     180
gataaagctg tgcaggcgat agaagaagcg gttgacaatg aagtaaagat aaccgtatac     240
ggcgattacg attgcgacgg cgttacatct accgttatgc ttttcacaca tcttgatgca     300
ataggtgctg acgtaaactg gtacataccc acacgtgaag aaggctacgg gctgaatgaa     360
aatgcgatac gcaaactgca cgaggacggt acgggtctta taataacggt tgacaacggc     420
gtttcagccg tcaacgaggc ggagcttata tatgaacttg gaatgaagct tgttgttacc     480
gaccaccatc agctccctga gattctgcct aaagcggagg ctatcgtaaa tccgcacaga     540
caagatgaca actctcccta taaagaactt gcaggctgcg gcgttgcgct aaagctcatt     600
atggctctgg aacgtgacgt tgaaggtgtt cttgagcagt atgccgacct tgcggctatc     660
ggcactatag gcgatgttgt cgcactgacg ggagaaaacc gcataatagt aaagcgtgga     720
cttcttgaaa tgcagtacag cgaaaatcag ggacttcagg cgcttatcaa tgcggcagga     780
cttgatgccg aaagtattac ttctacaggc atagcgttcg gcttatgccc ccgtataaat     840
gccgcaggac gttatgacag tccgaaagcg gcggcagagc ttcttatggc tcagaccgga     900
cagatagccg agataaaagc gcaggaactg aatgaactga acgctaagag aaaacagatc     960
gaaagcgata ttctcgaaat ggcaaaggct cagcttattg ccgaccctaa agcgttcaac    1020
tcccgtgtgc ttattgtttg cggcgagggt tggaatcacg aattatagg tatagtcagc    1080 gcaagacttc ttgaactta cgaaaaaccc tgtatcgtca taggaatag gggcgatgag    1140 gcaagaggct cagcgagaag catcgaaggc ttttcacttt ataccgcact tgatgcgtgc    1200
agtgagcatc ttacacgttt cggaggtcat acgaaggcgg ctggctttc gcttccgaaa    1260 gacaaggtag atgattttat agctcagctg agaagctatg cggatgaaaa attcccttca    1320
atgccggtta tgacaacgga ggctgatatt gagccggagc tgtccgacct tgaaatatct    1380
tcaatcgaga atcttcgtca tttacagcct tacggcgaag aaaacaacgc tccgctgttt    1440
ttgatgagaa actgcacgat catatcatca agaccgctaa aagacggtaa atatacatcg    1500
tttagcgcag agtataaagg ctcacagttt aaatttctct gcttcggaac atcgtttgat    1560
aagttcggat attatcccgg agataaggtc gatgtgctga gccatatcga aataaacgaa    1620
tataatgata aaaaaagcgt cagcgtaaga gtaaaggaca tacgcagaag tgattttacg    1680
caggataagt attttgccgc aagaaatttc tatgaaaaaa tcctcagagg cgaaaaaacc    1740
gattcaagac ttcttaaacg tatcctgccc gataaggaga acatgaagct cccgttcgac    1800
cttgcaagaa agctgacctc tatagattca gccgcacaga ttgcaatgtc gcacggtatg    1860
aattactgcc tttttatgat gtgccttcat gttttttgcgg aattcggtca tcttgagctg    1920
gacagaataa acggtacgat gaatttcata aaaggcggca gacgtataga acttgaaaac    1980
tcggcagtga taagaagaat aatgaaatcc tgcagctga                          2019
```

-continued

<210> SEQ ID NO 71
<211> LENGTH: 1977
<212> TYPE: DNA
<213> ORGANISM: Eubacterium siraeum

<400> SEQUENCE: 71
atggcagtat atcttatact tatggcactt gtgcttgtgc tagcttatcc gctcatcgag          60
cataagccga atgtggtgaa gaagctctgt tatgttatcg tgacattcgg ggcaatgtat         120
cttataagcg tattcagata cggactggga aacgattatt attcgtatat ctatattttc        180
tggaatatca agaatgcacc cggactttcg atattcaact acgggtatga gccgggcttt        240
acaatcgtca caaagctgat ctcgatgttt accgcagatg tgaatataat gtatgcggtg        300
tacgcactgc tgatacttat acctacggcg tatgcgatat tccgttacag tgaaaatata        360
tggatgtcaa cgatgatgtt catatcgctg acgttcttct actgctcgct gagctttatc        420
cgtcagtcga tagcgtttgc aatcatactc tgcgcttaca gatttatgaa ggaacgcaat        480
catttcatgg tgctgttgtt tattttctta gcgtgtctgt tccacagtac agtaatagtg        540
ctgataccgc tgtatctgat tgcggcgttc ataaagccca caaagataac cgtaccgata        600
tatgcgatat tgacagcgct tgtatatctg ctttcgtggc cgatactgcg gtttgcggtt        660
gtgcttcttc cgcagtacaa gggctacctt gaacttaact ttatcacgca gggctattca        720
cctgtttata ttatagtgcc tgcgataatc acggcacttg cgcttatcgc acatttcacg        780
ggatacggaa aggcatatcc gaaagagtcg gcactgttca cgaactttgc gatattcaac        840
ttcataatat ggtttatagc gacaaagcac tttgttatcg agcgtttctc gatgtatctg        900
tacattatga tgataatgtt cataccgtca atagcaaggt actatatgaa ctgcgcaaag        960
gtttatcttg cacgcaggaa aaatcccgat gctgtggttg aattcgataa aacggtagat       1020
gaggtcatac gttccaagca tcccgaaaaa tatgccaaga agtatgccgc cgaacccaaa       1080
aaggaaaaag cggtttcgca gcccgtaccc gaaaaggcgg agcctgaact gagcgatata       1140
gaaaaggaaa agcagagaat tttagccgaa atcatggctg aggacggcgg cgacagcaat       1200
atagtgacaa agccgattga agctgtggaa aacaaaaagc ccgaaaagca gaagaagtat       1260
tcgtctgtat tcggagagca gtttaatgct gacgaaagat atatgccgaa gaacagggta       1320
ttcaaaaaga gaaggaacgg ttttgtgaac ttcgttacac gtcctgttac gatatttgcg       1380
gctttccttg ttgtagtggt gggcgctaac ctgtggtaca actatttcgg ccttacggta       1440
tcgaagaagg gcttccacgg agttatgccg tacaagagca ttgctccgca gtatacagaa       1500
tttgtgcttt caaaagaaag caaggacgaa aagaacacta acctcagaag cgaggataat       1560
ttccttaact atatgtacag gctgaaagag ggcgagaatt tcactgccat aatctcggca       1620
agaggagatg tgacgggcgg atataacgac ggtgctttat cggctgtaaa ggatctgggg       1680
cttgaaaagc tgcttacggc tcagaaaaac cagcgttata ttgcgataat agaaggcggc       1740
aaggttgtcc gtgaggaact gtcggatgac aggatcgata caggcgttat tgatgtgctg       1800
ggctataaga cacagataat cagcgacgca gatgaatcga ttgtcaaaat gggcaacaag       1860
aactactcgc taaacgagcg tggaatgaat atcgtggtgc ttgacaacac aacgagaaac       1920
attgttgaca aggtacgttt caagacgtat tacgttatgc tgtcggcaac aagataa          1977

<210> SEQ ID NO 72
<211> LENGTH: 1881
<212> TYPE: DNA
<213> ORGANISM: Eubacterium siraeum -continued

```
<400> SEQUENCE: 72
atgaaaatat ttgtatatga gatgaaaaag atactgataa aacagtacgc aataataatt    60
ctggcagctg tagtaatagt aagactgcta tcttctctgc cgcttgcaaa gcagacatac   120
ggatttgact ctgctacaga gagagagaaa tattttgaga taatctctcc gtttatagga   180
gcagtgaccg aagaaaaaac tgaccgtgca gacgagcttg aaaagcagct tgaaacggca   240
agtcaacaat acgataagct gattgatcag cgtctggaac acaaaatatc ggatattgaa   300
tattacgagc agatgaagct gtacgaaccg accctcaata tcaaaaagca gattgaaaaa   360
actgtcgaac aggtacggca ggcgcaagaa cgccaatgcg atattctgcc tgtaagctat   420
atccctataa tatgcgaagc gtcggccgat tacctttttg tgcttgcaat ctgtcttata   480
tgcagtctga gtgtaatcac agagtataca agcaagacaa gatatatcct gtgtactact   540
ccagcaggac agtcacgcag tatggcggca aaaacgacag ttctgctctt ttcggtcgca   600
gtggcatcgg ttttgctctc ggcggttgag ggatactgtc tttcaaaaca gcttcccttt   660
gaatactggg cgtattccgc aagaggtata gtgataatga cgaattgtac ggcggagctt   720
tctataggca gtctgtttat tcagacccag cttattaaac tggtgggaag tattttcatc   780
gcctcggttg caattcttat ttccgagctt tttaaaagct attccgcaag cgtatttcg    840 cttgtaaccg tgcagatagt tgtcgactat gtcggcaatc gctcaaatct cagctatctt   900
ctgccgacag gggctatgcg tggctacggt tattttttacg gcgatgtcac gccgaccgcc   960
gaaaacaatt atatgcagtt ttcgggagtg cctctttggt atactgcagt gcttatgtgc  1020
ggtttgctga ttttttctgt ggcagcttgt gcaggaacga ttctttcctg caataaccga  1080
ctgaaaagaa aaaggaaaaa gatacgcaag gcggcacttt tgtcaacgat gtgcattgtc  1140
acttcactgc ttctgtcctc gtgcagtgtt gcgaataacc gctacgaccc cgaagataca  1200
atgaagcttg taggcggctc atataccttg atcggcgaat ataacatccc ttttacagaa  1260
ggactgaaaa caagcaaata tgaaatcgtt cttgagacca atcagtcttc cggtggattt  1320
tcaatatcgc tgatcgatct tgcaagcaat gaaaagctcg atattccgca gagctatttt  1380
tcggacgaaa ctttcattca ttgctttata accgagcatt acattttagt cgagtatatc  1440
gccaaagacg gaaccgaagc aatgcggtac tatgacctga atgacttttc gacacaaaca  1500
attgctcaga acacccgagg agtagaaaaa aatctgttcg gacttacctt taaggacagc  1560
gaaagcatat ttacgacaag ctccttggtt ttcaccgatg acagagattt tttctttgtt  1620
acagacagcg gtttgtataa ggtaggcgta aataaaaatg cgtcactgat aatagacgag  1680
cctgtaactg aaggcttgat ttacgatgct cacagcatct attttatcag cgaaaaggac  1740
agcatcaagc gttacgacct ttcaacaggc attctcagcg aaattgtaag cggtgaaaaa  1800
ataatcccac gttcgctgtg gggagattac gattatattt attacacaag cgagaacggc  1860
gaacaaaagt tagcaaaata g                                            1881

<210> SEQ ID NO 73
<211> LENGTH: 20
<212> TYPE: DNA
<213> ORGANISM: Alistipes senegalensis

<400> SEQUENCE: 73
gcggaaggta aggtcgaaca                                                20

<210> SEQ ID NO 74
<211> LENGTH: 20
```

```
<212> TYPE: DNA
<213> ORGANISM: Alistipes senegalensis

<400> SEQUENCE: 74 aatactttttc cgcctcggca                                              20

<210> SEQ ID NO 75
<211> LENGTH: 20
<212> TYPE: DNA
<213> ORGANISM: Alistipes senegalensis

<400> SEQUENCE: 75
gtttcggtcg aagccggata                                              20

<210> SEQ ID NO 76
<211> LENGTH: 20
<212> TYPE: DNA
<213> ORGANISM: Alistipes senegalensis

<400> SEQUENCE: 76
atcgtgcaga tgcatggtga                                              20

<210> SEQ ID NO 77
<211> LENGTH: 20
<212> TYPE: DNA
<213> ORGANISM: Alistipes senegalensis

<400> SEQUENCE: 77
ttcgagcagg ccaatgctaa                                              20

<210> SEQ ID NO 78
<211> LENGTH: 20
<212> TYPE: DNA
<213> ORGANISM: Alistipes senegalensis

<400> SEQUENCE: 78
gtattcagtt gtccgcccca                                              20

<210> SEQ ID NO 79
<211> LENGTH: 20
<212> TYPE: DNA
<213> ORGANISM: Alistipes senegalensis

<400> SEQUENCE: 79
gtgaccgtct ggctgaaaga                                              20

<210> SEQ ID NO 80
<211> LENGTH: 20
<212> TYPE: DNA
<213> ORGANISM: Alistipes senegalensis

<400> SEQUENCE: 80
cgatgccgcg gattttgaat                                              20

<210> SEQ ID NO 81
<211> LENGTH: 20
<212> TYPE: DNA
<213> ORGANISM: Alistipes senegalensis

<400> SEQUENCE: 81
cgacgatccg gaagatgagg                                              20

<210> SEQ ID NO 82
```

-continued

```
<211> LENGTH: 20
<212> TYPE: DNA
<213> ORGANISM: Alistipes senegalensis

<400> SEQUENCE: 82
acctcccgaa cagaggatga                                                    20

<210> SEQ ID NO 83
<211> LENGTH: 20
<212> TYPE: DNA
<213> ORGANISM: Alistipes senegalensis

<400> SEQUENCE: 83
gctacacgtt cgacaatcgc                                                    20

<210> SEQ ID NO 84
<211> LENGTH: 20
<212> TYPE: DNA
<213> ORGANISM: Alistipes senegalensis

<400> SEQUENCE: 84
cgaaatgccg taagaagcgg                                                    20

<210> SEQ ID NO 85
<211> LENGTH: 20
<212> TYPE: DNA
<213> ORGANISM: Alistipes senegalensis

<400> SEQUENCE: 85
tcagatcagc ggtgatgacg                                                    20

<210> SEQ ID NO 86
<211> LENGTH: 20
<212> TYPE: DNA
<213> ORGANISM: Alistipes senegalensis

<400> SEQUENCE: 86
gcaccttgta gcttttgccc                                                    20

<210> SEQ ID NO 87
<211> LENGTH: 20
<212> TYPE: DNA
<213> ORGANISM: Alistipes senegalensis

<400> SEQUENCE: 87
ttcctgaatc ggttgctggc                                                    20

<210> SEQ ID NO 88
<211> LENGTH: 20
<212> TYPE: DNA
<213> ORGANISM: Alistipes senegalensis

<400> SEQUENCE: 88
cctcggcgaa atagtccgaa                                                    20

<210> SEQ ID NO 89
<211> LENGTH: 20
<212> TYPE: DNA
<213> ORGANISM: Alistipes senegalensis

<400> SEQUENCE: 89
cgtgccgctg aagaaaaaca                                                    20
```

<210> SEQ ID NO 90
<211> LENGTH: 20
<212> TYPE: DNA
<213> ORGANISM: Alistipes senegalensis

<400> SEQUENCE: 90
cgtaggttcc cgaatagggc                                              20

<210> SEQ ID NO 91
<211> LENGTH: 20
<212> TYPE: DNA
<213> ORGANISM: Alistipes senegalensis

<400> SEQUENCE: 91
aggtcgaaag ccgaacttcc                                              20

<210> SEQ ID NO 92
<211> LENGTH: 20
<212> TYPE: DNA
<213> ORGANISM: Alistipes senegalensis

<400> SEQUENCE: 92
tgcgtatatg ggcgttctct                                              20

<210> SEQ ID NO 93
<211> LENGTH: 20
<212> TYPE: DNA
<213> ORGANISM: Alistipes senegalensis

<400> SEQUENCE: 93
cgtcagtcga agaggtacgg                                              20

<210> SEQ ID NO 94
<211> LENGTH: 20
<212> TYPE: DNA
<213> ORGANISM: Alistipes senegalensis

<400> SEQUENCE: 94
cgacggcctc catctgtatc                                              20

<210> SEQ ID NO 95
<211> LENGTH: 20
<212> TYPE: DNA
<213> ORGANISM: Clostridium boltae

<400> SEQUENCE: 95
gaggcatagg cggaagtacc                                              20

<210> SEQ ID NO 96
<211> LENGTH: 20
<212> TYPE: DNA
<213> ORGANISM: Clostridium boltae

<400> SEQUENCE: 96
accccgccgg aattaatgtt                                              20

<210> SEQ ID NO 97
<211> LENGTH: 21
<212> TYPE: DNA
<213> ORGANISM: Clostridium boltae

<400> SEQUENCE: 97
gtccggcgaa aacaggtctg a                                            21

-continued

```
<210> SEQ ID NO 98
<211> LENGTH: 20
<212> TYPE: DNA
<213> ORGANISM: Clostridium boltae

<400> SEQUENCE: 98
cctgcaccat gtcccctttt                                              20

<210> SEQ ID NO 99
<211> LENGTH: 20
<212> TYPE: DNA
<213> ORGANISM: Clostridium boltae

<400> SEQUENCE: 99
cgggacattt gcatgaacgg                                              20

<210> SEQ ID NO 100
<211> LENGTH: 20
<212> TYPE: DNA
<213> ORGANISM: Clostridium boltae

<400> SEQUENCE: 100
ctatgcgctc cgctagcaat                                              20

<210> SEQ ID NO 101
<211> LENGTH: 20
<212> TYPE: DNA
<213> ORGANISM: Clostridium boltae

<400> SEQUENCE: 101
ccggaccttt tggctcagat                                              20

<210> SEQ ID NO 102
<211> LENGTH: 20
<212> TYPE: DNA
<213> ORGANISM: Clostridium boltae

<400> SEQUENCE: 102
tccgcagcct cgatgtattc                                              20

<210> SEQ ID NO 103
<211> LENGTH: 20
<212> TYPE: DNA
<213> ORGANISM: Clostridium boltae

<400> SEQUENCE: 103
gggcagtatt cgcggtatca                                              20

<210> SEQ ID NO 104
<211> LENGTH: 20
<212> TYPE: DNA
<213> ORGANISM: Clostridium boltae

<400> SEQUENCE: 104
ttcggcagca ccatcagaat                                              20

<210> SEQ ID NO 105
<211> LENGTH: 20
<212> TYPE: DNA
<213> ORGANISM: Clostridium boltae

<400> SEQUENCE: 105
ggcgataacc tgtgtgtgga                                              20
```

-continued

```
<210> SEQ ID NO 106
<211> LENGTH: 20
<212> TYPE: DNA
<213> ORGANISM: Clostridium boltae

<400> SEQUENCE: 106
cccgctgtaa aatccccctg                                           20

<210> SEQ ID NO 107
<211> LENGTH: 20
<212> TYPE: DNA
<213> ORGANISM: Clostridium boltae

<400> SEQUENCE: 107
gacaggccat aaggtggctt                                           20

<210> SEQ ID NO 108
<211> LENGTH: 20
<212> TYPE: DNA
<213> ORGANISM: Clostridium boltae

<400> SEQUENCE: 108
agcctgtagt tgggaatggc                                           20

<210> SEQ ID NO 109
<211> LENGTH: 20
<212> TYPE: DNA
<213> ORGANISM: Clostridium boltae

<400> SEQUENCE: 109
gggggacaca tggactgttt                                           20

<210> SEQ ID NO 110
<211> LENGTH: 20
<212> TYPE: DNA
<213> ORGANISM: Clostridium boltae

<400> SEQUENCE: 110
gttcccttca tgtctggcga                                           20

<210> SEQ ID NO 111
<211> LENGTH: 20
<212> TYPE: DNA
<213> ORGANISM: Clostridium boltae

<400> SEQUENCE: 111
tattccagcc cctacggaca                                           20

<210> SEQ ID NO 112
<211> LENGTH: 20
<212> TYPE: DNA
<213> ORGANISM: Clostridium boltae

<400> SEQUENCE: 112
tcaacggcct cgcatatctc                                           20

<210> SEQ ID NO 113
<211> LENGTH: 22
<212> TYPE: DNA
<213> ORGANISM: Clostridium boltae

<400> SEQUENCE: 113
```

-continued attctccggt atttgcccaa tg                                        22

<210> SEQ ID NO 114
<211> LENGTH: 20
<212> TYPE: DNA
<213> ORGANISM: Clostridium boltae

<400> SEQUENCE: 114
taccagtgta aggcggtcat                                           20

<210> SEQ ID NO 115
<211> LENGTH: 20
<212> TYPE: DNA
<213> ORGANISM: Clostridium boltae

<400> SEQUENCE: 115
ccgcgctaaa gattcatggc                                           20

<210> SEQ ID NO 116
<211> LENGTH: 20
<212> TYPE: DNA
<213> ORGANISM: Clostridium boltae

<400> SEQUENCE: 116
gcttgcaagg ctgtggtttt                                           20

<210> SEQ ID NO 117
<211> LENGTH: 20
<212> TYPE: DNA
<213> ORGANISM: Clostridium boltae

<400> SEQUENCE: 117
ctgtgtaccc tctgtgcctg                                           20

<210> SEQ ID NO 118
<211> LENGTH: 20
<212> TYPE: DNA
<213> ORGANISM: Clostridium boltae

<400> SEQUENCE: 118
agattccgtt tcagcccctg                                           20

<210> SEQ ID NO 119
<211> LENGTH: 20
<212> TYPE: DNA
<213> ORGANISM: Clostridium clostridioforme

<400> SEQUENCE: 119
tgcatggatg ataccgaccg                                           20

<210> SEQ ID NO 120
<211> LENGTH: 20
<212> TYPE: DNA
<213> ORGANISM: Clostridium clostridioforme

<400> SEQUENCE: 120
ccgcgtttgt ggtttccaat                                           20

<210> SEQ ID NO 121
<211> LENGTH: 20
<212> TYPE: DNA
<213> ORGANISM: Clostridium clostridioforme

<400> SEQUENCE: 121

-continued

```
tcaaagatgc ggcagaggag                                          20

<210> SEQ ID NO 122
<211> LENGTH: 20
<212> TYPE: DNA
<213> ORGANISM: Clostridium clostridioforme

<400> SEQUENCE: 122
caactcctga tacgcctccc                                          20

<210> SEQ ID NO 123
<211> LENGTH: 20
<212> TYPE: DNA
<213> ORGANISM: Clostridium clostridioforme

<400> SEQUENCE: 123
gggacgccct tctgattgaa                                          20

<210> SEQ ID NO 124
<211> LENGTH: 20
<212> TYPE: DNA
<213> ORGANISM: Clostridium clostridioforme

<400> SEQUENCE: 124
agtgcaaaca aggccggata                                          20

<210> SEQ ID NO 125
<211> LENGTH: 20
<212> TYPE: DNA
<213> ORGANISM: Clostridium clostridioforme

<400> SEQUENCE: 125
ccatcggatg tctggttgct                                          20

<210> SEQ ID NO 126
<211> LENGTH: 20
<212> TYPE: DNA
<213> ORGANISM: Clostridium clostridioforme

<400> SEQUENCE: 126
tcctccaata gccaaacgca                                          20

<210> SEQ ID NO 127
<211> LENGTH: 20
<212> TYPE: DNA
<213> ORGANISM: Clostridium clostridioforme

<400> SEQUENCE: 127
gcccagtgca gacatggata                                          20

<210> SEQ ID NO 128
<211> LENGTH: 20
<212> TYPE: DNA
<213> ORGANISM: Clostridium clostridioforme

<400> SEQUENCE: 128
agccaatgca ccatagacgg                                          20

<210> SEQ ID NO 129
<211> LENGTH: 20
<212> TYPE: DNA
<213> ORGANISM: Clostridium clostridioforme
```

-continued

```
<400> SEQUENCE: 129
tgtgccagga acgggataac                                               20

<210> SEQ ID NO 130
<211> LENGTH: 20
<212> TYPE: DNA
<213> ORGANISM: Clostridium clostridioforme

<400> SEQUENCE: 130
cagattcagc tgcccaggaa                                               20

<210> SEQ ID NO 131
<211> LENGTH: 20
<212> TYPE: DNA
<213> ORGANISM: Clostridium clostridioforme

<400> SEQUENCE: 131
gccgtggtta atgcatcgtt                                               20

<210> SEQ ID NO 132
<211> LENGTH: 20
<212> TYPE: DNA
<213> ORGANISM: Clostridium clostridioforme

<400> SEQUENCE: 132
tgccggttgc cttcgattat                                               20

<210> SEQ ID NO 133
<211> LENGTH: 20
<212> TYPE: DNA
<213> ORGANISM: Clostridium clostridioforme

<400> SEQUENCE: 133
gctggcagga gtagtttcgt                                               20

<210> SEQ ID NO 134
<211> LENGTH: 20
<212> TYPE: DNA
<213> ORGANISM: Clostridium clostridioforme

<400> SEQUENCE: 134
tggcggcaat tgtttccttg                                               20

<210> SEQ ID NO 135
<211> LENGTH: 20
<212> TYPE: DNA
<213> ORGANISM: Clostridium clostridioforme

<400> SEQUENCE: 135
gccgtcaggc gtattatgga                                               20

<210> SEQ ID NO 136
<211> LENGTH: 20
<212> TYPE: DNA
<213> ORGANISM: Clostridium clostridioforme

<400> SEQUENCE: 136 ccctttggc gtcttcctct                                                20

<210> SEQ ID NO 137
<211> LENGTH: 20
<212> TYPE: DNA
<213> ORGANISM: Clostridium clostridioforme
```

-continued

```
<400> SEQUENCE: 137
ccgttacgtt gaggctctgt                                               20

<210> SEQ ID NO 138
<211> LENGTH: 20
<212> TYPE: DNA
<213> ORGANISM: Clostridium clostridioforme

<400> SEQUENCE: 138
gtgcatacgg tcatgggtga                                               20

<210> SEQ ID NO 139
<211> LENGTH: 20
<212> TYPE: DNA
<213> ORGANISM: Clostridium clostridioforme

<400> SEQUENCE: 139
tagcggctgc aaatagcctt                                               20

<210> SEQ ID NO 140
<211> LENGTH: 20
<212> TYPE: DNA
<213> ORGANISM: Clostridium clostridioforme

<400> SEQUENCE: 140
tgggctggat gaaaccacaa                                               20

<210> SEQ ID NO 141
<211> LENGTH: 20
<212> TYPE: DNA
<213> ORGANISM: Clostridium hathewayi

<400> SEQUENCE: 141
aaggcggtaa atggcggtta                                               20

<210> SEQ ID NO 142
<211> LENGTH: 20
<212> TYPE: DNA
<213> ORGANISM: Clostridium hathewayi

<400> SEQUENCE: 142
cgtctgcttc atcaatggcg                                               20

<210> SEQ ID NO 143
<211> LENGTH: 20
<212> TYPE: DNA
<213> ORGANISM: Clostridium hathewayi

<400> SEQUENCE: 143
tatttaccgt cagcggcagg                                               20

<210> SEQ ID NO 144
<211> LENGTH: 20
<212> TYPE: DNA
<213> ORGANISM: Clostridium hathewayi

<400> SEQUENCE: 144
gttgctgaat tccactccgc                                               20

<210> SEQ ID NO 145
<211> LENGTH: 20
<212> TYPE: DNA
```

-continued

<213> ORGANISM: Clostridium hathewayi

<400> SEQUENCE: 145
accacaattc tctgtgccgt                                                    20

<210> SEQ ID NO 146
<211> LENGTH: 20
<212> TYPE: DNA
<213> ORGANISM: Clostridium hathewayi

<400> SEQUENCE: 146
tgccgggata accaaactcc                                                    20

<210> SEQ ID NO 147
<211> LENGTH: 20
<212> TYPE: DNA
<213> ORGANISM: Clostridium hathewayi

<400> SEQUENCE: 147
cgcatcggga atcgaagaga                                                    20

<210> SEQ ID NO 148
<211> LENGTH: 20
<212> TYPE: DNA
<213> ORGANISM: Clostridium hathewayi

<400> SEQUENCE: 148
attcagccct ccgcctattg                                                    20

<210> SEQ ID NO 149
<211> LENGTH: 20
<212> TYPE: DNA
<213> ORGANISM: Clostridium hathewayi

<400> SEQUENCE: 149
ttctggaaaa ggctgcggat                                                    20

<210> SEQ ID NO 150
<211> LENGTH: 20
<212> TYPE: DNA
<213> ORGANISM: Clostridium hathewayi

<400> SEQUENCE: 150
cactggctct caagtcctcg                                                    20

<210> SEQ ID NO 151
<211> LENGTH: 20
<212> TYPE: DNA
<213> ORGANISM: Clostridium hathewayi

<400> SEQUENCE: 151
ggcttctacg gaccgtttca                                                    20

<210> SEQ ID NO 152
<211> LENGTH: 20
<212> TYPE: DNA
<213> ORGANISM: Clostridium hathewayi

<400> SEQUENCE: 152
ttggcaatcc agaatgggct                                                    20

<210> SEQ ID NO 153
<211> LENGTH: 20

-continued

<212> TYPE: DNA
<213> ORGANISM: Clostridium hathewayi

<400> SEQUENCE: 153
accaaccggc tgattacgtt                                            20

<210> SEQ ID NO 154
<211> LENGTH: 20
<212> TYPE: DNA
<213> ORGANISM: Clostridium hathewayi

<400> SEQUENCE: 154
gcctctgttc ctcctcacac                                            20

<210> SEQ ID NO 155
<211> LENGTH: 20
<212> TYPE: DNA
<213> ORGANISM: Clostridium hathewayi

<400> SEQUENCE: 155
tcacccagga cttaaaccgc                                            20

<210> SEQ ID NO 156
<211> LENGTH: 20
<212> TYPE: DNA
<213> ORGANISM: Clostridium hathewayi

<400> SEQUENCE: 156
gaggcgctta tccagctcat                                            20

<210> SEQ ID NO 157
<211> LENGTH: 20
<212> TYPE: DNA
<213> ORGANISM: Clostridium hathewayi

<400> SEQUENCE: 157
cggctgggga agattgtgat                                            20

<210> SEQ ID NO 158
<211> LENGTH: 20
<212> TYPE: DNA
<213> ORGANISM: Clostridium hathewayi

<400> SEQUENCE: 158
caaaagcact gcaagcgact                                            20

<210> SEQ ID NO 159
<211> LENGTH: 20
<212> TYPE: DNA
<213> ORGANISM: Clostridium hathewayi

<400> SEQUENCE: 159
gccggaggct atgactatcg                                            20

<210> SEQ ID NO 160
<211> LENGTH: 20
<212> TYPE: DNA
<213> ORGANISM: Clostridium hathewayi

<400> SEQUENCE: 160
aatgagaatg cggccgtttg                                            20

<210> SEQ ID NO 161

-continued

```
<211> LENGTH: 20
<212> TYPE: DNA
<213> ORGANISM: Clostridium hathewayi

<400> SEQUENCE: 161
ggccctgatt cgggatcatt                                          20

<210> SEQ ID NO 162
<211> LENGTH: 20
<212> TYPE: DNA
<213> ORGANISM: Clostridium hathewayi

<400> SEQUENCE: 162
ttccgcacat tctcgacctc                                          20

<210> SEQ ID NO 163
<211> LENGTH: 20
<212> TYPE: DNA
<213> ORGANISM: Clostridium hathewayi

<400> SEQUENCE: 163
caagccaaca gagagccaga                                          20

<210> SEQ ID NO 164
<211> LENGTH: 20
<212> TYPE: DNA
<213> ORGANISM: Clostridium hathewayi

<400> SEQUENCE: 164
actccaggtc ccttctctcc                                          20

<210> SEQ ID NO 165
<211> LENGTH: 20
<212> TYPE: DNA
<213> ORGANISM: Dorea longicatena

<400> SEQUENCE: 165
accggaagaa tggacttcgg                                          20

<210> SEQ ID NO 166
<211> LENGTH: 20
<212> TYPE: DNA
<213> ORGANISM: Dorea longicatena

<400> SEQUENCE: 166
agcggctggt tacttttcca                                          20

<210> SEQ ID NO 167
<211> LENGTH: 20
<212> TYPE: DNA
<213> ORGANISM: Dorea longicatena

<400> SEQUENCE: 167
agcttctgac gggagcaatg                                          20

<210> SEQ ID NO 168
<211> LENGTH: 20
<212> TYPE: DNA
<213> ORGANISM: Dorea longicatena

<400> SEQUENCE: 168
caccgtctga tttcccgcat                                          20
```

-continued

```
<210> SEQ ID NO 169
<211> LENGTH: 20
<212> TYPE: DNA
<213> ORGANISM: Dorea longicatena

<400> SEQUENCE: 169
tttatctggc agaagccgca                                              20

<210> SEQ ID NO 170
<211> LENGTH: 20
<212> TYPE: DNA
<213> ORGANISM: Dorea longicatena

<400> SEQUENCE: 170
tgaacgccat gctgcaattc                                              20

<210> SEQ ID NO 171
<211> LENGTH: 20
<212> TYPE: DNA
<213> ORGANISM: Dorea longicatena

<400> SEQUENCE: 171
cgatgatccg ggcaacaatg                                              20

<210> SEQ ID NO 172
<211> LENGTH: 20
<212> TYPE: DNA
<213> ORGANISM: Dorea longicatena

<400> SEQUENCE: 172
ccggcatctt ctggtacgaa                                              20

<210> SEQ ID NO 173
<211> LENGTH: 20
<212> TYPE: DNA
<213> ORGANISM: Dorea longicatena

<400> SEQUENCE: 173
atggcgacgg aagtgcatta                                              20

<210> SEQ ID NO 174
<211> LENGTH: 20
<212> TYPE: DNA
<213> ORGANISM: Dorea longicatena

<400> SEQUENCE: 174
cggtacagca aacggtggta                                              20

<210> SEQ ID NO 175
<211> LENGTH: 20
<212> TYPE: DNA
<213> ORGANISM: Dorea longicatena

<400> SEQUENCE: 175
aagctcaggc acagacgaaa                                              20

<210> SEQ ID NO 176
<211> LENGTH: 20
<212> TYPE: DNA
<213> ORGANISM: Dorea longicatena

<400> SEQUENCE: 176
ttccgtccgc cagatcaaaa                                              20
```

-continued

<210> SEQ ID NO 177
<211> LENGTH: 20
<212> TYPE: DNA
<213> ORGANISM: Dorea longicatena

<400> SEQUENCE: 177
tcgattctgg cgatagcagg                                                       20

<210> SEQ ID NO 178
<211> LENGTH: 20
<212> TYPE: DNA
<213> ORGANISM: Dorea longicatena

<400> SEQUENCE: 178
tgccaaaggg aggctgtaag                                                       20

<210> SEQ ID NO 179
<211> LENGTH: 20
<212> TYPE: DNA
<213> ORGANISM: Dorea longicatena

<400> SEQUENCE: 179
tgcggacggg cagtattatc                                                       20

<210> SEQ ID NO 180
<211> LENGTH: 20
<212> TYPE: DNA
<213> ORGANISM: Dorea longicatena

<400> SEQUENCE: 180
tctttccgtc aaccgcagaa                                                       20

<210> SEQ ID NO 181
<211> LENGTH: 20
<212> TYPE: DNA
<213> ORGANISM: Dorea longicatena

<400> SEQUENCE: 181
ggccgctgtc tattcgatga                                                       20

<210> SEQ ID NO 182
<211> LENGTH: 20
<212> TYPE: DNA
<213> ORGANISM: Dorea longicatena

<400> SEQUENCE: 182
agcagaaaac tgcacccgat                                                       20

<210> SEQ ID NO 183
<211> LENGTH: 20
<212> TYPE: DNA
<213> ORGANISM: Dorea longicatena

<400> SEQUENCE: 183
tctgggggca ttcgcatatc                                                       20

<210> SEQ ID NO 184
<211> LENGTH: 20
<212> TYPE: DNA
<213> ORGANISM: Dorea longicatena

<400> SEQUENCE: 184
accgacatct gtcatcgtcg                                                       20

-continued

```
<210> SEQ ID NO 185
<211> LENGTH: 19
<212> TYPE: DNA
<213> ORGANISM: Dorea longicatena

<400> SEQUENCE: 185
ttggctgggc gacattagg                                                    19

<210> SEQ ID NO 186
<211> LENGTH: 21
<212> TYPE: DNA
<213> ORGANISM: Dorea longicatena

<400> SEQUENCE: 186
acgtatttct cgccaaagca c                                                 21

<210> SEQ ID NO 187
<211> LENGTH: 20
<212> TYPE: DNA
<213> ORGANISM: Dorea longicatena

<400> SEQUENCE: 187
tccgaaaatg tgcaggggaa                                                   20

<210> SEQ ID NO 188
<211> LENGTH: 20
<212> TYPE: DNA
<213> ORGANISM: Dorea longicatena

<400> SEQUENCE: 188
acgccagttg tcctgctatc                                                   20

<210> SEQ ID NO 189
<211> LENGTH: 20
<212> TYPE: DNA
<213> ORGANISM: Eubacterium siraeum

<400> SEQUENCE: 189
taggcgatgt aacgctcgac                                                   20

<210> SEQ ID NO 190
<211> LENGTH: 20
<212> TYPE: DNA
<213> ORGANISM: Eubacterium siraeum

<400> SEQUENCE: 190
acaagcgtct ttgcgttgtc                                                   20

<210> SEQ ID NO 191
<211> LENGTH: 23
<212> TYPE: DNA
<213> ORGANISM: Eubacterium siraeum

<400> SEQUENCE: 191
gagatatgca gagaagcccg aac                                               23

<210> SEQ ID NO 192
<211> LENGTH: 21
<212> TYPE: DNA
<213> ORGANISM: Eubacterium siraeum

<400> SEQUENCE: 192
```

-continued

```
aggcgtggaa acagcgtaat a                                          21

<210> SEQ ID NO 193
<211> LENGTH: 20
<212> TYPE: DNA
<213> ORGANISM: Eubacterium siraeum

<400> SEQUENCE: 193
catcaaagcg gtttgtcgca                                            20

<210> SEQ ID NO 194
<211> LENGTH: 20
<212> TYPE: DNA
<213> ORGANISM: Eubacterium siraeum

<400> SEQUENCE: 194
cactcagcgg cttttatcgc                                            20

<210> SEQ ID NO 195
<211> LENGTH: 20
<212> TYPE: DNA
<213> ORGANISM: Eubacterium siraeum

<400> SEQUENCE: 195
atggaggagg aaaccgcaag                                            20

<210> SEQ ID NO 196
<211> LENGTH: 20
<212> TYPE: DNA
<213> ORGANISM: Eubacterium siraeum

<400> SEQUENCE: 196
taccgatgct accggtgctg                                            20

<210> SEQ ID NO 197
<211> LENGTH: 20
<212> TYPE: DNA
<213> ORGANISM: Eubacterium siraeum

<400> SEQUENCE: 197
gctgccgtct gctgttttac                                            20

<210> SEQ ID NO 198
<211> LENGTH: 20
<212> TYPE: DNA
<213> ORGANISM: Eubacterium siraeum

<400> SEQUENCE: 198
aggtctttgt tgtcagcccc                                            20

<210> SEQ ID NO 199
<211> LENGTH: 20
<212> TYPE: DNA
<213> ORGANISM: Eubacterium siraeum

<400> SEQUENCE: 199
aggctcccaa tccgtacaac                                            20

<210> SEQ ID NO 200
<211> LENGTH: 21
<212> TYPE: DNA
<213> ORGANISM: Eubacterium siraeum

<400> SEQUENCE: 200
```

-continued

```
cttaacgtcg aacctccgtg a                                          21

<210> SEQ ID NO 201
<211> LENGTH: 25
<212> TYPE: DNA
<213> ORGANISM: Eubacterium siraeum

<400> SEQUENCE: 201
gagatggaca attcgcagaa tgcaa                                      25

<210> SEQ ID NO 202
<211> LENGTH: 20
<212> TYPE: DNA
<213> ORGANISM: Eubacterium siraeum

<400> SEQUENCE: 202
gccgatgacg taaggctcag                                            20

<210> SEQ ID NO 203
<211> LENGTH: 20
<212> TYPE: DNA
<213> ORGANISM: Eubacterium siraeum

<400> SEQUENCE: 203
gcggacaaga agaccgaaga                                            20

<210> SEQ ID NO 204
<211> LENGTH: 19
<212> TYPE: DNA
<213> ORGANISM: Eubacterium siraeum

<400> SEQUENCE: 204
caccgtgacc gcctatgtt                                             19

<210> SEQ ID NO 205
<211> LENGTH: 22
<212> TYPE: DNA
<213> ORGANISM: Eubacterium siraeum

<400> SEQUENCE: 205
catttgaaaa gggtgcggct gt                                         22

<210> SEQ ID NO 206
<211> LENGTH: 19
<212> TYPE: DNA
<213> ORGANISM: Eubacterium siraeum

<400> SEQUENCE: 206
cacattccca gtgccgact                                             19

<210> SEQ ID NO 207
<211> LENGTH: 22
<212> TYPE: DNA
<213> ORGANISM: Eubacterium siraeum

<400> SEQUENCE: 207
ttttgtgcag tctgcttgtc ag                                         22

<210> SEQ ID NO 208
<211> LENGTH: 18
<212> TYPE: DNA
<213> ORGANISM: Eubacterium siraeum
```

-continued

```
<400> SEQUENCE: 208
gccttcttca cgtgtgggg                                              18

<210> SEQ ID NO 209
<211> LENGTH: 20
<212> TYPE: DNA
<213> ORGANISM: Eubacterium siraeum

<400> SEQUENCE: 209
ttgtccgtga ggaactgtcg                                             20

<210> SEQ ID NO 210
<211> LENGTH: 20
<212> TYPE: DNA
<213> ORGANISM: Eubacterium siraeum

<400> SEQUENCE: 210
cattccacgc tcgtttagcg                                             20

<210> SEQ ID NO 211
<211> LENGTH: 20
<212> TYPE: DNA
<213> ORGANISM: Eubacterium siraeum

<400> SEQUENCE: 211
cttctgtcct cgtgcagtgt                                             20

<210> SEQ ID NO 212
<211> LENGTH: 23
<212> TYPE: DNA
<213> ORGANISM: Eubacterium siraeum

<400> SEQUENCE: 212
agggatgtta tattcgccga tca                                         23

<210> SEQ ID NO 213
<211> LENGTH: 20
<212> TYPE: DNA
<213> ORGANISM: Clostridium boltae

<400> SEQUENCE: 213
atgcctccag aacctccgcc                                             20

<210> SEQ ID NO 214
<211> LENGTH: 20
<212> TYPE: DNA
<213> ORGANISM: Clostridium boltae

<400> SEQUENCE: 214
cagctgctgc ttccggaata                                             20

<210> SEQ ID NO 215
<211> LENGTH: 20
<212> TYPE: DNA
<213> ORGANISM: Clostridium boltae

<400> SEQUENCE: 215
aattcatcag tatttacggc                                             20

<210> SEQ ID NO 216
<211> LENGTH: 20
<212> TYPE: DNA
<213> ORGANISM: Clostridium boltae
```

-continued

```
<400> SEQUENCE: 216
tccgcatctg ctcatcatat                                              20

<210> SEQ ID NO 217
<211> LENGTH: 20
<212> TYPE: DNA
<213> ORGANISM: Clostridium boltae

<400> SEQUENCE: 217
gtatttcaca ctgtcactgc                                              20

<210> SEQ ID NO 218
<211> LENGTH: 20
<212> TYPE: DNA
<213> ORGANISM: Clostridium boltae

<400> SEQUENCE: 218
ctggagccgc atgttatcaa                                              20

<210> SEQ ID NO 219
<211> LENGTH: 20
<212> TYPE: DNA
<213> ORGANISM: Clostridium boltae

<400> SEQUENCE: 219
gaggaagcgg ccagggaggc                                              20

<210> SEQ ID NO 220
<211> LENGTH: 20
<212> TYPE: DNA
<213> ORGANISM: Clostridium boltae

<400> SEQUENCE: 220
cagacgagga atattctgta                                              20

<210> SEQ ID NO 221
<211> LENGTH: 20
<212> TYPE: DNA
<213> ORGANISM: Clostridium boltae

<400> SEQUENCE: 221
acggtctgga acaagaggaa                                              20

<210> SEQ ID NO 222
<211> LENGTH: 20
<212> TYPE: DNA
<213> ORGANISM: Clostridium boltae

<400> SEQUENCE: 222
caggtacaga gtcagttacc                                              20

<210> SEQ ID NO 223
<211> LENGTH: 20
<212> TYPE: DNA
<213> ORGANISM: Clostridium boltae

<400> SEQUENCE: 223
agcccgccgc ccaattaccg                                              20

<210> SEQ ID NO 224
<211> LENGTH: 20
<212> TYPE: DNA
```

-continued

<213> ORGANISM: Clostridium boltae

<400> SEQUENCE: 224
agcctacttg ctggcaggac                                                  20

<210> SEQ ID NO 225
<211> LENGTH: 20
<212> TYPE: DNA
<213> ORGANISM: Clostridium clostridioforme

<400> SEQUENCE: 225
cgcatcaaca gcgaaccgga                                                  20

<210> SEQ ID NO 226
<211> LENGTH: 20
<212> TYPE: DNA
<213> ORGANISM: Clostridium clostridioforme

<400> SEQUENCE: 226
cgattcaagc agcatctgac                                                  20

<210> SEQ ID NO 227
<211> LENGTH: 20
<212> TYPE: DNA
<213> ORGANISM: Clostridium clostridioforme

<400> SEQUENCE: 227
cctaagctcc gtctcatcta                                                  20

<210> SEQ ID NO 228
<211> LENGTH: 20
<212> TYPE: DNA
<213> ORGANISM: Clostridium clostridioforme

<400> SEQUENCE: 228
catgctgctg caaactccga                                                  20

<210> SEQ ID NO 229
<211> LENGTH: 20
<212> TYPE: DNA
<213> ORGANISM: Clostridium clostridioforme

<400> SEQUENCE: 229
gcttatttat ggaagatatc                                                  20

<210> SEQ ID NO 230
<211> LENGTH: 20
<212> TYPE: DNA
<213> ORGANISM: Clostridium clostridioforme

<400> SEQUENCE: 230
cagtgacggc tattcctata                                                  20

<210> SEQ ID NO 231
<211> LENGTH: 20
<212> TYPE: DNA
<213> ORGANISM: Clostridium clostridioforme

<400> SEQUENCE: 231
gaacgggatt ggaaacagtg                                                  20

<210> SEQ ID NO 232
<211> LENGTH: 20

-continued

```
<212> TYPE: DNA
<213> ORGANISM: Clostridium clostridioforme

<400> SEQUENCE: 232
gcaaccggca acaggtaaac                                          20

<210> SEQ ID NO 233
<211> LENGTH: 20
<212> TYPE: DNA
<213> ORGANISM: Clostridium clostridioforme

<400> SEQUENCE: 233
gtacacgaag ccccggaaca                                          20

<210> SEQ ID NO 234
<211> LENGTH: 20
<212> TYPE: DNA
<213> ORGANISM: Clostridium clostridioforme

<400> SEQUENCE: 234
gccccagtcc aggcggattg                                          20

<210> SEQ ID NO 235
<211> LENGTH: 20
<212> TYPE: DNA
<213> ORGANISM: Clostridium clostridioforme

<400> SEQUENCE: 235
cagcttaaac cgttacgttg                                          20

<210> SEQ ID NO 236
<211> LENGTH: 20
<212> TYPE: DNA
<213> ORGANISM: Clostridium clostridioforme

<400> SEQUENCE: 236
aattggactt ggaagtcatc                                          20

<210> SEQ ID NO 237
<211> LENGTH: 20
<212> TYPE: DNA
<213> ORGANISM: Clostridium hathewayi

<400> SEQUENCE: 237
cggattatca ggcggaacta                                          20

<210> SEQ ID NO 238
<211> LENGTH: 20
<212> TYPE: DNA
<213> ORGANISM: Clostridium hathewayi

<400> SEQUENCE: 238
tttcatatga tccgtcatac                                          20

<210> SEQ ID NO 239
<211> LENGTH: 20
<212> TYPE: DNA
<213> ORGANISM: Clostridium hathewayi

<400> SEQUENCE: 239
cttctttcga tggatttgca                                          20

<210> SEQ ID NO 240
```

-continued

```
<211> LENGTH: 20
<212> TYPE: DNA
<213> ORGANISM: Clostridium hathewayi

<400> SEQUENCE: 240
agctgcgggc cggtacggca                                               20

<210> SEQ ID NO 241
<211> LENGTH: 20
<212> TYPE: DNA
<213> ORGANISM: Clostridium hathewayi

<400> SEQUENCE: 241
tcagcgggga cggagtcacc                                               20

<210> SEQ ID NO 242
<211> LENGTH: 20
<212> TYPE: DNA
<213> ORGANISM: Clostridium hathewayi

<400> SEQUENCE: 242
aagcggtatc tacagaagcg                                               20

<210> SEQ ID NO 243
<211> LENGTH: 20
<212> TYPE: DNA
<213> ORGANISM: Clostridium hathewayi

<400> SEQUENCE: 243
gtcccgctgg ataagatcgt                                               20

<210> SEQ ID NO 244
<211> LENGTH: 20
<212> TYPE: DNA
<213> ORGANISM: Clostridium hathewayi

<400> SEQUENCE: 244
cggccagaaa cggcgacagc                                               20

<210> SEQ ID NO 245
<211> LENGTH: 20
<212> TYPE: DNA
<213> ORGANISM: Clostridium hathewayi

<400> SEQUENCE: 245
tccgtacatt acaagtacga                                               20

<210> SEQ ID NO 246
<211> LENGTH: 20
<212> TYPE: DNA
<213> ORGANISM: Clostridium hathewayi

<400> SEQUENCE: 246
acatgtgcgt gctggtggac                                               20

<210> SEQ ID NO 247
<211> LENGTH: 20
<212> TYPE: DNA
<213> ORGANISM: Clostridium hathewayi

<400> SEQUENCE: 247
cagttaaagg aactgcagag                                               20
```

-continued

```
<210> SEQ ID NO 248
<211> LENGTH: 20
<212> TYPE: DNA
<213> ORGANISM: Clostridium hathewayi

<400> SEQUENCE: 248
gattactgga tgccgtttaa                                                        20
```

MICROBIAL COMPOSITIONS FOR IMPROVING THE EFFICACY OF ANTICANCER TREATMENTS BASED ON IMMUNE CHECKPOINT INHIBITORS AND/OR TYROSINE KINASE INHIBITORS AND MARKERS OF RESPONSIVENESS TO SUCH TREATMENTS

FIELD OF THE INVENTION

The present invention relates to the field of anticancer treatment. In particular, the present invention concerns the role of the gut microbiota in the efficacy of treatments comprising administration of an immune checkpoint inhibitor (ICI) and/or a tyrosine kinase inhibitor (TKI), in the treatment of cancer. The present invention provides "metagenomics-based gut oncomicrobiome signatures" (GOMS) at diagnosis prior to ICI and/or TKI administration and/or after initiation of the treatment, as novel predictors of response or resistance to the treatment. The present invention also provides theranostic methods to identify patients in need of a bacterial compensation treatment before receiving an ICI and/or TKI and/or during the therapy with such ICI and/or TKI, as well as novel bacterial species appropriate for such a bacterial compensation.

BACKGROUND AND PRIOR ART

Metastatic renal cell carcinoma (RCC) have long been considered as "immunogenic malignancies" susceptible to immunotherapies (Rosenberg et al., 1993; Escudier et al., 1994). In this tumor type, the prognostic role of the immune contexture was broadly heralded. In both primary and metastatic RCC, CD38+ tumor associated macrophages, immature dendritic cells (DC), the absence of tertiary lymphoid organs or overt expression of T cell inhibitory receptors and tumoral PD-L1 are associated with shorter overall survival (OS) in both primary and metastatic RCC (Ascierto et al., 2016; Becht et al., 2015, 2016; Chevrier et al., 2017; Giraldo et al., 2015, 2017). Despite the success seen with interleukin-2, an immuno-oncological revolution has been truly precipitated by the regulatory approval of immune checkpoint blockers, agents that release latent anticancer immunity. After positive trials in second line (2L) setting (Motzer et al., 2015), the Checkmate 214 trial combining anti-PD-1 and anti-CTLA-4 (CICB) in first line (1L) metastatic RCC (Motzer et al., 2018), new data from randomized Phase Ill trials (JAVELIN Renal 101, KEYNOTE-426, and IMmotion 151) provide evidence that immune-based combination therapy (anti-PD-(L)1 and tyrosine kinase inhibitors (TKI)) is superior to standard care sunitinib (Motzer et al., 2019; Porta and Rizzo, 2019; Rini et al., 2019b, 2019a). In this rapidly expanding field, patients stratification is now required to predict tumor aggressiveness. Moreover, immune-related adverse events are common and lead to complex treatment paradigms. These obstacles can be overcome by exploring the impact of neo-angiogenesis/hypoxia patterns and Th1 geared-inflammatory profile to generate novel molecular classification of RCC (Beuselinck et al., 2015; Casuscelli et al., 2017). In addition, several arguments are currently in favor of the influence of the intestinal microbiome in oncogenesis and response to therapy, some establishing cause-effect relationships between the fecal composition and clinical outcome in mice and humans. First, distinct commensals exert protumorigenic effects, as observed in colon and pancreatic cancers (Kroemer and Zitvogel, 2018). Second, antibiotics (ATB) compromise the efficacy of (combined) immune checkpoint blockade (ICB), independently of the tumor histology (Derosa et al., 2018; Elkrief et al., 2019; Routy et al., 2018). Third, microbiome profiling revealed different fingerprints between responders and non-responders to ICB across groups and countries (Gopalakrishnan et al., 2018; Matson et al., 2018; Routy et al., 2018). Finally, selecting immuno-stimulatory bacteria species (*Akkermansia muciniphila* (Routy et al., 2018), *Bifidobacterium longum* (Matson et al., 2018; Sivan et al., 2015), *Bacteroides fragilis* (Vétizou et al., 2015)) or strains (*Enterococcus* hirae 13144 but not 13344 (Daillère et al., 2016)) can elicit systemic immune responses and reprogram the tumor microenvironment (TME) in mouse tumors treated with anti-CTLA-4 and/or anti-PD-1 antibodies.

The results disclosed in the present application show that the composition of the microbiome is influenced by antibiotics, tyrosine kinase inhibitors (TKI) and immune checkpoint blockers (ICB), and that the composition of the microbiome has an impact on the success of immunotherapy by modulating the cancer-immune set point of the host and can be modified to increase the response to these treatments.

SUMMARY OF THE INVENTION

According to a first aspect, the present invention pertains to a composition comprising bacteria selected from the group consisting of *Alistipes senegalensis, Dorea longicatena, Eubacterium siraeum* and mixtures thereof, for use for treating a cancer, in combination with an immune checkpoint inhibitor (ICI)-based therapy and/or a tyrosine kinase inhibitor (TKI)-based therapy wherein said composition induces immunostimulation in a cancer patient.

The invention also pertains to a fecal microbial composition, for use in treating a cancer, in combination with an ICI-based therapy and/or a TKI-based therapy, wherein said composition has been enriched with a composition as above-described.

Method of in vitro determining if an individual having a cancer is likely to respond to a treatment with an ICI-based therapy and/or a TKI-based therapy are also part of the present invention. One is based on determining the relative abundances of *Clostridium hathewayi, Clostridium clostridioforme* and/or *Clostridium boltae* in a biological sample of said individual, wherein overrepresentation of at least one of these species indicates that the individual is likely to be a poor responder to said treatment.

Another method of in vitro determining if a cancer patient is likely to respond to an ICI-based and/or a TKI-based therapy comprises:

(i) determining the relative abundance of at least two immunotolerant species selected from the group consisting of *Clostridium hathewayi, Clostridium clostridioforme* and *Clostridium boltae* in the gut microbiota of said patient;

(ii) determining the relative abundance of at least two (e.g., 2, 3, 4 or 5) immunostimulatory species selected from the group consisting of *Akkermansia muciniphila, Bacteroides salyersiae, Alistipes senegalensis, Dorea longicatena*, and *Eubacterium siraeum* in the patient's gut microbiota;

(iii) calculating the ratio of the relative abundance of the immunotolerant species of step (i) to the relative abundance of the immunostimulatory species of step (ii);

wherein the lower the ratio calculated in step (iii), the higher the probability that the individual responds to the treatment.

Other methods for in vitro determining if a cancer patient is likely to respond to an ICI-based and/or a TKI-based therapy are based on assessing, in a blood sample from said patient, the presence of memory Th1 or Tc1 cells towards *Alistipes senegalensis, Dorea longicatena* and/or *Eubacterium siraeum*, and/or the presence of memory Tr cells towards *Clostridium hathewayi, Clostridium clostridioforme* and/or *Clostridium boltae*, wherein the presence of memory Th1 or Tc1 cells towards *Alistipes senegalensis, Dorea longicatena* and/or *Eubacterium siraeum* indicates that the patient is likely to be a good responder to said treatment and the presence of memory CD4+ Tr cells (IL-10 producing) or TH17 regulatory Rorct/foxp3 towards *Clostridium hathewayi, Clostridium clostridioforme* and/or *Clostridium boltae* indicates that the patient is likely to be a poor responder to said treatment.

Theranostic methods for determining whether an individual needs a bacterial compensation with a bacterial composition and/or by FMT before receiving an ICI-based therapy and/or a TKI-based treatment are also part of the invention.

The invention also pertains to the use of an endonuclease (e.g., a CRISPR/Cas9) capable of inducing a double-stranded break in a sequence specific for *Clostridium hathewayi, Clostridium clostridioforme* or *Clostridium boltae*, as a medication for treating cancer, in combination with a TKI and/or an ICB-based therapy.

Figure 1A:
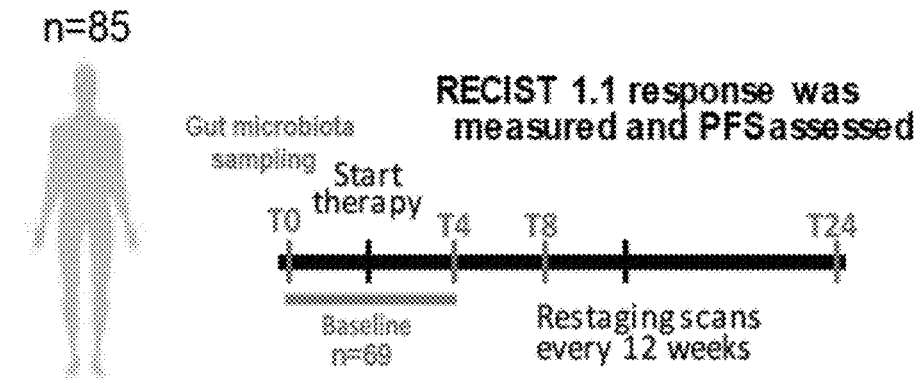
FIG. 1A-1D: Antibiotics compromise the efficacy of PD-1 blockade and affect the intestinal composition of feces in advanced renal cell carcinoma patients.
Figure 1B:
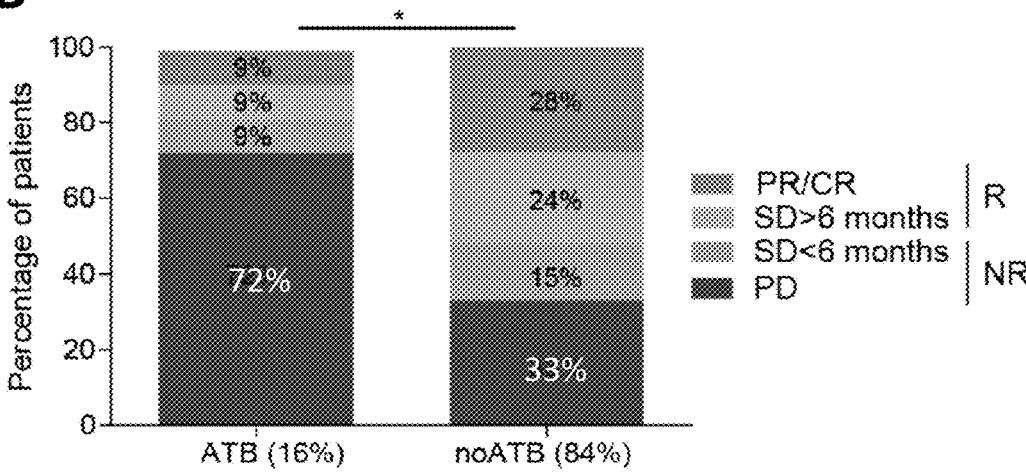

(A) Patients with advanced renal cell carcinoma (n=85) were evaluated for clinical outcomes and correlative fecal microbiota (n=69) analyses prior to and following initiation of anti-PD-1 blockade. Tumor response was assessed using the Response Evaluation Criteria in Solid Tumors version 1.1 (RECIST v1.1).

(B) The best overall response was stratified by use of ATB (ATB=11, patients who took antibiotics; noATB=58, patients who did not take antibiotics). P value was obtained with two-tailed chi-squared test and Yates correction and significant p values are indicated with * (*p<0.05, p<0.01, *p<0.001).

(C) Beta-diversity ordination plot based on Principal Coordinate Analysis (PCoA) of normalized and standardized data of fecal microbiota composition in pre-treatment (T0-T4) samples (n=69). Bacterial relative abundances were obtained with MetaOmineR package developed in 'R' by INRA. Percentage of variance embraced by each new coordinate is reported in percentages for each axis. Ellipses describing the 95% of confidence are even depicted for each cohort. ANOSIM metrics was implemented with 999 permutations to assess differences among ATB (gold) and noATB (blue) cohorts.

(D) LEfSe graph was implemented in Python v2.7 on bacterial species undergoing two-stages Benjamini-Hochberg False Detection Rate (FDR) at 10%, resulting in the identification of the most discriminant species for each cohort based on LDA score.

FIG. 2A-2D: Metagenomic analyses of fecal samples predict response of anti-PD-1 mAb in renal cell carcinoma patients.

(A) Shotgun sequencing of fecal microbiota in no-ATB basal (T0-T4) samples (n=58) with representation of gene richness and MGS count for all cancer patients according to clinical outcome (PFS at 3, 6, 9, 12 months). Mean±SEM of count are depicted for patients who experienced PFS more or less 3, 6, 9, 12 months. Of note gene richness and MGS count predict PFS at 12 months, while gene richness alone predicts PFS at 6 months.

(B) Beta-diversity ordination plot based on Principal Coordinate Analysis (PCoA) of normalized and standardized data of fecal microbiota composition in no-ATB basal (T0-T4) samples (n=58). Bacterial relative abundances were obtained with MetaOmineR package developed in 'R' by MetaGenoPolis (INRA). Percentage of variance embraced by each new coordinate is reported in percentages for each axis. Ellipses describing the 95% of confidence are even depicted for each cohort. ANOSIM and PERMANOVA metrics were implemented with 999 permutations to assess differences according to R (complete response or partial response or stable disease more than 6 months) and NR (death or progressive disease or stable disease less than 6 months).

(C) Variable Importance Plot (VIP) was implemented within Partial Least Square Discriminant Analysis (PLS-DA, inset differentiating NR and R), describing the 35 most discriminant species in descending order of importance. Each bar reports the following information: i) length, VIP score; ii) bar color, cohort in which the species has the highest mean relative abundance (high); iii) edge color, cohort in which the species has the lowest mean relative abundance (low); iv) thickness, Fold Ratio (FR) among high and low; v) significance of Mann-Whitney U test among high and low (*p<0.05, p<0.01, *p<0.001).

(D) Barplots of relative abundances (within the 0-1 interval) and prevalence of selected species (*A. muciniphila* and *B. salyersiae*). P values for relative abundances were obtained after two-tailed Mann-Whitney U test, while P values for prevalence were retrieved by chi-square test.

FIG. 3A-3E: Oral gavage with immunostimulatory commensals or feces from responders-RCC patients rescues the primary resistance in RCC tumor bearing mice.

(A) Experimental setting: Fecal microbial transplantation (FMT) was performed following 3 days of ATB in specific pathogen free (SPF) BALB/c mice. Two weeks later, luciferase engineered RENal cell CArcinoma (RENCA) were orthotopically inoculated and anti-PD-1 plus anti-CTLA-4 mAbs (CICB) or isotype control mAb (Ctrl) were inoculated intraperitoneally every 4 days starting from day-7. ATB induced dysbiosis were restored by oral administration of commensals *A. muciniphila* (Am), *B. salyersiae* (Bs), control bacteria *B. xylanosolvens* (Bx) or feces from responder patients (R) to recipient mice receiving CICB.

(B) Proportion of 15 FMT donors feces (human-responders, HR; human-non-responders, HNR) reflected in BALB/c mice (mice-responders, MR; mice-non-responders, MNR), as described in Table 7.

(C-D-E) Monitoring of RENCA progression using bioluminescence imaging of luciferase activity (C, E) or tumor weight (C-D) in ATB-treated mice post FMT with feces from 5 R and 10 NR RCC patients, treated with CICB, and compensated by oral administration of commensals *A. muciniphila* (Am), *B. salyersiae* (Bs) or feces from responder patients (R). All experiments were composed of 5-7 mice/group and were performed at least twice in similar conditions yielding similar results. ANOVA & Student T test statistical analyses of means±SEM: (*p<0.05, p<0.01, *p<0.001). Dx: last IVIS measurement, DO day of randomization.

FIG. 4A-4D: The gut microbiota influences the systemic and local immune tonus in RCC tumor bearing mice.

(A) Correlations of splenocyte profiles with selected bacterial consortium in isotype control (Ctrl) treatment group. Standardized relative abundances of species selected in Tables 6 and 7 were correlated with splenocyte profiles following a spearman correlation method and Benjamini-Hochberg correction. Splenocyte profiles were obtained by flow cytometry analyses at 48 h after $2^{nd}$ injection of Ctrl in mice bearing orthotopic RENCA post NR FMT. Significant p values<0.05 are indicated with star.

(B) Flow cytometry analyses of CD103+CD11b− DC in CD45 measured in the spleen of Ctrl treatment group in orthotopic RENCA tumor-bearer post NR FMT mice. Differences between each group were assessed by an ANOVA (ANalysis Of Variance) and significant p values are indicated with stars (*p<0.05, p<0.01, *p<0.001).

(C) Correlations of Tumor infiltrated lymphocytes (TIL) profiles with selected bacterial consortium in Ctrl treatment group in orthotopic RENCA tumor-bearer post NR FMT mice. Standardized relative abundances of species selected in Tables 6 and 7 were correlated with TIL profiles following a spearman correlation method and Benjamini-Hochberg correction. TIL profiles were obtained by flow cytometry analyses in tumors at 48 h after $2^{nd}$ injection of Ctrl in RENCA tumor-bearer post NR FMT mice. Significant p values<0.05 are indicated with a star.

(D) Flow cytometry analyses of TIL CXCR3+CD4 in CD45 measured in the kidney of Ctrl treatment group in RENCA tumor-bearer post NR FMT mice. Differences between each group were assessed by an ANOVA (ANalysis Of Variance) and significant p values are indicated with * (*p<0.05, p<0.01, *p<0.001).

FIG. 5A-5F: Immuno-stimulatory versus -tolerant commensals govern the cancer-immune set point of tumor bearers.

(A) Correlations of TIL profiles with selected bacteria. Standardized relative abundances of species selected from Tables 6 and 7 were correlated to fold-ratio of CICB (anti-PD-1 & anti-CTLA-4 Abs) TIL divided by isotype control (Ctrl) TIL following a spearman correlation method and Benjamini-Hochberg correction. TIL profiles were obtained by flow cytometry analyses in tumors at 48 h after $2^{nd}$ injection of CICB in RENCA tumor-bearer post NR FMT mice. Significant p values<0.05 are indicated with a star.

(B) Percentages of TIL CXCR3+CD4+ in CD45 in CICB treatment group (B, left panel) and percentages of TIL CXCR3+CD8+ in CD45 in CICB treatment group (B, right panel) measured in the kidney of RENCA tumor-bearer post NR FMT mice. TIL profiles were obtained by flow cytometry analyses in tumors at 48 h after $2^{nd}$ injection of CICB or Ctrl in RENCA tumor-bearer post NR FMT mice. Differences between each group were assessed by an ANOVA (ANalysis Of Variance) and significant p value are indicated with * (*p<0.05, p<0.01, *p<0.001).

(C-D) Linear correlation plots were performed on normalized and standardized relative abundances of selected bacterial species and normalized total flux (C) or splenocytes and TIL phenotypes (D) obtained by flow cytometry analyses (CICB+Bs (*B. salyersiae*) on CICB or CICB+Bs on Ctrl). Pearson coefficient and corresponding P values are reported within each graph as inset.

(E) Clustermap of normalized total flux of RENCA tumor-bearer post NR (7 donors) FMT mice and treated with CICB+Bs (*B. salyersiae*) or CICB or Ctrl. Logarithm in base 2 and a Bray-Curtis distance metrics were implemented.

(F) Kaplan-Meier curves showing progression-free survival of patients in relation to their microbial composition. Bs_Am: with detectable *B. salyersiae* and *A. muciniphila*, Bs: with detectable *B. salyersiae*, Am: with detectable *A. muciniphila*, NoBs_NoAm: without detectable *B. salyersiae* and *A. muciniphila* in the upper panel; Ch: with detectable *C. hathewayi* and NoCh: without detectable *C. hathewayi*, in the middle panel; Dl: with detectable *D. longicatena* and NoDl: without detectable *D. longicatena* in the lower panel. Significant p values<0.05 are indicated with a star.

Figure 6B:
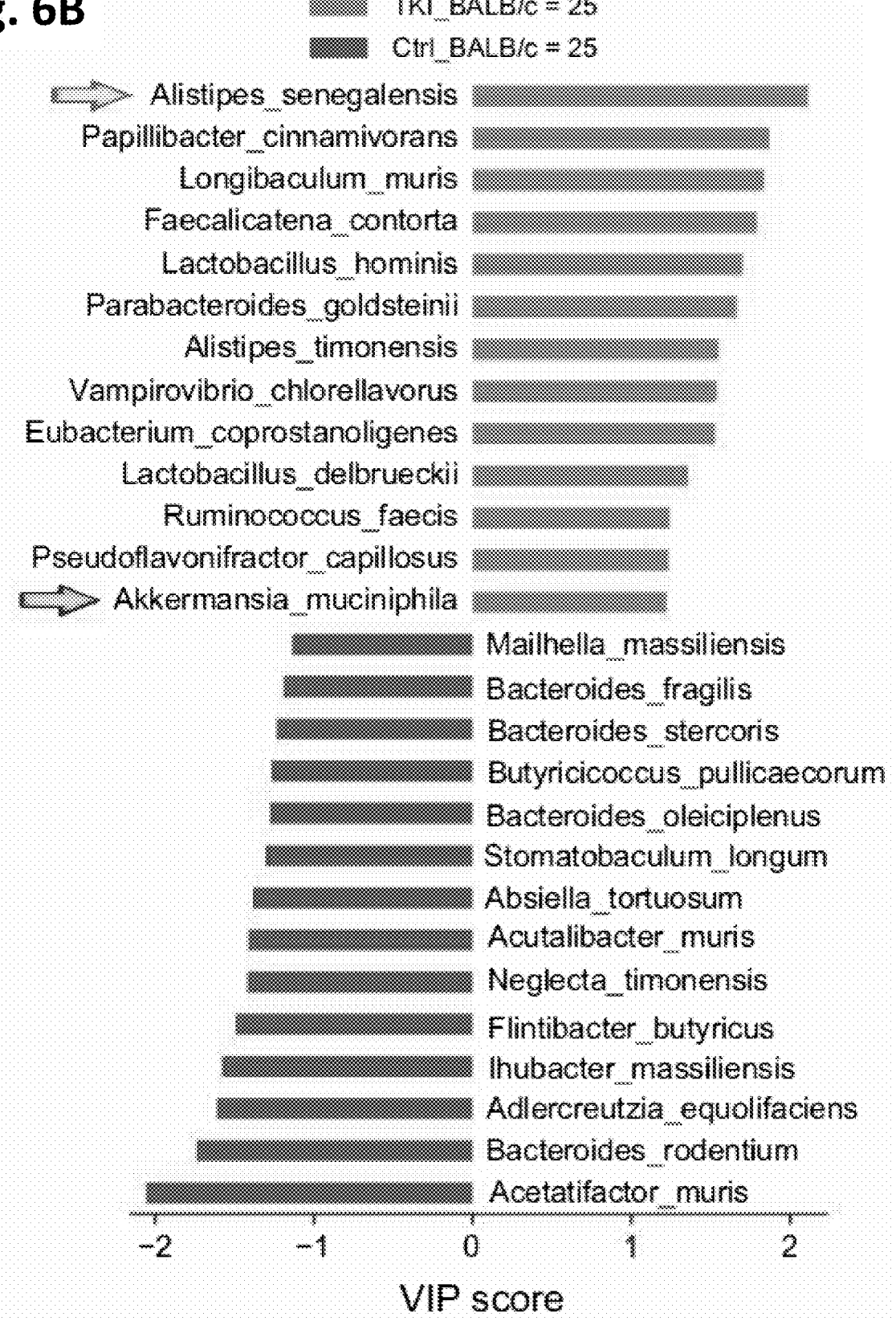
Figure 6C:
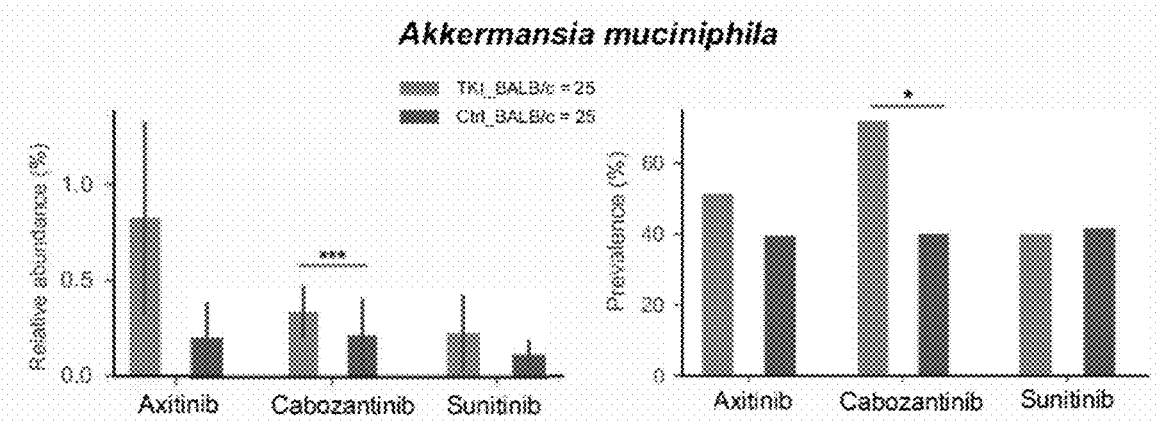

FIG. 6A-6C: Fecal microbiota differences in patients and mice treated with TKI. Fecal microbiota compositional differences of patients who underwent first-line TKI treatment and control adults (A) and BALB/c mice (B) which underwent TKI treatment (axitinib, sunitinib, cabozantinib) were analyzed. LEfSe (Linear discriminant analysis Effect Size) and Partial Least Square Discriminant Analysis (PLS-DA) coupled to Variable Importance Plot (VIP) were implemented for humans and mice, respectively, in order to describe the most discriminant species in descending order of importance. In humans we considered first-line TKI treatment compared to literature-based controls (A), while in mice we considered the mean VIP score taken from the combined TKI. Briefly, VIP scores of all bacterial species which were present in at least two mice VIP plots were averaged and classified in descending order according to the species belonging to TKI or control cohort (B). Arrows highlight relevant bacterial species. Relative abundance and prevalence of the most discriminant species for TKI group, *Alistipes senegalensis* and *Akkermansia muciniphila* were reported (C) for the three different treatments (axitinib, sunitinib, cabozantinib), and a Mann-Whitney U test was used to assess statistical differences (*p<0.05, p<0.01, *p<0.001).

Figure 7A:
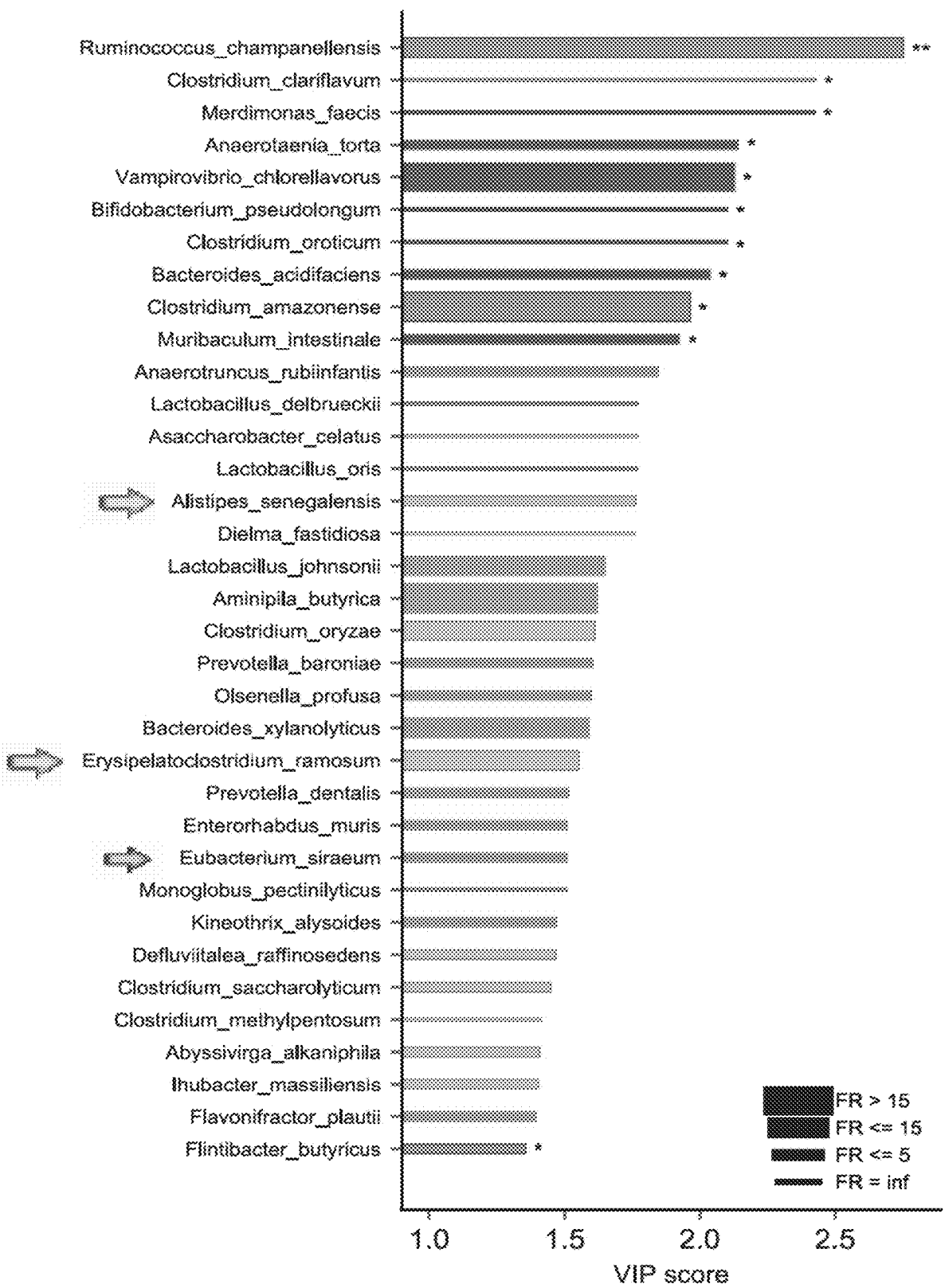

FIG. 7A-7C: Antiangiogenic tyrosine kinase inhibitors induce an immuno-stimulatory intestinal microbiome shift.

(A) Variable Importance Plot (VIP) was implemented to describe the 35 most discriminant species in descending order of importance among BALB/c and C57BL6 mice treated with axitinib and sunitinib. Each bar reports the following information: i) length, VIP score; ii) face color, cohort in which the species has the highest mean relative abundance (high); iii) edge color, cohort in which the species has the lowest mean relative abundance (low); iv) thickness, Fold Ratio (FR) among high and low; v) significance of Mann-Whitney U test among high and low (*p<0.05, p<0.01, *p<0.001).

(B) Monitoring of RENCA progression using bioluminescence imaging of luciferase activity in ATB-treated mice post FMT with feces from 1 NR RCC patients and treated with CICB or CICB with oral administration of *B. salyersiae* (Bs) or ICB with oral administration of axitinib or Ctrl.

(C) Survival curves of RENCA bearing mice treated with CICB or Ctrl or ICB with oral administration of axitinib with or without oral gavage with *Akkermansia muciniphila*. Each line represents one survival curve for each group of 5 mice from 2 independent experiment. Log-rank (mantel-Cox) statistical analyses: (*p<0.05, p<0.01, *p<0.001).

All experiments were composed of 5-7 mice/group and were performed at least twice in similar conditions yielding similar results. ANOVA & Student T test statistical analyses of means±SEM: (*p<0.05, p<0.01, *p<0.001). Dx: last IVIS measurement, DO day of randomization.

FIG. 8: Antibiotics compromise the efficacy of anti-PD-1 mAb in renal cell carcinoma patients.

Kaplan-Meier estimates for progression-free survival (PFS) or overall survival (OS) of renal cell carcinoma patients. P values are shown [log-rank (Mantel-Cox) analysis].

Figure 9B:
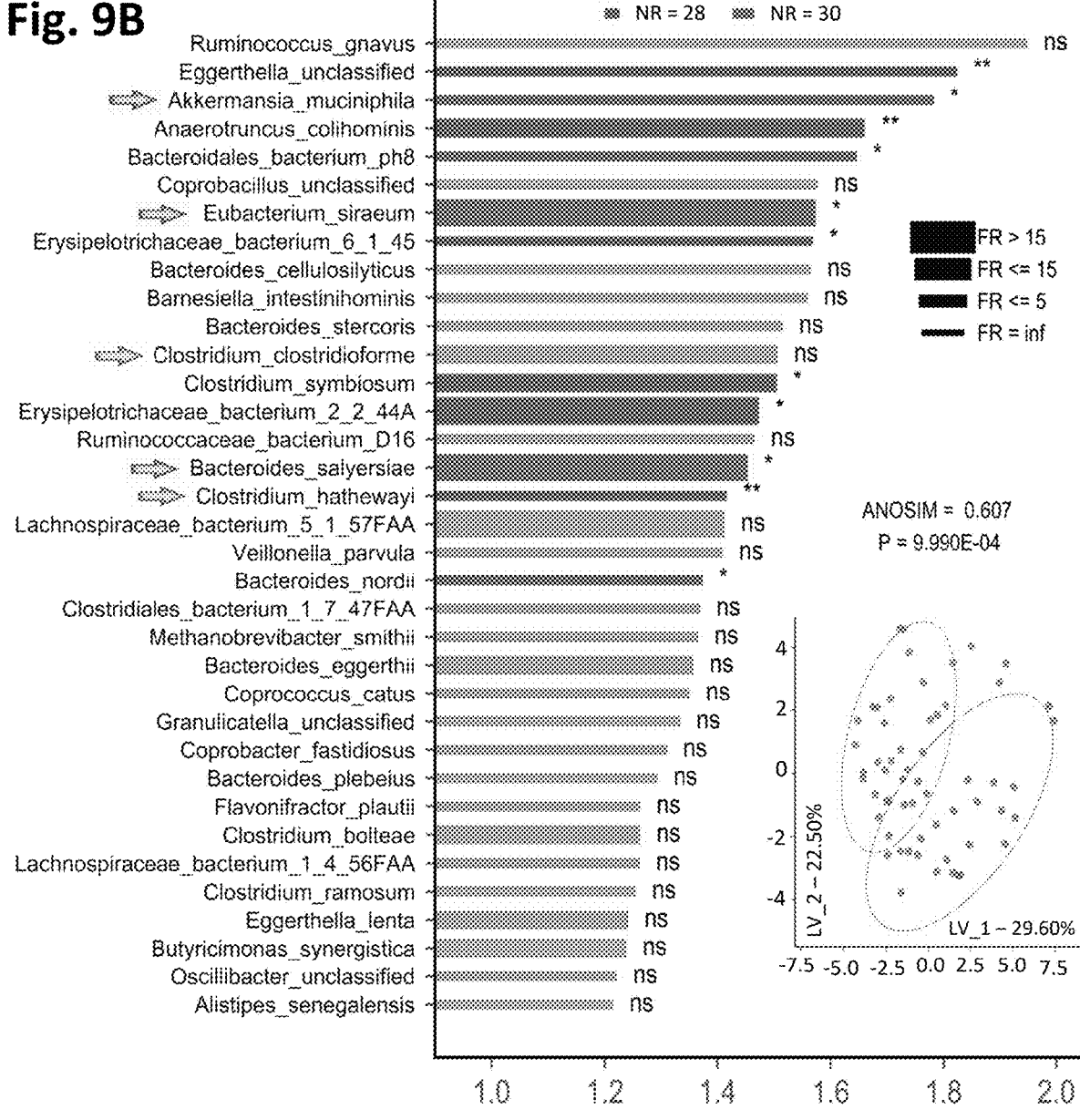
Figure 11C:
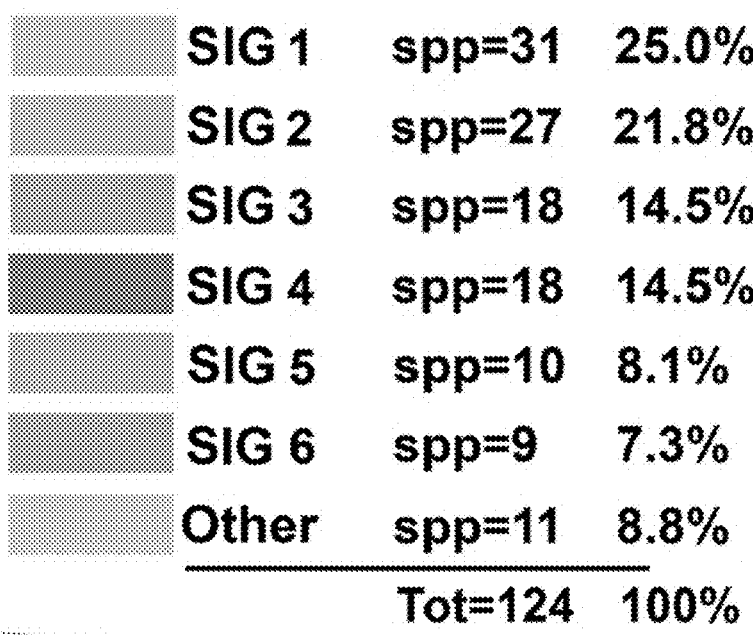
Figure 11D:
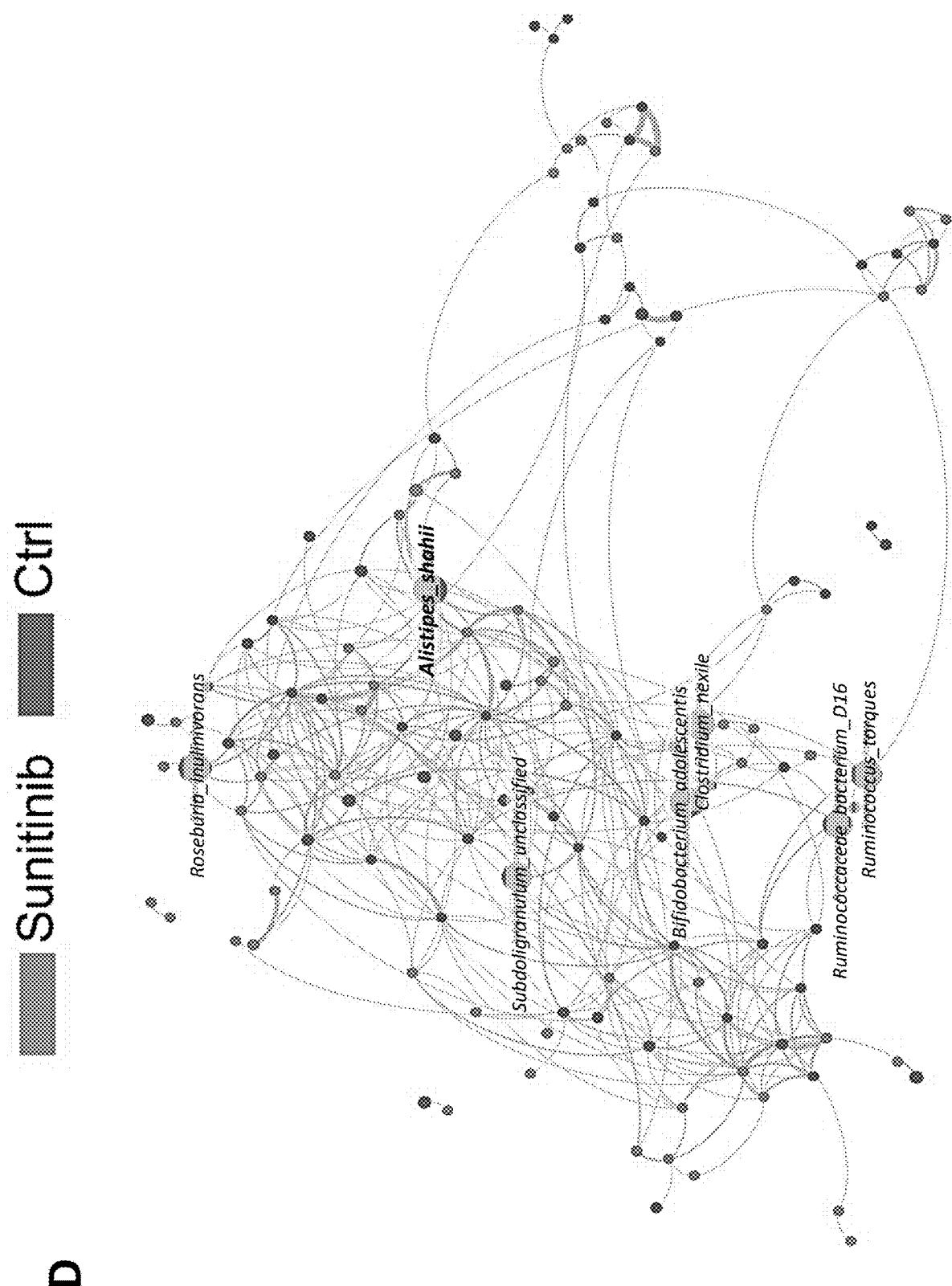
Figure 11E:
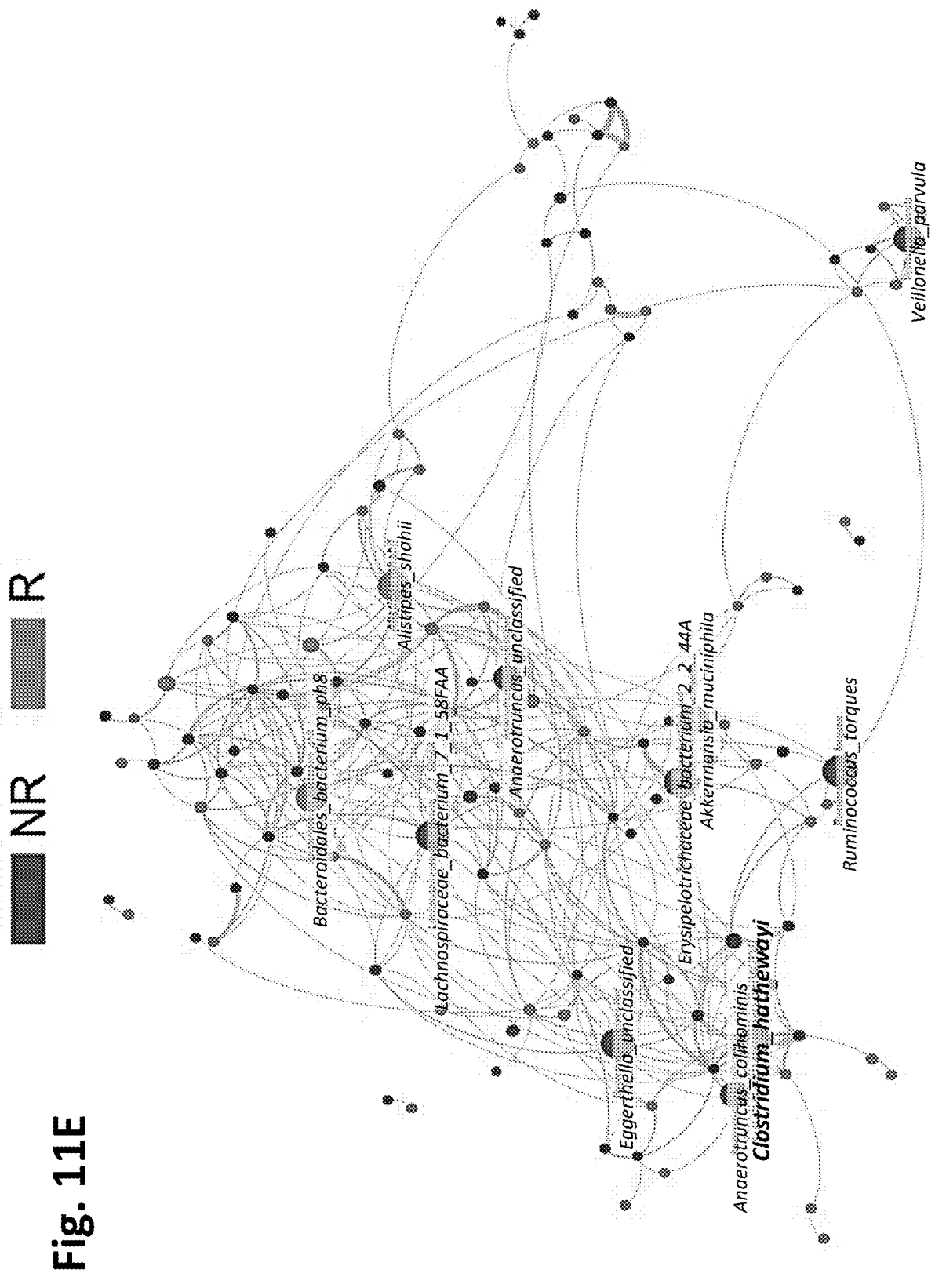
Figure 11F:
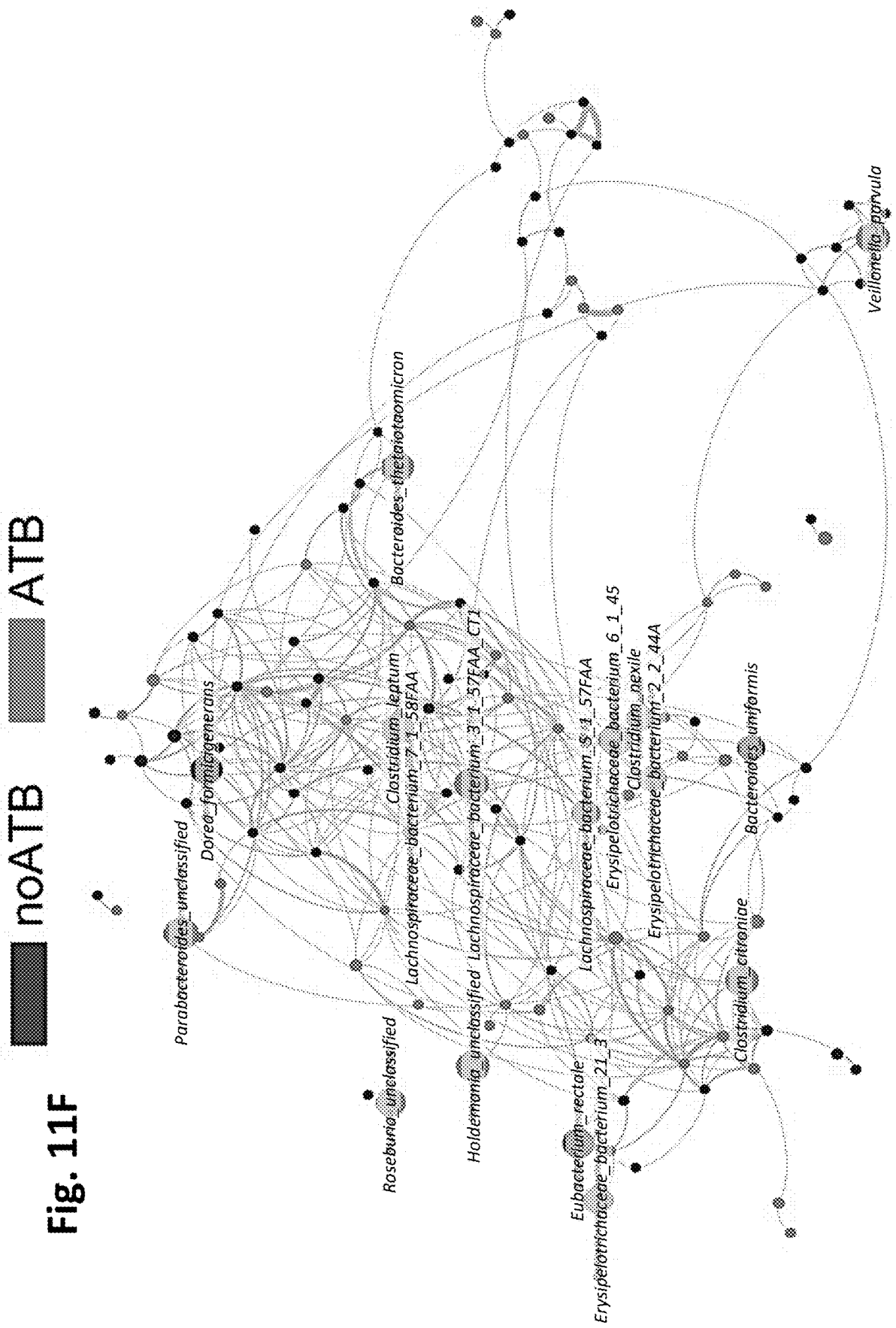
Figure 11G:
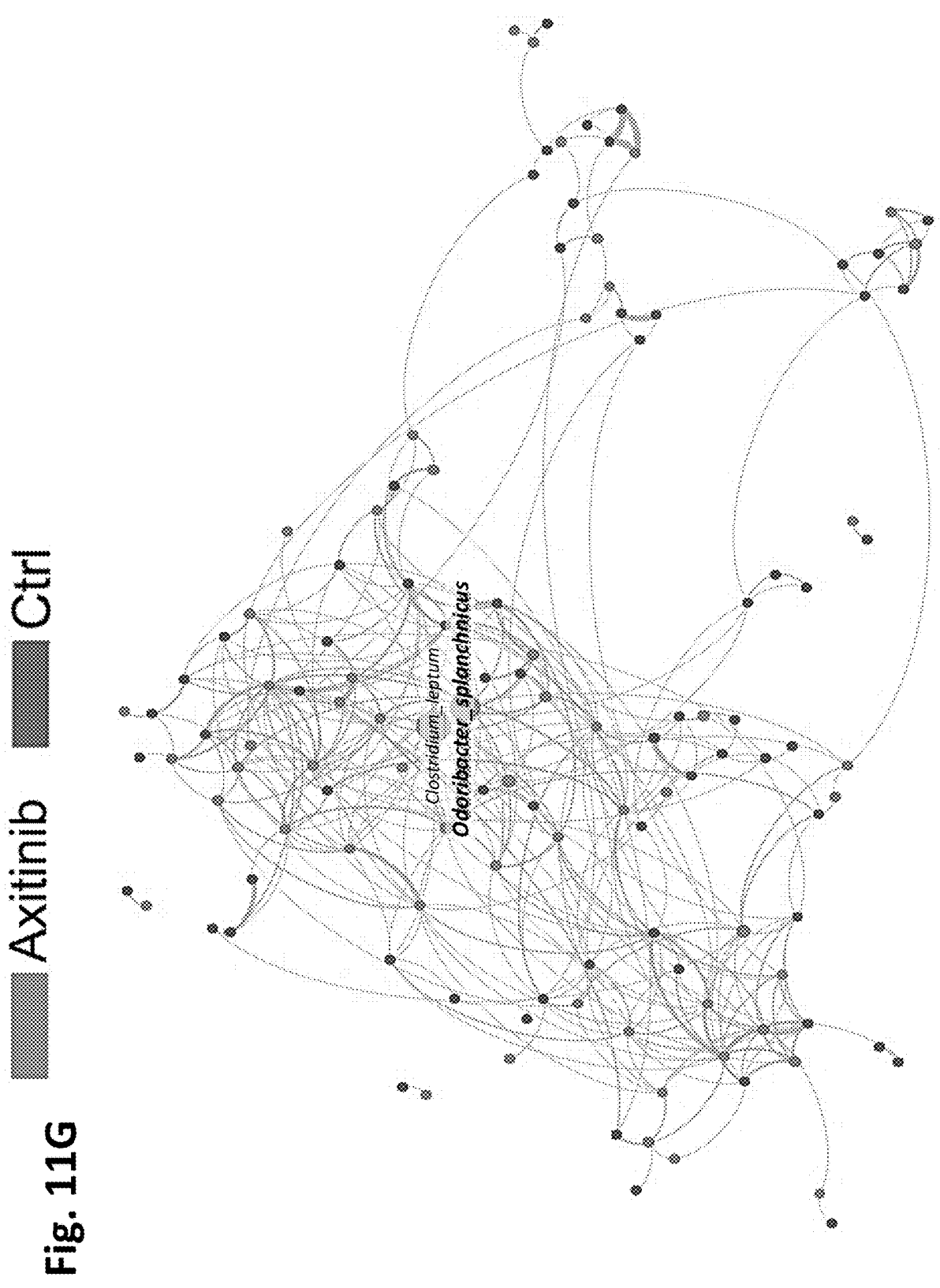

FIG. 9A-9C: Metagenomic analyses (MetaPhlAn2 pipeline) of fecal samples predict response of anti-PD-1 mAb in renal cell carcinoma patients.

(A) Beta-diversity ordination plot based on Principal Coordinate Analysis (PCoA) of normalized and standardized data of fecal microbiota composition in no-ATB pre-treatment (T0-T4) samples (n=58). Bacterial relative abundances were obtained with MetaPhlAn2 package developed in Python 2.7 by Center for Integrative Biology (CIBIO). Percentage of variance embraced by each new coordinate is reported in percentages for each axis. Ellipses describing the 95% of confidence are even depicted for each cohort. ANOSIM and PERMANOVA metrics were implemented with 999 permutations to assess differences according to R (complete response or partial response or stable disease more than 6 months) and NR (death or progressive disease or stable disease less than 6 months).

(B) Variable Importance Plot (VIP) was implemented within Partial Least Square Discriminant Analysis (PLS-DA, inset differentiating NR and R), describing the 35 most discriminant species in descending order of importance. Arrows are depicted to highlight species of importance. Each bar reports the following information: i) length, VIP score; ii) bar color, cohort in which the species has the highest mean relative abundance (high); iii) edge color, cohort in which the species has the lowest mean relative abundance (low); iv) thickness, Fold Ratio (FR) among high and low; v) significance of Mann-Whitney U test among high and low (*p<0.05, p 0.01, *p<0.001).

(C) Barplots of relative abundances (within the 0-1 interval) and prevalence of selected species (*A. muciniphila* and *B. salyersiae*). P values for relative abundances were obtained after two-tailed Mann-Whitney U test, while P values for prevalence were retrieved by chi-square test.

FIG. 10A-10B: GC and MGS count varies longitudinally with time. Heat maps of $Log_2$ fold ratio (FR) of R versus NR (left) and R(Tx) versus R(T0) (right) for outcome (A) and PFS12 (B). Both GC and MGS counts were considered for FR calculation in overall pre-treatment samples (n=69) and in no-ATB pre-treatment samples (n=58). Patients' numbers are considered at TO, and significance was assessed by Mann-Whitney U test (*p<0.05, p<0.01, *p<0.001).

Figure 11A:
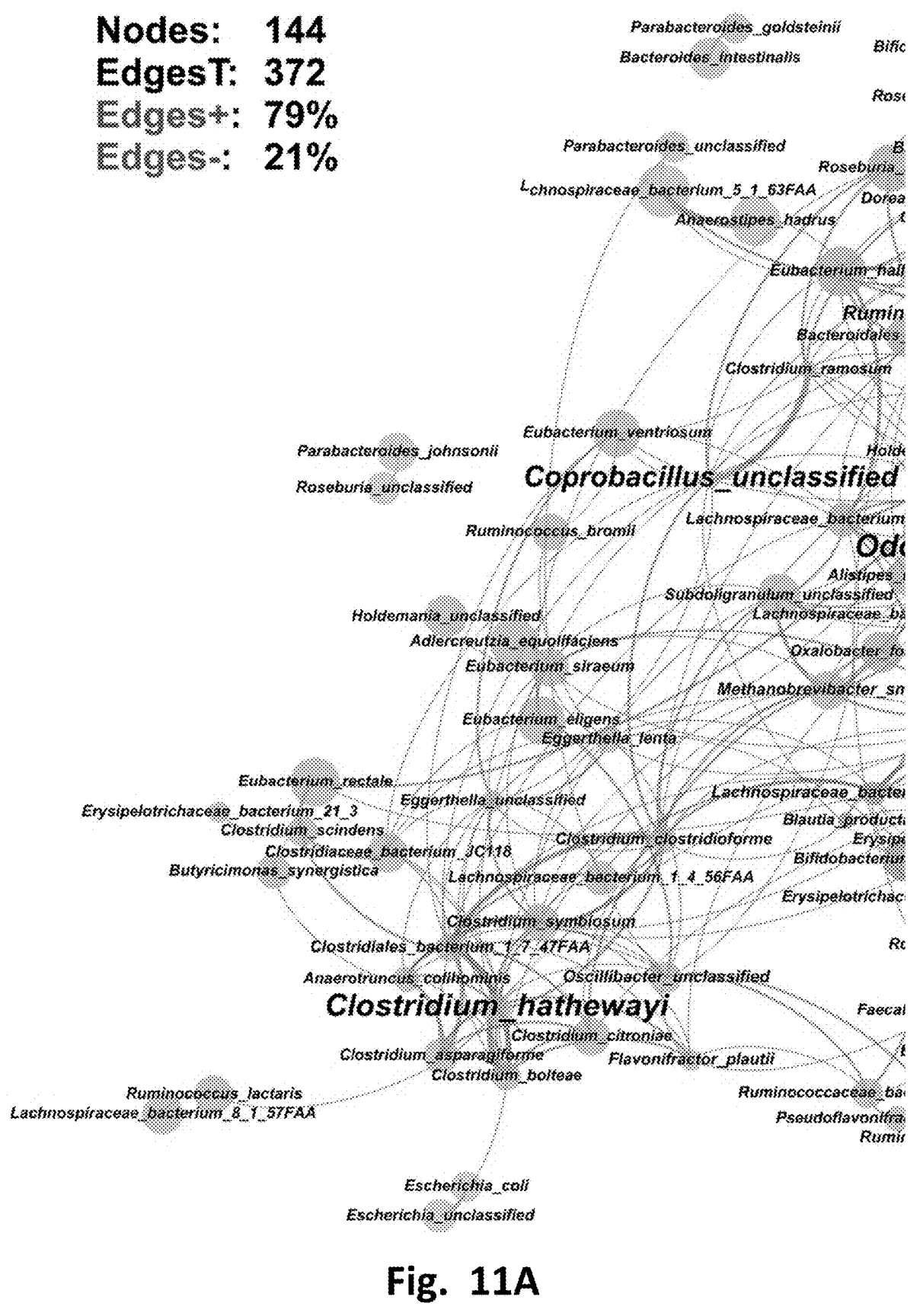
Figure 11B:
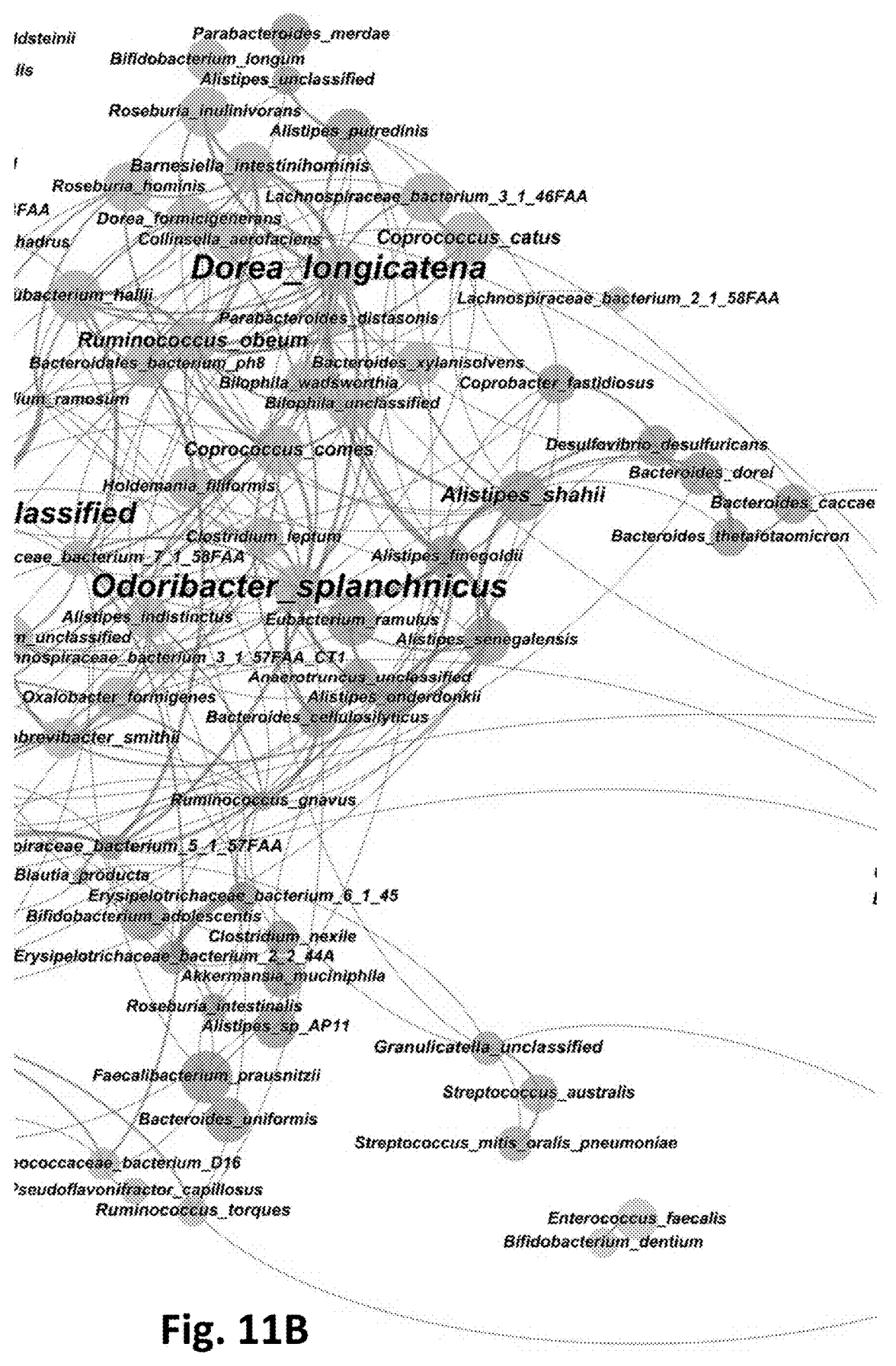

FIG. 11A-11G: Bacterial network of RCC patients (regardless ATB usage). Network was created by co-occurrences of 124 bacterial species (the nodes) and concomitant significance of pair-wise Pearson correlation coefficient (the edges). In order to fulfil the formal requirements for patents figures, FIG. 11A-11C has been divided to be represented in three pages (23/39, 24/39 and 25/39), which can be put side-by-side to reconstitute the network. (A-C). Node properties are as follows: i) size, normalized and standardized bacterial relative abundances; ii) color, 'guilds' (GIG) retrieved by Blondel algorithm to detect bacterial communities; iii) name size, betweenness centrality (a measure of the importance within the network). Edge properties: i) thickness, proportional to P value of Pearson correlation coefficient divided into 8 categories from the most significant (thicker) to the lesser one (thinner); ii) color, red for positive and blue for negative Pearson correlation coefficient. Spp, number of species within each GIG. EdgesT, total number of edges. Edges+, percentage of edges with positive correlation. Edges-, percentage of edges with negative correlation. The same network underwent four different node coloring (panel D, sunitinib; panel E, OUTCOME2; panel F, ATB; panel G, axitinib) taking into account the cohort in which each species had the highest average relative abundance, while the node size derived from the importance for that species in dividing the cohorts following the random forest algorithm. Within panels B-D edge coloring was discarded to ameliorate node visualization and interpretation.

Figure 12A:
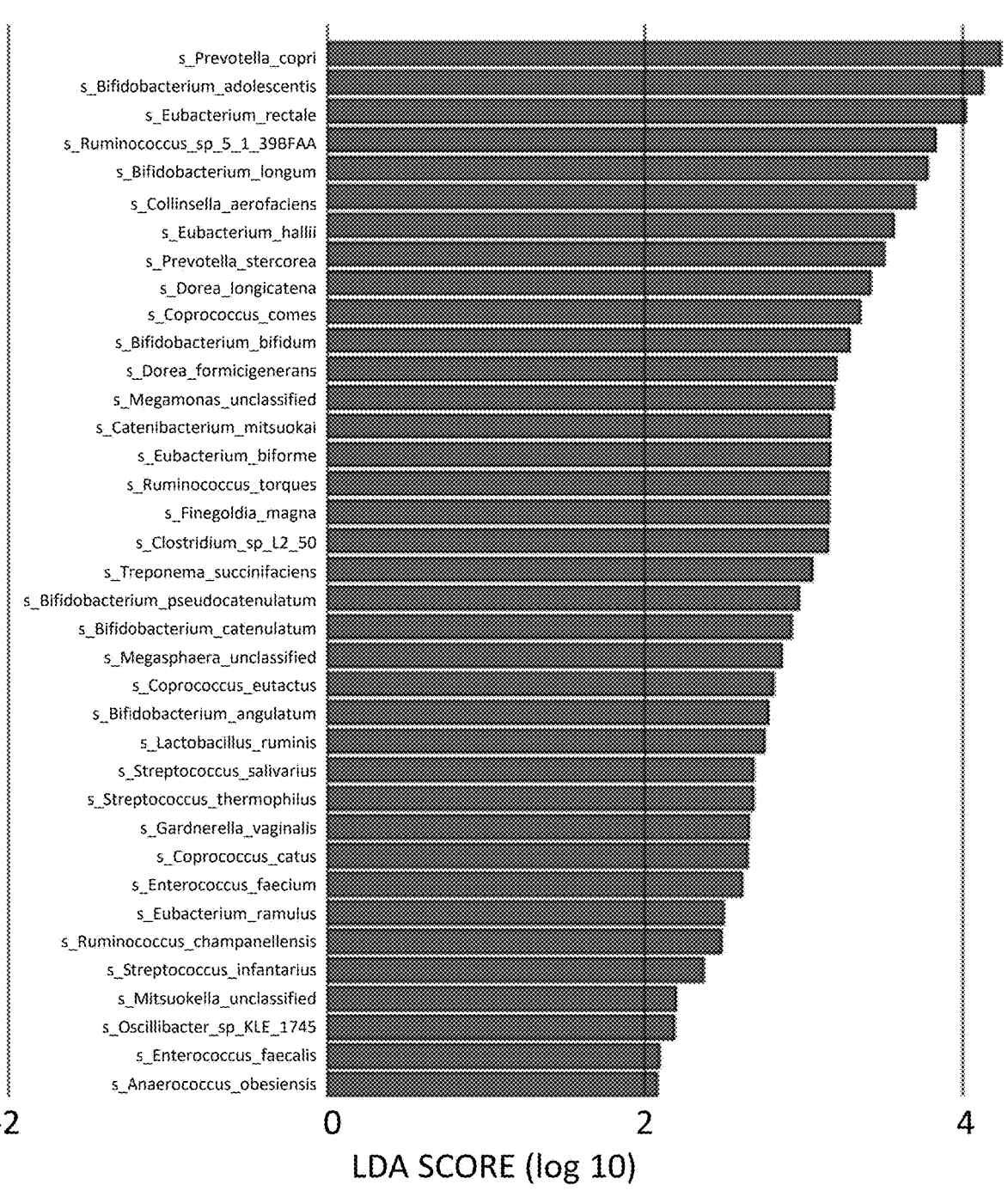
Figure 12B:
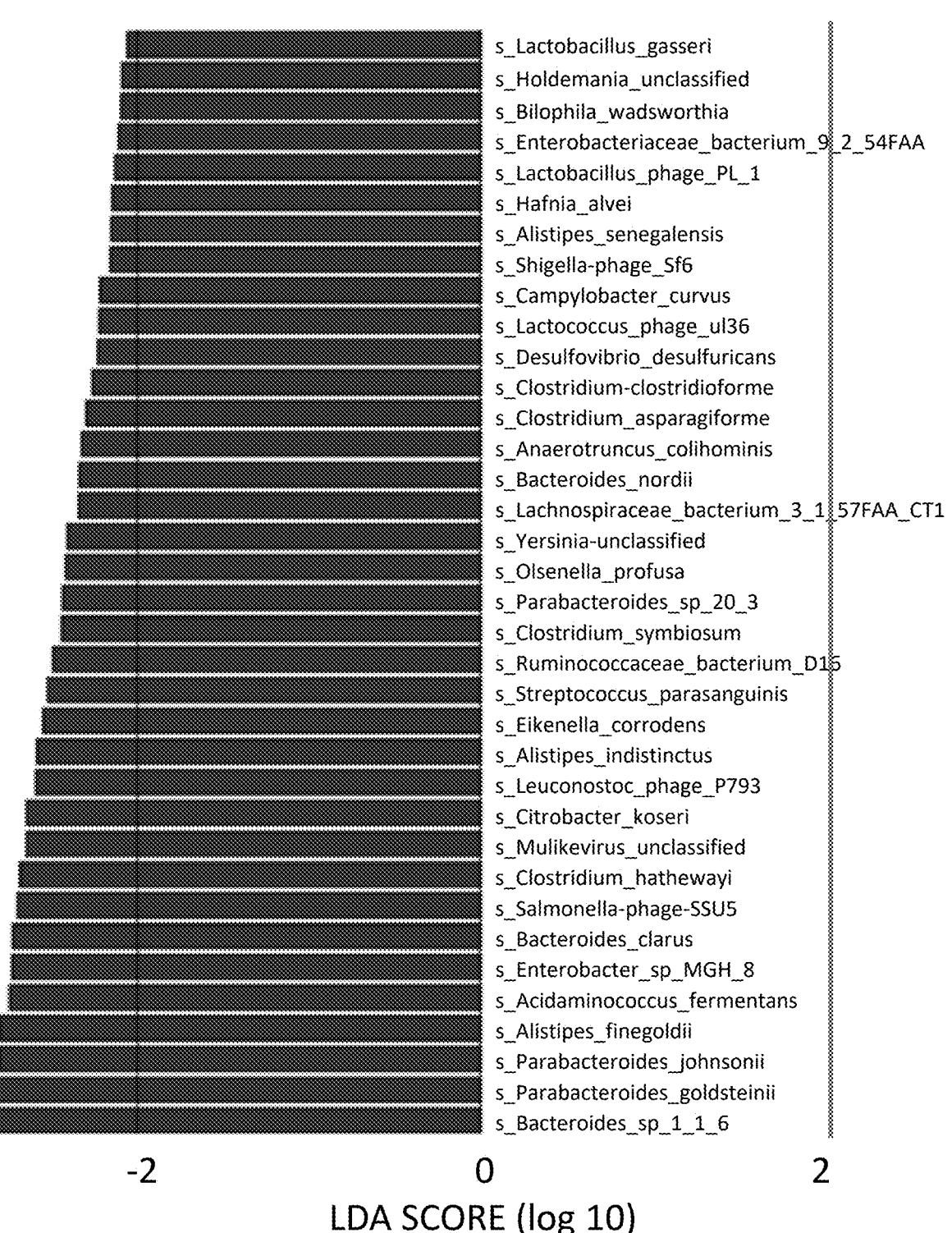
Figure 12C:
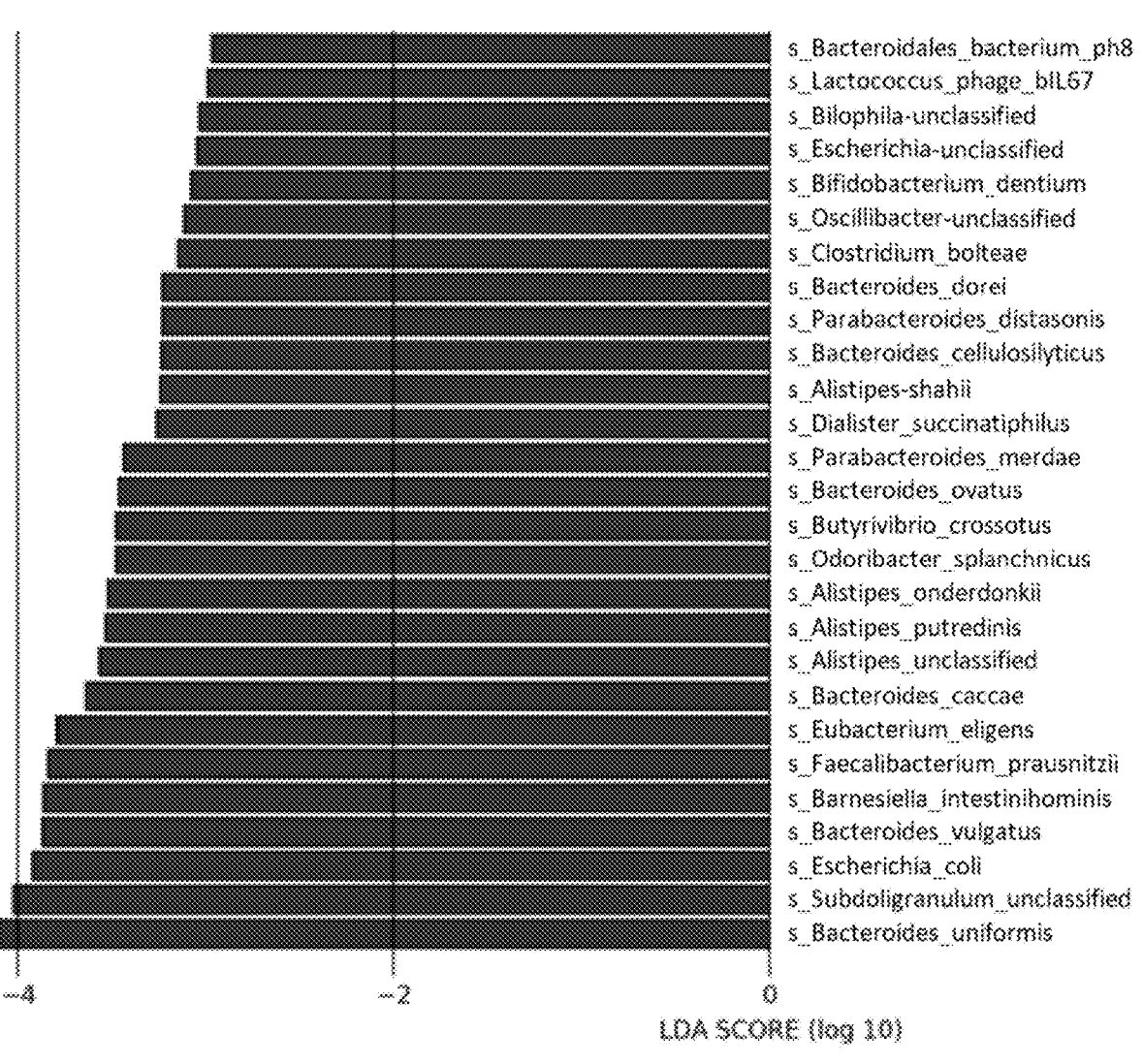

FIG. 12A-12C: Analysis of the bacteria discriminating RCC from control adults The 69 RCC samples were analyzed and compared with 2994 control adults acquired from publicly available repositories and spanning multiple countries and lifestyles. This set of control samples was enlarged by 54 Italian samples newly acquired and sequenced in the current study. Bacterial species discriminating RCC from control adults were determined using LefSe.

Figures 13A, 13B:
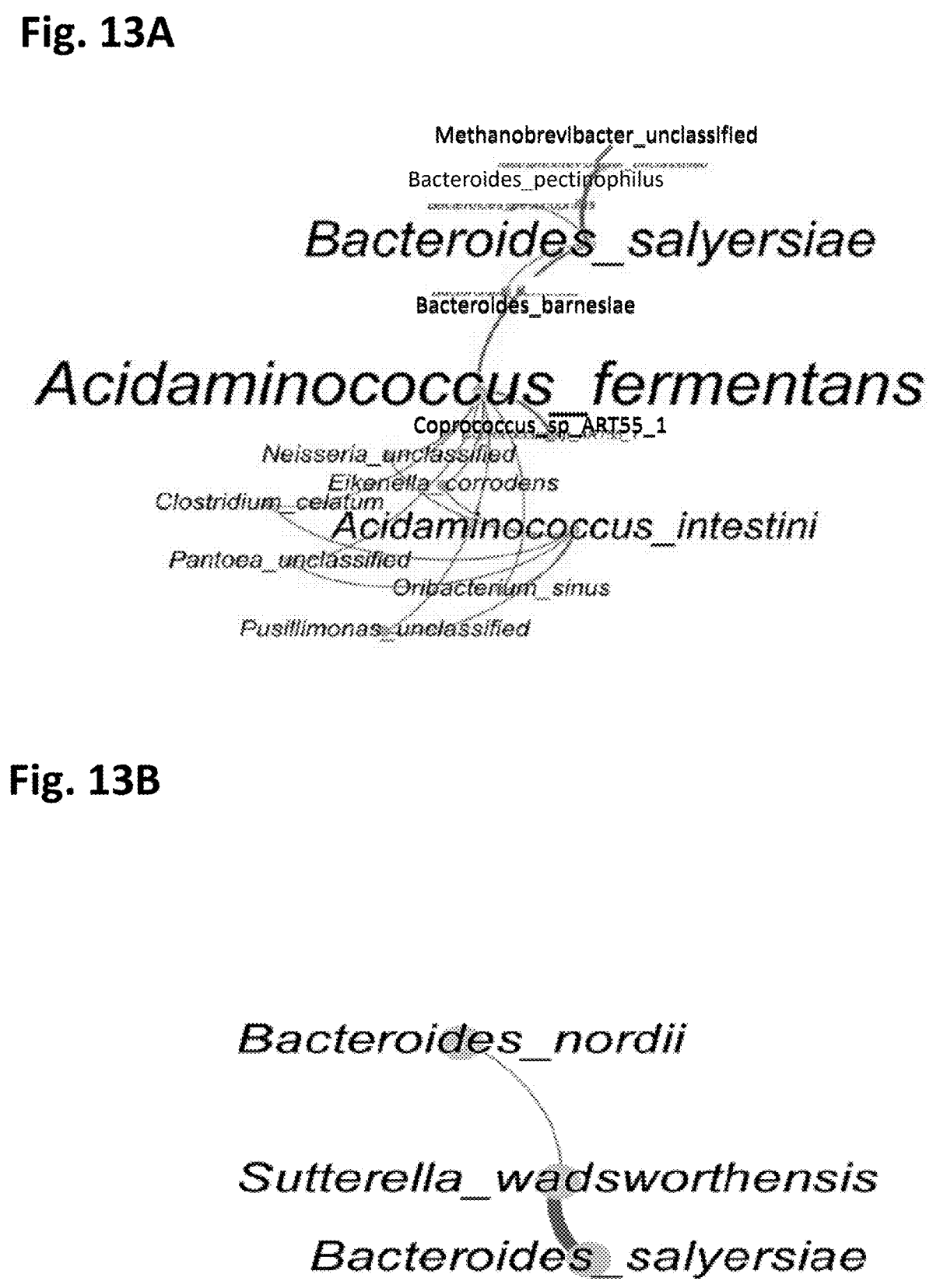
Figure 13C:
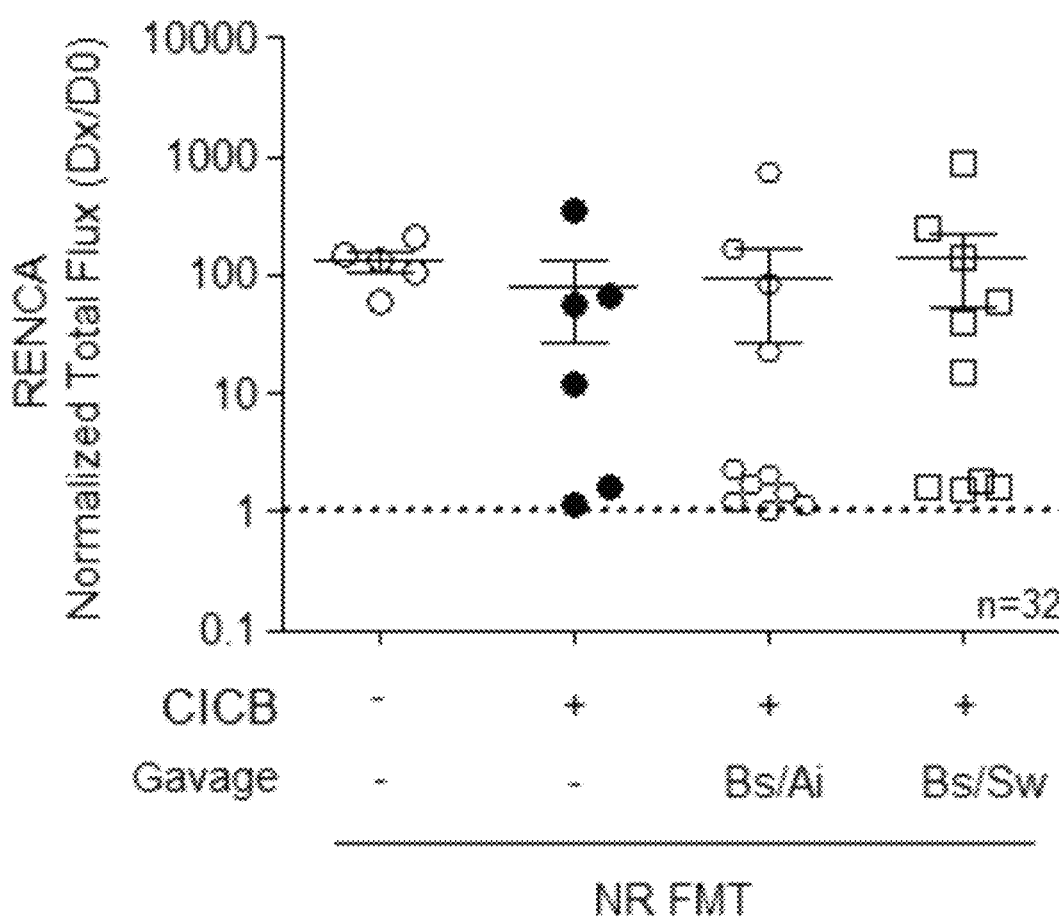

FIG. 13A-13C: Local network of *B. salyersiae*

(A-B) Local network of *B. salyersiae* within 69 patients regardless ATB usage (A) and within 58 patients who did not take ATB (B). Network properties (nodes, edges) as per Figure S.1.

(C) Monitoring of RENCA progression using bioluminescence imaging of luciferase activity in ATB-treated mice post FMT with feces from 1 NR RCC patients and treated with CICB or CICB with oral administration of *B. salyersiae* (Bs) and Acidaminococcus intestini (Ai) or CICB with oral administration of *B. salyersiae* (Bs) and *Sutterella wadswothensis* (Sw) or Ctrl.

Figure 14A:
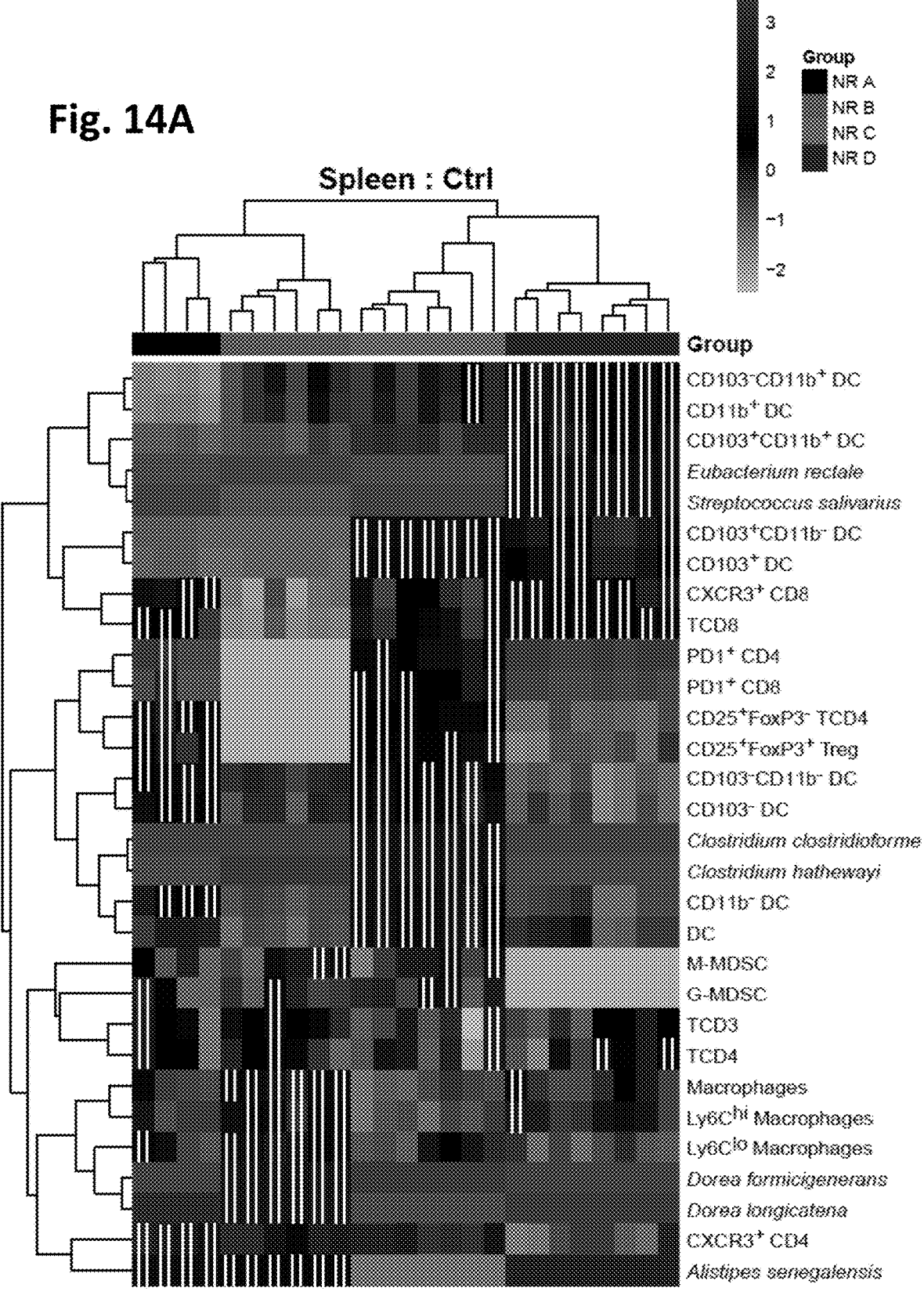
Figure 14B:
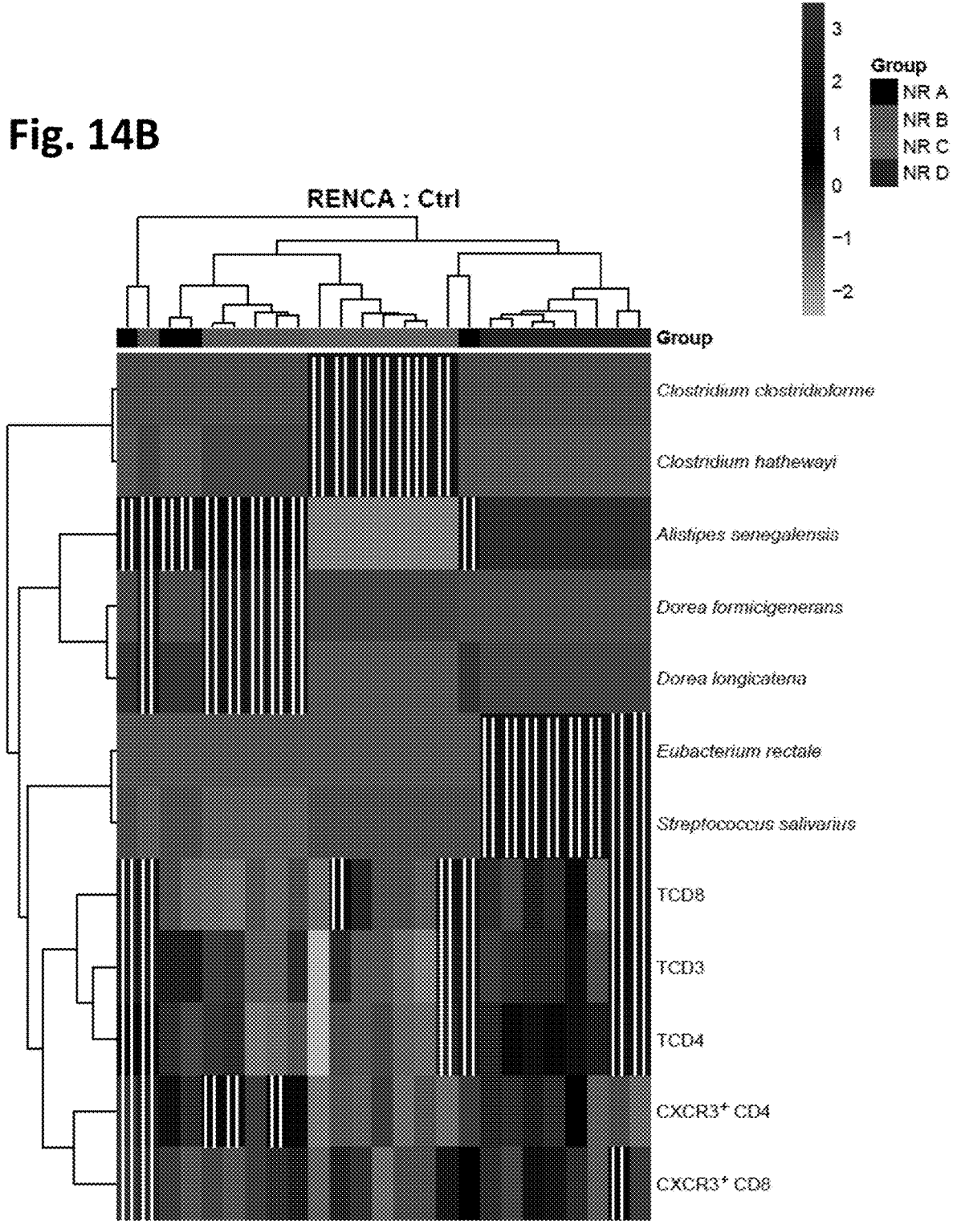

FIG. 14A-14B: The gut microbiota controls the cancer-immune set point in RCC tumor bearing mice (A) Splenocyte profiles in isotype control (Ctrl) treatment group in RENCA tumor-bearer post-FMT mice.

(B) Tumor infiltrated lymphocyte (TIL) profiles in isotype control (Ctrl) treatment group in RENCA tumor-bearer post-FMT mice. Splenocyte or TIL profiles obtained by cytometry and standardized relative abundances of species selected in Tables 6 and 7 were clustered following a hierarchical clustering (Euclidean distance and complete method).

Figure 15C:
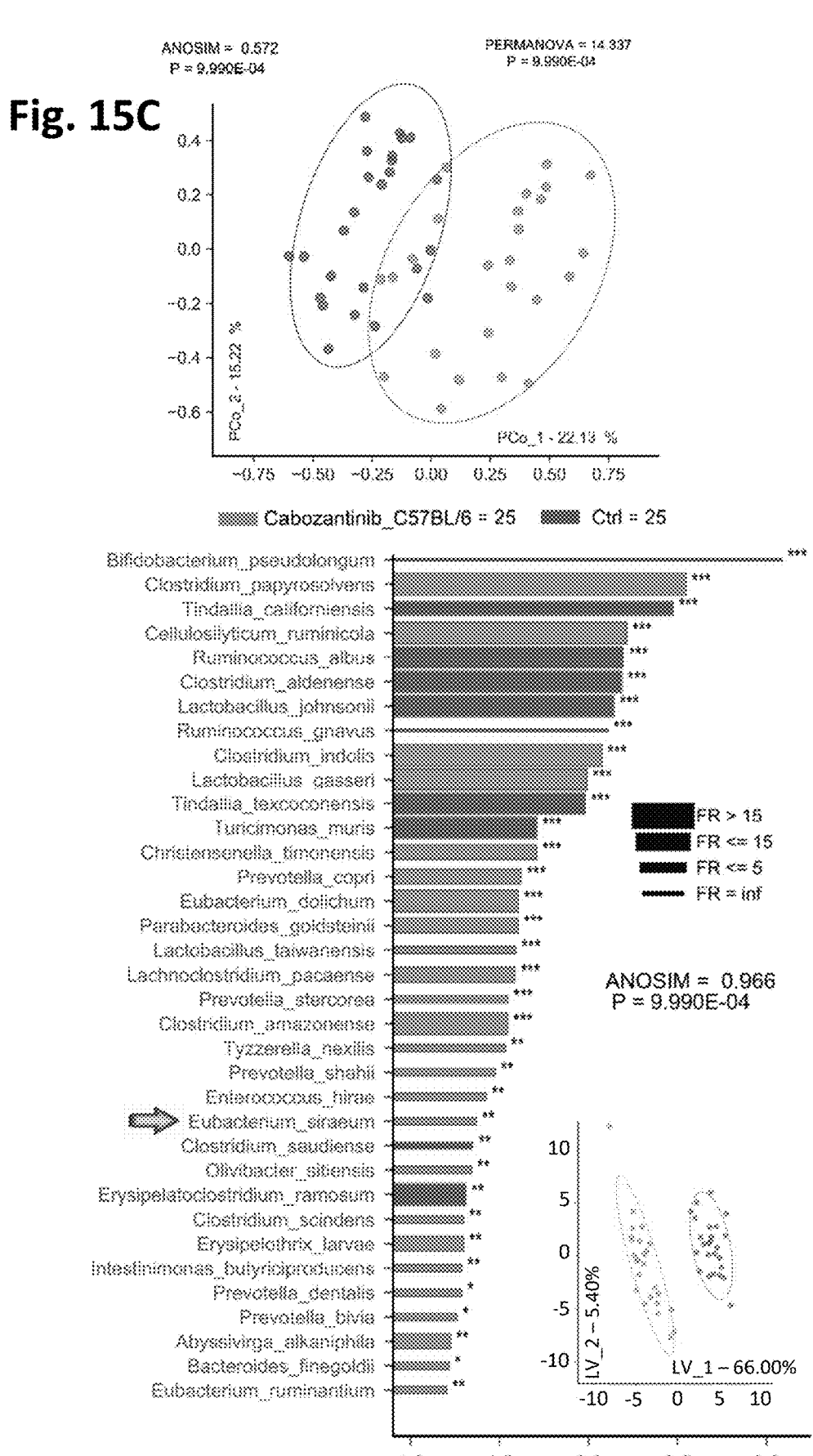

FIG. 15A-15C: Fecal microbiota differences in C57BL6 mice treated with TKI. Fecal microbiota compositional differences of C57BL6 mice which underwent TKI treatment (sunitinib, panel A; axitinib, panel B; cabozantinib, panel C) were analyzed. In order to assess beta-diversity, Principal Coordinate Analysis (PcoA, insets) was implemented, while ANOSIM and PERMANOVA metrics were used with 999 permutations to assess differences among the patients' cohorts. Variable Importance Plot (VIP) were generated by Partial Least Square Discriminant Analysis (PLS-DA) to describe the 35 most discriminant species in descending order of importance for each TKI treatment. Each bar reports the following information: i) length, VIP score; ii) face color, cohort in which the species has the highest mean relative abundance (high); iii) edge color, cohort in which the species has the lowest mean relative abundance (low); iv) thickness, Fold Ratio (FR) among high and low; v) significance of Mann-Whitney U test among high and low ($*p<0.05$, $p<0.01$, $*p<0.001$).

DETAILED DESCRIPTION OF THE PREFERRED EMBODIMENTS

In the present text, the following definitions are used:

An "immune checkpoint inhibitor" (ICI) designates any drug, molecule or composition which blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1 and CTLA-4/B7-1/B7-2. In particular, ICIs encompass anti-PD1 antibodies (such as Nivolumab or Pembrolizumab), anti-PD-L1 antibodies (such as Atezolizumab or Durvalumab), anti-CTLA-4 antibodies and anti-PD-L2 antibodies. In the scientific literature, ICIs are also designated as "drugs blocking an immune checkpoint", or "immune checkpoint blockers" (ICB) or "immune checkpoint blockade drugs".

An "anti-PD1/PD-L1/PD-L2 Ab-based therapy" herein designates any therapy including the use of a drug that antagonizes PD1, PD-L1 or PD-L2. These include therapies mainly based on an ICI such as a drug antagonizing PD1 or PD-L1 or PD-L2, as well as combined therapies using several ICIs and/or additional anticancer drugs such as chemotherapeutic drugs. Non-limitative examples of combined therapies encompassed by the phrase "anti-PD1/PD-L1/PD-L2 Ab-based therapy" include anti-PD1+anti-CTLA4, anti-PD1+polychemotherapy (pemetrexed+ carboplatin), anti-Lag3+anti-PD1, anti-NKG2A+anti-PD1, IDO inhibitor+anti-PD1 and anti-ICOS+anti-PD1. Although the currently used drugs antagonizing immune checkpoint proteins are monoclonal antibodies, other molecules specifically binding to PD1, PD-L1, PD-L2 or other proteins could be used for the development of future ICIs such as, for example, antibody fragments or specifically designed aptamers. Of course, the phrase "anti-PD1/PD-L1/PD-L2 Ab-based therapy" encompasses any therapy including an active molecule that antagonizes PD1 or PD-L1 or PD-L2.

A "tyrosine kinase inhibitor" (TKI) designates any drug, molecule or composition which inhibits tyrosine kinases. Tyrosine kinases are enzymes responsible for the activation of many proteins by signal transduction cascades. The proteins are activated by adding a phosphate group to the protein (phosphorylation), a step that TKIs inhibit. Non-limitative examples of TKIs are listed below.

TABLE 1

| | | tyrosine kinase inhibitors | | |
|---|---|---|---|---|
| TKI | Time to market | Development company | Target | Examples of diseases |
| Sorafenib | 2005 | Bayer | Raf, VEGFR, PDGER | Advanced RCC |
| Axitinib | 2012 | Pfizer | VEGFR | Advanced RCC |
| Pazopanib | 2009 | GlaxoSmithKline | VEGFR, PDGFR, FGFR | Advanced RCC, STS, NSCLC |
| Cabozantinib | 2018 | Ipsen | VEGFR2, AXL, cMET | Advanced RCC, Advanced Thyroid cancer |
| Sunitinib | 2006 | Pfizer | PDGFR, VEGFR, | Advanced RCC, GIST |
| Lenvatinib | 2015 | Eisai | VEGFR | Advanced RCC |
| Crizotinib | 2011 | Pfizer | ALK | Advanced papRCC, NSCLC |
| Vandetanib | 2011 | AstraZeneca | VEGFR, EGFR | Advanced Thyroid cancer |
| Lapatinib | 2007 | GlaxoSmithKline | EGFR | Breast cancer |
| Neratinib | 2017 | Puma | HER2 | Breast cancer |
| Nilotinib | 2004 | Novartis | Bcr-Abl, PDGFR | CML |
| Dasatinib | 2006 | Bristol-Myers Squibb | Bcr-Abl, SRC, PDGFR | CML |
| Bosutinib | 2012 | Wyeth | Abl, SRC | CML |
| Imatinib | 2001 | Novartis | Abl, PDGFR, SCFR | CML, GIST |
| Regorafenib | 2017 | Bayer | VEGFR, EGFR | HCC, CRC, GIST |
| Ruxolitinib | 2011 | Novartis | JAK1, JAK2 | myelofibrosis |
| Gefitinib | 2003 | AstraZeneca | EGFR | NSCLC |
| Afatinib | 2013 | Boehringer Ingelheim | EGFR | NSCLC |
| Erlotinib | 2013 | Roche | EGFR | NSCLC |
| Ceritinib | 2014 | Novartis | ALK | NSCLC |
| Osimertinib | 2015 | AstraZeneca | EGFR | NSCLC |
| Alectinib | 2015 | Roche | ALK | NSCLC |
| Brigatinib | 2017 | Ariad | ALK | NSCLC |

"NR" defines a non-responder status to PD-1/PDL-1/PDL-2 blockade

"R" defines a responder status to PD-1/PDL-1/PDL-2 blockade

"NGS" defines any Next Generation Sequencing platform available in the past, present or in the future.

In the present text, each "bacterial species" is defined by a Co-Abundance gene Group ("CAG"), which is a group of bacterial genes from the gut microbiome (i.e., the gene repertoire of the gut microbiota), which abundance level varies in the same proportion among different individual samples. In other words, a bacterial species according to the invention is defined by a cluster of bacterial gene sequences which abundance levels in samples from distinct subjects are statistically linked rather than being randomly distributed.

Most current approaches for analyzing metagenomic data rely on comparisons to reference genomes, but the human gut microbiota diversity extends beyond what is currently covered by reference databases. In the results disclosed herein, the inventors used a method based on binning co-abundant genes across a series of metagenomic samples, that enables comprehensive discovery of new microorganisms without the need for reference sequences. In what follows, some species identified as likely to play a role in the patients' response to therapies based TKI or ICI may be newly-identified species, not yet precisely referenced in public databases. For each of the identified species (both newly-identified and species very close to already referenced species), the present application discloses a set of bacterial genes which are non-redundant sequences and can be used, alone or in combination, as tracer genes to assess the presence and relative abundance to the corresponding species. Of course, once the species are identified, either by the set of non-redundant genes disclosed herein, or later on by their further identification and/or inclusion into a data base, the skilled in the art can assess their relative abundance by any appropriate means, such as, for example, by measuring the copy number of another non-redundant gene that co-varies with the sequences disclosed in the present application, or even by identifying a signature of this species at the protein level rather than in a nucleic acids sample. Hence, the present invention is not limited to the use of the disclosed sequences to measure the relative abundance of the corresponding species.

The "relative abundance" of a definite bacterial is defined as the fraction of the entire bacterial ecosystem belonging to this bacterial species. Throughout the present text, all relative abundances are expressed within the closed interval [0:1], where 1 stands for the maximum fraction available for a single bacterial species (i.e., a bacterial species with a relative abundance equal to 1 means that 100% of the bacteria present in the sample are of the considered species). Using a NGS technique, the relative abundance of a bacterial species is considered as the number of reads of that selected species divided by the total number of reads representing the overall bacterial community. Using a qPCR technique, the relative abundance of a bacterial species is considered as the ΔCt value of that species X (amplified by a pair of primers specific for X) divided by the ΔCt value of the total bacteria (amplified by an universal primers pair able to catch all the eubacteria present in a sample, the pair consisting of primers PRK341F and PRK806R or the pair consisting of primers 27F and 1492R).

When necessary, other definitions are provided later in the present text.

According to a first aspect, the present invention concerns a composition comprising bacteria selected amongst *Alistipes senegalensis, Dorea longicatena* and *Eubacterium siraeum*, for use in treating a cancer, in combination with an immune checkpoint inhibitor (ICI)-based therapy and/or a tyrosine kinase inhibitor (TKI)-based therapy wherein said composition induces immunostimulation in a cancer patient.

According to a particular embodiment, the composition comprises a mix of at least two species selected amongst *Alistipes senegalensis, Dorea longicatena* and *Eubacterium siraeum*.

Other immunostimulating bacterial compositions have already been described, for example in WO 2016/063263 and in WO 2018/115519. The bacterial compositions according to the present invention can also comprise one or several of the bacterial species of the previously described compositions, in order to combine the favorable effects of the bacterial species.

According to a particular embodiment, the composition according to the present invention further comprises bacteria of at least one species selected amongst *Enterococcus hirae, Akkermansia muciniphila* and *Bacteroides salyersiae*. For example, the composition can comprise a mix of *Alistipes senegalensis* and *Bacteroides salyersiae*, or a mix of *Alistipes senegalensis* and *Akkermansia muciniphila*.

Non-limitative additional examples of bacterial strains which can be included in the compositions according to the invention are: Blautia strains, *Coprococcus comes* strains, *Alistipes shahii*, other *Alistipes* species (e.g. *Alistipes indistinctus* and/or onderdonkii and/or *finegoldii*), Ruminococcacae, Clostridiales species, Bacteroidales species, Actinobacteria, Coriobacteriales species, *Methanobrevibacter smithii, Burkholderia cepacia, Bacteroides fragilis, Actinotignum schaalii*, as well as Clostridiales bacteria of the species *Christensenella minuta*; Erysipelotrichia of the species *Dielma fastidiosa* or *Erysipelatoclostridium ramosum; Eubacterium limosum; Barnesiella intestinihominis*; Coriobacteriales bacteria of the species *Collinsella intestinalis* and/or *Collinsella tanakaei*; and Firmicutes bacteria of the species *Flavonifractor plautii*.

The present invention also pertains to a fecal microbial composition enriched with a bacterial composition as above-described, and to its use in treating a cancer, in combination with an ICI-based therapy and/or a TKI-based therapy. A fecal microbial composition is a composition of matter derived from one or several feces sample(s), preferably obtained (directly or indirectly) from a stool sample from (a) healthy individual(s) and/or from (a) responder(s) to a treatment with an ICI- and/or TKI-based therapy, or at least from an individual exhibiting a gut microbiota profile that identifies him/her as likely to respond to the envisioned treatment. The fact that the fecal microbial composition can be obtained indirectly from a healthy individual's stool sample means that banks of fecal microbial material may be created, with possible mixes of stool samples, and possible creation of "standard healthy fecal microbial compositions", possibly adapted to certain conditions requiring FMT (e.g., a fecal microbial composition for treating a *Clostridium* infection may be different from a fecal microbial composition for use in a cancer context) and/or to other characteristics of patients (age, ethnic origin, food regimen etc.). Several ways of conditioning fecal microbial material and conducting FMT have been described and are currently developed, and the skilled artisan is free to choose appropriate techniques for preparing the fecal microbial composition according to the invention, which can be freshly-prepared liquid, freeze-dried material or any other conditioning.

In what follows, the word "composition(s)" indifferently designates bacterial compositions and fecal microbial compositions according to the invention.

The above compositions are particularly useful for inducing immunostimulation in patients having a cancer that can be treated with a TKI, such as (but not limited to) any of those listed in Table 1, especially breast cancer, chronic myeloid leukemia (CML), GIST and sarcoma, glioblastoma, thyroid cancers, (advanced) renal cell cancer (RCC) and non-small cell lung cancer (NSCLC).

According to another particular embodiment, the composition according to the invention is used in combination with an ICI-based therapy and a TKI-based therapy.

The present invention also pertains to the use of the above bacterial compositions or fecal microbial compositions, as a medicament for compensating dysbiosis in a cancer patient. A "dysbiosis" can be defined as a disequilibrium between potentially "detrimental" and "beneficial" bacteria in the gut or any deviation to what is considered a healthy microbiota in terms of main bacterial groups composition and diversity. Dysbiosis may be linked to health problems, including cancer (as shown in WO 2018/115519). It can also be the consequence of a treatment, such as a cytotoxic treatment or an antibiotic treatment.

It is to be understood that when a composition according to the invention is used "in combination with" a TKI and/or an ICI-based therapy, the bacterial or fecal material composition and the TKI and/or ICI can be administered either concomitantly or sequentially. For example, the patient is first treated with the TKI (first-line therapy in RCC), followed by a second treatment sequence in which the patient receives a TKI and an ICB, as well as a bacterial composition comprising *Alistipes senegalensis* and/or *Akkermansia muciniphila*.

According to another aspect, the present invention pertains to a protocol for treating a patient having a cancer (e.g., a RCC or another TKI-sensitive cancer such as those listed above), in which: (i) the patient receives a first-line TKI-based therapy, (ii) the patient's microbiota is analyzed to assess whether an intestinal microbiome shift has occurred (compared to the intestinal microbiota before TKI uptake), and (iii) depending on the result of step (ii), the TKI-based therapy is maintained in combination with an ICI-based therapy, if necessary accompanied by administration of a compensating composition as the bacterial compositions and fecal material compositions described above. In particular, if the result of step (ii) shows that the relative abundance of *Alistipes senegalensis* has increased in the intestinal microbiota following TKI administration, the ICI-based immunotherapy comprising anti-PD1 Ab could be combined to TKI for the rest of the clinical management, or the combination of anti-CTLA4+anti-PD1 could be the main therapy. If the result of step (ii) shows that the relative abundance of *Alistipes senegalensis* or *E. siraeum* has not increased in the intestinal microbiota following TKI administration, the ICI-based immunotherapy comprising anti-PD1 Ab could be combined to FMT or administration of beneficial bacterial compositions (described above) for the rest of the clinical management, or the combination of anti-CTLA4+anti-PD1 together with the benefical bacteria.

In the above method, the patient's microbiota is analyzed in an appropriate sample from the patient, such as, for example, a feces sample, a biopsy from the patient's ileum or colon mucosae or a tumor biopsy.

The present invention also pertains to a method of in vitro determining if an individual having a cancer is likely to respond to a treatment with an ICI-based therapy and/or a TKI-based therapy, comprising the following steps:

(i) determining the relative abundances of *Clostridium hathewayi* (previously known as *Hungatella hathewayi*), *Clostridium clostridioforme* and/or *Clostridium boltae* in a biological sample of said individual, and (ii) comparing each of the relative abundances measured in step (i) to a control value, wherein overrepresentation of at least one of *Clostridium hathewayi*, *Clostridium clostridioforme* and *Clostridium boltae* indicates that the individual is likely to be a poor responder to said treatment.

In the above method, step (i) can be performed by measuring, in an appropriate sample from the patient (as defined above), the relative abundances of *Clostridium hathewayi, Clostridium clostridioforme* and/or *Clostridium boltae*. The obtained values are then compared, in step (ii), to control values based on relative abundances of the same species in normal volunteers (healthy volunteers who did not take antibiotics recently). A given species is considered as "overrepresented" when its relative abundance in the sample from the patient is superior to the control value, it being understood that (a) for species that are normally not present in healthy volunteers (e.g., the value is zero in healthy volunteers in novel data bases such as MetaphLan or Meta HIT at the plateau of worldwide machine learning), the mere presence of the bacterium is considered of negative predictive value and (b) for species which are normally present in healthy volunteers, the control values are determined so that a relative abundance above this value is significantly superior (for a skilled person) to what is observed in healthy volunteers.

Alternatively, the above method can be performed by determining, in the patient's serum, IgG responses directed against *Clostridium hathewayi, Clostridium clostridioforme* and/or *Clostridium boltae*. These responses are then compared to control values, such as those observed in healthy volunteers.

The present invention also pertains to a method for in vitro determining if an individual having a cancer is likely to respond to a treatment with an ICI-based therapy and/or a TKI-based therapy, comprising the following steps:

(i) from an appropriate biological sample of said individual, determining the relative abundance of at least two immunotolerant species selected from the group consisting of *Clostridium hathewayi, Clostridium clostridioforme* and *Clostridium boltae;*

(ii) from an appropriate biological sample of said individual, determining the relative abundance of at least three immunostimulatory species selected from the group consisting of *Akkermansia muciniphila, Bacteroides salyersiae, Alistipes senegalensis, Dorea longicatena* and *Eubacterium siraeum;*

(iii) calculating the ratio of the relative abundance of the immunotolerant species of step (i) to the relative abundance of the immunostimulatory species of step (ii);

wherein the lower the ratio calculated in step (iii), the higher the probability that the individual responds to the treatment.

In the above method, the terms "immunostimulatory" and "immunotolerant" reflect the effects of the recited bacteria on the response or the resistance of the patient to the treatment with an ICI and/or TKI. Indeed, as shown in Example 4 below, some species, which disappear during cancer development or antibiotics uptake, appear associated with an efficient response to a treatment by, e.g., anti-PD-1 blockade. These species are defined as "immunostimulatory". Other species, on the contrary, are specifically selected following antibiotics administration and during cancer development, and may confer primary resistance to this therapy. Such species are referred to as "immunotolerant" herein.

When performing the above method, the ratio obtained in step (iii) can be compared to one or several predetermined thresholds to obtain a probability score that the patient responds to the treatment. These thresholds can be calculated by the skilled person based on the results obtained in patients cohorts. One particular threshold is also calculated based on the relative abundancies observed in healthy volunteers, it being understood that if the ratio is inferior to this threshold, the patient is likely to be a good responder.

In particular, the above methods can be performed by using the following control values, obtained in healthy volunteers:

"immunotolerant" bacteria are considered as overrepresented when their relative abundances are:
>0.09%+/−0.017% for *C. clostridiofome,*
>0.21%+/−0.024% for *C. boltae* and
>0.06%+/−0.009% for *C. hathewayi*

"immunstimulatory" bacteria are considered as overrepresented when their relative abundances are:
>0.855%+/−0.022% for *D. longicatena*
>1.11%+/−0.058% for *E. siraeum,*
>1.89%+/−0.10% for *A. muciniphila,*
>0.05%+/−0.0022% for *A. senegalensis,* and
>0.15%+/−0.01% for *B. salyersae*

These data can be used also to calculate the control value for the ratio of the relative abundance of the immunotolerant species of step (i) to the relative abundance of the immunostimulatory species of step (ii) in the above method. For example, if this method is based on the measure of the relative abundances of *C. boltae, C. hathewayi, D. longicatena* and *A. muciniphila,* one can compare the ratio
[RA(*C. boltae*)+RA(*C. hathewayi*)]/[RA(*D. longicatena*)+RA(*A. muciniphila*)] to 2 control values calculated as follows $$V1=[(0.21+0.024)+(0.06+0.009)]/[(0.855-0.022)+ (1.89\%-0.10)]$$

$$V2=[(0.21-0.024)+(0.06-0.009)]/[(0.855+0.022)+ (1.89\%+0.10)]$$

and consider that if the measured ratio is superior to V1, the patient is likely to be a poor responder to the treatment, and/or if the measured ratio is inferior to V2, the patient is likely to respond to the treatment.

When performing the methods according to the invention, the skilled person can use any technique to measure the relative abundances of the bacterial species, such as NGS (through any past or future NGS platform, from the first generation to the last available on the market and those in development, using any NGS output file provided as fastq, BAM, SAM, or other kind of files extensions) or any other technique such as, for example, qPCR (quantitative polymerase chain reaction) and microarrays to express the relative abundances of selected bacterial species.

Specific genome sequences and primer pairs are disclosed herein (Table 2), which can be used to detect the bacterial species mentioned above and measure their relative abundance according to the invention.

TABLE 2

| genome sequences and primers specific for the recited bacterial species. | | |
| --- | --- | --- |
| Bacterial species | Specific sequence (SEQ ID No:) | Primers* (SEQ ID No:) |
| *A. senegalensis* | 1-12 | 73-94 |
| *C. boltae* | 13-24 | 95-118 |
| *C. clostridioforme* | 25-36 | 119-140 |
| *C. hathewayi* | 37-48 | 141-164 |
| *D. longicatena* | 49-60 | 165-188 |
| *E. siraeum* | 61-72 | 189-212 |

*primer pairs for specifically amplifying fragments (of a length comprised between 70 and 350 pb) of the recited species are formed with primers having two consecutive numbers (SEQ ID No: 2n + 1 and SEQ ID No: 2n + 2, n being an integer)

Other methods for ex vivo determining whether a cancer patient is likely to benefit from a treatment with an ICI-based therapy and/or a TKI-based therapy are also part of the present invention, based on the analysis of memory immune responses directed against the immunostimulatory and/or immunotolerant bacterial species defined above.

Thus, the present invention pertains to a method for ex vivo determining whether a cancer patient is likely to benefit from a treatment with an ICI-based therapy and/or a TKI-based therapy, comprising assessing the presence of memory Th1 or Tc1 cells towards *Alistipes senegalensis, Dorea longicatena* and/or *Eubacterium siraeum* in a blood sample from said patient, wherein the presence of memory Th1 or Tc1 cells towards *Alistipes senegalensis, Dorea longicatena* and/or *Eubacterium siraeum* indicates that the patient is likely to be a good responder to said treatment.

Another method according to the invention for ex vivo determining whether a cancer patient is likely to benefit from a treatment with an ICI-based therapy and/or a TKI-based therapy, comprises assessing the presence of memory Tr cells towards *Clostridium hathewayi, Clostridium clostridioforme* and/or *Clostridium boltae* in a blood sample from said patient, wherein the presence of memory CD4+Tr cells (IL-10 producing) or TH17 regulatory Rorct/foxp3 towards *Clostridium hathewayi, Clostridium clostridioforme* and/or *Clostridium boltae* indicates that the patient is likely to be a poor responder to said treatment.

The skilled person can of course decide to combine two of the above described methods, to better assess the patient's profile. For example, the memory immune response against both the immunostimulatory bacterial species and the immunotolerant bacterial species can be assessed according to the invention. According to another example, method based on the measure of the relative abundance of immunotolerant bacterial species can be combined with that based on assessing the memory immune response against immunostimulatory bacterial species, etc. Such combined methods are also part of the present invention.

Alternatively or complementarily, one or several of the above methods is (are) combined with another method for determining, from a feces sample from a cancer patient, whether said patient is likely to be a good responder to a treatment with an ICI, based on an animal model. Such a method was already described in a previous application from the inventors' team (WO2016/063263) and comprises the steps of (i) performing a fecal microbial transplantation (FMT) of a feces sample from the patient into germ free (GF) model animals (e.g., GF mice); (ii) at least 7 to 14 days after step (i), inoculating said mice with a transplantable tumor model; (iii) treating the inoculated mice with the ICI; and (iv) measuring the tumor size in the treated animals. The results of step (iv) are illustrative of the response that can be expected for said patient to said treatment.

A nucleic acid microarray designed to perform a method according to the invention is also part of the present invention. Such a nucleic acid microarray comprises nucleic acid probes specific for each of the microorganism species to be detected in said method. In a specific embodiment, the nucleic acid microarray is an oligonucleotide microarray comprising at least one oligonucleotide specific for at least one sequence selected from SEQ ID NOs: 1-72. For example, the said microarray comprises at least 6 oligonucleotides, each oligonucleotide being specific for one sequence of a distinct species. The microarray of the invention can of course comprise more oligonucleotides specific for sequences of SEQ ID NOs: 1-72. The microarray according to the invention may further comprise at least one oligonucleotide for detecting at least one gene of at least one control bacterial species. A convenient bacterial species may be e.g. a bacterial species the abundance of which does not vary between individuals having a R or a NR status. Preferably, the oligonucleotides are about 50 bases in length. Suitable microarray oligonucleotides specific for any gene of SEQ ID NOs: 1-72 may be designed, based on the genomic sequence of each gene, using any method of microarray oligonucleotide design known in the art. In particular, any available software developed for the design of microarray oligonucleotides may be used, such as, for instance, the OligoArray software, the GoArrays software, the Array Designer software, the Primer3 software, or the Promide software, all known by the skilled in the art.

The above methods can also be performed for determining if a cancer patient needs a bacterial compensation before or during administration of an ICB-based therapy and/or a TKI-based therapy. Indeed, if the patient is identified as likely to be a poor responder to the treatment, his/her situation can be improved by bacterial compensation. According to this aspect of the invention, the bacterial compensation can be done either by fecal microbiota transplant (FMT), using microbiota from one or several donors (for example, from responders to the treatment), or by administration of a fecal microbial composition or a bacterial composition as above-described. The inventors already described other bacterial compositions that can be used for such a compensation and restore the ability, for the patient, to respond to the treatment (e.g., in WO 2016/063263 and in WO 2018/115519). The present invention thus pertains to a theranostic method for determining if a cancer patient needs a bacterial compensation before or during administration of an ICB-based therapy and/or a TKI-based therapy, comprising assessing, by any method as above-described, whether the patient is likely to respond to the treatment, wherein if the patient is likely to be a poor responder to the treatment, he/she needs a bacterial compensation, for example with a composition according to the invention.

The above methods for determining whether a cancer patient is likely to benefit from a treatment with an ICI-based therapy and/or a TKI-based therapy, and/or whether this patient need a bacterial compensation are especially useful for patients having a breast cancer, chronic myeloid leukemia (CML), GIST and sarcoma, glioblastoma, thyroid cancers, (advanced) renal cell cancer (RCC) and non-small cell lung cancer (NSCLC).

Recently, attempts to directly manipulate the gut microbiome in a targeted manner in situ have been described, using gene editing tools such as the CRISPR/Cas9 system (Ramachandran and Bikard, 2019; Lee et al., 2018). This strategy can be used to design "precision" antimicrobials that target immunotolerant bacterial species in a DNA sequence-specific manner.

The present invention thus pertains to the use of an endonuclease capable of inducing a double-stranded break in a sequence specific for *Clostridium hathewayi, Clostridium clostridioforme* or *Clostridium boltae*, as a medicament for treating cancer, in combination with a TKI and/or an ICB-based therapy.

Several sequence-specific endonucleases useful for gene editing have been described, such as TALE nucleases (TALENs) or zinc-finger nucleases (ZFNs) and CRISPR/Cas systems. According a particular embodiment of the invention, the endonuclease is a CRISR/Cas9. The skilled person can choose any appropriate delivery methods for vectorising the endonuclease according to the invention, such as, for example, transduction (via a phage) or conjugation.

Specific endonucleases according to the invention target sequences listed in Table 3 below. In particular, when CRISPR/Cas is used with a guide RNA targeting a sequence disclosed in this table, the corresponding PAM sequence is indicated. The present invention thus pertains to an endonuclease which targets a sequence selected from the group consisting of SEQ ID Nos: 213 to 248.

TABLE 3 target sequences and corresponding PAM for CRISPR/Cas gRNA

| Targeted species | Guide Sequence | SEQ ID No | PAM |
|---|---|---|---|
| *C. boltae* | ATGCCTCCAGAACCTCCGCC | 213 | TGG |
| | CAGCTGCTGCTTCCGGAATA | 214 | CGG |
| | AATTCATCAGTATTTACGGC | 215 | GGG |
| | TCCGCATCTGCTCATCATAT | 216 | AGG |
| | GTATTTCACACTGTCACTGC | 217 | CGG |
| | CTGGAGCCGCATGTTATCAA | 218 | AGG |
| | GAGGAAGCGGCCAGGGAGGC | 219 | CGG |
| | CAGACGAGGAATATTCTGTA | 220 | TGG |
| | ACGGTCTGGAACAAGAGGAA | 221 | CGG |
| | CAGGTACAGAGTCAGTTACC | 222 | AGG |
| | AGCCCGCCGCCCAATTACCG | 223 | AGG |
| | AGCCTACTTGCTGGCAGGAC | 224 | CGG |
| *C. clostridioforme* | CGCATCAACAGCGAACCGGA | 225 | TGG |
| | CGATTCAAGCAGCATCTGAC | 226 | AGG |
| | CCTAAGCTCCGTCTCATCTA | 227 | TGG |
| | CATGCTGCTGCAAACTCCGA | 228 | GGG |
| | GCTTATTTATGGAAGATATC | 229 | TGG |
| | CAGTGACGGCTATTCCTATA | 230 | CGG |
| | GAACGGGATTGGAAACAGTG | 231 | CGG |
| | GCAACCGGCAACAGGTAAAC | 232 | AGG |
| | GTACACGAAGCCCCGGAACA | 233 | TGG |
| | GCCCCAGTCCAGGCGGATTG | 234 | TGG |

TABLE 3-continued target sequences and corresponding PAM for
CRISPR/Cas gRNA

| Targeted species | Guide Sequence | SEQ ID No | PAM |
|---|---|---|---|
| | CAGCTTAAACCGTTACGTTG | 235 | AGG |
| | AATTGGACTTGGAAGTCATC | 236 | AGG |
| C. hathewayi | CGGATTATCAGGCGGAACTA | 237 | CGG |
| | TTTCATATGATCCGTCATAC | 238 | CGG |
| | CTTCTTTCGATGGATTTGCA | 239 | CGG |
| | AGCTGCGGGCCGGTACGGCA | 240 | CGG |
| | TCAGCGGGGACGGAGTCACC | 241 | TGG |
| | AAGCGGTATCTACAGAAGCG | 242 | CGG |
| | GTCCCGCTGGATAAGATCGT | 243 | TGG |
| | CGGCCAGAAACGGCGACAGC | 244 | CGG |
| | TCCGTACATTACAAGTACGA | 245 | TGG |
| | ACATGTGCGTGCTGGTGGAC | 246 | CGG |
| | CAGTTAAAGGAACTGCAGAG | 247 | AGG |
| | GATTACTGGATGCCGTTTAA | 248 | CGG |

Other characteristics of the invention will also become apparent in the course of the description which follows of the biological assays which have been performed in the framework of the invention and which provide it with the required experimental support, without limiting its scope.

EXAMPLES

In the experimental examples, the following abbreviations are used: 1L: first line therapy, 2L: second line therapy, ATB: antibiotics, "ATB": patient who took antibiotics, CICB: combined immune checkpoint blockade using anti-PD-1/anti-CTLA-4 antibodies, Ctrl: isotype control, DC: dendritic cells, FMT: fecal microbial transplantation, GC: gene count, GIG: genome interaction group, GOMS: Gut OncoMicrobiome Signature, HV: healthy volunteers, ICB: immune checkpoint inhibitor anti-PD1 antibody, LEfSe: linear discriminant analysis of effect size, MGS: metagenomic species, "noATB": patient who did not take antibiotics, NR: non-responders, OS: overall survival, PCoA: principal coordinate analyses, PD: progressive disease, PFS: progression free survival, R: responders, RCC: renal cell carcinoma, RENCA: renal cell carcinoma murine model, SD: stable disease, Tc1: IFNγ producing CD8+T lymphocyte, TH1: IFNγ producing CD4+T lymphocyte, TIL: tumor infiltrating lymphocytes, TKI: tyrosine kinase inhibitors, TME: tumor microenvironment, VEGF: anti-vascular endothelial growth factor, WGS: wall genome sequencing.

Materials and Methods
A. Patient Characteristics and Clinical Study Details:
Medical Centers and Regulatory Approvals for Translational Research.

The clinical study was conducted according to the ethical guidelines and approval of the local CCPRB. For feces collection, the study name was "Oncobiotics", E2M ethics protocol number PP: 15-013. Written informed consent in accordance with the Declaration of Helsinki was obtained from all patients.

Collection of Patient Feces.

The patients were included from Gustave Roussy Cancer Campus, France. Inclusion criteria were patients with stage IV clear cell or non-clear cell RCC histology and disease progression during or after >1 prior anti-angiogenic therapy regimens who received nivolumab intravenously (i.v.) 3 mg/kg every 2 weeks until disease progression or intolerable toxicity in the NIVOREN GETUG-AFU 26 Phase II trial (EudraCT: 2015-004117-24) (Albiges et al., 2018). Computer tomography (CT) scans were performed at baseline and every 8 to 12 weeks for the first year and then every 12 to 15 weeks until disease progression. Tumor response was assessed using the Response Evaluation Criteria in Solid Tumors version 1.1 (RECIST v1.1) (Eisenhauer et al., 2009). Data were collected from a case report form (CRF). All patents were followed-up until death or data lock (September 2018). We evaluated objective response rate defined as the number of patients with a complete response and a partial response. The best overall response was defined as the investigator-assessed best response (complete response, partial response, stable disease, or progressive disease) from the start date of nivolumab to objectively documented disease progression or subsequent therapy, whichever occurred first. Patient were divided into 2 groups: responders (those in complete response, partial response or stable disease for more than 6 months) and non-responders (who either progressed or were in stable disease for less than 6 months or died). Progression-free survival (PFS) was defined as the time from the start date of nivolumab to first documented RECIST-defined tumor progression or death from any cause. Four median PFS values (3, 6, 9 and 12 months) were used to examine the impact of PFS time on metagenomics. Feces were collected according to International Human Microbiome Standards (IHMS) guidelines (SOP 03 V1) at different timepoints: before the first injection (0-1 month before) (T0), after the 2nd (T4-4 weeks), after the 4th (T8-8 weeks) and after the 12th (T24-24 weeks) injection (FIG. 1). In brief, a collection kit including an anaerobic generator (Biomerieux) was given to patients. Samples were collected by patients at home, and frozen 4 to 24 h later at −80° C. at Gustave Roussy Cancer Campus in plastic tubes (Plastic vessel by 1000-Sarstedt) with or without BHI+2% glycerol. Forty patients were analyzed in addition to 60 non-small cell lung cancer patients in the *Science* 2018 paper (Routy et al., 2018). Finally, from February 2016 to September 2018, a total of 85 patients with RCC were enrolled in the NIVOREN trial at Gustave Roussy and we collected T0-T4 feces of 69 patients. For the first time, RCC were analyzed as a single and independent cohort in this paper.

Metagenomic analysis of patient stools.

Total fecal DNA was extracted as described (Godon et al., 1997; Suau et al., 1999) and sequenced using ion-proton technology (ThermoFisher) resulting in 22.7±0.9 million (mean±SD) single-end short reads of 150-base-long single-end reads as a mean. Reads were cleaned using (Criscuolo et al., 2013). AlienTrimmer in order (i) to remove resilient sequencing adapters and (ii) to trim low quality nucleotides at the 3' side using a quality and length cut-off of 20 and 45 bp, respectively. Cleaned reads were subsequently filtered from human and other possible food contaminant DNA (using Human genome RCh37-p10, *Bos taurus* and *Arabidopsis thaliana* and an identity score threshold of 97%). For the MetaOMineR analyses the gene abundance profiling was performed using the 9.9 million gene integrated reference catalog of the human microbiome (Li et al., 2014). Filtered high-quality reads were mapped with an identity threshold of 95% to the 9.9 million-gene catalogue using (Langmead et Salzberg, 2012) Bowtie 2 included in METEOR software (Cotillard et al., 2013). The gene abundance profiling table was generated by means of a two-step procedure using METEOR. The gene abundance table was processed for rarefaction and normalization and further analysis using the MetaOMineR (momr R) package (Le Chatelier et al., 2013). The gene abundance table was rarefied to 13 million reads per sample (a threshold chosen to include all samples, but 1 with 12.5 million reads) by random sampling of 13 million mapped reads without replacement. The resulting rarefied gene abundance table was normalized according to the FPKM strategy (normalization by the gene size and the number of total mapped reads reported in frequency) to give the gene abundance profile table. Metagenomic species (MGS) are co-abundant gene groups with more than 500 genes corresponding to microbial species. 1436 MGS were clustered from 1267 human gut microbiome samples used to construct the 9.9 million-gene catalogue (Li et al., 2014), as described (Nielsen et al., 2014). Differentially abundant MGS between different patients' groups were selected using the Wilcoxon test (p<0.05). Microbial gene richness (gene count) was calculated by counting the number of genes that were detected at least once in a given sample, using the average number of genes counted in 10 independent rarefaction experiments. MGS richness (MGS count) was calculated directly from the MGS abundance matrix. For the MetaPh/An2 analyses fastq files were cleaned/filtered as described above and underwent an additional filtering for possible human contaminants (reference database GRCh37/hg19) and contextual quality control using KneadData. This wrapper entangles Bowtie2 ("--very-sensitive" and "--dovetail" settings) to rule out contaminant sequences and Trimmomatic (sliding window 20, min-length 50) to exclude low-quality reads. Filtered reads underwent MetaPhlAn2 pipeline (default settings) for unambiguous taxonomic classification and to generate a table of relative abundances for bacterial, archaeal, eukaryotic and viral species. Only taxa that were present in at least 20% of all samples were considered. Raw tabular data were firstly normalized then standardized using QuantileTransformer and StandardScaler methods from Sci-Kit learn package v0.20.3. Normalization using the output_distribution='normal' option make each variable to strictly have a gaussian shape distribution, while the standardization makes each variable to have zero mean and unit variance. Measurements of a diversity (within sample diversity) such as observed_otus and Shannon index, were calculated at OTU level using the SciKit-learn package v.0.4.1. Exploratory analysis of β-diversity (between sample diversity) was calculated using the Bray-Curtis measure of dissimilarity and represented in Principal Coordinate Analyses (PCoA), while for Hierarchical Clustering Analysis (HCA) 'Bray-Curtis' metrics and 'complete linkage' method was implemented using custom scripts (Python v.2.7.11). We implemented Partial Least Square Discriminant Analysis (PLS-DA) and the subsequent Variable Importance Plot (VIP) as a supervised analysis in order to find out the most discriminant bacterial species. Mann-Whitney U and Kruskall-Wallis tests were employed to assess significance for pair-wise or multiple comparisons, respectively, taking into account a p-value≤0.05 as significant. For the Network analysis cross-correlation Pearson matrices for network analysis (metric=Bray-Curtis, method=complete linkage) were generated with in-house scripts (Python v.2.7) and visualized with Gephi v.0.9.2, considering species having a prevalence≥20% and a significant Pearson correlation coefficients divided into eight categories to define edge thickness (Li et al., 2008). A network analysis was performed on each dataset using co-occurrences and concomitant significance of pair-wise Pearson correlation coefficient, taking care of an optimized visual representation as proposed by current guidelines (Merico et al., 2009; Berry and Widder, 2014; Faust et al., 2012a; Faust et al., 2012b; Lozupone et al., 2012). The degree value, measuring the in/out number of edges linked to a node, and the betweenness centrality, measuring how often a node appears on the shortest paths between pairs of nodes in a network, were computed with Gephi v.0.9.2. Intranetwork communities (here called 'guilds') were retrieved using the Blondel community detection algorithm (Blondel et al., 2008) by means of randomized composition and edge weights, with a resolution equal to 1 (Lambiotte et al., 2014).

Analysis of the Impact of Antibiotics or Tyrosine Kinase Inhibitors (TKI) on Anti-PD-1 mAb Efficacy.

Patients who received any oral or intravenous antibiotics within 60 days before the first injection of nivolumab were defined "ATB" and compared to "noATB" patients. The class of antibiotics, the indication route of administration and the duration were collected. Best overall response differences (as defined before) between "ATB" and "noATB" patients were analyzed using Chi-squared test. Prior regimens (anti-angiogenic therapy—TKI, i.e, sunitinib, axitinib or other—or mTOR (mammalian target of rapamycin)) used before starting nivolumab were collected and underwent network analysis to highlight putative differences in the species distribution among 'guilds' previously found. The feature group belonging (e.g., TKI, ATB, mTOR) for each species was computed taking into account when the mean relative abundance was higher for that distinctive feature. Nodes within Networks where then re-colored according to the new classification and two different distribution criteria within each guild were computed: i) feature distribution; ii) taxonomical distribution (phylum, class, order level). Chi-square test with Yates correction was used to assess putative differences within the distributions, and a P value less than or equal to 0.05 was considered significant.

Analyses of the Bacteria Discriminating RCC from Control Adults (HV)

The 69 RCC samples were analyzed and compared with 2994 control adults acquired from publicly available repositories and spanning multiple countries and lifestyles (Pasolli et al., 2017). This set of control samples was enlarged by 54 Italian samples newly acquired and sequenced in the current study. Bacterial species discriminating RCC from HV were determined using LefSe (Segata et al., 2011).

Analyses of the Bacteria Discriminating RCC from Lung Cancer Patients (NSCLC).

The 69 RCC samples were analyzed and compared with 118 NSCLC samples acquired and sequenced in the "Oncobiotics' study. Bacterial species discriminating NR from R in NSCLC cohort were determined using MetaOMineR analyses as previously described for RCC cohort.

B. Pre-Clinical Study Details:

Mice

All animal experiments were carried out in compliance with French and European laws and regulations. The local institutional animal ethics board and French Ministere de la Recherche approved all mouse experiments (permission numbers: 2016-049-4646, 2018-078-17530). Experiments were performed in accordance with Government and institutional guidelines and regulations. Female BALB/c were purchased from Janvier (France). Mice were used between 7 and 12 weeks of age. All mouse experiments were performed at the animal facility in Gustave Roussy Cancer Campus where animals were housed in specific pathogen-free conditions.

Cell Culture, Reagents and Tumor Cell Line.

Luciferase-transfected RENCA cell lines (syngeneic for BALB/c mice, kindly provided by Transgene, Illkirch, France) were cultured at 37° C. in the presence of 5% CO2 in RPMI 1640 containing 10% FCS, 2 mM L-glutamine, 100 UI/ml penicillin/streptomycin, 1 mM sodium pyruvate and MEM non-essential amino acids (henceforth referred to as complete RPMI 1640). All reagents were purchased from Gibco-Invitrogen (Carlsbad, CA, USA). Renca cells were maintained in RPMI 1640 medium in the presence of 0.7 mg/ml geneticin (G418).

Antibiotic Treatments.

Mice were treated with an antibiotic solution (ATB) containing ampicillin (1 mg/ml), streptomycin (5 mg/ml), and colistin (1 mg/ml) (Sigma-Aldrich), with or without the addition vancomycin (0.25 mg/ml) added in the drinking water of mice. Antibiotic activity was confirmed by cultivating fecal pellets resuspended in BHI+15% glycerol at 0.1 g/ml on COS (Columbia Agar with 5% Sheep Blood) plates for 48 h at 37° C. in aerobic and anaerobic conditions. In brief, in the context of fecal microbial transplantation experiments, mice received 3 days of ATB before undergoing fecal microbial transplantation the next day by oral gavage using animal feeding needles.

Orthotopic Luciferase Engineered-Renal Cell Carcinoma (RENCA)

BALB/c mice were anesthetized with isoflurane. A lateral incision was made on the dorsolateral right flank of each mouse, 104 Renca-Luc cells in 30 μL PBS were injected into the subcapsular space of the right kidney. The skin incision was then closed with surgical clips. Tumor growth was monitored once weekly on an IVIS Imaging System 50 Series (Analytic Jenap). Treatment began on day 7 after tumor inoculation. Mice were injected intraperitoneally 4 times every 4 days with anti-PD-1 (250 mg/mouse; clone RMPI-14) with anti-CTLA-4 mAbs (100 mg of clone 9D9) or anti-PD-1 mAb and axitinib or isotype control mAb (clone 2A3 and clone MPC11, respectively) with or without oral gavage of fecal samples from responding patients or of commensal species.

FMT Experiments

Fecal microbiota transfer (FMT) was performed by thawing fecal material. Two hundred μL of the suspension was then transferred by oral gavage into ATB pre-treated recipient. In addition, another 100 μL was applied on the fur of each animal. Two weeks after FMT, tumor cells were injected subcutaneously or orthotopically and mice were treated with anti-PD-1 and CTLA-4 mAbs or anti-PD-1 mAb and axitinib or isotype controls with or without oral gavage of fecal samples from responding patients or of commensal species, as mentioned above.

Gut Colonization with Commensal Species.

*A. muciniphila* CSUR P2261 and *A. indistinctus* CSUR P723 were provided by the Institut hospitalo-universitaire Mediterranée Infection, Marseille, France. *Bacteroides salyersiae* was isolated from the feces of an RCC patient while *Bacteroides xylanisolvens* was isolated from the ileal mucosa of a colorectal cancer patient. Both patients responded to therapy. *Sutterella wadsworthensis* was isolated from the ileal mucosa of a non-responder colorectal cancer patient. *A. muciniphila* was grown on COS plates in an anaerobic atmosphere created using 3 anaerobic generators (Biomerieux) at 37° C. for at least 72 h. *Alistipes indistinctus, Bacteroides salyersiae, Sutterella wadsworthensis* and *Bacteroides xylanisolvens* were also grown on 5% sheep blood enriched Columbia agar (BioMerieux) in an anaerobic atmosphere created using a single anaerobic generator at 37° C. for 48 h. Bacteria were verified using a Matrix-Assisted Laser Desorption/Ionization Time of Flight (MALDI-TOF) mass spectrometer (Microflex LT analyser, Bruker Daltonics, Germany). Colonization of ATB pre-treated mice was performed by oral gavage with 100 μl of suspension containing $1 \times 10^8$ bacteria. For bacterial gavage: suspensions of $10^9$ CFU/mL were obtained using a fluorescence spectrophotometer (Eppendorf) at an optical density of 600 nm in PBS. Five bacterial gavages were performed for each mouse, the first 24 h before the first injection of anti-PD-1 and CTLA-4 mAbs and subsequently four times on the same day anti-PD-1 and CTLA-4 mAbs injections.

Flow Cytometry Analyses.

Tumor-bearer kidneys and spleens were harvested at different time points, 48 h days after the second injection of anti-PD-1+anti-CTLA-4 mAbs into mice bearing RENCA tumors. Excised tumors were cut into small pieces and digested in RPMI medium containing Liberase™ at 25 μg/mL (Roche) and DNase1 at 150 UI/mL (Roche) for 30 minutes at 37° C. and then crushed and filtered twice using 70 μm cell strainers (Becton & Dickinson). Spleen were crushed in RPMI medium and subsequently filtered through a 100 μm cell strainer. Four million tumor cells or splenocytes were pre-incubated with purified anti-mouse CD16/CD32 (clone 93; eBioscience) for 30 minutes at 4° C., before membrane staining. For intracellular staining, the Foxp3 staining kit (eBioscience) was used. Dead cells were excluded using the Live/Dead Fixable Aqua dead cell stain kit (Life Technologies). Anti-mouse antibodies for CD3 (145-2C11), CD4 (RM4-5), CD8 (53-6.7), CD44 (IM7), CD45 (30-F11), CD62L (MEL-14), Foxp3 (FJK-16s), CD25 (PC61), CXCR3 (CXCR3-173), PD-1 (J43) and PD-L1 (MIH5), Ly6C (HK1.4), Ly6G (1A8), CD11c (N418), F4/80 (BM8), IA/IE (M5/114.15.2), CD103 (2E7), CD11b (M1/70), XCR1 (ZET), Tim3 (B8.2C12), Lag3 (eBioC9B7W), 4-1BB (CD137, 1785), CTLA-4 (CD152, UC10-4B9), CD86 (GL1) (BD, BioLegend, R&D and eBioscience) were used to stain cells. Stained samples were acquired on Cytoflex cytometer (Beckman Coulter) and analyses were performed with Kaluza software (Beckman Coulter). T central memory (TCM) gating: after gating on CD3+ alive, CD4+ or CD8+ then, TCM were identified as being CD62L+ and CD44+. Effector memory T (TEM) cells were selected as being CD62L− and CD44+. Treg were gated on CD45+ alive, CD3+, CD4+, CD25+, FoxP3+. Dendritic cells were gated on CD45+ alive, CD3−, Ly6G−, CD11chi, IA/IE+, F4/80−. Macrophages were gated on, CD45+ alive, CD3−, CD11b+F4/80+.Myeloid-derived suppressor cells (MDSC) were gated after exclusion of Macrophages, on CD45+ alive, CD3−, CD11b+, Ly6Clo Ly6G+ for G-MDSC (granulocytic) and Ly6Chi Ly6G-for M-MDSC (monocytic). T central memory (TCM) gating: after gating on CD3+ alive, CD4+ were selected excluding CD8+ and CD4+CD8+ then, TCM were identified as being either CD62L+ and CD44+ or CD45RB−. Effector memory T (TEM) cells were selected as being CD62L− and CD44+ or CD45RB−.

Mouse Samples for TKI Experiment

BALB/c and C57BL6 mice were treated with sunitinib (40 mg/Kg/day) or axitinib (30 mg/Kg/day) (Diaz-Montero et al., 2016) or cabozantinib (60 mg/Kg/day) (Doran et al., 2014) or PBS by oral gavage. At least 5 longitudinal stool samples were collected from mice and stored at −80° C. until DNA extraction. Preparation and sequencing of mouse fecal samples was performed at IHU Méditerranée Infection, Marseille, France. Briefly, DNA was extracted using two protocols. The first protocol consisted of physical and chemical lysis, using glass powder and proteinase K respectively, then processing using the Macherey-Nagel DNA Tissue extraction kit (Duren, Germany)(Dridi et al., 2009). The second protocol was identical to the first protocol, with the addition of glycoprotein lysis and deglycosylation steps (Angelakis et al., 2016). The resulting DNA was sequenced, targeting the V3-V4 regions of the 16S rRNA gene as previously described (Million et al., 2016). Raw FASTQ files were analyzed with Mothur pipeline v.1.39.5 for quality check and filtering (sequencing errors, chimerae) on a Workstation DELL T7910 (Round Rock, Texas, United States). Raw reads (12692043 in total, on average 127 k per sample) were filtered (2949373 in total, on average 30 k per sample) and clustered into Operational Taxonomic Units (OTUs), followed by elimination of low-populated OTUs (till 5 reads) and by de novo OTU picking at 97% pair-wise identity using standardized parameters and SILVA rDNA Database v.1.19 for alignment. In all, considering BALB/c and C57BL6 samples, 188 bacterial species were identified. Sample coverage was computed with Mothur and resulted to be on average higher than 99% for all samples, thus meaning a suitable normalization procedure for subsequent analyses. Bioinformatic and statistical analyses on recognized OTUs were performed with Python v.2.7.11. The most representative and abundant read within each OTU (as evidenced in the previous step with Mothur v.1.39.5) underwent a nucleotide Blast using the National Center for Biotechnology Information (NCBI) Blast software (ncbi-blast-2.3.0) and the latest NCBI 16S Microbial 722 Database accessed at the end of April 2019 (ftp://ftp.ncbi.nlm.nih.gov/). A matrix of bacterial relative abundances was built at each taxon level (phylum, class, order, family, genus and species) for subsequent multivariate statistical analyses. Raw data were firstly normalized then standardized using QuantileTransformer and StandardScaler methods from Sci-Kit learn package v0.20.3. Normalization using the output_distribution='normal' option transforms each variable to a strictly Gaussian-shaped distribution, whilst the standardization results in each normalized variable having a mean of zero and variance of one. These two steps of normalization followed by standardization ensure the proper comparison of variables with different dynamic ranges, such as bacterial relative abundances, tumor size, or colonic infiltrate score. Measurements of a diversity (within sample diversity) such as observed_otus and Shannon index, were calculated at OTU level using the SciKit-learn package v.0.4.1. Exploratory analysis of β-diversity (between sample diversity) was calculated using the Bray-Curtis measure of dissimilarity calculated with Mothur and represented in Principal Coordinate Analyses (PCoA), while for Hierarchical Clustering Analysis (HCA) 'Bray-Curtis' metrics and 'complete linkage' method were implemented using custom scripts (Python v.2.7.11). We implemented Partial Least Square Discriminant Analysis (PLS-DA) and the subsequent Variable Importance Plot (VIP) as a supervised analysis in order to identify the most discriminant bacterial species among the different cohorts of mice treated or not. Where needed, univariate/multivariate statistics and correlation analysis were performed with Python v2.7 and related packages (Scipy, Scikit-learn).

Example 1: Antibiotics Compromise the Efficacy of ICB

From February 2016 to September 2018, a total of 85 patients with RCC were enrolled in the NIVOREN trial (Albiges et al., 2018). We collected baseline (T0-T4) feces from 69 patients (FIG. 1A). Results from 40 patients were previously reported in a pooled analysis with 60 NSCLC patients in the Science 2018 paper (Routy et al., 2018). Here, RCC have been analyzed for the first time as a single cohort after inclusion of additional patients. The demographic and clinical characteristics of the patients are illustrated in Table 4.

TABLE 4

| Baseline characteristics of renal cell carcinoma patients. | | |
|---|---|---|
| Patient characteristics | | Total (N = 69) |
| Age-yr | Median | 62 |
| | Range | 30-82 |
| Age-yr-no.(%) | <65 | 40 (58) |
| | ≥65 <75 | 22 (32) |
| | ≥75 | 7 (10) |
| Gender-no.(%) | Male | 48 (69) |
| | Female | 21 (31) |
| Histology-no.(%) | Clear cell | 67 (97) |
| | Non-clear cell | 2 (3) |
| Nephrectomy-no.(%) | Yes | 63 (91) |
| | No | 6 (9) |
| IMDC risk group-no.(%) | Good | 14 (20) |
| | Intermediate | 39 (57) |
| | Poor | 14 (20) |
| | Unknown | 2 (3) |
| Number of prior treatments-no.(%) | 1 | 47 (68) |
| | 2 | 17 (25) |
| | ≥3 | 5 (7) |
| Previous systemic cancer therapy-no.(%) | Sunitinib | 49 (71) |
| | Axitinib | 13 (19) |
| | Other TKI | 20 (29) |
| | mTOR | 12 (17) |
| ATB-no.(%) | Yes | 11 (16) |
| | β-lactam ± inhibitors | 7 (64) |
| | Quinolones | 1 (9) |
| | Unknown | 3 (27) |
| | No | 58 (84) |

Figure 1C:
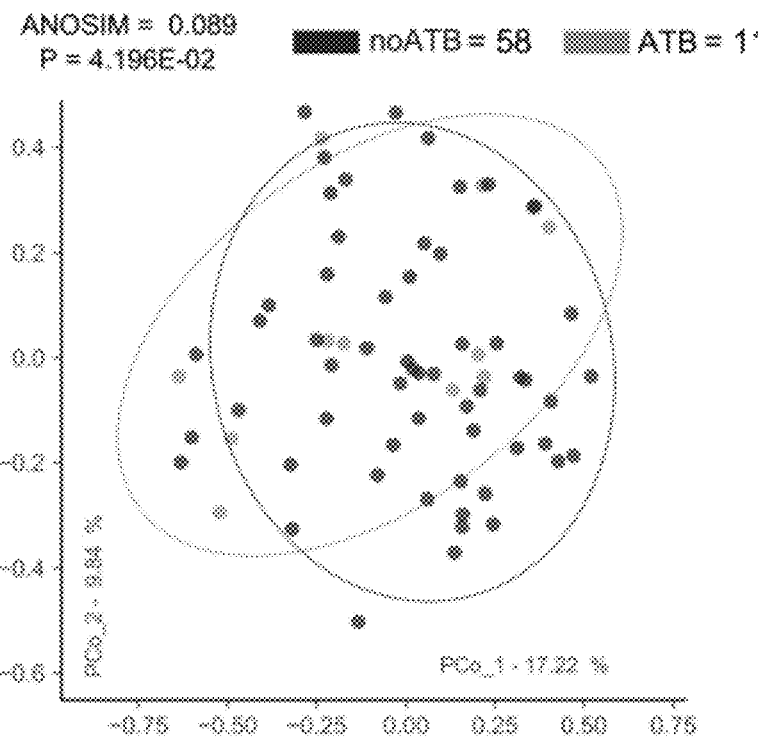
Figure 1D:
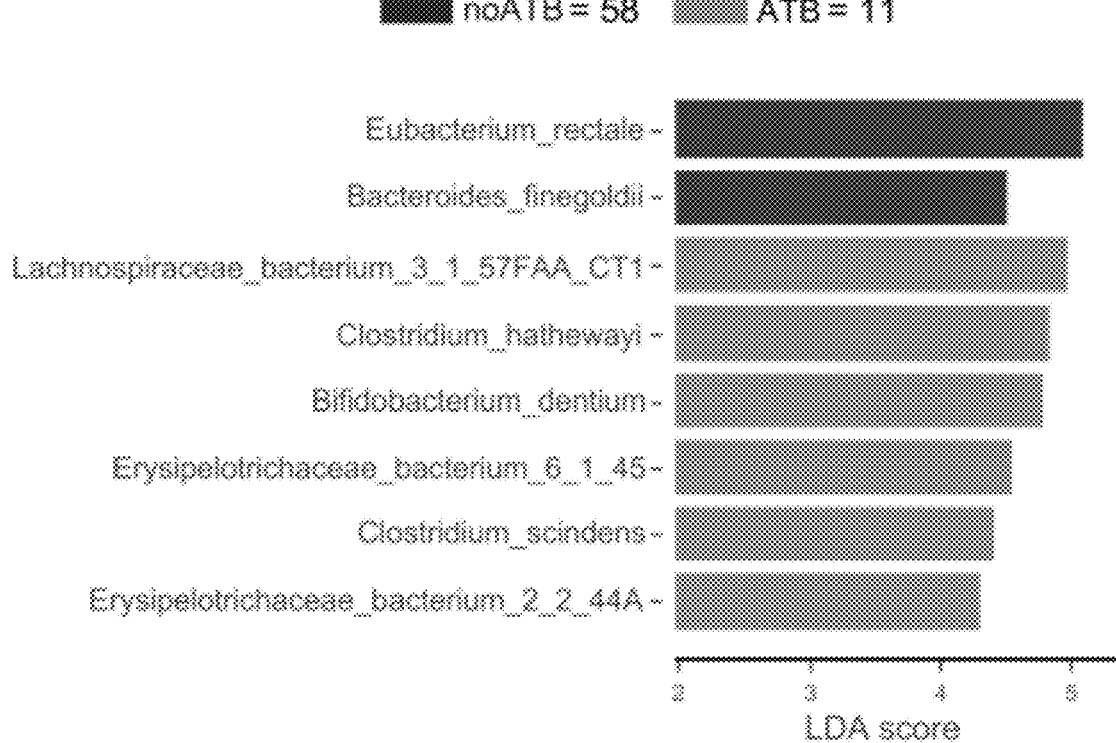

IMDC, International Metastatic Renal Cell Carcinoma Database Consortium (includes: Karnofsky performance status, time from diagnosis to treatment, hemoglobin, serum calcium concentration, neutrophil and platelet counts); ATB, Antibiotics; TKI, tyrosine kinase inhibitor; mTOR, mammalian target of rapamycin Tumor response was assessed using the Response Evaluation Criteria in Solid Tumors version 1.1 (RECIST v1.1) (Eisenhauer et al., 2009). Patients who received "ATB" (n=11, 16%) had a lower objective response rate (ORR, number of patients with a complete response and a partial response) compared to the noATB subgroup (9% versus 28%, p<0.03) (FIG. 1A-B) and lower PFS and OS (FIG. 8). Based on prior studies demonstrating a higher diversity of the gut microbiome in R melanoma patients to anti-PD-1 blockade (Gopalakrishnan et al., 2018) we first compared the median alpha diversity in noATB versus ATB, and observed no significant differences which was preserved across multiple diversity metrics (Shannon or observed OTUs or Simpson index, not shown). We then performed principal coordinate analyses (PCoA) for microbial beta diversity, which provides a measure of the overall relatedness (or lack thereof) between samples. Significant differences separated bacterial species from feces of ATB versus noATB individuals (ANOSIM=0.089; p<0.04) (FIG. 1C). Using linear discriminant analysis of effect size (LEfSe) (Segata et al., 2011), coupled to a pairwise comparison of relative taxonomic abundances (for species having a prevalence equal or greater than 20%) within each level using bootstrapping of two-tailed Mann-Whitney U tests (with 1000 permutations and correction for continuity and ties), we concluded that selected bacterial taxa were overrepresented in noATB stools such as *Eubacterium rectale* (p=0.02) while others were overrepresented in "ATB" fecal materials such as Erysipelotrichaceae bacterium_2_2_44A (p=0.02) and *Clostridium hathewayi* (p<0.02) (FIG. 1D). Altogether, we confirmed that ATB compromised the clinical efficacy of ICB in RCC patients and altered the taxonomic beta diversity and composition of intestinal microbiota.

Example 2: The Intestinal Microbiota Composition Predicts Clinical Outcome to ICB in the Cohort that Did not Take Antibiotics Given the confounding factor of ATB uptake on microbiota composition, we firstly considered only noATB patients (n=58). We started analyzing whether metagenomic profiles of baseline stools (T0-T4) could predict PFS (at 3, 6, 9, 12 months).

The taxonomical annotation of each MGS was performed based on gene homology to previously sequenced organisms (using blastN against the nt and whole genome sequencing (WGS, Meta-Hit) (Li et al., 2014) as well as the MetaPhLan database and pipeline (Segata et al., 2011)). The higher richness (alpha-diversity) of the samples evaluated both at the gene richness count (GC) or metagenomic species (MGS) levels correlated with the clinical response defined by the absence of PD at 12 months after initiation of ICB (FIG. 2A).

Figure 2C:
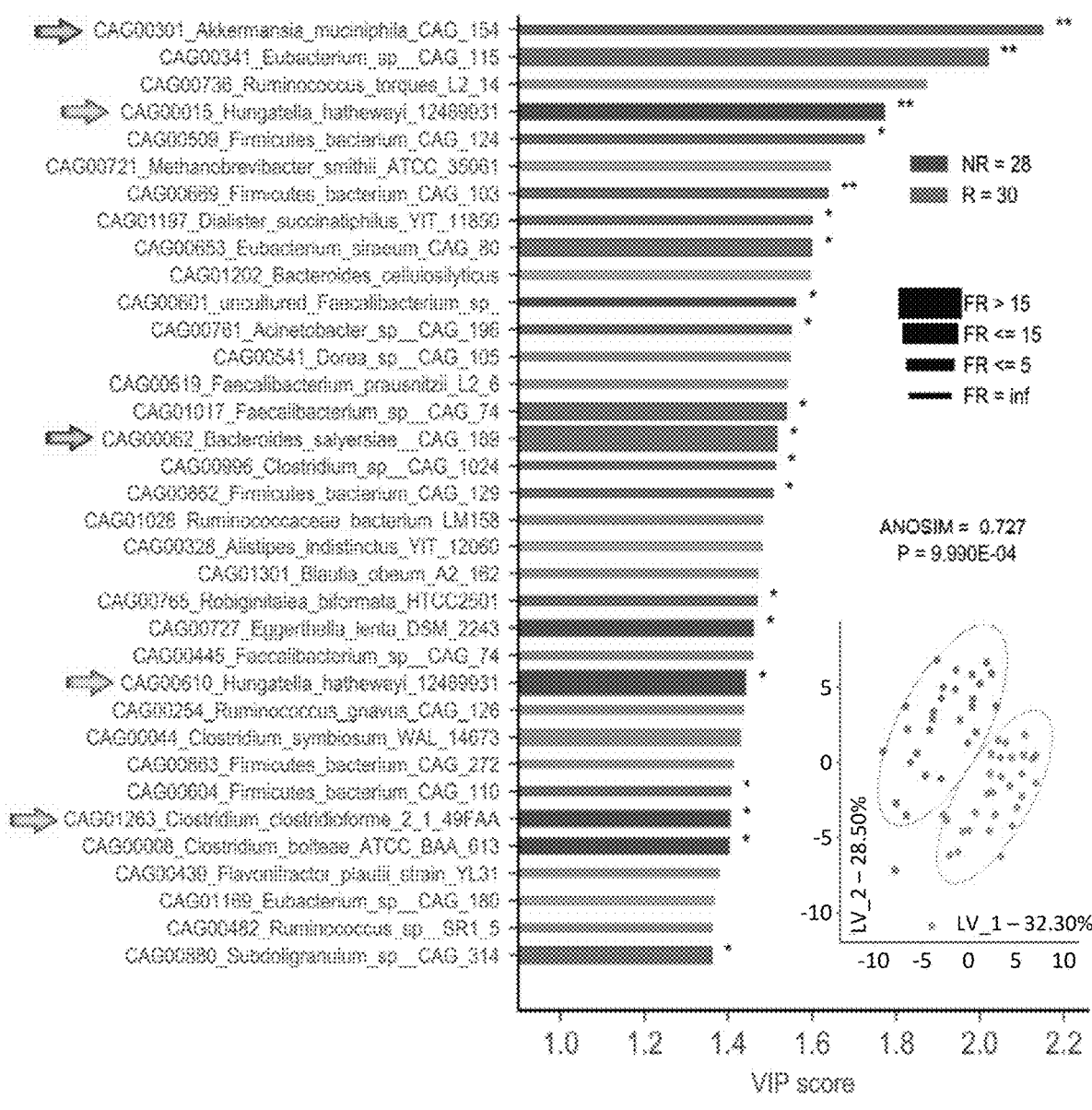
Figure 2D:
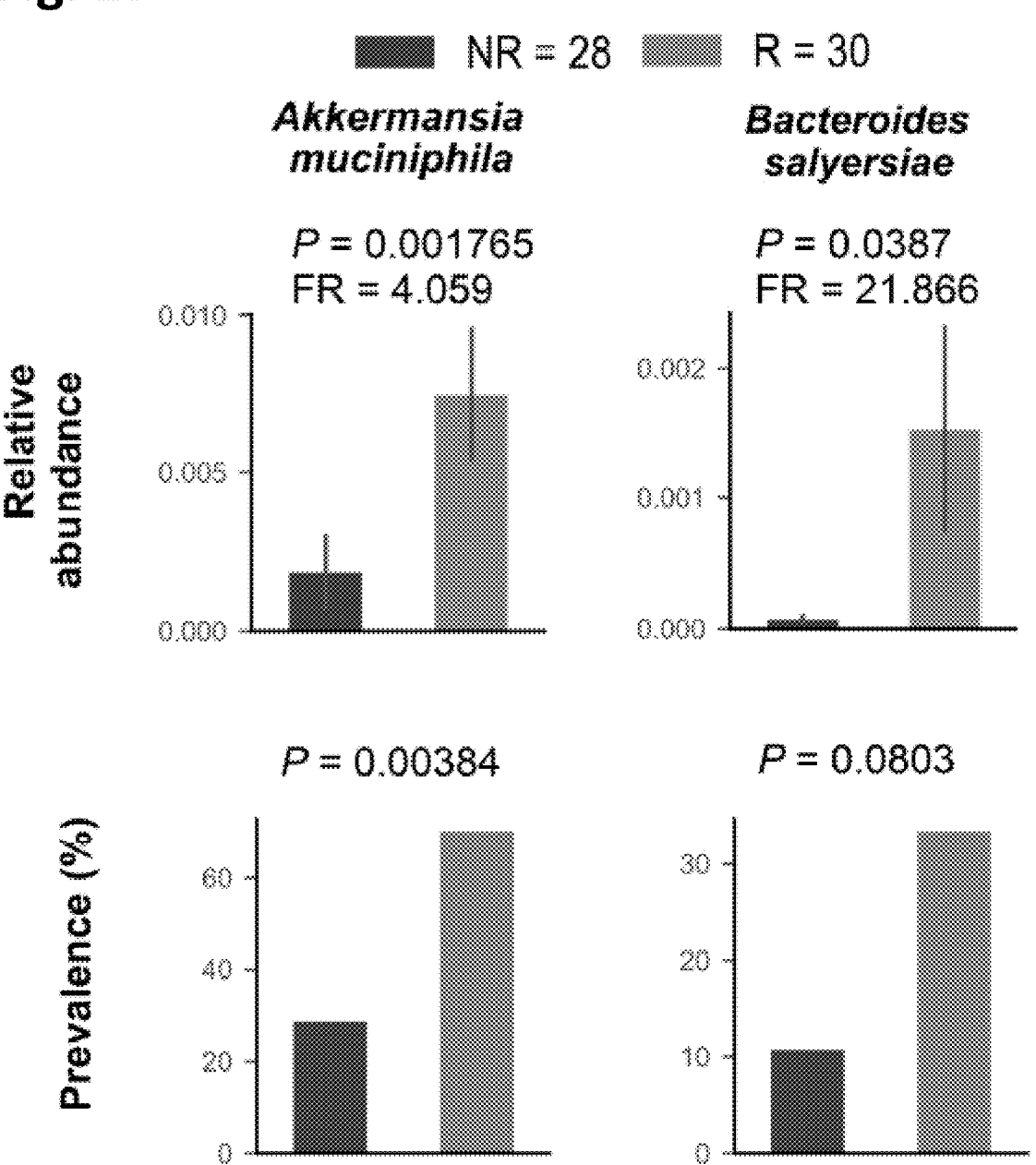

Then, we performed the PCoA (beta-diversity) using a threshold of bacteria prevalence>20%. When segregating patients into non-responders (NR) (i.e., progressive disease (PD) or stable disease (SD) for less than 6 months) and responders (R) to nivolumab according to the best overall response (BOR, the investigator-assessed best response: complete response, partial response, stable disease, or progressive disease), we observed a significant bacterial composition contrasting R versus NR (FIG. 2B), with an overrepresentation of distinct species including *Akkermansia muciniphila* (p<0.02), *Bacteroides salyersiae* (p=0.04), *Eubacterium siraeum* (p=0.01) and a trend towards *Clostridium ramosum* (ns) and *Alistipes senegalensis* (ns), in R, using both, the MetaPhlAn2 pipeline (FIG. 9) or using the MetaOMiner pipeline (FIG. 2C) and of Erysipelotrichaceae bacterium_2_2_44A (p<0.01) and *Clostridium hathewayi* (p<0.01) and *Clostridium clostridioforme* in NR (ANOSIM=0.727; p<0.0009, FIG. 2C) as observed in ATB (FIG. 1D). The prevalence and relative abundance of *A. muciniphila* and *B. salyersiae* were both higher in R versus NR in RCC patients' stools, using either one of these catalogs (FIG. 2D).

Considering higher GC and MGS counts at baseline in patients with PFS longer than 12 months and significant beta-diversity between R and NR (BOR) (FIG. 2A,C), we addressed whether paired metagenomic profiles could change over time under ICB therapy by performing a longitudinal analysis of stools (TO, T4, T8, T12) correlating with BOR or PFS at 12 months. When excluding ATB usage (n=58), MGS count was significantly higher in R compared to NR at T0 and T4 (FIG. 10A, left). At the same way, MGS count was significantly higher in patients with PFS longer than 12 months compared to those with PFS shorter than 12 months at T0 and T8 (FIG. 10B, left). Interestingly, we observed higher GC only in patients with PFS longer than 12 months compared to those with PFS shorter than 12 months at T0 and T8 (FIG. 10B, left).

Finally, to perform a robustness test across at least 3 clinical parameters (BOR (with SD>6 months and partial response), PFS3, PFS6, PFS9, PFS12)), we took into consideration all 69 individuals and we found 27 reliable MGS (out of 1347) contrasting R (n=21) and NR (n=6) (based on the cliff delta for each MGS recovered in >50% tests). Four among these selected MGS are in common with NSCLC microbiome profiles (listed in Table 5), especially encompassing *A. muciniphila* associated with favorable outcome during anti-PD-1 blockade. Of note, the robustness of MGS for the prediction was superior in the long-term clinical readouts (not shown).

TABLE 5

Bacteria species associated with resistance to therapy in renal cell carcinoma patients (RCC) and in non-small cell lung cancer patients (NSCLC).

| Non-Responders (NR) | | Responders (R) | |
|---|---|---|---|
| RCC | NSCLC | RCC | NSCLC |
| *Holdemanella biformis* | | unclassified *Lachnoclostridium* | *Akkermansia muciniphila* |
| *Clostridium* sp. | | *Bacteroides* sp. CAG:144 | *Eubacterium* sp. CAG:115 |
| *Prevotella timonensis* | | *Eubacterium* sp. CAG:115 | unclassified *Candidatus Gastranaerophilales* |
| *Clostridium bolteae* | | *Clostridiaceae bacterium* CIM:MAG 755/*Clostridium* sp. CAG:230 | *Phascolarctobacterium* sp. CAG:266 |
| *Hungatella effluvii* | | *Akkermansia muciniphila* | |
| *Eggerthella lenta* | | *Clostridium* sp. CAG:167 | |
| | | *Clostridium* sp. CAG:349 | |
| | | unclassified *Clostridiales* | |
| | | *Phascolarctobacterium* sp. CAG:266 | |
| | | *Bacteroides salyersiae* | |
| | | *Clostridium* sp. CAG:245 & CIM:MAG 941 | |

TABLE 5-continued

| Bacteria species associated with resistance to therapy in renal cell carcinoma patients (RCC) and in non-small cell lung cancer patients (NSCLC). | | | |
|---|---|---|---|
| Non-Responders (NR) | | Responders (R) | |
| RCC | NSCLC | RCC | NSCLC |
| | | unclassified *Clostridiales* | |
| | | unclassified *Clostridiales* | |
| | | unclassified *Clostridiales* | |
| | | unclassified *Candidatus Gastranaerophilales* | |
| | | *Ruminococcaceae bacterium* UBA6353 | |
| | | unclassified *Clostridia* | |
| | | unclassified *Firmicutes* | |
| | | unclassified *Ruminococcaceae* | |
| | | unclassified *Clostridiales* | |
| | | unclassified *Bacteroidales* | |

Summary of the contrasting species found in 100 robustness tests (100 Wilcoxon tests on 80% of the total RCC samples randomly sampled, N=55 samples for each test) and comparison with the contrasting species of the NSCLC cohort (Routy et al.). MGS are selected based on the contrasting tests (MGS need to be significantly contrasted for more than 50% of the robustness tests, N=98 MGS) and on the number of clinical parameter for which MGS is found contrasted (more than three clinical parameters over nine clinical parameters in total, N=27 MGS out of the 98). Among these species, 4 also show a signal in NSCLC cohort for at least one tested clinical parameter.

Altogether, we conclude that the alpha and beta diversity of stool composition could be considered to stratify the RCC patient's population in responder and non-responder and to predict patients with PFS longer than 12 months.

Example 3: RCC-Associated Gut Dysbiosis Fingerprint

Given the commonalities observed between MGS resulting from ATB-induced dysbiosis and species associated with primary resistance to immunotherapy, and in order to better appreciate the magnitude of intestinal "dysbiosis" in NR (as opposed to R), we analyzed MGS discriminating RCC cancer patients from control adults (HV, n=2994). Significant differences in stool composition were observed between RCC and HV (PCOA not shown, p<0.001; LEfSe FIG. 11). Hence, by merging only significant species in each intersection (ATB yes/no, RCC yes/no, NR yes/no), we only found two distinct species shared between the fecal repertoires of diseased groups (ATB yes, RCC yes, NR yes) i.e *C. hathewayi* and *C. clostridioforme*. Conversely, there were no common species shared between the opposite groups. Interestingly, *Alistipes senegalensis* and *C. ramosum* were the only 2 common spp. between R and noATB subgroups, while *Dorea longicatena*, *Dorea formicigenerans*, *Eubacterium rectale* and *Streptococcus salivarius* were all shared between HV and noATB cancer patients (Tables 6-7, FIG. 11).

TABLE 6

| Bacteria species associated with resistance to therapy and ATB in renal cell carcinoma patients. | | |
|---|---|---|
| | NR versus R (noATB) | ATB versus noATB |
| (NR > R) or (ATB > noATB) | *Anaerotruncus colihominis* | *Alistipes putredinis* |
| | *Bacteroides eggerthii* | *Bifidobacterium dentium* |
| | *Bacteroides stercoris* | *Blautia producta* |
| | *Barnesiella intestinihominis* | |
| | *Clostridiales bacterium_1_7_47FAA* | *Clostridiales bacterium_1_7_47FAA* |
| | *Clostridium boltae* | |
| | *Clostridium clostridioforme* | *Clostridium clostridioforme* |
| | *Clostridium hathewayi* | *Clostridium hathewayi* |
| | *Clostridium symbiosum* | *Clostridium nexile* |
| | *Coprobacter fastidiosus* | *Clostridium scindens* |
| | *Coprococcus catus* | *Coprobacillus* unclassified |
| | *Eggerthella lenta* | *Desulfovibrio piger* |
| | *Eggerthella* unclassified | *Erysipelotrichaceae bacterium_2_2_44A* |
| | *Erysipelotrichaceae bacterium_2_2_44A* | *Erysipelotrichaceae bacterium_21_3* |
| | *Erysipelotrichaceae bacterium_6_1_45* | *Erysipelotrichaceae bacterium_6_1_45* |
| | *Flavonifractor plautii* | *Faecalibacterium prausnitzii* |

TABLE 6-continued

Bacteria species associated with resistance to therapy and ATB in renal cell carcinoma patients.

|  | NR versus R (noATB) | ATB versus noATB |
|---|---|---|
| (R > NR) or (noATB > ATB) | Lachnospiraceae bacterium_1_4_56FAA | Lachnospiraceae bacterium_3_1_57FAA_CT1 |
|  | Lachnospiraceae bacterium_5_1_57FAA | Lachnospiraceae bacterium_5_1_57FAA |
|  | Oscillibacter unclassified |  |
|  | Ruminococcaceae bacterium D16 | Ruminococcus callidus |
|  | Ruminococcus gnavus | Ruminococcus gnavus |
|  | Veillonella parvula | Ruminococcus lactaris |
|  | Akkermansia muciniphila | Alistipes senegalensis |
|  | Alistipes senegalensis | Alistipes sp_AP11 |
|  | Bacteroidales bacterium_ph8 | Bacteroides finegoldii |
|  | Bacteroides cellulosilyticus | Bacteroides uniformis |
|  | Bacteroides nordii | Barnesiella intestinihominis |
|  | Bacteroides plebeius |  |
|  | Bacteroides salyersiae |  |
|  | Butyricimonas synergistica |  |
|  | Clostridium ramosum | Clostridiaceae bacterium_JC118 |
|  | Coprobacillus unclassified | Clostridium ramosum |
|  | Eubacterium siraeum | Dorea formicigenerans |
|  |  | Dorea longicatena |
|  |  | Escherichia unclassified |
|  |  | Eubacterium rectale |
|  | Granulicatella unclassified | Lachnospiraceae bacterium_1_4_56FAA |
|  | Methanobrevibacter smithii | Parabacteroides merdae |
|  |  | Roseburia inulinivorans |
|  |  | Streptococcus salivarius |
|  |  | Subdoligranulum unclassified |

Refers to discriminant species taken from PLS-DA variable importance plot (VIP) drawn to differentiate NR (non-responder) and R (responder) to nivolumab using RECIST1.1 best overall response in the RCC patient cohort. Bacterial species which are in common among NR and "ATB" or among R and "noATB" are in bold. Bacterial species which are in common among NR, RCC and ATB or among Control adults and noATB (data from Tables 4-7 and FIG. 9) are bold underlined.

TABLE 7

Bacteria species associated with resistance (NR > R or cancer > HV) or sensitivity (R > NR or HV > cancer) to therapy and cancer.

|  | NR versus R (noATB) | RCC cancer versus Control adults | |
|---|---|---|---|
| (NR>R) or (RCC > Controls) | Anaerotruncus colihominis | Acidaminococcus fermentans | Bacteroides dorei |
|  | Bacteroides eggerthii | Alistipes finegoldii | Bacteroides nordii |
|  | Bacteroides stercoris | Alistipes indistinctus | Bacteroides ovatus |
|  | Barnesiella intestinihominis | Alistipes onderdonkii | Bacteroides sp_1_1_6 |
|  |  | Alistipes putredinis | Bacteroides uniformis |
|  |  | Alistipes senegalensis | Bacteroides vulgatus |
|  |  | Alistipes_shahii |  |
|  |  | Alistipes unclassified | Barnesiella intestinihominis |
|  |  | Anaerotruncus colihominis | Bifidobacterium dentium |
|  |  | Bacteroidales bacterium_ph8 | Bilophila unclassified |
|  |  | Bacteroides caccae | Bilophila wadsworthia |
|  |  | Bacteroides cellulosilyticus | Butyrivibrio crossotus |
|  |  | Bacteroides clarus |  |
|  | Clostridiales bacterium_1_7_47FAA | Campylobacter curvus | Eikenella corrodens |
|  | Clostridium boltae | Citrobacter koseri | Enterobacter sp_MGH_8 |
|  | Clostridium clostridioforme | Clostridium asparagiforme | Enterobacteriaceae bacterium_9_2_54FAA |
|  | Clostridium hathewayi | Clostridium boltae | Escherichia coli |
|  | Clostridium symbiosum | Clostridium clostridioforme | Escherichia unclassified |
|  | Coprobacter fastidiosus | Clostridium hathewayi | Eubacterium eligens |
|  | Coprococcus catus | Clostridium symbiosum | Faecalibacterium prausnitzii |

TABLE 7-continued

Bacteria species associated with resistance (NR > R or cancer > HV)
or sensitivity (R > NR or HV > cancer) to therapy and cancer.

| | NR versus R (noATB) | RCC cancer versus Control adults | |
|---|---|---|---|
| | *Eggerthella lenta* | *Dialister succinatiphilus* | |
| | *Eggerthella* unclassified | *Desulfovibrio desulfuricans* | |
| | *Erysipelotrichaceae bacterium_2_2_44A* | | |
| | *Erysipelotrichaceae bacterium_6_1_45* | | |
| | *Flavonifractor plautii* | | |
| | *Lachnospiraceae bacterium_1_4_56FAA* | *Hafnia alvei* | *Parabacteroides distasonis* |
| | *Lachnospiraceae bacterium_5_1_57FAA* | *Holdemania* unclassified | *Parabacteroides goldstenii* |
| | *Oscillibacter* unclassified | *Lachnospiraceae bacterium_3_1_57FAA_CT1* | *Parabacteroides johnsonii* |
| | *Ruminococcaceae bacterium_D16* | *Lactobacillus gasseri* | *Parabacteroides merdae* |
| | *Ruminococcus gnavus* | *Lactobacillus phage_PL_1* | *Parabacteroides sp_20_3* |
| | *Veillonella parvula* | *Lactococcus phage_bIL67* | *Ruminococcaceae bacterium_D16* |
| | | *Lactococcus phage_ul36* | *Salmonella phage_SSU5* |
| | | *Leuconostoc phage_P793* | *Shigella phage_Sf6* |
| | | *Mulikevirus* unclassified | *Streptococcus parasanguinis* |
| | | *Odoribacter splanchnicus* | *Subdoligranulum* unclassified |
| | | *Olsenella profusa* | *Yersinia* unclassified |
| | | ***Oscillibacter*unclassified** | |
| (R>NR) or (Controls > RCC) | *Akkermansia muciniphila* | *Anaerococcus obesiensis* | *Bifidobacterium catenulatum* |
| | *Alistipes senegalensis* | *Bifidobacterium adolescentis* | *Bifidobacterium longum* |
| | *Bacteroidales bacterium_ph8* | *Bifidobacterium angulatum* | *Bifidobacterium pseudocatenulatum* |
| | *Bacteroides cellulosilyticus* | *Bifidobacterium bifidum* | |
| | *Bacteroides nordii* | | |
| | *Bacteroides plebeius* | | |
| | *Bacteroides salyersiae* | | |
| | *Butyricimonas synergistica* | | |
| | *Clostridium ramosum* | *Catenibacterium mitsuokai* | *Enterococcus faecalis* |
| | *Coprobacillus* unclassified | *Clostridium sp_L2_50* | *Enterococcus faecium* |
| | *Eubacterium siraeum* | *Collinsella aerofaciens* | *Eubacterium biforme* |
| | | *Coprococcus catus* | *Eubacterium hallii* |
| | | *Coprococcus comes* | *Eubacterium ramulus* |
| | | *Coprocacus eutactus* | *Eubacterium rectale* |
| | | *Dorea formicigenerans* *Dorea longicatena* | *Finegoldia magna* |
| | *Granulicatella* unclassified | *Gardnerella vaginalis* | *Ruminococcus champanellensis* |
| | *Methanobrevibacter smithii* | *Lactobacillus ruminis* | *Ruminococcus torques* |
| | | *Megamonas* unclassified | *Ruminococus sp_5_1_39BFAA* |
| | | *Megasphaera* unclassified | *Streptococcus infantarius* |
| | | *Mitsuokella* unclassified | *Streptococcus salivarius* |
| | | *Oscillibacter sp_KLE_1745* | *Streptococcus termophilus* |
| | | *Prevotella copri* | *Treponema succinifaciens* |
| | | *Prevotella stercorea* | |

Refers to discriminant species taken from PLS-DA variable importance plot (VIP) drawn to differentiate between NR (non-responder) and R (responder) (RCC patient cohort, best overall response) and between RCC and control adults (>2500 control adults acquired from publicly available repositories and spanning multiple countries and lifestyles, enlarged by 54 Italian samples newly acquired). Bacterial species which are in common among NR and RCC or R and control adults are in bold. Bacterial species which are in common among NR, RCC and ATB or Control adults and noATB (data from Tables 4-5-6-7 and FIG. 9) are bold underlined.

Example 4: Prior Tyrosine Kinase Inhibitors (TKI) and ATB Use are Associated with Distinct Gut Microbiota 'Guilds' in RCC Patients The majority of RCC patients (n=55, 80%) received two previous lines of treatment for their advanced RCC before starting nivolumab (Table 4). Sunitinib (n=49, 71%) or axitinib (n=13, 19%) were the most frequent previous TKI. Co-occurrence network analysis revealed six 'species interaction groups' referred as 'SIG'(Zhao et al., 2018), highlighting that i) ATB and axitinib were the most powerful medications shifting fecal microbiota (using cross-validation model, predictive power for ATB=84%; for axitinib=81%; for sunitinib=69%); ii) defined bacterial species drove the stratification of the whole RCC network into 'SIG', such as *A. muciniphila* for R and *Dorea formicigenerans* for noATB (random forest analysis) (FIG. 12).

Altogether, the stool composition of RCC patients is influenced by ATB and axitinib and distinct species, missing during cancer development or ATB uptake, appear associated with BOR and PFS during anti-PD-1 blockade ("immunostimulatory" *D. longicatena*) while others, specifically selected following ATB administration and the cancer status (*C. hathewayi*), may confer primary resistance to this therapy and will be referred to as "immunotolerant" henceforth.

Figure 3B:
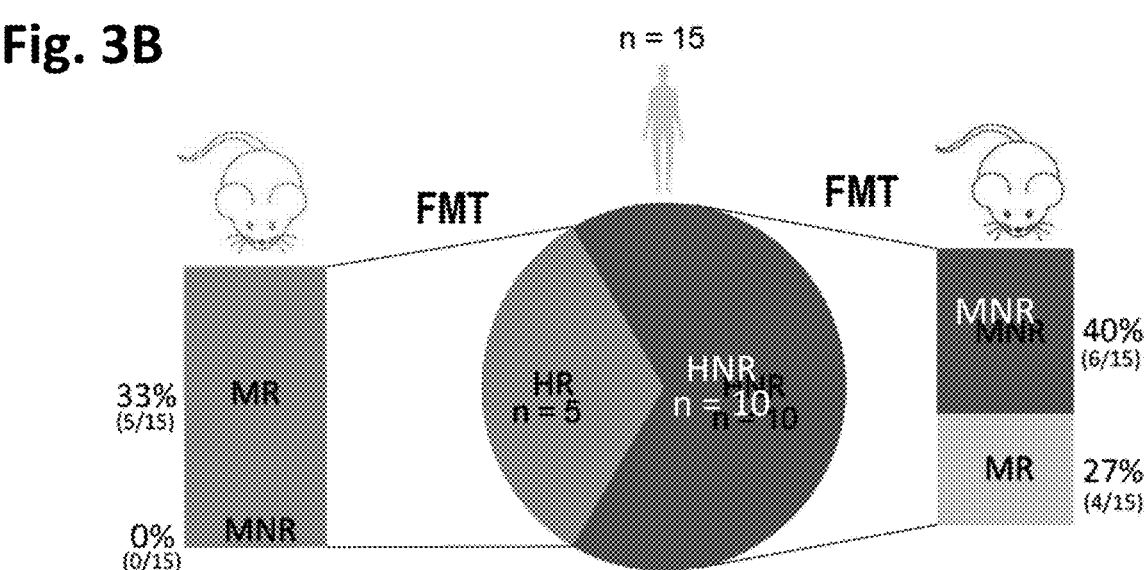
Figure 3C:
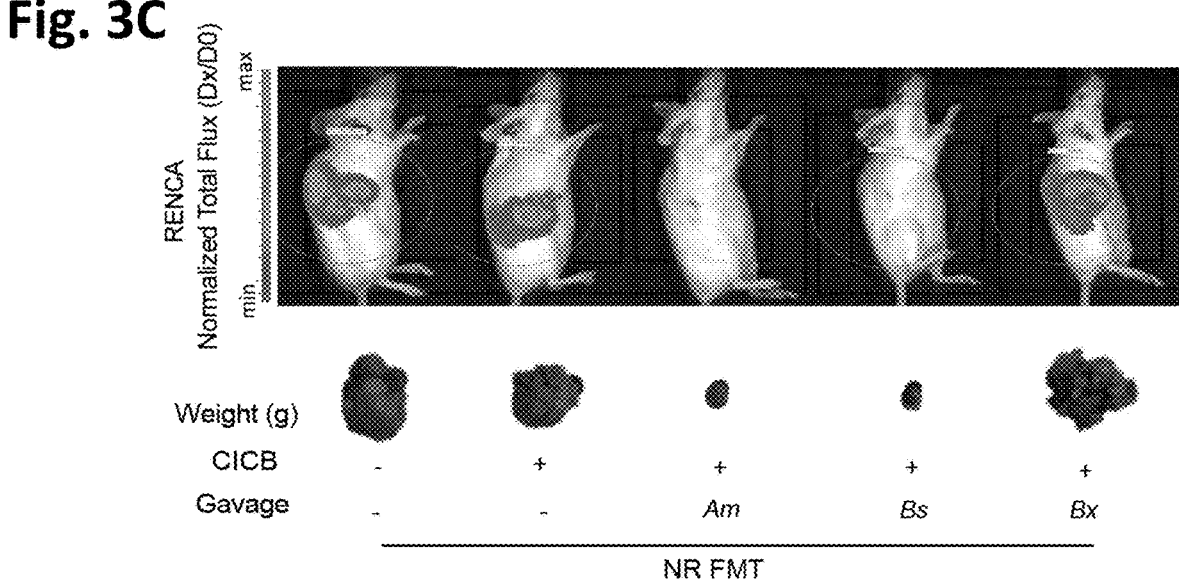
Figure 3D:
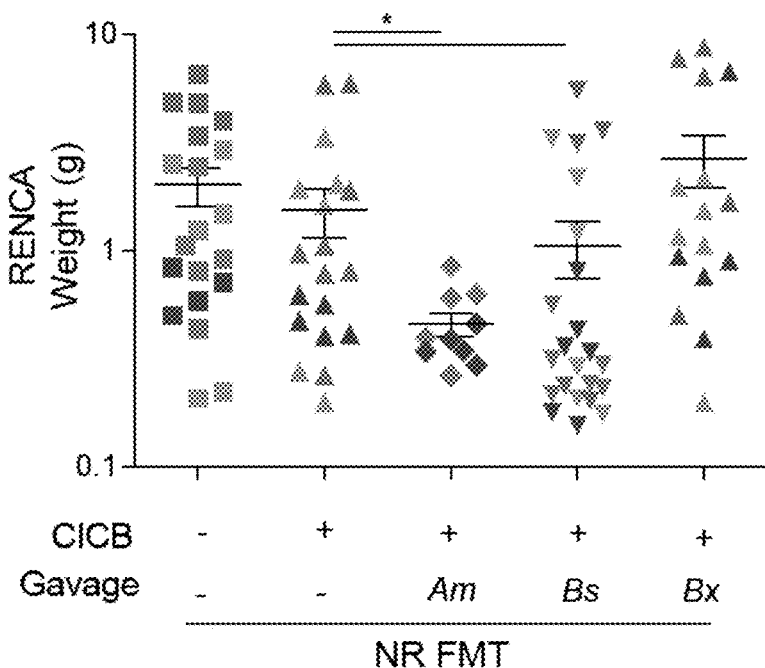
Figure 3E:
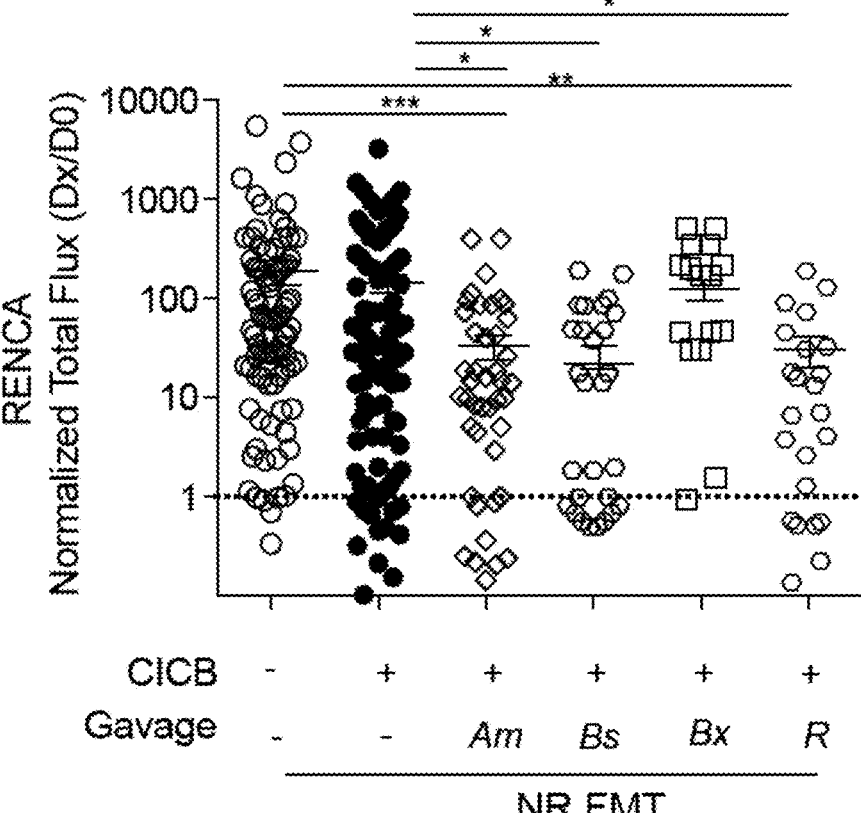

Example 5: Oral Gavage with Immunostimulatory or Beneficial Commensals or Feces from Responding RCC Patients Rescues Primary Resistance in RCC Tumor Bearing Mice To further provide evidence of a cause-effect relationship between bacterial fecal composition and therapy outcome, we humanized BALB/c mice sterilized by ATB with RCC patient stools, 15 days prior to orthotopic inoculation of luciferase engineered-RENCA (FIG. 3A). Transfer of 15 FMT (5R and 10NR) patient stools by oral gavage (referred to as "FMT" henceforth) in ATB-treated avatar mice that were subsequently implanted with RENCA induced significant responses (for FMT R) or resistance (for FMT NR) to CICB. It should be noted that we observed only 27% of exceptions of concordance between patient's response and mouse recipient's response to ICB: only 4 stools above 15 FMT used (Table 8, FIG. 3A-B). However, compensation of NR-FMT (that did not contain *A. muciniphila* or *B. salyersiae*) with oral administration of immunostimulatory *A. muciniphila* or *B. salyersiae* or R-FMT prior to each CICB cycle restored sensitivity to therapy, as evidenced by kidney weight at sacrifice (FIG. 3D) and decreased luminescence (FIG. 3E)). Despite strong co-occurrence of *B. salyersiae* with other commensal species (FIG. 13A-B) varying in their identity in the R versus NR networks, the antitumor efficacy of the former bacterium was not boosted by coadministration of a neighboring species (FIG. 13C).

In conclusion, bacteria contrasting R and NR in our 69 RCC cohort compensate the lack of responsiveness observed with NR-FMT in avatar mice, establishing cause-effect relationship between favorable bacterial composition of feces and clinical outcome.

TABLE 8

Patient stools mostly retain best overall response (BOR) in mice host after FMT.

| Patients | | Mice | | |
|---|---|---|---|---|
| FMT | BOR | Outcome | FR (CICB/Ctrl) | log2FR |
| 1 | NR | R | 0.1216396 | −30 393 151 |
| 2 | R | R | 0.3652943 | −14 528 689 |
| 3 | NR | NR | 11 980 702 | 0.2607124 |
| 4 | NR | NR | 12 889 166 | 0.3661589 |
| 5 | NR | NR | 11 106 782 | 0.1514409 |
| 6 | NR | R | 0.4636201 | −11 089 851 |
| 7 | R | R | 0.3586016 | −14 795 461 |
| 8 | R | R | 0.2497193 | −20 016 208 |
| 9 | R | R | 0.3898888 | −13 588 655 |
| 10 | R | R | 0.4224561 | −12 431 266 |
| 11 | NR | R | 0.1845931 | −24 375 793 |
| 12 | NR | NR | 54 836 224 | 24 551 292 |
| 13 | NR | NR | 14 994 432 | 0.5844269 |

TABLE 8-continued

Patient stools mostly retain best overall response (BOR) in mice host after FMT.

| Patients | | Mice | | |
|---|---|---|---|---|
| FMT | BOR | Outcome | FR (CICB/Ctrl) | log2FR |
| 14 | NR | NR | 10 287 575 | 0.040903 |
| 15 | NR | R | 0.6221715 | −0.6846157 |

SPF BALB/c mice were gavaged with fecal material (FMT) from 15 patients: 5 responders (R) and 10 non-responders (NR) patient donors (RCC patient cohort, best overall response). We calculated fold ratio (FR) of total flux 015/DO among mice treated with anti-PD1 plus anti-CTLA-4 (CICB) and control (Ctrl). Underlined the discrepancies between human outcome and mice outcome.

Figures 4A, 4B:
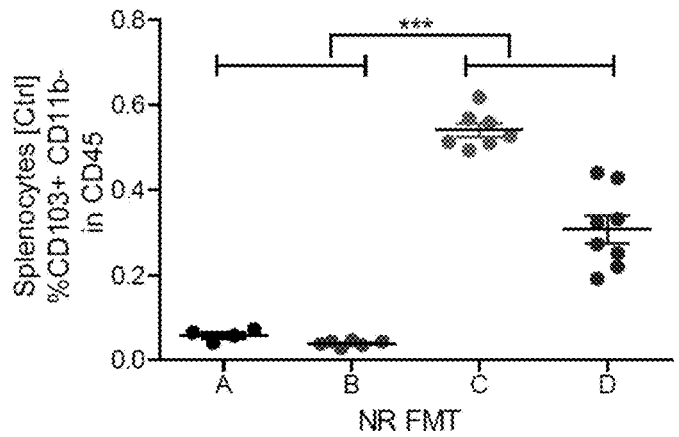
Figures 4C, 4D:
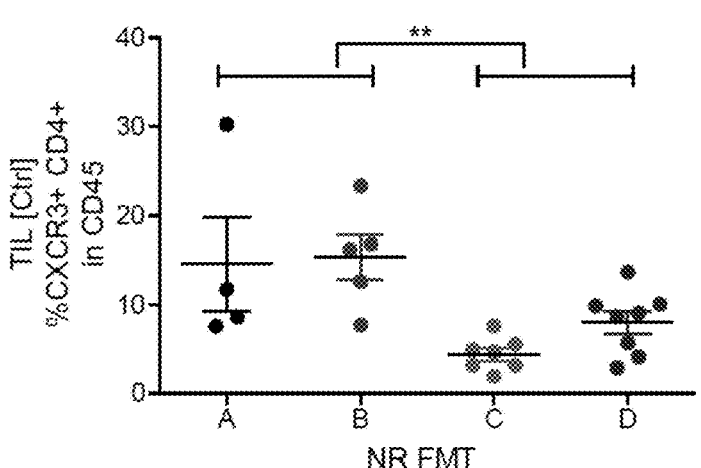
Figures 5A, 5B:
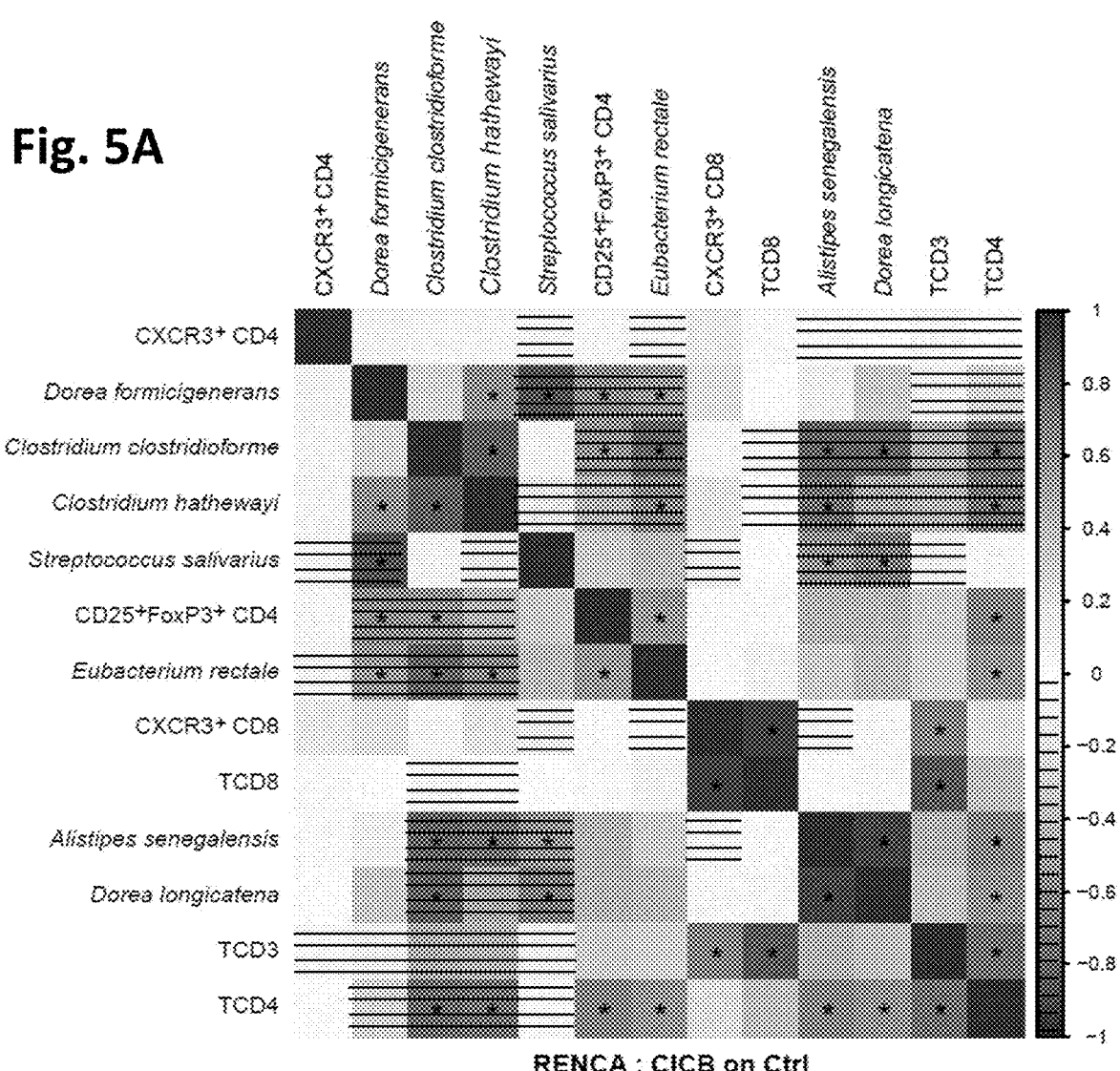

Example 6: The Gut Microbiota Controls the Cancer-Immune Set Point in RCC Tumor Bearing Mice To analyze how NR FMT could influence the systemic (spleen) and tumor (RENCA) immune tonus or contexture, we performed multicolor flow cytometric analyses of splenocytes 48 h after the second cycle of CICB in five NR FMT (from independent donors). Indeed, we observed major differences in the relative capacity of each FMT to influence the splenic residence of CD103$^+$XCR1$^+$ cross-presenting DC and effector IFNγ-producing CD4$^+$ and CD8$^+$ Th1 or Tc1 lymphocytes, according to patient's stool composition (FIG. 4A-B). Indeed, donor stools containing immunotolerant spp. (Clostridia) clustered with CD103+DC and anticorrelated with those containing immunostimulatory spp. (*A. senegalensis* and *D. longicatena*) inducing Ly6C$^{high}$ myeloid cells and CD4+ T cells. Moreover, homeostatic bacteria (*D. formicigenerans*) enriched feces resulted in the accumulation of splenic Th1 cells and Ly6C$^{low}$ macrophages, in contrast to stools containing *E. rectale* and *S. salivarius* clustering with high abundancy of Tc1 and CD103+CD11b+DC (FIG. 4A, FIG. 14A). Similar influences were observed in the TME (FIG. 4C-D, FIG. 14B), stools containing immunostimulatory spp. (*A. senegalensis* and *D. longicatena*) inducing Th1 tumor infiltrating lymphocytes (TIL), a phenomenon anti-correlated with the fecal presence of immunotolerant Clostridia spp. or *S. salivarius* in the donor material (FIG. 4F-G-B-C). During CICB therapy, the induction of tumor immunosurveillance based on CD3+ and CD4+ accumulation in TIL was blunted after transfer of stools containing Clostridia spp. while presence of *A. senegalensis* and *D. longicatena* clustered together and were associated with increased CD3+, CD4+, CD8+ and Tc1 TIL accumulation (FIG. 5A-B). This tumor contexture mirrored the strong association between stool immunostimulatory bacteria and Th1/Tc1 systemic immunity in contrast to immunotolerant commensals that favored the overrepresentation of myeloid cells (FIG. 14).

Figures 5C, 5D:
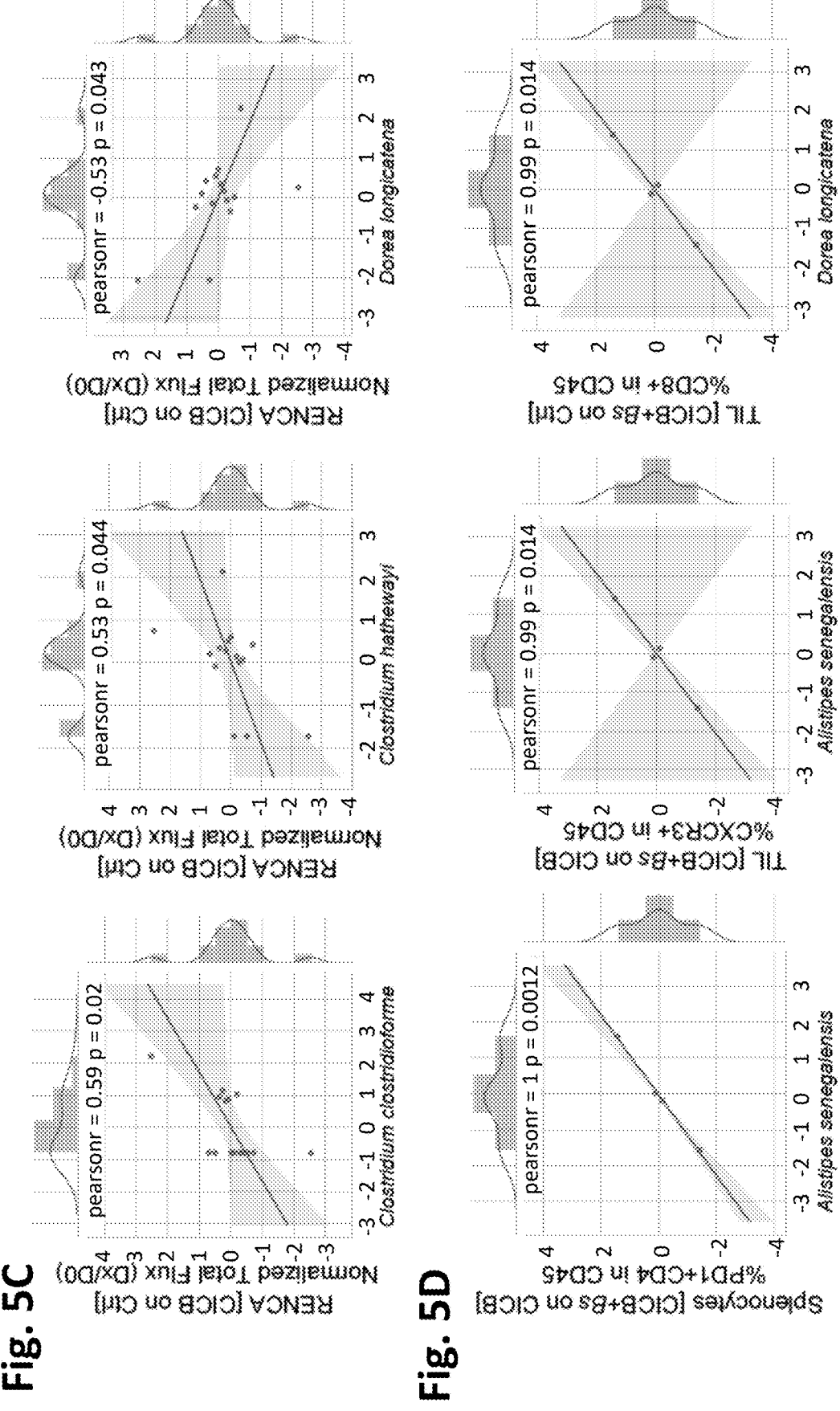

To illustrate the pathophysiological relevance of the NR FMT RENCA avatar model system, we show first that the CICB/Ctrl ratio of the bioluminescence flux in the retroperitoneum of avatar mice was significantly proportional to the relative abundance of the immunotolerant versus immunostimulatory commensals; correlated and anticorrelated with *C. hathewayi* or *C. clostridioforme* versus *D. longicatena* respectively (FIG. 5C). Secondly, oral gavage with *B. salyersiae* to compensate for FMT NR-mediated immunomodulation culminated in induction of splenic CD4+PD1+ T cells and Tc1 TIL proportional to the relative abundance of *A. senegalensis* in donor stools while CD8+ TIL were correlated with the relative abundance of *D. longicatena* (FIG. 5D). Finally, Kaplan Meier survival curves illustrated the clinical relevance of some of these commensals for PFS during anti-PD-1 blockade, namely *D. longicatena* associated with longer PFS, and presence of *C. hathewayi* or absence of both *A. muciniphila*+*B. salyersiae* for shorter PFS (FIG. 5E).

Altogether, we infer from these findings that the relative abundance of immuno-stimulatory versus -tolerant commensals will govern the cancer-immune set point of tumor bearers, paving the way to CICB-induced tumor control.

Example 7: Antiangiogenic Tyrosine Kinase Inhibitors (TKI) Induce an Immuno-Stimulatory Intestinal Microbiome Shift Data from the co-occurrence network analysis revealed six species interaction groups called 'SIG' (FIG. 12). Interestingly, axitinib (like ATB) appeared to markedly influence SIG distribution within network topology (RF importance), more specifically SIG2, centered by *Odoribacter splanchnicus*, belonging to the same community as *Dorea longicatena* (FIG. 12). To assess the distinct bacteria related to TKI, we compared a subgroup of patient who taken TKI in 1 L (within our 69 RCC patients' stools, regardless of ATB) with HV. An overrepresentation of *A. senegalensis* and *A. muciniphila* induced by TKI (LEfSe, FIG. 6A) was observed in these patients. LEfSe performed to assess distinct species associated with TKI versus mTOR inhibitors taken as 2L therapy in subgroup analysis within our 69 RCC patients' stools (regardless of ATB) revealed significant beta diversities contrasting these 2 subgroups for fecal composition and a trend for an overrepresentation of *A. senegalensis* induced by TKI (not shown). Since we enrolled patients after failure of 1L (or more) TKI, feces collection preceding introduction of TKI were not available to uncouple the effects of tumor progression from that of TKI on the microbiome shift. To circumvent this limitation, we administered in two mouse genetic backgrounds a tumoricidal antiangiogenic dose of various TKI (sunitinib, axitinib, or cabozantinib) over 3 weeks and collected longitudinally stools. Strikingly, all three TKI markedly induced significant changes in the alpha and beta diversity of the microflora over time, in both BALB/c (FIG. 6B) and C57BL/6 mice with a common dominant deviation of the microbiota composition (FIG. 15). In BALB/c intestines, there was a prototypic TKI signature, with an over representation of *Eubacterium coprostanoligenes, Vampirovibrio chlorellavorus, Longibaculum muris, Parabacteroides goldsteinii, Alistipes timonensis, Faecalicatena contorta*, with a relative lower dominance of *Neglecta timonensis, Adlercreutzia equolifaciens*, and *Bacteroides fragilis* at 15 days of all three TKI uptake (mean VIP score). Importantly, sunitinib and cabozantinib favored a higher abundance of immunostimulatory *Alistipes senegalensis* as observed in humans (FIG. 6A-B). Accordingly, in C57BL/6 intestines, there was an over representation of the immunostimulatory *E. siraeum*, among other species shared by all three TKI (FIG. 15). Importantly, TKI favored a higher abundance of immunostimulatory *A. senegalensis* and *A. muciniphila* (FIG. 6B), especially for cabozantinib. Overall, TKI induced a significant and prototypic microbiota shift including immunostimulatory commensals (such as *E. siraeum, A. senegalensis, A. muciniphila*) that could be harnessed to improve the efficacy of ICB in RCC patients.

In patients, axitinib and sunitinib-induced microbiome shifts could be contrasted, with axitinib favoring the immunogenic *A. senegalensis* and *C. ramosum*. (FIG. 7A). Therefore, to circumvent resistance to ICB in RENCA (Routy et al., 2018), we undertook experiments using axitinib alone or in combination with *A. muciniphila*. Indeed, we observed a markedly increased efficacy combining axitinib with ICB and *A. muciniphila* in tumor bearers with or without FMT NR (FIG. 7B-C).

Overall, TKI induced a significant and prototypic microbiome shift including immunostimulatory commensals that could be harnessed to improve the efficacy of ICB in RCC patients.

DISCUSSION

RCC encompasses a wide spectrum of morphologically and molecularly distinct cancer subtypes. The introduction of targeted therapies (inhibiting VEGF, PFGF, MET, AXL tyrosine kinases) and immune checkpoint inhibitors into clinical practice has markedly improved the median overall survival (OS) in clear cell RCC patients, the most common subtype. With 12 approved drugs acting through 6 different effective mechanisms, novel biomarkers are needed to stratify and simplify this therapeutic landscape, to improve efficacy and reduce side effects. Based on pan-omics approaches integrating genetics, transcriptomics and immunoscoring, molecular stratifications of RCC identified subgroups of patients with dismal prognosis that may benefit more specifically from antiangiogenic or immunotherapies (Casuscelli et al., 2017). However, it appears that some tumors are a desert of immune reactivities while others are invaded with overt inflammatory and/or exhausted cell infiltrates that do not convey long term protection, suggesting that the immune tonus of RCC patients is not properly triggered or controlled.

Our study highlights the potential of harnessing the intestinal microbiome to better control the "cancer-immune set point" (Chen and Mellman, 2017), i.e., the threshold beyond which ICB triggers a clinical benefit. Mapping the gut holobiont to identify a minimalist ecosystem governing the cancer-immune set point and more specifically immunogenic versus tolerogenic commensals and medications tilting their balance remains an open conundrum. By applying various bioinformatic and clinical subgroup analyses (LEfSe, PLS-DA VIP, networks), we identified a limited set of species (phylum Firmicutes, family Clostridiaceae, species *C. clostridioforme, C. hathewayi*) that were associated with primary resistance and enriched by ATB use and metastatic cancer status.

The "*C. clostridioforme* group" comprises three principal species that differ in virulence and antimicrobial susceptibility despite similar colony and microscopic morphology. *C. bolteae* and *C. clostridioforme* are observed with approximately equal frequency, but *C. hathewayi* is seen with much greater frequency (Dababneh et al., 2014; Finegold et al., 2005). Infections with the "*C. clostridioforme* group" are the second most frequently isolated species of *Clostridium*, after *Clostridium perfringens* (Dababneh et al., 2014; Finegold et al., 2005). *C. hathewayi* has been reported to be part of the pathobionts associated with the diagnosis of colon cancers (Liang et al., 2017) and could mitigate antigen-specific T cell responses in mice (Rossi et al., 2016).

Conversely, we identified some commensals associated with favorable prognosis and the intestinal homeostatic status, which belong to Eubacteriaceae (*E. rectale, E. siraeum*), Lachnospiraceae (*Dorea longicatena*), Verrucomicrobioaceae (*A. muciniphila*) families and to the Bacteroidales order (Rikenellaceae family/*Alistipes/Alistipes senegalensis*, Bacteroidaceae family/*Bacteroides/Bacteroides salyersiae*). While *A. senegalensis* and *A. muciniphila* alone or together within minimalist communities were clearly associated with the elicitation of adaptive immune responses beneficial against murine cancers (Routy et al., 2018; Tanoue et al., 2019), Eubacteriaceae and *Dorea longicatena* have been described as pivotal to keep in check the homeostasis of the intestinal barrier (Kamo et al., 2017).

Experiments initially conducted in mice showed that broad-spectrum ATB blunt the activity of ICB against a wide range of transplantable and orthotopic tumors, suggesting that a minimalist intestinal ecosystem is required for the function of the mammalian host immune system. These pioneering observations in preclinical models encouraged retrospective analyses in cancer patients to determine if premedication with ATB would influence the clinical response to ICB. In the literature, 11 retrospective analyses assessed the impact of ATB taken shortly before or after the initiation of ICB on clinical outcome of patients treated with ICB in several malignancies. Eleven out of the 12 analyses reported a negative impact of ATB uptake in PFS and/or OS, mirroring the murine data (Derosa et al., 2018; Elkrief et al., 2019; Routy et al., 2018). However, the impact of these puzzling findings on the clinical management of cancer patients remains controversial. Here, we describe how ATB (mostly betalactams and quinolones) affect the intestinal composition of feces of 69 RCC patients. ATB markedly affected the beta diversity, leading to the underrepresentation of Eubacteriaceae family members as already described (Raymond et al., 2016) (such as *Eubacterium rectale*) for the benefit of pathobiont species (Erysipelotrichaceae bacterium_2_2_44A and *Clostridium hathewayi*). This microbiome shift is associated with reduced ORR during ICB therapy (73% of primary resistance in ATB versus 33% in the no ATB subgroups, p<0.03).

Given the incidence of gastrointestinal toxicity associated with TKI, pioneering studies investigated TKI-induced dysbiosis and the impact of ATB on diarrhea and survival. Pal et al. evaluated a population of 20 RCC patients receiving VEGF-TKI and reported a positive and negative association between *Bacteroides* spp. and *Prevotella* spp. and diarrhea, respectively (Pal et al., 2015). When comparing their TKI-RCC stool data with those from HV, they observed a relative loss of *Bifidobacterium* spp. Accordingly, Gong et al. followed up 5 RCC patients treated with TKI and showed that *Bacteroides, Barnesiella and Phascolarctobacterium* were elevated in responders while *Bifidobacterium* were elevated in non-responders (Gong et al., 2019). However, in parallel, Hahn et al. showed that ATB targeting stool *Bacteroides* spp. improved PFS in patients receiving 1 L VEGF-TKI in a duration-dependent manner (Hahn et al., 2018). Our data fuel this hypothesis of an unconventional mode of action of VEGF-TKI whereby a treatment-induced prototypic gut microbiome fingerprint might influence therapeutic outcome. We observed a relative loss of *Bifidobacterium* and overrepresentation of distinct species of the Bacteroidales order (*A. timonensis, P. goldsteinii*) post-TKI in naive mice and showed that axitinib could compensate NR FMT induced dysbiosis and reduced responsiveness to ICB, in a microbiota-dependent manner.

Limitations of our study include that this conclusion relies on a single cohort of 69 RCC patients including only 11 cases who took ATB and in 2L therapy with the interference of many confounding factors (prior therapies, comedications, and other factors such as hemoglobin (Maier et al., 2018; Pasolli et al., 2019)). Prospective studies in 1 L therapy should validate this fingerprint as a new predictor of primary resistance to ICB.

REFERENCES

Albiges L, Negrier S, Dalban C, Gravis G, Chevreau C, Oudard S, et al. Safety and efficacy of nivolumab in metastatic renal cell carcinoma (mRCC): Results from the NIVOREN GETUG-AFU 26 study. J Clin Oncol 2018; 36:577-577. doi:10.1200/JCO.2018.36.6_suppl.577.

Angelakis E, Bachar D, Henrissat B, Armougom F, Audoly G, Lagier J C, Robert C, Raoult D (2016) Glycans affect DNA extraction and induce substantial differences in gut metagenomic studies.—Sci Rep. May 18; 6:26276

Ascierto, M. L., McMiller, T. L., Berger, A. E., Danilova, L., Anders, R. A., Netto, G. J., Xu, H., Pritchard, T. S., Fan, J., Cheadle, C., et al. (2016). The Intratumoral Balance between Metabolic and Immunologic Gene Expression Is Associated with Anti-PD-1 Response in Patients with Renal Cell Carcinoma. Cancer Immunol. Res.

Becht, E., Giraldo, N. A., Beuselinck, B., Job, S., Marisa, L., Vano, Y., Oudard, S., Zucman-Rossi, J., Laurent-Puig, P., Sautès-Fridman, C., et al. (2015). Prognostic and theranostic impact of molecular subtypes and immune classifications in renal cell cancer (RCC) and colorectal cancer (CRC). Oncoimmunology 4, e1049804.

Becht, E., Giraldo, N. A., Lacroix, L., Buttard, B., Elarouci, N., Petitprez, F., Selves, J., Laurent-Puig, P., Sautès-Fridman, C., Fridman, W. H., et al. (2016). Estimating the population abundance of tissue-infiltrating immune and stromal cell populations using gene expression. Genome Biol. 17, 218.

Berry D, Widder S. Deciphering microbial interactions and detecting keystone species with co-occurrence networks. Front Microbiol 2014; 5:219. doi:10.3389/fmicb.2014.00219.

Beuselinck, B., Job, S., Becht, E., Karadimou, A., Verkarre, V., Couchy, G., Giraldo, N., Rioux-Leclercq, N., Molinie, V., Sibony, M., et al. (2015). Molecular subtypes of clear cell renal cell carcinoma are associated with sunitinib response in the metastatic setting. Clin. Cancer Res. Off. J. Am. Assoc. Cancer Res. 21, 1329-1339.

Blondel V D, Guillaume J-L, Lambiotte R, Lefebvre E. Fast unfolding of communities in large networks. J Stat Mech Theory Exp 2008; 2008:P10008. doi:10.1088/1742-5468/2008/10/P10008.

Casuscelli, J., Vano, Y.-A., Fridman, W. H., and Hsieh, J. J. (2017). Molecular Classification of Renal Cell Carcinoma and Its Implication in Future Clinical Practice. Kidney Cancer 1, 3-13.

Chen, D. S., and Mellman, I. (2017). Elements of cancer immunity and the cancer-immune set point. Nature 541, 321-330.

Chevrier, S., Levine, J. H., Zanotelli, V. R. T., Silina, K., Schulz, D., Bacac, M., Ries, C. H., Ailles, L., Jewett, M. A. S., Moch, H., et al. (2017). An Immune Atlas of Clear Cell Renal Cell Carcinoma. Cell 169, 736-749.e18.

Criscuolo A, Brisse S. AlienTrimmer: a tool to quickly and accurately trim off multiple short contaminant sequences from high-throughput sequencing reads. Genomics 2013; 102:500-6. doi:10.1016/j.ygeno.2013.07.011.

Cotillard A, Kennedy S P, Kong L C, Prifti E, Pons N, Le Chatelier E, et al. Dietary intervention impact on gut microbial gene richness. Nature 2013; 500:585-8. doi: 10.1038/nature12480.

Dababneh, A. S., Nagpal, A., Palraj, B. R. V., and Sohail, M. R. (2014). *Clostridium hathewayi* bacteraemia and surgical site infection after uterine myomectomy. BMJ Case Rep. 2014.

Daillère, R., Vetizou, M., Waldschmitt, N., Yamazaki, T., Isnard, C., Poirier-Colame, V., Duong, C. P. M., Flament, C., Lepage, P., *Roberti*, M. P., et al. (2016). *Enterococcus hirae* and *Barnesiella intestinihominis* Facilitate Cyclophosphamide-Induced Therapeutic Immunomodulatory Effects. Immunity 45, 931-943.

Derosa, L., Hellmann, M. D., Spaziano, M., Halpenny, D., Fidelle, M., Rizvi, H., Long, N., Plodkowski, A. J., Arbour, K. C., Chaft, J. E., et al. (2018). Negative association of antibiotics on clinical activity of immune checkpoint inhibitors in patients with advanced renal cell and non-small-cell lung cancer. Ann. Oncol. Off. J. Eur. Soc. Med. Oncol. 29, 1437-1444.

Diaz-Montero C M, Mao F J, Barnard J, Parker Y, Zamanian-Daryoush M, Pink J J, et al. MEK inhibition abrogates sunitinib resistance in a renal cell carcinoma patient-derived xenograft model. Br J Cancer 2016; 115:920-8. doi:10.1038/bjc.2016.263.

Doran M G, Spratt D E, Wongvipat J, Ulmert D, Carver B S, Sawyers C L, et al. Cabozantinib resolves bone scans in tumor-naive mice harboring skeletal injuries. Mol Imaging 2014; 13. doi:10.2310/7290.2014.00026.

Dridi B, Henry M, Khéchine A, Raoult D, Drancourt M. (2009) High prevalence of *Methanobrevibacter smithii* and Methanosphaera stadtmanae detected in the human gut using an improved DNA detection protocol. PLoS One. 2009 Sep. 17; 4(9):e7063. doi: 10.1371/journal.pone.0007063

Eisenhauer, E. A., Therasse, P., Bogaerts, J., Schwartz, L. H., Sargent, D., Ford, R., Dancey, J., Arbuck, S., Gwyther, S., Mooney, M., et al. (2009). New response evaluation criteria in solid tumours: revised RECIST guideline (version 1.1). Eur. J. Cancer Oxf. Engl. 1990 45, 228-247.

Elkrief, A., El Raichani, L., Richard, C., Messaoudene, M., Belkaid, W., Malo, J., Belanger, K., Miller, W., Jamal, R., Letarte, N., et al. (2019). Antibiotics are associated with decreased progression-free survival of advanced melanoma patients treated with immune checkpoint inhibitors. Oncoimmunology 8, e1568812.

Escudier, B., Farace, F., Angevin, E., Charpentier, F., Nitenberg, G., Triebel, F., and Hercend, T. (1994). Immunotherapy with interleukin-2 (IL2) and lymphokine-activated natural killer cells: improvement of clinical responses in metastatic renal cell carcinoma patients previously treated with IL2. Eur. J. Cancer Oxf. Engl. 1990 30A, 1078-1083.

Faust K, Sathirapongsasuti J F, Izard J, Segata N, Gevers D, Raes J, et al. Microbial Co-occurrence Relationships in the Human Microbiome. PLOS Comput Biol 2012; 8:e1002606. doi:10.1371/journal.pcbi.1002606.

Faust K, Raes J. Microbial interactions: from networks to models. Nat Rev Microbiol 2012; 10:538-50. doi: 10.1038/nrmicro2832.

Finegold, S. M., Song, Y., Liu, C., Hecht, D. W., Summanen, P., Könönen, E., and Allen, S. D. (2005). *Clostridium clostridioforme*: a mixture of three clinically important species. Eur. J. Clin. Microbiol. Infect. Dis. 24, 319-324.

Giraldo, N. A., Becht, E., Pagès, F., Skliris, G., Verkarre, V., Vano, Y., Mejean, A., Saint-Aubert, N., Lacroix, L., Natario, I., et al. (2015). Orchestration and Prognostic Significance of Immune Checkpoints in the Microenvironment of Primary and Metastatic Renal Cell Cancer. Clin. Cancer Res. Off. J. Am. Assoc. Cancer Res. 21, 3031-3040.

Giraldo, N. A., Becht, E., Vano, Y., Petitprez, F., Lacroix, L., Validire, P., Sanchez-Salas, R., Ingels, A., Oudard, S., Moatti, A., et al. (2017). Tumor-Infiltrating and Peripheral Blood T-cell Immunophenotypes Predict Early Relapse in Localized Clear Cell Renal Cell Carcinoma. Clin. Cancer Res. Off. J. Am. Assoc. Cancer Res. 23, 4416-4428.

Gong, J., Noel, S., Pluznick, J. L., Hamad, A. R. A., and Rabb, H. (2019). Gut Microbiota-Kidney Cross-Talk in Acute Kidney Injury. Semin. Nephrol. 39, 107-116.

Gopalakrishnan, V., Spencer, C. N., Nezi, L., Reuben, A., Andrews, M. C., Karpinets, T. V., Prieto, P. A., Vicente, D., Hoffman, K., Wei, S. C., et al. (2018). Gut microbiome modulates response to anti-PD-1 immunotherapy in melanoma patients. Science 359, 97-103.

Godon J J, Zumstein E, Dabert P, Habouzit F, Moletta R. Molecular microbial diversity of an anaerobic digestor as determined by small-subunit rDNA sequence analysis. Appl Environ Microbiol 1997; 63:2802-13.

Hahn, A. W., Froerer, C., VanAlstine, S., Rathi, N., Bailey, E. B., Stenehjem, D. D., and Agarwal, N. (2018). Targeting *Bacteroides* in Stool Microbiome and Response to Treatment With First-Line VEGF Tyrosine Kinase Inhibitors in Metastatic Renal-Cell Carcinoma. Clin. Genitourin. Cancer 16, 365-368.

Kamo, T., Akazawa, H., Suda, W., Saga-Kamo, A., Shimizu, Y., Yagi, H., Liu, Q., Nomura, S., Naito, A. T., Takeda, N., et al. (2017). Dysbiosis and compositional alterations with aging in the gut microbiota of patients with heart failure. PloS One 12, e0174099.

Kroemer, G., and Zitvogel, L. (2018). Cancer immunotherapy in 2017: The breakthrough of the microbiota. Nat. Rev. Immunol. 18, 87-88.

Lambiotte R, Delvenne J-C, Barahona M. Random Walks, Markov Processes and the Multiscale Modular Organization of Complex Networks. IEEE Trans Netw Sci Eng 2014; 1:76-90. doi:10.1109/TNSE.2015.2391998.

Langmead B, Salzberg S L. Fast gapped-read alignment with Bowtie 2. Nat Methods 2012; 9:357-9. doi:10.1038/nmeth.1923.

Le Chatelier E, Nielsen T, Qin J, Prifti E, Hildebrand F, Falony G, et al. Richness of human gut microbiome correlates with metabolic markers. Nature 2013; 500:541-6. doi:10.1038/nature12506.

Lee H L, Shen H, Hwang I Y, Ling H, Yew W S, Lee Y S, Chang M W. (2018) Targeted Approaches for In Situ Gut Microbiome Manipulation. Genes (Basel). July 12; 9(7).

Li M, Wang B, Zhang M, Rantalainen M, Wang S, Zhou H, et al. Symbiotic gut microbes modulate human metabolic phenotypes. Proc Natl Acad Sci USA 2008; 105:2117-22. doi:10.1073/pnas.0712038105.

Li, J., Jia, H., Cai, X., Zhong, H., Feng, Q., Sunagawa, S., Arumugam, M., Kultima, J. R., Prifti, E., Nielsen, T., et al. (2014). An integrated catalog of reference genes in the human gut microbiome. Nat. Biotechnol. 32, 834-841.

Liang, Q., Chiu, J., Chen, Y., Huang, Y., Higashimori, A., Fang, J., Brim, H., Ashktorab, H., Ng, S. C., Ng, S. S. M., et al. (2017). Fecal Bacteria Act as Novel Biomarkers for Noninvasive Diagnosis of Colorectal Cancer. Clin. Cancer Res. Off. J. Am. Assoc. Cancer Res. 23, 2061-2070.

Lozupone C A, Stombaugh J I, Gordon J I, Jansson J K, Knight R. Diversity, stability and resilience of the human gut microbiota. Nature 2012; 489:220-30. doi:10.1038/nature11550.

Maier, L., Pruteanu, M., Kuhn, M., Zeller, G., Telzerow, A., Anderson, E. E., Brochado, A. R., Fernandez, K. C., Dose, H., Mori, H., et al. (2018). Extensive impact of non-antibiotic drugs on human gut bacteria. Nature 555, 623-628.

Matson, V., Fessler, J., Bao, R., Chongsuwat, T., Zha, Y., Alegre, M.-L., Luke, J. J., and Gajewski, T. F. (2018). The commensal microbiome is associated with anti-PD-1 efficacy in metastatic melanoma patients. Science 359, 104-108.

Merico D, Gfeller D, Bader G D. How to visually interpret biological data using networks. Nat Biotechnol 2009; 27:921-4. doi:10.1038/nbt.1567.

Million, M. et al. (2016) Increased Gut Redox and Depletion of Anaerobic and Methanogenic Prokaryotes in Severe Acute Malnutrition. Sci. Rep. 6, 26051; doi: 10.1038/srep26051Motzer, R. J., Escudier, B., McDermott, D. F., George, S., Hammers, H. J., Srinivas, S., Tykodi, S. S., Sosman, J. A., Procopio, G., Plimack, E. R., et al. (2015). Nivolumab versus Everolimus in Advanced Renal-Cell Carcinoma. N. Engl. J. Med. 373, 1803-1813.

Motzer, R. J., Tannir, N. M., McDermott, D. F., Aren Frontera, O., Melichar, B., Choueiri, T. K., Plimack, E. R., Barthelemy, P., Porta, C., George, S., et al. (2018). Nivolumab plus Ipilimumab versus Sunitinib in Advanced Renal-Cell Carcinoma. N. Engl. J. Med. 378, 1277-1290.

Motzer, R. J., Penkov, K., Haanen, J., Rini, B., Albiges, L., Campbell, M. T., Venugopal, B., Kollmannsberger, C., Negrier, S., Uemura, M., et al. (2019). Avelumab plus Axitinib versus Sunitinib for Advanced Renal-Cell Carcinoma. N. Engl. J. Med. 380, 1103-1115.

Nielsen H B, Almeida M, Juncker A S, Rasmussen S, Li J, Sunagawa S, et al. Identification and assembly of genomes and genetic elements in complex metagenomic samples without using reference genomes. Nat Biotechnol 2014; 32:822-8. doi:10.1038/nbt.2939.

Pal, S. K., Li, S. M., Wu, X., Qin, H., Kortylewski, M., Hsu, J., Carmichael, C., and Frankel, P. (2015). Stool Bacteriomic Profiling in Patients with Metastatic Renal Cell Carcinoma Receiving Vascular Endothelial Growth Factor-Tyrosine Kinase Inhibitors. Clin. Cancer Res. Off. J. Am. Assoc. Cancer Res. 21, 5286-5293.

Pasolli E, Schiffer L, Manghi P, Renson A, Obenchain V, Truong D T, et al. Accessible, curated metagenomic data through ExperimentHub. Nat Methods 2017; 14:1023-4. doi:10.1038/nmeth.4468.

Pasolli, E., Asnicar, F., Manara, S., Zolfo, M., Karcher, N., Armanini, F., Beghini, F., Manghi, P., Tett, A., Ghensi, P., et al. (2019). Extensive Unexplored Human Microbiome Diversity Revealed by Over 150,000 Genomes from Metagenomes Spanning Age, Geography, and Lifestyle. Cell 176, 649-662.e20.

Porta, C., and Rizzo, M. (2019). Immune-based combination therapy for metastatic kidney cancer. Nat. Rev. Nephrol. 15, 324-325.

Ramachandran G, Bikard D. (2019) Editing the microbiome the CRISPR way. Philos Trans R Soc Lond B Biol Sci. 2019 May 13; 374(1772):20180103.

Raymond, F., Ouameur, A. A., Deraspe, M., Iqbal, N., Gingras, H., Dridi, B., Leprohon, P., Plante, P.-L., Giroux,

44

R., Bérubé, È., et al. (2016). The initial state of the human gut microbiome determines its reshaping by antibiotics. ISME J. 10, 707-720.

Rini, B. I., Plimack, E. R., Stus, V., Gafanov, R., Hawkins, R., Nosov, D., Pouliot, F., Alekseev, B., Soulières, D., Melichar, B., et al. (2019a). Pembrolizumab plus Axitinib versus Sunitinib for Advanced Renal-Cell Carcinoma. N. Engl. J. Med. 380, 1116-1127.

Rini, B. I., Powles, T., Atkins, M. B., Escudier, B., McDermott, D. F., Suarez, C., Bracarda, S., Stadler, W. M., Donskov, F., Lee, J. L., et al. (2019b). Atezolizumab plus bevacizumab versus sunitinib in patients with previously untreated metastatic renal cell carcinoma (IMmotion151): a multicentre, open-label, phase 3, randomised controlled trial. Lancet Lond. Engl.

Rosenberg, S. A., Lotze, M. T., Yang, J. C., Topalian, S. L., Chang, A. E., Schwartzentruber, D. J., Aebersold, P., Leitman, S., Linehan, W. M., Seipp, C. A., et al. (1993). Prospective Randomized Trial of High-Dose Interleukin-2 Alone or in Conjunction With Lymphokine-Activated Killer Cells for the Treatment of Patients With Advanced Cancer. JNCI J. Natl. Cancer Inst. 85, 622-632.

Rossi, O., van Berkel, L. A., Chain, F., Tanweer Khan, M., Taverne, N., Sokol, H., Duncan, S. H., Flint, H. J., Harmsen, H. J. M., Langella, P., et al. (2016). *Faecalibacterium prausnitzii* A2-165 has a high capacity to induce IL-10 in human and murine dendritic cells and modulates T cell responses. Sci. Rep. 6, 18507.

Routy, B., Le Chatelier, E., Derosa, L., Duong, C. P. M., Alou, M. T., Daillère, R., Fluckiger, A., Messaoudene, M., Rauber, C., *Roberti*, M. P., et al. (2018). Gut microbiome influences efficacy of PD-1-based immunotherapy against epithelial tumors. Science 359, 91-97.

Segata, N., Izard, J., Waldron, L., Gevers, D., Miropolsky, L., Garrett, W. S., and Huttenhower, C. (2011). Metagenomic biomarker discovery and explanation. Genome Biol. 12, R60.

Sivan, A., Corrales, L., Hubert, N., Williams, J. B., Aquino-Michaels, K., Earley, Z. M., Benyamin, F. W., Lei, Y. M., Jabri, B., Alegre, M.-L., et al. (2015). Commensal *Bifidobacterium* promotes antitumor immunity and facilitates anti-PD-L1 efficacy. Science 350, 1084-1089.

Suau A, Bonnet R, Sutren M, Godon J J, Gibson G R, Collins M D, et al. Direct analysis of genes encoding 16S rRNA from complex communities reveals many novel molecular species within the human gut. Appl Environ Microbiol 1999; 65:4799-807.

Tanoue, T., Morita, S., Plichta, D. R., Skelly, A. N., Suda, W., Sugiura, Y., Narushima, S., Vlamakis, H., Motoo, I., Sugita, K., et al. (2019). A defined commensal consortium elicits CD8 T cells and anti-cancer immunity. Nature 565, 600.

Vétizou, M., Pitt, J. M., Daillère, R., Lepage, P., Waldschmitt, N., Flament, C., Rusakiewicz, S., Routy, B., *Roberti*, M. P., Duong, C. P. M., et al. (2015). Anticancer immunotherapy by CTLA-4 blockade relies on the gut microbiota. Science 350, 1079-1084.

Zhao, L., Zhang, F., Ding, X., Wu, G., Lam, Y. Y., Wang, X., Fu, H., Xue, X., Lu, C., Ma, J., et al. (2018). Gut bacteria selectively promoted by dietary fibers alleviate type 2 diabetes. Science 359, 1151-1156.

The invention claimed is:

1. A method for treating a patient with a renal cell cancer comprising administering a composition enriched for bacteria selected from the group consisting of *Dorea longicatena* and *Eubacterium siraeum* in combination with an immune checkpoint inhibitor (ICI)-based therapy or a tyrosine kinase inhibitor (TKI)-based therapy, wherein said bacterial administration results in a relative abundance of >0.855% for *D. longicatena* or generates a relative abundance of >1.11% for *E. siraeum* in a feces sample from the patient and induces immunostimulation in the cancer patient and improves efficacy of the (ICI)-based or (TKI)-based therapy.

2. The method of claim 1, comprising administering *Dorea longicatena* bacteria.

3. The method of claim 1, comprising administering *Eubacterium siraeum* bacteria.

4. The method of claim 1, comprising administering *Dorea longicatena* bacteria and *Eubacterium siraeum* bacteria.

5. The method of claim 2, further comprising administering *Alistipes senegalensis* bacteria.

6. The method of claim 3, further comprising administering *Alistipes senegalensis* bacteria.

7. The method of claim 4, further comprising administering *Alistipes senegalensis* bacteria.

8. The method of claim 1, further comprising administering bacteria of at least one species selected from the group consisting of *Enterococcus hirae, Akkermansia muciniphila* and *Bacteroides salyersiae.*

9. The method of claim 1, wherein said bacteria are administered in a fecal microbial composition.

10. The method of claim 1, wherein the bacteria are administered in combination with an ICI-based therapy.

11. The method of claim 1, wherein the bacteria are administered in combination with a TKI-based therapy.

12. The method of claim 1, wherein the bacteria are administered in combination with an ICI-based therapy and a TKI-based therapy.

13. The method of claim 1, further comprising the following steps prior to administering the bacteria:

(i) determining relative abundance of at least two immunotolerant species selected from the group consisting of *Clostridium hathewayi, Clostridium clostridioforme* and *Clostridium bolteae* in a biological sample from said patient;

(ii) determining relative abundance of at least two immunostimulatory species selected from the group consisting of *Akkermansia muciniphila, Bacteroides salyersiae, Alistipes senegalensis, Dorea longicatena, Eubacterium siraeum* in the biological sample; and (iii) calculating the ratio of the relative abundance of the immunotolerant species of step (i) to the relative abundance of the immunostimulatory species of step (ii).

14. The method of claim 13, comprising determining the relative abundance of at least two immunostimulatory species selected from the group consisting of *Alistipes senegalensis, Dorea longicatena,* and *Eubacterium siraeum.*

15. The method of claim 10, wherein the ICI-based therapy is an anti-CTLA-4 and/or anti-PD-1 antibody therapy.

16. The method of claim 11, wherein the TKI-based therapy is a sunitinib, axitinib, and/or cabozantinib therapy.

* * * * *